(12) United States Patent
Zhang et al.

(10) Patent No.: US 9,221,838 B2
(45) Date of Patent: Dec. 29, 2015

(54) INHIBITORS OF AKT ACTIVITY

(75) Inventors: Lixin Zhang, Craigavon (GB); Graham Peter Trevitt, Craigavon (GB); Hugues Miel, Craigavon (GB); Frank Burkamp, Craigavon (GB); Timothy Harrison, Craigavon (GB); Andrew John Wilkinson, Craigavon (GB); Charles-Henry Fabritius, Craigavon (GB)

(73) Assignee: ALMAC DISCOVERY LIMITED, Craigavon (IE)

( * ) Notice: Subject to any disclaimer, the term of this patent is extended or adjusted under 35 U.S.C. 154(b) by 438 days.

(21) Appl. No.: 13/517,219

(22) PCT Filed: Dec. 23, 2010

(86) PCT No.: PCT/GB2010/002329
§ 371 (c)(1),
(2), (4) Date: Sep. 14, 2012

(87) PCT Pub. No.: WO2011/077098
PCT Pub. Date: Jun. 30, 2011

(65) Prior Publication Data
US 2013/0116243 A1    May 9, 2013

(30) Foreign Application Priority Data

Dec. 23, 2009 (GB) .................................. 0922589.7

(51) Int. Cl.
| | | |
|---|---|---|
| *C07D 498/04* | (2006.01) | |
| *C07D 498/14* | (2006.01) | |
| *C07D 405/04* | (2006.01) | |
| *C07D 471/04* | (2006.01) | |

(52) U.S. Cl.
CPC ............ *C07D 498/04* (2013.01); *C07D 471/04* (2013.01); *C07D 498/14* (2013.01)

(58) Field of Classification Search
CPC ... C07D 498/04; C07D 498/14; C07D 405/04
See application file for complete search history.

(56) References Cited

U.S. PATENT DOCUMENTS

2008/0207666 A1 * 8/2008 Debenham et al. ........... 514/278

FOREIGN PATENT DOCUMENTS

| WO | WO 2006/065601 A2 | 6/2006 |
|---|---|---|
| WO | WO 2008/070016 A2 | 6/2008 |
| WO | WO 2008/070041 A2 | 6/2008 |
| WO | WO 2008/070134 A1 | 6/2008 |
| WO | WO 2009/148887 A1 | 12/2009 |
| WO | WO 2009/148916 A1 | 12/2009 |

OTHER PUBLICATIONS

Golub et al., Science, vol. 286, Oct. 15, 1999, pp. 531-537.*
Wu Z et al: "Rapid assembly of diverse and potent allosteric Akt inhibitors", Bioorganic & Medicinal Chemistry Letters, Pergamon, Elseuier Science, GB, vol. 18, No. 6, Mar. 15, 2008, pp. 2211-2214.
International Search Report & Written Opinion from PCT/GB2010/002329, dated Mar. 17, 2011.

\* cited by examiner

*Primary Examiner* — Samira Jean-Louis
(74) *Attorney, Agent, or Firm* — Lathrop & Gage LLP; Brian C. Trinque; Jana A. Lewis

(57) ABSTRACT

The invention relates to a series of compounds with particular activity as inhibitors of the serine-threonine kinase AKT. Also provided are pharmaceutical compositions comprising same as well as methods for treating cancer.

16 Claims, No Drawings

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide: 5' FAM Crosstide
<220> FEATURE:
<221> NAME/KEY: misc_feature
<222> LOCATION: (1)..(1)
<223> OTHER INFORMATION: Modification with 5' FAM

<400> SEQUENCE: 1

Gly Arg Pro Arg Thr Ser Ser Phe Ala Glu Gly
1               5                   10
```

INHIBITORS OF AKT ACTIVITY

RELATED APPLICATIONS

This application is a 35 U.S.C. §371 filing of International Patent Application No: PCT/GB2010/002329, which was filed on Dec. 23, 2010, and which claims priority to Great Britain Patent Application No: 0922589.7, which was filed on Dec. 23, 2009. The entire contents of the aforementioned applications are hereby incorporated herein by reference.

The present invention relates to compounds that are useful as inhibitors of the activity of one or more isoforms of the serine/threonine kinase, AKT. The present invention also relates to pharmaceutical compositions comprising these compounds and to methods of using these compounds in the treatment of cancer and methods of treating cancer.

BACKGROUND TO THE INVENTION

The AKT protein family, also known as protein kinases B (PKB), are known to be involved in a wide variety of biological processes including cell proliferation, differentiation, apoptosis, tumorigenesis, as well as glycogen synthesis and glucose uptake. These enzymes are members of the serine/threonine-specific protein kinase family.

The PKB/AKT pathway has been identified as an important regulator of cell survival signalling and apoptosis in cells. Signalling is thought to occur through a range of growth factor receptors including platelet derived growth factor, insulin growth factor and nerve growth factor, resulting in activation of phosphatidylinositol 3-OH kinase (PI-3K). This activation in turn leads to the generation of phosphatidylinositol (3,4,5)triphosphate (PIP3). Activated PIP3 binds to and in turn phosphorylates the enzyme PDK-1, the main activator of AKT, through its pleckstrin homology domain. Activated PDK-1 is responsible for a phosphorylation event at Thr308 of AKT, which induces a conformational change that facilitates further phosphorylation of AKT at Ser 473 by PDK-2.

PDK-1 phosphorylation of downstream kinases is not unique to AKT, as it has been reported to activate p70 S6 kinase and protein kinase C.

The activation of AKT influences multiple events within the cell including the inhibition of apoptosis, the progression of the cell cycle, cellular survival, metabolism, angiogenesis and hormone resistance.

Presently three family members of AKT have been identified, AKT 1, AKT 2 and AKT 3 (also known as PKBα, PKBβ and PKBγ). The family members share 80% amino acid sequence homology and all retain similar regional structure. They possess a C-terminal pleckstrin homology (PH) domain, a catalytic domain, a short α helical linker region and a carboxyl terminal domain. The PH domain permits binding of proteins to the cell membrane through a phospholipid interaction. The catalytic domain of AKT family members contains two residues essential for kinase activation, namely Thr308 and Ser 473. In turn AKT can phosphorylate any protein containing the RXRXXS/T-B motif where X represents any amino acid and B represents bulky hydrophobic residues.

Turning to the cellular function of AKT, hyper activation of AKT has been linked to the inhibition of cellular apoptosis due to phosphorylation and negative regulation of the forkhead family of transcription factors which regulate various genes responsible for instigating death processes including FKHR, FKHRL1 and AFX. Conversely AKT has been reported to up-regulate genes which are known to be anti-apoptotic including IKK and CREB. It is this mixture of positive and negative regulation which highlights the importance of AKT in regulating apoptosis. AKT promotes unwanted cell survival through its' phosphorylation of several key apoptotic proteins including Bad and Pro-caspase 9, thus rendering them inactive and preventing signalling through this pathway. AKT activates and inhibits multiple mechanisms which have a major role in the progression of the cell cycle, ultimately leading to cell proliferation. The best characterised cell cycle regulator and tumour suppressor proteins p53 can be dysregulated via AKT phosphorylation and activation of the main p53 negative regulator MDM2. Phosphorylated MDM2 translocates to the nucleus where it prevents p53 transcription. The inhibition of p53 allows aberrant proliferation of the cell and progression towards a benign state.

In a similar fashion, AKT can also phosphorylate p27kip1 and p21; two main inhibitors of cell cycle progression, leading to loss of function, resulting in unchecked cell cycle progress and excessive proliferation.

AKT activation causes an increase in the rate of glycolysis by increasing the rate of glucose metabolism. It has also been reported that activated AKT stimulates the transport of amino acids and supports mTOR dependent increases in protein translation. Proangiogenic factors such as vascular endothelial growth factor (VEGF), have been reported to activate AKT, ultimately resulting in inhibition of endothelial apoptosis, as well as activating endothelial nitric oxide synthase (eNOS). The sum result of this is rapid neo-vascularisation and cell migration.

Hypoxia driven angiogenesis, primarily mediated by hypoxia inducible factor (HIF 1α) can lead to the induction of multiple proteins including VEGF. Increased activated AKT has been reported to increase HIF-1α expression leading to an increase in angiogenesis independent of a hypoxic environment. Recent data has shown that HIF-1α activity in invasive breast cancer is correlated with increased activated AKT-1 phosphorylation.

Estrogen receptor (ER) and androgen receptor (AR) inhibitors designed to inhibit cell signalling and induce apoptosis, are vital tools in cancer therapies. Incidence of resistance to these drugs arises rapidly in cancers including prostate, breast and ovarian. AKT has been reported to phosphorylate androgen receptors, leading to inhibition of AR activity and blockade of normal apoptotic signalling in prostate cancer induced by androgens.

In a similar manner, activation of AKT leads to phosphorylation of ERα resulting in an inhibition of tamoxifen mediated apoptosis or tumour regression, coupled with the creation of an estrogen independent signalling pathway. Activated AKT-2 has been identified as a promoter of ERα transcription in the presence or absence of estrogen increasing the rate of proliferation of breast cancer cells.

Hyper-activated AKT has been reported in a range of cancers compared to normal tissues including breast, lung, prostate, gastric, ovary, pancreas, thyroid, glioblastoma and haemological cancers. Phosphorylation of AKT has also been associated with clinical characteristics including increased stage and grade of tumour and increased poor prognosis. The activation of AKT can arise from a number of different genetic mutations in the AKT/PI-3K pathway.

Somatic mutations in the PI-3KCA gene have been widely reported in a large variety of tumours including breast, prostate and head and neck. A large number of these mutations will increase the copy number of the gene leading to an increase in PI-3K activity. A recent study has identified a PI-3K mutation which selectively phosphorylates AKT in colon cancer which results in increase cell proliferation and invasion.

Any mutation which increases the activity of the PI-3K pathway will ultimately result in an increased activation of AKT. Gene amplifications are common occurrences in cancer. Amplifications of AKT-2 have been reported in ovarian, pancreatic, breast and head and neck squamous cell carcinoma. No amplifications or mutations in AKT-3 have been reported to date although deletion mutations leading to hyperactivation and amplification mutations have been reported associated with AKT-1. One mutation; E17K, results in pathological localization of AKT-1 to the cell membrane, inducing its activation and resulting in down-stream signalling and cellular transformation. In vivo, this mutation has been shown to induce leukaemia in mice.

Phosphatase and tensin homolog deleted on chromosome 10 (PTEN) is a tumour suppressor gene known to negatively regulate AKT function. In cancer, loss of PTEN function results in constitutive phosphorylation of AKT and other down-stream effectors of the PI-3K pathway. Loss of PTEN, due to deletion mutations or promoter methylation, has been reported in a number of different cancers including glioblastoma, endometrial, lung, breast, prostate and thyroid. This loss is commonly associated with hyperactivation of AKT. Recent studies have shown that loss of heterozygosity (LOH) at the PTEN gene was directly correlated to increased AKT activation and chemoresistance in gastric carcinomas and decreased progesterone receptor expression in breast carcinomas.

AKT activation is commonly initiated at the cell surface through a signalling event at a receptor, usually one of the tyrosine kinase family. Two tyrosine kinase receptors commonly amplified or over-expressed in cancer are HER2 and EGFR. In HER2 over-expressing tumours there is often a hyper-activation of AKT, this has been reported in ovarian, stomach and bladder cancer. Similarly in EGFR over-expressing tumours, particularly those with the EGFRvIII activating mutation, selective activation of AKT has been reported in a range of cancers including non-small cell lung cancers, breast, ovarian and most commonly high grade gliomas.

Examples of AKT inhibitors are provided in WO 2008/070134, WO 2008/070016 and WO 2008/070041. These documents provide specific naphthyridine compounds fused to a five membered heterocycle. Other inhibitors of AKT may be found in, for example, WO 2009/148887 and WO 2009/148916.

SUMMARY OF THE INVENTION

In a first aspect the present invention provides a compound according to Formula (I):

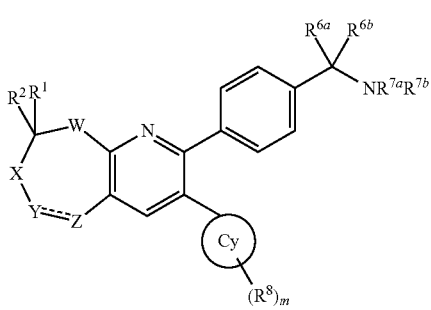
(I)

wherein:

$R^1$ and $R^2$ are each independently selected from hydrogen, aryl, C1-C10 alkyl, CN, CHO, $CO_2H$, $CONH_2$, $CONHR^3$, $CONR^{3a}R^{3b}$, $COR^3$, $CO_2R^3$, $NH_2$, $NHR^3$, $NR^{3a}R^{3b}$, $NHCOR^3$, $NHSO_2R^3$, $NR^{3a}COR^{3b}$, $NR^{3a}SO_2R^{3b}$, OH, $OR^3$, SH, $SR^3$, $SOR^3$, $SO_2R^3$, $SO_2NHR^3$, $SO_2NR^{3a}R^{3b}$, F, Cl, Br and I, wherein each $R^3$, $R^{3a}$ and $R^{3b}$ is independently selected from C1-C10 alkyl, including wherein $R^{3a}$ and $R^{3b}$ are joined to one another to form a heterocycle that includes the nitrogen to which they are attached.

Wherein separate $R^1$ and $R^2$ may be joined to one another to form an optionally substituted and optionally saturated heterocycle or carbocycle that includes the C atom to which they are attached; or $R^1$ and $R^2$ together are oxo or optionally C1-C10 alkyl O-substituted oxime;

W is O, S, SO, $SO_2$, NR', or $CR^aR^b$ where R' is either hydrogen or C1-C10 alkyl, and where $R^a$ and $R^b$ are each independently selected from the members of the group from which $R^1$ and $R^2$ are selected above;

X is either absent or is $CR^4R^5$ where $R^4$ and $R^5$ are each independently selected from the members of the group from which $R^1$ and $R^2$ are selected above;

Y and Z are independently either substituted or unsubstituted nitrogen or carbon and where carbon is substituted by substituents independently selected from the members of the group from which $R^1$ and $R^2$ are selected above or when nitrogen then the substituent is selected from aryl, C1-C10 alkyl, $SO_2R^3$, $CONHR^3$, $CONR^{3a}R^{3b}$, $COR^3$ and $CO_2R^3$ where $R^3$, $R^{3a}$ and $R^{3b}$ are as defined above, or where Y and Z together form an optionally substituted heterocyclyl or carbocyclic group, or where Y is $SO_2$;

$R^{7a}$ and $R^{7b}$ are independently selected from H and alkyl, including wherein $R^{7a}$ and $R^{7b}$ are joined to one another to form a heterocycle that includes the nitrogen to which they are attached; and $R^{6a}$ and $R^{6b}$ are independently selected from: H, $(C_1-C_6)$ alkyl, $(C_1-C_6)$alkenyl, and $(C_1-C_6)$alkynyl, wherein said alkyl is optionally substituted with up to three substituents selected from: OH and halo; or $R^{6a}$ and $R^{6b}$ can be taken together to form a monocyclic or bicyclic carbo- or heterocycle with 3-7 members in each ring, said heterocycle having one or more heteroatoms selected from N, O and S, and said carbo- or heterocycle is optionally substituted with one or more substituents selected from: $(C_1-C_6)$alkyl, $(C_3-C_6)$cycloalkyl, $(C_1-C_6)$alkoxy, $CO_2H$, halo, OH, CN and $NR^{3a}R^{3b}$, said alkyl, cycloalkyl and alkoxy is optionally substituted with one or more substituents selected from halo, CN, OH and $NR^{3a}R^{3b}$; and ring Cy is selected from ($C_3$ to $C_8$)cycloalkyl, alkylcycloalkyl, heterocycloalkyl, heteroaryl and aryl, wherein m is 0, 1, 2, 3, 4 or 5, and each $R^9$ is independently selected from alkyl, CN, CHO, $CO_2H$, $CONH_2$, $CONHR^9$, $CONHR^{9a}R^{9b}$, $COR^9$, $CO_2R^9$, $NH_2$, $NHR^9$, $NR^{9a}R^{9b}$, $NHCOR^9$, $NHSO_2R^9$, $NR^{9a}COR^{9b}$, $NR^{9a}SO_2R^{9b}$, OH, $OR^9$, SH, $SR^9$, F, Cl, Br and I, wherein each $R^9$, $R^{9a}$ and $R^{9b}$ is independently selected from alkyl, including wherein $R^{9a}$ and $R^{9b}$ form a heterocycle that includes the nitrogen to which they are attached or Cy may be iodine;

and pharmaceutically acceptable salts, stereoisomers and tautomers thereof.

One aspect of the invention also provides compounds selected from the following group of structures:

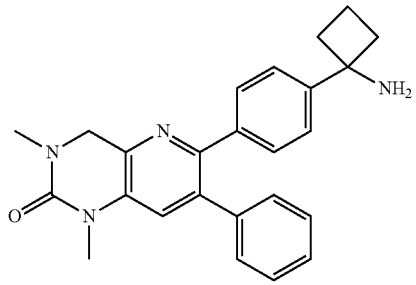

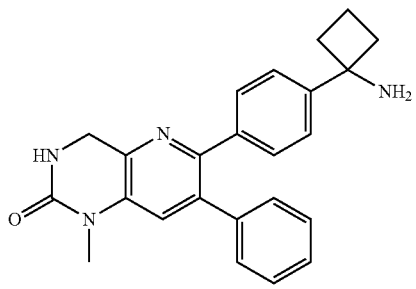

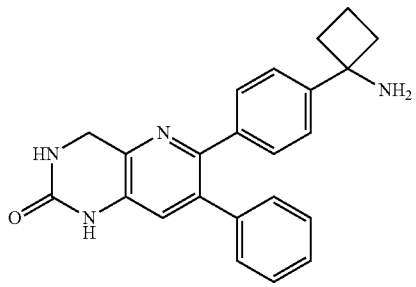

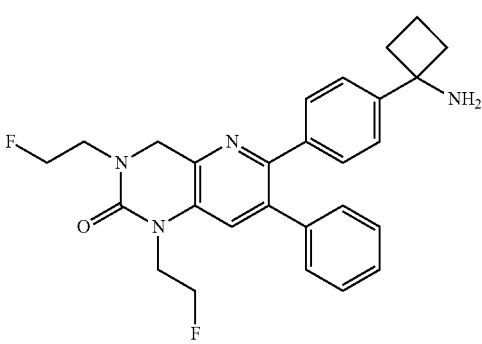

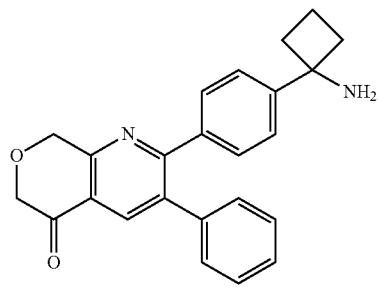

and pharmaceutically acceptable salts, stereoisomers and tautomers thereof.

In preferred embodiments X is absent.

In preferred embodiments $R^{6a}$ and $R^{6b}$ together form

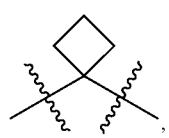 [SMILES: *C1(*)CCC1]

that is they preferably form cyclobutane. In further preferred embodiments the group bound to the phenyl ring in structure I is 1-aminocyclobutyl.

In preferred embodiments $R^{6a}$ and $R^{6b}$ together form

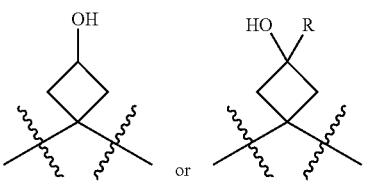

where R is an alkyl group, preferably a C1 to C6 alkyl group.

In preferred embodiments the ring Cy is unsubstituted $C_6$ aryl, that is phenyl.

In a further embodiment of the compound of the invention the phenyl ring shown in Formula (I) is replaced with a pyridine ring.

The bond between Y and Z is optionally either a single or a double bond. In preferred embodiments the bond between Y and Z is a single bond.

In preferred embodiments X is absent, Y is carbonyl and Z is optionally substituted amino, or X is absent, Y is optionally substituted amino and Z is carbonyl. In these embodiments W is preferably $CH_2$ or O, more preferably O. In these same embodiments $R^1$ and $R^2$ are preferably hydrogen. In these embodiments when amino is substituted it is preferably methyl or acetamido substituted.

In preferred embodiments the substituents bound to Y and Z together with Y and Z themselves form a 5 or 6 membered optionally substituted carbocyclic or heterocyclic ring.

In particularly preferred embodiments the substituents bound to Y and Z together with Y and Z themselves form a moiety selected from the group:

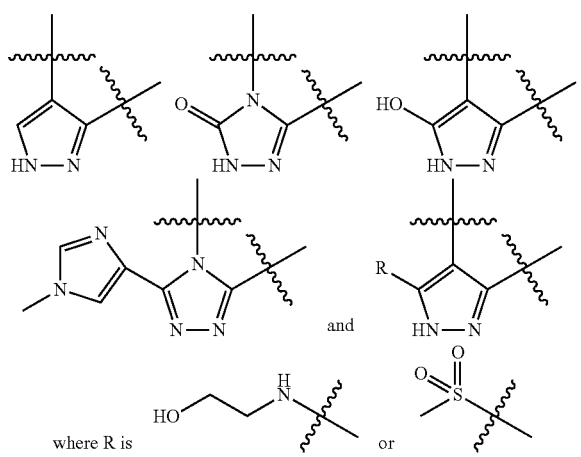

where R is 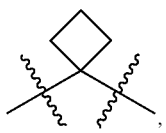 [SMILES: *C1(*)CCC1] or

In one particularly preferred embodiment of the compound of the invention the ring Cy is replaced with an iodine atom.

In preferred embodiments where Cy is alkylcycloalkyl, Cy is methylcyclopropyl.

In preferred embodiments W is either $CH_2$ or O. In one particularly preferred embodiment W is $CH_2$. In another particularly preferred embodiment W is O.

Where the compound of the invention has $R^{6a}$ and $R^{6b}$ groups cooperating so as to together form that is they preferably form cyclobutane, which additionally has a polar substituent at the position distal to the benzene ring to which the cyclobutane ring is bound, the polar substituent is preferably in a trans relationship to the nitrogen atom having groups $R^{7a}$ and $R^{7b}$ pendant therefrom.

Other preferred embodiments of the compounds according to the invention appear throughout the specification and in particular in the examples. Particularly preferred are those named compounds having greater activity as tested. Compounds having higher activity are more preferred over those having lower activity.

DETAILED DESCRIPTION OF THE INVENTION

The term "alkyl group" refers to an aliphatic group containing at least carbon and hydrogen and containing 1 to 15 carbon atoms, such as 1 to 10 carbon atoms. Attachment to the alkyl group occurs through a carbon atom.

A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms.

An alkyl group may be straight chained or it may be branched.

An alkyl group may contain no ring structures or it may contain one or more rings.

For example, a "cycloalkyl" group contains at least one ring. It is understood that attachment to a cycloalkyl group is via a ring of the cycloalkyl group. Each ring may contain 3 to 10 atoms, such as 4 to 8 or 5 to 7 atoms. Each ring may be independently selected to contain just carbon atoms or to contain both carbon atoms and from 1 to 4 heteroatoms selected from O, N and S. For cyclo-heteroalkyl groups (i.e. cycloalkyl groups that contain one or more heteroatoms), attachment to the cycloalkyl group may occur either through a carbon atom or, if one or more heteroatoms are contained in a ring, attachment may also occur through a heteroatom contained in a ring.

For example, a cycloalkyl group may be mono-cyclic or bi-cyclic.

Thus, a "$C_n$ cycloalkyl" group contains n carbon atoms. All n carbon atoms may be contained in the ring(s) of the cycloalkyl group or one or more of the carbons may not be contained in the ring(s) and may instead form one or more chains branching from the ring, If a $C_n$, alkyl group is joined to a separate $C_m$ alkyl group containing m carbon atoms to form, for example, a heterocycle, the two alkyl groups contain a total number of m+n carbon atoms.

An alkyl group may be saturated or unsaturated. Thus, the alkyl group may be an alkenyl group (i.e. contain a carbon-carbon double bond) and/or an alkynyl group (i.e. contain a carbon-carbon triple bond). If the alkyl group is unsaturated, it may contain at least 2 carbon atoms. It is understood that any unsaturated portions of an alkyl group are non-aromatic (aromatic groups fall within the scope of the definition of "aryl"). Any part of the alkyl group may be unsaturated, for example the straight, branched or cyclic portion of an alkyl group may contain a carbon-carbon double bond or a carbon-carbon triple bond. Attachment to an unsaturated alky group may occur through the unsaturated part of the alkyl group or may occur through the unsaturated part of the group.

For example, an unsaturated alkyl group may contain 1 to 4 carbon-carbon double bonds or 1 to 3 carbon-carbon triple bonds or 1 to 4 of a combination of carbon-carbon double bonds and carbon-carbon triple bonds.

An alkyl group may be substituted with one or more heteroatoms or it may be unsubstituted (i.e. not contain any heteroatoms). If more than one hetero-substituent is present, the substituents are independently selected from one another unless they form a part of a particular functional group (e.g. an amide group).

The heteroatom substituents may in turn be substituted with further carbon-containing groups. In this case, the $C_n$ or $C_m$ prefix that defines the substituted alkyl group refers to the total number of carbons contained in the group, i.e. including the carbon atoms contained in any substituted heteroatomic groups, and the total alkyl group contains 1 to 15 carbon atoms as defined previously.

Accordingly, if the alkyl group is substituted, it may, for example, contain one or more of CN, $CO_2H$, $CONH_2$, CONHR, $CONR^aR^b$, $CO_2R$, $NH_2$, NHR, $NR^aR^b$, OH, OR, SH, SR, F, Cl, Br and I, wherein each R, $R^a$ and $R^b$ are independently selected groups (e.g. alkyl/aryl groups) attached to the atom to which the group joins through a carbon atom of each group, including wherein $R^a$ and $R^b$ form a heterocycle that includes the heteroatom to which they are attached. A group containing two $C_m$-$C_n$ alkyl moieties that form a cycle that includes, for example, the heteroatom to which they are attached may contain from $C_{2m}$ to $C_{2n}$ carbon atoms.

Examples of unsubstituted saturated alkyl groups containing no cyclic structures include methyl, ethyl, n-propyl, sec-propyl, n-butyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

Examples of unsubstituted saturated cyclic alkyl groups include cyclopropyl, cyclobutyl, cyclopentyl and cyclohexyl.

Examples of unsaturated alkyl groups include ethenyl, propenyl, butenyl, 2-methylbutenyl and cyclohexenyl.

The term "aryl group" refers to a group containing at least one ring that is aromatic and containing 1 to 15 carbon atoms, such as 1 to 10 carbon atoms. Where an aryl group is stated as being substituted at a particular position, attachment of the position to the aryl group is onto the aromatic ring of the aryl group itself rather than the position being joined to the aryl group through any non-aromatic side-chain of the aryl group. For example, when $R^1$ is an aryl group in $CR^1$, the C is attached to the aromatic part of the aryl group.

Each ring may be independently selected to contain only carbon atoms or to contain both carbon atoms and from 1 to 4 heteroatoms selected from O, N and S. For heteroaryl groups (i.e. aryl groups that contain one or more heteroatoms), attachment to the aryl group may occur either through a carbon atom or, if one or more heteroatoms are contained in a ring, attachment may also occur through a heteroatom contained in a ring.

It is noted that the heteroatoms contained in a ring of a heteroaryl group may be substituted, for example forming an N-oxide.

For example, the aromatic group may be mono-cyclic or bi-cyclic, wherein one or both of the rings of a bi-cyclic system is aromatic.

Examples of aryl groups include acridinyl, phenyl, carbazolyl, cinnolinyl, quinoxalinyl, pyrazolyl, benzotriazolyl, furanyl, naphthyl, thienyl, thiazolyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline, benzimidazolyl and melaminyl.

It is noted that the term "heterocycle" includes within its scope both cycloalkyl groups containing one or more heteroatoms within the ring system and aryl groups containing one or more heteroatoms within the ring system.

Heterocyclic groups may be any of the various pyrazoles, imidazoles and triazoles and may include the oxygen and/or sulfur containing analogues of the various pyrazoles, imidazoles and triazoles, that is oxazoles, isoxazoles, thiazoles and isothiazoles and derivatives.

The term "halo" refers to a group selected from chlorine, fluorine, bromine and iodine.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

For completeness, it is also noted that certain chemical formulae used herein define delocalized systems. This definition is known in the art as a definition of aromaticity and may indicate the presence of, for example, a mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and I or planes and/or axes. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein. For example, a prodrug may be formed by protecting the amine appending the cyclobutane as a physiological hydrolyzable amide. Alternatively or additionally, Y or Z or any moieties appended thereto are NH, one or more of these may be protected as a physiological hydrolyzable amide.

In those compounds of the invention where X is 'absent' there is instead a single covalent bond such that W and Y are bound to the same carbon atom, that atom with $R^1$ and $R^2$ substitution.

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulphate, bisulphate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The compounds of the present invention are useful in the treatment of medical conditions associated with disordered cell growth, including, but not restricted to, cancer, in particular cancers associated with overactivity of AKT occurring either from a direct change within the kinase itself such as may occur following a mutation within any of its subunits or from increased upstream activity including but not restricted to increased PI3K or PDK activity. Increased PI3K activity may have occurred through loss of the tumor suppressor PTEN.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers.

For example, cancers include adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharyngeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, esophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar.

The compounds of the present invention are also useful in preparing a medicament that is useful in treating the diseases described above, in particular cancer.

The compounds of the present invention may selectively inhibit one or two of the AKT protein family over the other AKT isoform(s). For example, the compounds may selectively inhibit one or two of AKT1, AKT2 or AKT3 over the other isoform(s) of AKT.

For example, the compounds of the present invention may inhibit at least AKT1 and/or AKT2. For example, the compounds may selectively inhibit AKT1 and I or AKT2 over AKT3.

The present invention is further directed to a method of inhibiting AKT activity which comprises administering to a mammal in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second drug in the treatment of cancer. The second drug may be a drug that is already known in the art in the treatment of cancer. The present invention also includes the use of the compounds of the invention in a regime including the step of radiotherapy.

In particular, cancers often become resistant to therapy. The development of resistance may be delayed or overcome by the administration of a combination of drugs that includes the compounds of the present invention.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

With regard to combination therapy the compounds of the present invention may be administered separately, sequentially, simultaneously, concurrently or may be chronologically staggered with one or more standard therapeutics such as any of those mentioned above.

The present invention also provides a pharmaceutical composition suitable for clinical use.

In particular, a pharmaceutical composition may comprise a pharmaceutical carrier and, dispersed therein, a therapeutically effective amount of the compounds of the invention. The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The anti-cancer agent may also be administered in the form of a suppository or pessary, or may be applied topically in the form of a lotion, solution, cream, ointment or dusting powder.

The present invention also relates to methods of treating or preventing cancer comprising administering a compound according to the present invention as described herein to a subject in need thereof. In preferred embodiments the method includes the use of one or more compounds of the present invention in a regime including the step of radiotherapy.

EXAMPLES

The present invention will now be described in relation to several examples.

Examples 1 to 153 were synthesised according to the methods described subsequently. Their IC50 values were then determined as described below and are represented in the following table, in which the compound numbers correspond to the numbers in the examples.

| Example Number | IC50 in IMAP assay vs AKT1 | IC50 in IMAP assay vs AKT2 | IC50 in IMAP assay vs AKT3 |
|---|---|---|---|
| 1 | ++ | ++ | + |
| 2 | +++ | ++ | + |
| 3 | ++ | + | + |
| 4 | ++++ | +++ | + |
| 5 | +++ | ++ | + |
| 6 | +++ | ++ | ++ |
| 7 | ++++ | ++ | + |
| 8 | +++ | +++ | + |
| 9 | +++ | ++ | + |
| 10 | +++ | ++ | + |
| 11 | +++ | +++ | + |
| 12 | ++++ | ++ | + |
| 13 | +++ | +++ | ++ |
| 14 | +++ | ++ | ++ |
| 15 | +++ | ++ | ++ |
| 16 | ++++ | +++ | ++ |
| 17 | +++ | ++ | ++ |
| 18 | ++ | ++ | + |
| 19 | +++ | +++ | + |
| 20 | +++ | ++ | + |
| 21 | +++ | ++ | + |
| 22 | ++++ | ++ | + |
| 23 | +++ | ++ | + |
| 24 | ++ | +++ | + |
| 25 | +++ | ++ | + |
| 26 | ++++ | ++ | + |
| 27 | ++ | + | + |
| 28 | ++ | +++ | + |
| 29 | ++++ | +++ | + |
| 30 | ++ | ++ | ++ |
| 31 | ++++ | +++ | ++ |
| 32 | +++ | +++ | + |
| 33 | ++++ | ++++ | +++ |
| 34 | ++ | ++ | + |
| 35 | ++ | +++ | + |
| 36 | +++ | ++ | ++ |
| 37 | +++ | ++ | + |
| 38 | +++ | +++ | ++ |
| 39 | +++ | ++ | + |
| 40 | +++ | ++ | + |
| 41 | ++ | +++ | + |
| 42 | ++ | +++ | ++ |
| 43 | +++ | ++++ | + |
| 44 | ++ | ++ | + |
| 45 | ++ | +++ | ++ |
| 46 | +++ | +++ | +++ |
| 47 | ++++ | +++ | ++ |
| 48 | +++ | ++++ | +++ |
| 49 | +++ | +++ | +++ |
| 50 | ++++ | +++ | ++ |
| 51 | +++ | +++ | ++ |
| 52 | +++ | ++++ | ++ |
| 53 | ++ | ++ | ++ |
| 54 | +++ | +++ | ++ |
| 55 | +++ | ++++ | +++ |
| 56 | +++ | +++ | +++ |
| 57 | ++ | +++ | ++ |
| 58 | ++ | +++ | ++ |
| 59 | ++ | +++ | ++ |
| 60 | +++ | ++++ | ++ |
| 61 | ++ | +++ | ++ |
| 62 | ++ | +++ | ++ |
| 63 | +++ | ++ | + |
| 64 | +++ | +++ | ++ |
| 65 | ++ | ++ | + |
| 66 | +++ | +++ | ++ |
| 67 | +++ | ++++ | ++ |
| 68 | +++ | +++ | + |
| 69 | ++++ | +++ | ++ |
| 70 | +++ | +++ | + |
| 71 | +++ | ++ | ++ |
| 72 | +++ | ++ | + |
| 73 | ++ | +++ | + |
| 74 | ++ | ++ | + |
| 75 | ++ | ++ | + |
| 76 | +++ | ++++ | + |
| 77 | +++ | ++ | + |
| 78 | +++ | +++ | + |
| 79 | ++++ | +++ | ++ |
| 80 | +++ | +++ | + |
| 81 | ++++ | +++ | ++ |
| 82 | ++ | ++++ | ++ |
| 83 | ++ | ++ | ++ |
| 84 | +++ | ++ | ++ |
| 85 | +++ | ++++ | +++ |
| 86 | +++ | ++++ | ++ |
| 87 | +++ | ++ | + |
| 88 | + | + | + |
| 89 | +++ | +++ | ++ |
| 90 | ++ | +++ | + |
| 91 | +++ | ++++ | ++ |
| 92 | +++ | ++ | ++ |
| 93 | ++++ | ++++ | ++ |
| 94 | +++ | ++ | + |
| 95 | +++ | +++ | + |
| 96 | +++ | ++ | + |
| 97 | +++ | ++ | ++ |
| 98 | ++++ | +++ | +++ |
| 99 | +++ | +++ | ++ |
| 100 | +++ | ++ | ++ |
| 101 | +++ | +++ | ++ |
| 102 | +++ | ++++ | ++ |
| 103 | ++ | +++ | ++ |
| 104 | +++ | ++ | + |
| 105 | ++++ | ++++ | ++ |
| 106 | +++ | +++ | ++ |
| 107 | ++++ | ++ | ++ |
| 108 | +++ | +++ | ++ |
| 109 | ++++ | ++++ | +++ |
| 110 | +++ | +++ | +++ |
| 111 | ++ | ++ | + |
| 112 | +++ | ++ | ++ |
| 113 | ++++ | +++ | ++ |
| 114 | ++ | ++ | + |
| 115 | +++ | +++ | ++ |
| 116 | ++ | ++ | ++ |

-continued

| Example Number | IC50 in IMAP assay vs AKT1 | IC50 in IMAP assay vs AKT2 | IC50 in IMAP assay vs AKT3 |
|---|---|---|---|
| 117 | ++ | ++ | ++ |
| 118 | +++ | ++ | ++ |
| 119 | +++ | +++ | ++ |
| 120 | ++++ | +++ | +++ |
| 121 | +++ | ++ | ++ |
| 122 | +++ | ++ | ++ |
| 123 | ++++ | ++ | ++ |
| 124 | ++ | ++ | ++ |
| 125 | +++ | ++ | ++ |
| 126 | +++ | +++ | ++ |
| 127 | ++ | + | + |
| 128 | ++++ | +++ | +++ |
| 129 | +++ | ++ | ++ |
| 130 | +++ | + | + |
| 131 | ++ | +++ | ++ |
| 132 | +++ | ++ | + |
| 133 | ++ | + | + |
| 134 | +++ | ++ | + |
| 135 | +++ | ++++ | ++ |
| 136 | +++ | ++ | ++ |
| 137 | ++++ | +++ | ++ |
| 138 | ++++ | +++ | ++ |
| 139 | +++ | +++ | ++ |
| 140 | +++ | +++ | ++ |
| 141 | +++ | +++ | +++ |
| 142 | ++ | ++ | ++ |
| 143 | ++++ | ++++ | +++ |
| 144 | +++ | ++++ | +++ |
| 145 | ++++ | ++++ | +++ |
| 146 | ++ | +++ | + |
| 147 | +++ | +++ | + |
| 148 | +++ | +++ | + |
| 149 | +++ | ++ | + |
| 150 | ++++ | ++++ | ++ |
| 151 | ++ | +++ | + |
| 152 | +++ | ++++ | ++ |
| 153 | ++ | ++ | + |

Key
+ IC50 > 10 μM
++ 1 μM < IC50 ≤ 10 μM
+++ 0.1 μM < IC50 ≤ 1 μM
++++ IC50 ≤ 0.1 μM

In addition, the phosphorylation status of various members of the AKT/PI3K pathway was investigated via ELISA. For example, Example 4 causes inhibition of GSK3β phosphorylation with an IC50<0.1 μM measured at 48 h.

It can be seen from the Table that several Examples exhibit selectivity for one or more AKT isoforms over the other isoform(s). For example, a greater activity for AKT1 and/or AKT2 is observed compared to AKT3.

In addition, the activity of compounds in in vitro cell proliferation assays was investigated. Representative examples (eg. 4, 28 and 31) show inhibition of proliferation of PC3 and/or LnCaP cell lines with an IC50<10 μM.

Abbreviations

AcOH: Acetic acid; nBuLi: n-Butyllithium; BINAP: 2,2'-bis(diphenylphosphino)-1,1'-binaphthyl; DBU: 1,8-Diazabicyclo[5.4.0]undec-7-ene; DCM: Dichloromethane; DIPEA: Diisopropylethylamine; DMA: N,N-Dimethyl acetamide; DMAP: 4-Dimethylaminopyridine; DME: Dimethoxyethane; DMF: N,N-Dimethylformamide; DMSO: Dimethylsulfoxide; EDCI: 1-Ethyl-3-(3'-dimethylaminopropyl)carbodiimide; EtOAc: Ethyl acetate; h:Hour: HATU: O-(7-Azabenzotriazol-1-yl)-N,N,N',N'-tetramethyluronium hexafluorophosphate; HCl: Hydrochloric acid; HOBt: 1-Hydroxybenzotriazole; HPLC: High Pressure Liquid Chromatography; IMS: Industrial methylated spirits: M: Molar; MeOH: Methanol; NMP: N-Methyl-2-pyrrolidone; NMR: Nuclear Magnetic Resonance; Min: Minutes; RT: Room temperature; SCX: SCX-strong cation exchange; TBAF: Tetra-n-butylammonium fluoride; TEA: Triethylamine; TFA: Trifluoroacetic acid; THF: Tetrahydrofuran; TMSCl: Trimethylsilyl chloride General Experimental Conditions $^1$H NMR spectra were recorded at ambient temperature using a Varian Unity Inova (400 MHz) spectrometer with a triple resonance 5 mm probe, a Bruker Avance DRX (400 MHz) with a 5 mm inverse detection triple resonance TXI probe, a Bruker Avance (500 MHz) spectrometer with a 5 mm QNP probe or a Bruker Avance DPX (300 MHz) spectrometer with a standard 5 mm dual frequency probe. Chemical shifts are expressed in ppm relative to tetramethylsilane.

High Pressure Liquid Chromatography—Mass Spectrometry (LCMS) experiments to determine retention times ($R_T$) and associated mass ions were performed using one of the following methods.

Method A: The system consists of ThermoFinnigan LCQ Advantage Mass Spectrometer with the Surveyor LC system and 200 position autosampler. The spectrometer has an electrospray source operating in positive and negative ion mode. An LC-MS experiment is performed on each sample submitted using the following conditions: LC Column—Luna 3 micron $C_{18}$ 50×2 mm; Mobile phase-A) Water 0.1% Formic Acid B) Acetonitrile 0.1% Formic Acid

| Gradient - Time | flow | % A | % B |
|---|---|---|---|
| 0.00 | 0.6 | 95 | 5 |
| 7.00 | 0.6 | 5 | 95 |
| 8.00 | 0.6 | 5 | 95 |
| 8.20 | 0.6 | 95 | 5 |
| 11.00 | 0.6 | 95 | 5 |

Split—100 μl/min split to the ESI source with inline Surveyor DAD detection.

Detection—MS, UV

MS ionisation method—Electrospray (positive and negative ion)

Total experiment time—11 mins (approx)

Method B: The system consists of a Waters ZMD quadrupole mass spectrometer linked to a Waters 1525 LC system with Waters 996 diode array detector. Sample injection is done by a Waters 2700 autosampler. The spectrometer has an electrospray source operating in positive and negative ion mode. Additional detection is achieved using a Sedex 85 evaporative light scattering detector.

An LC-MS experiment is performed on each sample submitted using the following conditions: LC Column—Luna 3 micron C18(2) 30×4.6 mm or equivalent. Mobile phase—A) Water 0.1% Formic Acid B) Methanol 0.1% Formic Acid

| Gradient - Time | flow | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—200 μl/min split to the ESI source with inline Waters 996 DAD detection.

Detection—MS, ELS, UV

MS ionisation method—Electrospray (positive and negative ion)

Total experiment time—6 mins (approx)

Method C: The system consists of a Waters Micromass ZQ2000 quadrupole mass spectrometer linked to a Waters Acquity HPLC system with a PDA UV detector. The spectrometer has an electrospray source operating in positive and negative ion mode. An LC-MS experiment is performed on each sample submitted using the following conditions: LC Column—Acquity BEH C18 1.7 um 100×2.1 mm, maintained at 40° C. or Acquity BEH Shield RP18 1.7 um 100×2.1 mm, maintained at 40° C. Mobile phase—A) Water 0.1% Formic Acid B) Acetonitrile 0.1% Formic Acid

| Gradient - Time | flow ml/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionisation method—Electrospray (positive/negative ion)

Method D: The system consists of an Agilent Technologies 6140 single quadrupole mass spectrometer linked to an Agilent Technologies 1290 Infinity LC system with UV diode array detector and autosampler. The spectrometer has a multimode ionization source (electrospray and atmospheric pressure chemical ionizations) operating in positive and negative ion mode. An LC-MS experiment is performed on each sample submitted using the following conditions: LC Column—Zorbax Eclipse Plus C18 RRHD 1.8 micron 50×2.1 mm maintained at 40° C. Mobile phase—A) Water 0.1% Formic Acid B) Acetonitrile 0.1% Formic Acid.

| Gradient - Time | Flow mL/min | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Detection—MS, UV

MS ionisation method—Multimode (positive and negative ion)

Total experiment time—2.50 mins (approx)

Method E: The system consists of a Agilent Technologies 6120 single quadrupole mass spectrometer linked to a Agilent Technologies 1200 Preparative LC system with Multiple Wavelength detector and autosampler. The spectrometer has a multimode ionization source (electrospray and atmospheric pressure chemical ionizations) operating in positive and negative ion mode. Fraction collection is mass-triggered. A purification experiment is performed on each sample submitted using the following conditions: LC Column—Waters XBridge™ Prep C18 5 μm OBD™ 19×50 mm column at room temperature. Mobile phase—A) Water 0.1% ammonium hydroxide B) Acetonitrile/Water 95: 5 with 0.1% ammonium hydroxide.

| Gradient - Time | Flow mL/min | % A | % B, |
|---|---|---|---|
| 0.00 | 20.0 | 95 | 5 |
| 7.00 | 20.0 | 0 | 100 |
| 8.00 | 20.0 | 0 | 100 |
| 8.20 | 20.0 | 95 | 5 |

Detection—MS, UV

MS ionisation method—Multimode (positive and negative ion)

Total experiment time—10 mins (approx)

Method F: The system consists of a Agilent Technologies 6120 single quadrupole mass spectrometer linked to a Agilent Technologies 1200 Preparative LC system with Multiple Wavelength detector and autosampler. The spectrometer has a multimode ionization source (electrospray and atmospheric pressure chemical ionizations) operating in positive and negative ion mode. Fraction collection is mass-triggered. A purification experiment is performed on each sample submitted using the following conditions: LC Column—Waters XBridge™ Prep C18 5 μm OBD™ 30×100 mm column at room temperature. Mobile phase—A) Water 0.1% ammonium hydroxide B) Acetonitrile/Water 95: 5 with 0.1% ammonium hydroxide.

| Gradient - Time | Flow mL/min | % A | % B |
|---|---|---|---|
| 0.00 | 60.0 | 95 | 5 |
| 14.00 | 60.0 | 0 | 100 |
| 16.00 | 60.0 | 0 | 100 |
| 16.50 | 60.0 | 95 | 5 |

Detection—MS, UV

MS ionisation method—Multimode (positive and negative ion)

Total experiment time—18 mins (approx)

Method G: The system consists of an Agilent 6110 quadrupole LC/MS mass spectrometer linked to an Agilent 1200 LC system with Agilent 1200 diode array detector. Sample injection is done by an Agilent 1200 autosampler. The spectrometer has an electrospray and APCI source operating in positive and negative ion mode. A purification experiment is performed on each sample submitted using the following conditions: LC Column—Sunfire 5 micron C18(2) 15×4.6 mm or equivalent. Mobile phase-A) Water 0.1% Formic Acid B) ACN 0.1% Formic Acid Split—40/min split to the ESI/APCI source Detection—MS, UV MS ionisation method—Electrospray and APCI (positive and negative ion)

Total experiment time—6 or 20 mins (approx)

Microwave experiments were carried out using a CEM Explorer™ or Biotage Initator™ instruments. Temperatures from 60-300° C. can be achieved, and pressures of up to 20 bar can be reached.

Unless otherwise indicated, the nomenclature of structures was using "structure=name" from ChemBioDraw 11 (CambridgeSoft). Some compounds named using the software mentioned above have stereocentres marked 'S' and 'R' where they would normally be designated 'cis' or 'trans'. For these compounds the structures presented are representative of the compounds made.

Unless otherwise indicated, starting materials and intermediates were obtained from commercial suppliers, prepared according to literature procedures (for example WO 2008/

Example 1

2-(4-(1-aminocyclobutyl)phenyl)-3-phenyl-7,8-dihydroquinolin-5(6H)-one

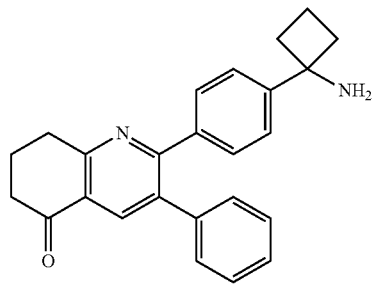 [SMILES: NC1(c2ccc(-c3nc4c(cc3-c3ccccc3)C(=O)CCC4)cc2)CCC1]

Step 1: tert-butyl(1-(4-(3-(dimethylamino)-2-phenylacryloyl)phenyl)cyclobutyl)carbamate A solution of tert-butyl(1-(4-(2-phenylacetyl)phenyl)cyclobutyl)carbamate (25.0 g, 68 mmol) in N,N-dimethylformamide dimethylacetal (150 mL) was heated to 80° C. under a nitrogen atmosphere for 18 hours. The resulting brown solution was allowed to cool to room temperature and concentrated to dryness under reduced pressure to give the desired product as a yellow/brown solid (30.6 g, quantitative yield). $^1$H-NMR (500 MHz, CDCl$_3$) δ 7.14-7.48 (10H, m), 5.09 (1H, br s), 2.74 (6H, s), 2.45-2.60 (4H, m), 2.04-2.16 (1H, m), 1.80-1.90 (1H, m), 1.10-1.52 (9H, br m).

Step 2: tert-butyl(1-(4-(5-oxo-3-phenyl-5,6,7,8-tetrahydroquinolin-2-yl)phenyl)cyclobutyl)carbamate To acetic acid (120 mL) was added molecular sieves (5 Å, 1.50 g), tert-butyl(1-(4-(3-(dimethylamino)-2-phenylacryloyl)phenyl)cyclobutyl)carbamate (8.00 g, 19.0 mmol) and 3-amino-2-cyclohexene-1-one (3.20 g, 28.8 mmol). The reaction mixture was heated to 100° C. under a nitrogen atmosphere for 2 hours. The mixture was allowed to cool to room temperature and concentrated under reduced pressure. The residue was partitioned between water (160 mL) and dichloromethane (160 mL) and decanted from the molecular sieves. The layers were separated and the aqueous phase extracted into dichloromethane (2×160 mL). The combined organic phases were washed with saturated NaHCO$_3$ solution (2×160 mL), brine (160 mL), dried over Na$_2$SO$_4$, filtered and concentrated to dryness under reduced pressure to give a yellow/brown solid. This was purified by Biotage chromatography (silica, hexane:ethyl acetate, gradient elution from 90:10 to 20:80) to give the desired product as a yellow solid (3.30 g, 37% yield). $^1$H-NMR (500 MHz, CDCl$_3$) δ 8.30 (1H, s), 7.37 (2H, d), 7.30 (2H, d), 7.24-7.27 (3H, m), 7.15-7.20 (2H, m), 5.01 (1H, br s), 3.26 (2H, t), 2.75 (2H, t), 2.42-2.55 (4H, m), 2.26 (2H, p), 2.00-2.10 (1H, m), 1.73-1.85 (1H, m), 1.12-1.44 (9H, br m). LCMS (Method A) RT=7.54 min, M+H$^+$=469.15.

Step 3: 2-(4-(1-aminocyclobutyl)phenyl)-3-phenyl-7,8-dihydroquinolin-5(6H)-one tert-butyl(1-(4-(5-oxo-3-phenyl-5,6,7,8-tetrahydroquinolin-2-yl)phenyl)cyclobutyl)carbamate (11 mg, 0.023 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (10 mg, 91% yield). $^1$H-NMR (500 MHz, CD$_3$OD) δ 8.29 (1H, s), 7.51 (2H, d), 7.45 (2H, d), 7.31 (3H, t), 7.21 (2H, dd), 3.26 (2H, t), 2.80 (2H, t), 2.72-2.81 (2H, m), 2.53-2.62 (2H, m), 2.30 (2H, t), 2.20-2.30 (1H, m), 1.92-2.01 (1H, m). LCMS (Method A) RT=4.09 min, M+H$^+$=368.91.

Example 2

2-(4-(1-aminocyclobutyl)phenyl)-3-phenyl-7,13-dihydroquinolin-5(6H)-one oxime

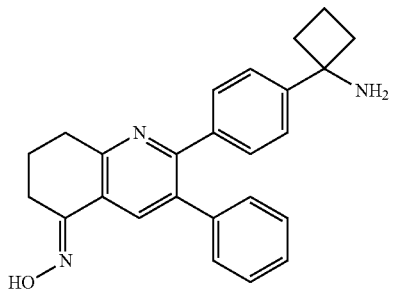 [SMILES: NC1(c2ccc(-c3nc4c(cc3-c3ccccc3)/C(=N/O)CCC4)cc2)CCC1]

Step 1: Tert-butyl (1-(4-(5-(hydroxyimino)-3-phenyl-5,6,7,8-tetrahydroquinolin-2-yl)phenyl)cyclobutyl)carbamate To a solution of tert-butyl-(1-(4-(1-aminocyclobutyl)phenyl)-3-phenyl-7,8-dihydroquinolin-5(6H)-one (80 mg, 0.17 mmol) in anhydrous ethanol (2.0 mL) was added hydroxylamine hydrochloride (65 mg, 0.9 mmol) and pyridine (75 μL, 0.9 mmol). The resulting yellow solution was heated to 90° C. for 2 hours under a nitrogen atmosphere. The reaction mixture was allowed to cool to room temperature and concentrated to dryness under reduced pressure. The residue was mixed with water (2.0 mL) and extracted into dichloromethane (3×2.0 mL). The combined organic phases were washed with brine (2×4.0 mL), dried over Na$_2$SO$_4$, filtered and concentrated to dryness under reduced pressure to give a yellow oil. The residue was purified by Biotage chromatography (silica, hexane:ethyl acetate, gradient elution from 95:5 to 60:40) to give the desired product as a white solid (47 mg, 56% yield). $^1$H NMR (500 MHz, CH$_3$OD) 8.30 (s, 1H), 7.30 (d, 2H), 7.26 (m, 5H), 7.19 (d, 2H), 3.19 (m, 2H), 2.87 (m, 2H), 2.45-2.50 (m, 4H), 2.0-2.1 (m, 1H), 1.90-1.99 (m, 2H), 1.80-1.86 (m, 1H), 1.2-1.4 (br s, 9H).

Step 2: 2-(4-(1-aminocyclobutyl)phenyl)-3-phenyl-7,8-dihydroquinolin-5(6H)-one oxime Tert-butyl (1-(4-(5-(hydroxyimino)-3-phenyl-5,6,7,8-tetrahydroquinolin-2-yl)phenyl)cyclobutyl)carbamate (7 mg, 0.017 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (3 mg, 35% yield). $^1$H NMR (500 MHz, CH$_3$OD) 8.45 (s, 1H), 7.46 (m, 5H), 7.34 (d, 2H), 7.21 (d, 2H), 3.10 (t, 2H), 2.90 (t, 2H), 2.74-2.78 (m, 2H), 2.56-2.6 (m, 2H), 2.20-2.28 (m, 1H), 2.02-2.10 (m, 2H), 1.93-1.98 (m, 1H).

Example 3

2-(4-(1-aminocyclobutyl)phenyl)-3-phenyl-7,8-dihydroquinolin-5(6H)-one O-methyl oxime

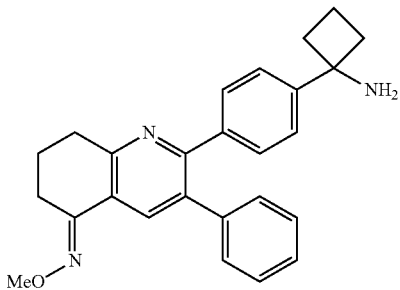 [SMILES: CO/N=C1\CCCc2nc(-c3ccc(C4(N)CCC4)cc3)c(-c3ccccc3)cc21]

Step 1: tert-butyl(1-(4-(5-(methoxyimino)-3-phenyl-5,6,7,8-tetrahydroquinolin-2-yl)phenyl)cyclobutyl) carbamate To a solution of tert-butyl(1-(4-(5-oxo-3-phenyl-5,6,7,8-tetrahydroquinolin-2-yl)phenyl)cyclobutyl)carbamate (90 mg, 0.19 mmol) in anhydrous ethanol (2.0 mL) was added O-methylhydroxylamine hydrochloride (80 mg, 0.96 mmol) and pyridine (80 µL, 0.99 mmol). The resulting yellow solution was heated to 90° C. under a nitrogen atmosphere. The reaction mixture was allowed to cool to room temperature and concentrated to dryness under reduced pressure. The residue was mixed with water (2.0 mL) and extracted into ethyl acetate (3×2.0 mL). The combined organic phases were washed with brine (2×4.0 mL), dried over Na$_2$SO$_4$, filtered and concentrated to dryness under reduced pressure to give a yellow oil. The residue was purified by Biotage chromatography (silica, hexane:ethyl acetate, gradient elution from 95:5 to 60:40) to give the desired product as a white solid (44 mg, 46% yield). $^1$H-NMR (500 MHz, CD$_3$OD) δ 8.29 (1H, s), 7.35 (2H, d), 7.26-7.32 (5H, m), 7.16-7.21 (2H, m), 4.01 (3H, s), 3.02 (2H, t), 2.83 (2H, t), 2.36-2.52 (4H, m), 2.04-2.16 (1H, m), 2.01 (2H, p), 1.81-1.92 (1H, m), 1.15-1.50 (9H, br m). LCMS (Method A) RT=8.28 min, M+H$^+$=498.10.

Step 2: 2-(4-(1-aminocyclobutyl)phenyl)-3-phenyl-7, 8-dihydroquinolin-5(6H)-one O-methyl oxime tert-butyl(1-(4-(5-(methoxyimino)-3-phenyl-5,6,7,8-tetrahydroquinolin-2-yl)phenyl)cyclobutyl)carbamate (44 mg, 0.088 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (32 mg, 73% yield). $^1$H-NMR (500 MHz, CD$_3$OD) δ 8.35 (1H, s), 7.48 (2H, d), 7.43 (2H, d), 7.30 (3H, t), 7.18-7.23 (2H, m), 4.02 (3H, s), 3.05 (2H, t), 2.85 (2H, t), 2.73-2.81 (2H, m), 2.54-2.63 (2H, m), 2.19-2.30 (1H, m), 2.03 (2H, p), 1.91-2.03 (1H, m). LCMS (Method A) RT=4.57 min, M+H$^+$=398.10.

Example 4

1-(4-(8-phenyl-4,5-dihydro-2H-pyrazolo[3,4-f] quinolin-7-yl)phenyl)cyclobutanamine

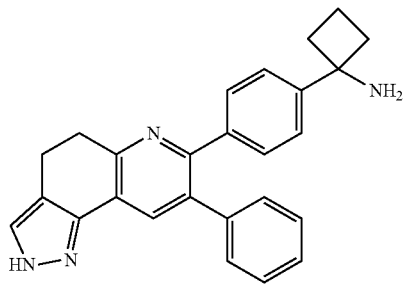 [SMILES: NC1(c2ccc(-c3nc4c(cc3-c3ccccc3)-c3n[nH]cc3CC4)cc2)CCC1]

Step 1: Tert-butyl 1-(4-(6-((dimethylamino)methylene)-5-oxo-3-phenyl-5,6,7,8-tetrahydronaphthalen-2-yl)phenyl)cyclobutyl)carbamate Tert-butyl (1-(4-(5-oxo-3-phenyl-5,6,7,8-tetrahydroquinolin-2-yl)phenyl)cyclobutyl)carbamate (500 mg, 1.06 mmol) was dissolved in 5 ml of anhydrous N,N-dimethylfomamide dimethyl acetate. The resulting mixture was heated to 100° C. under a nitrogen atmosphere for 2.5 hours. TLC and LC-MS analysis showed complete consumption of the starting material. The reaction mixture was concentrated to dryness under reduced pressure. The crude residue was slurried in n-hexane (10 ml) for 1 hour. The suspension was filtered and the solid was dried until constant weigh to give the desired product as a bright yellow solid (420 mg, 76% yield). LCMS (Method A): R$_T$=6.89 min, M+H$^+$=524; R$_T$=8.37 min, M+H$^+$=497

Step 2: tert-butyl(1-(4-(8-phenyl-4,5-dihydro-2H-pyrazolo[3,4-f]quinolin-7-yl)phenyl)cyclobutyl)carbamate To a solution of tert-butyl 1-(4-(6-((dimethylamino)methylene)-5-oxo-3-phenyl-5,6,7,8-tetrahydronaphthalen-2-yl) phenyl)cyclobutyl)carbamate (40 mg, 0.07 mmol) in anhydrous ethanol (1500 µL) was added hydrazine monohydrate (15 µL, 0.23 mmol). The reaction mixture was stirred at room temperature under a nitrogen atmosphere for 2.5 hours. The reaction mixture was concentrated to dryness under reduced pressure, purified by Biotage chromatography (silica, hexane:ethyl acetate, gradient elution from 95:5 to 60:40) and slurried in diethyl ether (1 mL) to give the desired product as a white solid (6 mg, 16% yield). $^1$H NMR (500 MHz, CH$_3$OD) 8.15 (s, 1H), 7.22-7.37 (m, 9H), 3.22 (t, 2H), 3.00 (t, 2H), 2.45-2.51 (m, 4H), 2.03-2.09 (m, 1H), 1.86-1.89 (m, 1H), 1.3-1.5 (br s, 9H).

Step 3: 1-(4-(8-phenyl-4,5-dihydro-2H-pyrazolo[3,4-f]quinolin-7-yl)phenyl)cyclobutanamine Tert-butyl (1-(4-(8-phenyl-4,5-dihydro-2H-pyrazolo[3,4-f]quinolin-7-yl)phenyl)cyclobutyl)carbamate (6 mg, 0.012 mmol) was dissolved in TFA (0.8 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (3 mg, 50% yield). $^1$H NMR (500 MHz, CH$_3$OD) 8.16 (s, 1H), 7.58 (s, 1H), 7.49 (d, 2H), 7.43 (d, 2H), 7.30 (m, 3H), 3.24 (t, 2H), 3.02 (t, 2H), 2.78 (m, 2H), 2.59 (m, 2H), 2.23 (m, 1H), 1.98 (m, 1H).

Example 5

1-(4-(2-methyl-8-phenyl-4,5-dihydro-2H-pyrazolo[3,4-f]quinolin-7-yl)phenyl)cyclobutanamine Example 6

1-(4-(1-methyl-8-phenyl-4,5-dihydro-1H-pyrazolo[3,4-f]quinolin-7-yl)phenyl)cyclobutanamine

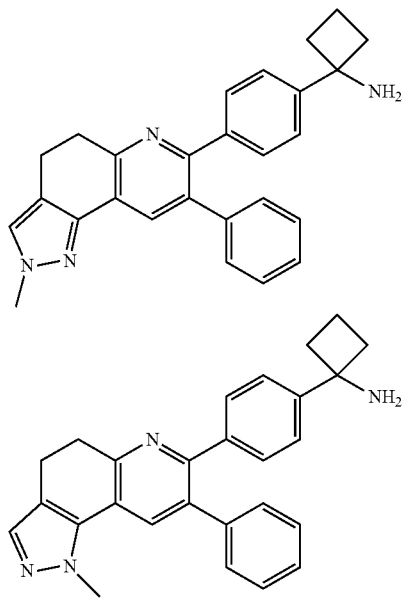

Step 1: tert-butyl(1-[4-(2-methyl-8-phenyl-4,5-dihydro-2H-pyrazolo[3,4-f]quinolin-7-yl)phenyl)cyclobutyl)carbamate and tert-butyl(1-4-(1-methyl-8-phenyl-4,5-dihydro-1H-pyrazolo-3,4-f]quinolin-7-yl)phenyl)cyclobutyl)carbamate To a solution of tert-butyl 1-(4-(6-((dimethylamino)methylene)-5-oxo-3-phenyl-5,6,7,8-tetrahydronaphthalen-2-yl)phenyl)cyclobutyl)carbamate (100 mg, 0.19 mmol) in anhydrous ethanol (2 mL) was added methyl hydrazine (30 μL, 0.57 mmol). The reaction mixture was stirred at room temperature under a nitrogen atmosphere for 2 hours. The reaction mixture was concentrated to dryness under reduced pressure, purified by Biotage chromatography (silica, hexane:ethyl acetate, gradient elution from 99:1 to 70:30) to give the desired product tert-butyl(1-(4-(2-methyl-8-phenyl-4,5-dihydro-2H-pyrazolo[3,4-f]quinolin-7-yl)phenyl)cyclobutyl)carbamate as a white solid (14 mg, 15% yield). $^1$H NMR (500 MHz, CH$_3$OD) 8.10 (s, 1H), 7.36 (d, 2H), 7.29 (d, 2H), 7.20-7.22 (m, 6H), 4.99 (s, 1H), 3.94 (s, 3H), 3.20-3.36 (br s, 2H), 2.86-3.01 (m, 4H), 2.43-2.55 (m, 2H), 1.99-2.10 (m, 1H), 1.74-1.85 (m, 1H), 1.49-1.68 (br s, 9H). $^1$H-$^1$H NOESY (500 MHz, CH$_3$OD) positive correlation between 7.22 (s, 1H) and 3.94 (s, 3H).

Mixed fractions from the column (45 mg) were purified by preparative HPLC (method G, gradient 5 to 95% 0.1% FA/ACN in 0.1% FA/H$_2$O, 20 minutes run) to give the desired product tert-butyl(1-(4-(1-methyl-8-phenyl-4,5-dihydro-1H-pyrazolo[3,4-f]quinolin-7-yl)phenyl)cyclobutyl)carbamate as a white solid (9 mg, 10% yield). $^1$H NMR (500 MHz, CH$_3$OD) 7.83 (s, 1H), 7.37 (m, 3H), 7.29 (m, 5H), 7.22 (m, 2H), 5.00 (s, 1H), 4.16 (s, 3H), 3.22-3.33 (br m, 2H), 2.87-2.94 (m, 2H), 2.41-2.55 (m, 4H), 2.04 (m, 1H), 1.57 (m, 1H), 1.50-1.62 (br s, 9H). LCMS (Method A): R$_T$=7.36 min, M+H$^+$=507.

Step 2A: 1-(4-(2-methyl-8-phenyl-4,5-dihydro-2H-pyrazolo[3,4-f]quinolin-7-yl) phenyl)cyclobutanamine

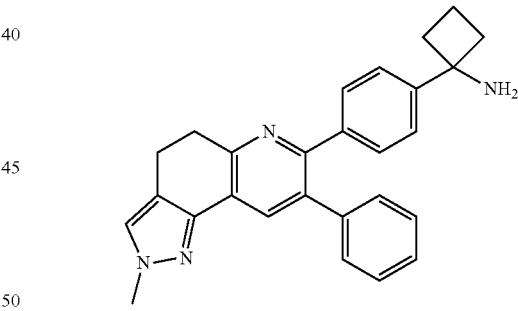

Tert-butyl (1-(4-(2-methyl-8-phenyl-4,5-dihydro-2H-pyrazolo[3,4-t]quinolin-7-yl)phenyl)cyclobutyl)carbamate (14 mg, 0.027 mmol) was dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (1 mL) and after settling the supernatant solvent removed by pipette. This was repeated three times. The remaining solvent was removed under reduced pressure and dried to give the desired product as an off-white solid (7 mg, 50% yield). $^1$H NMR (500 MHz, CH$_3$OD) 8.20 (s, 1H), 7.50 (s, 1H), 7.47 (d, 2H), 7.43 (d, 2H), 7.28 (m, 3H), 7.22 (m, 2H), 3.94 (s, 1H), 3.24 (t, 2H), 2.97 (t, 2H), 2.70-2.80 (br m, 2H), 2.52-2.61 (br m, 2H), 2.15-2.29 (br m, 1H), 1.88-2.00 (br m, 1H).

Step 2B: 1-(4-(1-methyl-8-phenyl-4,5-dihydro-1H-pyrazolo[3,4-f]quinolin-7-yl)phenyl)cyclobutan-amine

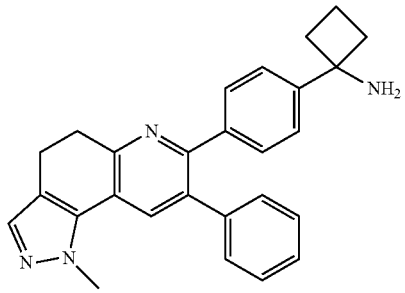 [SMILES: Cn1ncc2c1-c1cc(-c3ccccc3)c(-c3ccc(C4(N)CCC4)cc3)nc1CC2]

Tert-butyl (1-(4-(1-methyl-8-phenyl-4,5-dihydro-1H-pyrazolo[3,4-f]quinolin-7-yl)phenyl)cyclobutyl)carbamate (3 mg, 0.006 mmol) was dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (1 mL) and after settling the supernatant solvent removed by pipette. This was repeated three times. The remaining solvent was removed under reduced pressure and dried to give the desired product as an off-white solid (0.65 mg, 22% yield). $^1$H NMR (500 MHz, CH$_3$OD) 8.06 (s, 1H), 7.50 (d, 2H), 7.43 (d, 3H), 7.27-7.36 (br m, 5H), 4.19 (s, 1H), 3.22 (t, 2H), 2.93 (t, 2H), 2.73-2.83 (br m, 2H), 2.54-2.66 (br m, 2H), 2.18-2.33 (br m, 1H), 1.92-2.03 (br m, 1H). LCMS (Method A): R$_T$=4.21 min, M+H$^+$=407

Example 7

7-(4-(1-aminocyclobutyl)phenyl)-8-phenyl-4,5-dihydro-2H-pyrazolo[3,4f]quinolin-3-ol

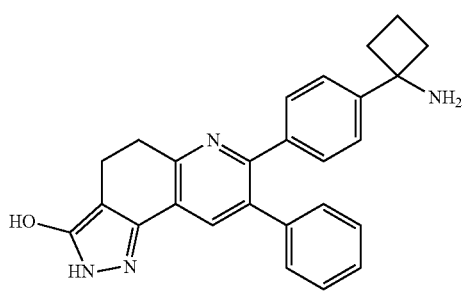 [SMILES: NC1(c2ccc(-c3nc4c(cc3-c3ccccc3)-c3n[nH]c(O)c3CC4)cc2)CCC1]

Step 1: tert-butyl(1-(4-(6-(bis(methylthio)methylene)-5-oxo-3-phenyl-5,6,7,8-tetrahydroquinolin-2-yl)phenyl)cyclobutyl)carbamate To a solution of tert-butyl(1-(4-(5-oxo-3-phenyl-5,6,7,8-tetrahydroquinolin-2-yl)phenyl)cyclobutyl)carbamate (1.00 g, 2.13 mmol) in anhydrous tetrahydrofuran (10 mL) was added dropwise potassium tert-butoxide, 1M in THF (4.69 mL, 4.69 mmol) over a period of 10 min to give a deep red suspension. The reaction mixture was stirred at room temperature under a nitrogen atmosphere for 15 min. To this was added dropwise carbon disulfide (142 µL, 2.35 mmol) over a period of 5 min to give a deep red solution. The reaction mixture was stirred at room temperature under a nitrogen atmosphere for 30 min. Methyl iodide (294 µl, 4.69 mmol) was added and the mixture stirred at room temperature for 90 min. The reaction mixture was diluted with saturated sodium bicarbonate solution (40 mL) and extracted with ethyl acetate (3×40 mL). The combined organic phases were washed with 50:50 water:brine (40 mL), then brine (40 mL), dried over Na$_2$SO$_4$, filtered and concentrated to dryness under reduced pressure to give the desired product as a bright yellow solid (1.21 g, 99% yield). $^1$H-NMR (500 MHz, CDCl$_3$) δ 8.40 (1H, s), 7.37 (2H, d), 7.31 (2H, d), 7.23-7.28 (3H, m), 7.17-7.21 (2H, m), 3.40 (2H, t), 3.31 (2H, br s), 2.50 (3H, s), 2.46 (3H,s), 2.42-2.57 (4H, m), 2.00-2.12 (1H, m), 1.75-1.87 (1H, m), 1.12-1.47 (9H, br m). LCMS (Method A) RT=8.64 min, M+H$^+$=573.13.

Step 2: methyl 2-(4-(1-((tert-butoxycarbonyl)amino) cyclobutyl)phenyl)-5-oxo-3-phenyl-5,6,7,8-tetrahydroquinoline-6-carboxylate To a stirred solution of tert-butyl(1-(4-(6-(bis(methylthio) methylene)-5-oxo-3-phenyl-5,6,7,8-tetrahydroquinolin-2-yl)phenyl)cyclobutyl)carbamate (140 mg, 0.24 mmol) in anhydrous tetrahydrofuran (2.8 mL) was added a solution of sodium hydroxide (96 mg, 2.4 mmol) in methanol (2.2 mL). The reaction mixture was heated to 50° C. under a nitrogen atmosphere for 2 hours. After allowing to cool to room temperature the mixture was diluted with 1M HCl solution (3 mL) and extracted into ethyl acetate (3×6 mL). The combined organic phases were washed with brine (3×6 mL), dried over Na$_2$SO$_4$, filtered and concentrated to dryness under reduced pressure to give the desired product as a brown solid (126 mg, quantitative yield). LCMS (Method A) RT=7.56 min, M+H$^+$= 527.14.

Step 3: tert-butyl(1-(4-(3-hydroxy-8-phenyl-4,5-dihydro-2H-pyrazolo[3,4-f]quinolin-7-yl)phenyl) cyclobutyl)carbamate To a solution of methyl 2-(4-(1-((tert-butoxycarbonyl) amino)cyclobutyl)phenyl)-5-oxo-3-phenyl-5,6,7,8-tetrahydroquinoline-6-carboxylate (60 mg, 0.11 mmol) in anhydrous ethanol (1500 µL) was added hydrazine monohydrate (9 µL, 0.19 mmol). The reaction mixture was heated to reflux under a nitrogen atmosphere for 18 hours. After cooling to room temperature the reaction mixture was concentrated to dryness under reduced pressure, purified by Biotage chromatography (silica, dichloromethane:methanol, gradient elution from 99:1 to 90:10) and slurried in diethyl ether (1 mL) to give the desired product as a white solid (19 mg, 33% yield). $^1$H-NMR (500 MHz, CD$_3$OD) δ 7.94 (1H, s), 7.32 (2H, d), 7.21-7.29 (5H, m), 7.14-7.21 (2H, m), 3.18 (2H, t), 2.81 (2H, t), 2.31-2.50 (4H, m), 2.00-2.12 (1, br m), 1.76-1.91 (1H, br m), 1.09-1.48 (br m). LCMS (Method A) RT=5.57 min, M+H$^+$= 509.17.

Step 4: 7-(4-(1-aminocyclobutyl)phenyl)-8-phenyl-4, 5-dihydro-2H-pyrazolo[3,4-f]quinolin-3-ol tert-butyl(1-(4-(3-hydroxy-8-phenyl-4,5-dihydro-2H-pyrazolo[3,4-f]quinolin-7-yl)phenyl)cyclobutyl)carbamate (19 mg, 0.037 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (3 mg, 17% yield). $^1$H-NMR (500 MHz, CD$_3$OD) δ 8.05 (1H, s), 7.49 (2H, d), 7.44 (2H, d), 7.27-7.34 (3H, m), 7.20-7.27 (2H, m), 3.25 (2H, t), 2.87 (2H, t), 2.72-2.82 (2H, m), 2.54-2.65 (2H, m), 2.18-2.30 (1H, m), 1.90-2.03 (1H, m). LCMS (Method A) RT=3.40 min, M+H$^+$=409.19.

Example 8

7-(4-(1-aminocyclobutyl) phenyl)-3a-methyl-8-phenyl-4,5-dihydro-2H-pyrazolo[3,4-f]quinolin-3(3aH)-one

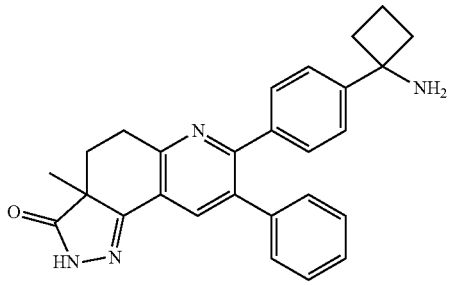

7-(4-(1-aminocyclobutyl)phenyl)-3a-methyl-8-phenyl-4,5-dihydro-2H-pyrazolo[3,4-f]quinolin-3(3aH)-one 7-(4-(1-aminocyclobutyl)phenyl)-3a-methyl-8-phenyl-4,5-dihydro-2H-pyrazolo[3,4-f]quinolin-3(3aH)-one Step 1: methyl 2-(4-(1-((tert-butoxycarbonyl)amino)cyclobutyl)phenyl)-6-methyl-5-oxo-3-phenyl-5,6,7,8-tetrahydroquinoline-6-carboxylate A solution of methyl 2-(4-(1-((tert-butoxycarbonyl)amino)cyclobutyl)phenyl)-5-oxo-3-phenyl-5,6,7,8-tetrahydroquinoline-6-carboxylate (65 mg, 0.12 mmol) in anhydrous THF (1.0 mL) was cooled to 0° C. under a nitrogen atmosphere, followed by the dropwise addition of potassium tert-butoxide solution (1M in THF, 150 µL, 0.15 mmol). The mixture was stirred at 0° C. for 15 minutes followed by the addition of methyl iodide (10 µL, 0.16 mmol). The reaction mixture was allowed to warm to room temperature and stirred for a further 4 hours. The mixture was diluted with ethyl acetate (2.0 mL), washed with 1M HCl solution (2.0 mL), brine (2×2.0 mL), dried over Na$_2$SO$_4$, filtered and concentrated to dryness under reduced pressure to give the desired product as a brown solid (54 mg, 83% yield). LCMS (Method A) RT=7.92 min, M+H$^+$=541.18.

Step 2: tert-butyl(1-(4-(3a-methyl-3-oxo-8-phenyl-3,3a,4,5-tetrahydro-2H-pyrazolo[3,4-f]quinolin-7-yl)phenyl)cyclobutyl)carbamate To a solution of methyl 2-(4-(1-((tert-butoxycarbonyl)amino)cyclobutyl)phenyl)-6-methyl-5-oxo-3-phenyl-5,6,7,8-tetrahydroquinoline-6-carboxylate (54 mg, 0.10 mmol) in anhydrous ethanol (1300 µL) was added hydrazine monohydrate (8 µL, 0.16 mmol). The reaction mixture was heated to reflux under a nitrogen atmosphere for 5 hours, additional hydrazine monohydrate (40 µL, 0.82 mmol) added, and the mixture heated at reflux for 18 hours. After cooling to room temperature the reaction mixture was concentrated to dryness under reduced pressure, purified by Biotage chromatography (silica, hexane:ethyl acetate, gradient elution from 88:12 to 0:100) to give the desired product as a yellow solid (12 mg, 23% yield). $^1$H-NMR (500 MHz, CDCl$_3$) δ 8.72 (1H, s), 8.09 (1H, s), 7.34 (2H, d), 7.30 (2H, d), 7.23-7.28 (3H, m), 7.16-7.22 (2H, m), 5.05 (1H, br s), 3.32-3.44 (1H, m), 3.19-3.32 (1H, br m), 2.41-2.60 (4H, br m), 2.26-2.35 (1H, dd), 1.97-2.11 (2H, m), 1.74-1.86 (1H, m), 1.45 (3H, s), 1.14-1.44 (9H, br m). LCMS (Method A) RT=6.60 min, M+H$^+$=523.17.

Step 3: 7-(4-(1-aminocyclobutyl)phenyl)-3a-methyl-8-phenyl-4,5-dihydro-2H-pyrazolo[3,4-f]quinolin-3(3aH)-one tert-butyl(1-(4-(3a-methyl-3-oxo-8-phenyl-3,3a,4,5-tetrahydro-2H-pyrazolo[3,4-f]quinolin-7-yl)phenyl)cyclobutyl)carbamate (12 mg, 0.023 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (9 mg, 60% yield). $^1$H-NMR (500 MHz, CD$_3$OD) δ 8.15 (1H, s), 7.49 (2H, d), 7.44 (2H, d), 7.29-7.36 (3H, m), 7.20-7.26 (2H, m), 3.35-3.45 (1H, m), 3.16-3.26 (1H, dd), 2.72-2.84 (2H, m), 2.54-2.66 (2H, m), 2.19-2.39 (2H, m), 1.92-2.09 (2H, m), 1.43 (3H, s). LCMS (Method A) RT=3.76 min, M+H$^+$=423.16.

Example 9

1-(4-(3-(methylthio)-8-phenyl-4,5-dihydro-2H-pyrazolo[3,4-f]quinolin-7-yl)phenyl)cyclobutanamine

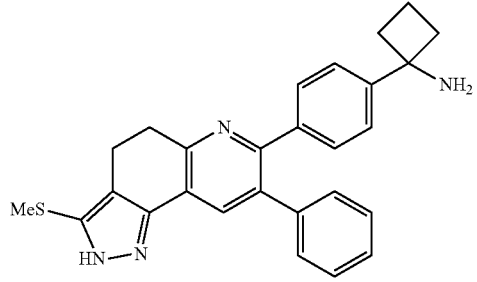 [SMILES: CSc1[nH]nc2c1CCc1nc(-c3ccc(C4(N)CCC4)cc3)c(-c3ccccc3)cc1-2]

Step 1: tert-butyl(1-(4-(3-(methylthio)-8-phenyl-4,5-dihydro-2H-pyrazolo[3,4-f]quinolin-7-yl)phenyl)cyclobutyl)carbamate To a solution of tert-butyl(1-(4-(6-(bis(methylthio)methylene)-5-oxo-3-phenyl-5,6,7,8-tetrahydroquinolin-2-yl)phenyl)cyclobutyl)carbamate (200 mg, 0.35 mmol) in anhydrous ethanol (1.7 mL) was added hydrazine monohydrate (25 µL, 0.52 mmol). The reaction mixture was heated to 80° C. under a nitrogen atmosphere for 2 hours. After cooling to room temperature the reaction mixture was concentrated to dryness under reduced pressure, purified by Biotage chromatography (silica, hexane:ethyl acetate, gradient elution from 90:10 to 80:20) to give the desired product as a yellow solid (53 mg, 28% yield). $^1$H-NMR (500 MHz, CDCl$_3$) δ 7.94 (1H, s), 7.16-7.24 (4H, m), 7.11-7.16 (3H, m), 7.06-7.10 (2H, m), 3.16 (2H, t), 2.83 (2H, t), 2.35 (3H, s), 2.15-2.45 (4H, br m), 1.88-2.01 (1H, m), 1.64-1.77 (1H, m), 1.00-1.35 (9H, br m). LCMS (Method A) RT=6.94 min, M+H$^+$=539.15.

Step 2: 1-(4-(3-(methylthio)-8-phenyl-4,5-dihydro-2H-pyrazolo[3,4-f]quinolin-7-yl)phenyl)cyclobutanamine tert-butyl(1-(4-(3-(methylthio)-8-phenyl-4,5-dihydro-2H-pyrazolo[3,4-f]quinolin-7-yl)phenyl)cyclobutyl)carbamate (53 mg, 0.098 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (24 mg, 37% yield). $^1$H-NMR (500 MHz, CD$_3$OD) δ 8.14 (1H, br s), 7.48 (2H, d), 7.43 (2H, d), 7.27-7.34 (3H, m), 7.21-7.27 (2H, m), 3.26 (2H, t), 2.97 (2H, br t), 2.72-2.82 (2H, m), 2.53-2.63 (2H, m), 2.49 (3H, s), 2.19-2.30 (1H, m), 1.91-2.02 (1H, m). LCMS (Method A) RT=4.06 min, M+H$^+$=439.14.

Example 10

1-(4-(3-(methylsulfonyl)-8-phenyl-4,5-dihydro-2H-pyrazolo[3,4-f]quinolin-7-yl)phenyl)cyclobutanamine

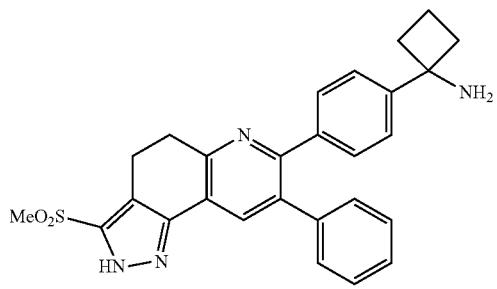 [SMILES: CS(=O)(=O)c1[nH]nc2c1CCc1nc(-c3ccc(C4(N)CCC4)cc3)c(-c3ccccc3)cc1-2]

Step 1: tert-butyl(1-(4-(3-(methylsulfonyl)-8-phenyl-4,5-dihydro-2H-pyrazolo[3,4-f]quinolin-7-yl)phenyl)cyclobutyl)carbamate To a solution of tert-butyl(1-(4-(3-(methylthio)-8-phenyl-4,5-dihydro-2H-pyrazolo[3,4-t]quinolin-7-yl)phenyl)cyclobutyl)carbamate (158 mg, 0.29 mmol) in a mixture of THF (2 mL) and methanol (2 mL) was added a solution of Oxone® (monopersulfate compound, 1.08 g, 1.76 mmol) in water (4 mL) dropwise. The reaction mixture was stirred at room temperature for 4 hours, then quenched by the dropwise addition of saturated NaHCO$_3$ solution (4 mL) and extracted into ethyl acetate (3×8 mL). The combined organic phases were washed with saturated NaHCO$_3$ solution (8 mL), brine (8 mL), dried over Na$_2$SO$_4$, filtered and concentrated to dryness under reduced pressure. The residue was purified by Biotage chromatography (silica, hexane:ethyl acetate, gradient elution from 92:12 to 100:0) to give the desired product as a white solid (44 mg, 26% yield). $^1$H-NMR (500 MHz, CDCl$_3$) δ 7.85 (1H, s), 7.27 (2H, d), 7.17-7.25 (5H, m), 7.11-7.16 (2H, m), 3.24 (2H, t), 3.14 (2H, t), 3.15 (3H, s), 2.18-2.51 (4H, br m), 1.96-2.10 (1H, br m), 1.68-1.80 (1H, br m), 1.09-1.38 (9H, br m). LCMS (Method A) RT=6.59 min, M+H$^+$=571.11.

Step 2: 1-(4-(3-(methylsulfonyl)-8-phenyl-4,5-dihydro-2H-pyrazolo[3,4-f]quinolin-7-yl)phenyl)cyclobutanamine tert-butyl(1-(4-(3-(methylsulfonyl)-8-phenyl-4,5-dihydro-2H-pyrazolo[3,4-f]quinolin-7-yl)phenyl)cyclobutyl)carbamate (40 mg, 0.070 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (18 mg, 37% yield). $^1$H-NMR (500 MHz, CD$_3$OD) δ 8.10 (1H, s), 7.50 (2H, d), 7.44 (2H, d), 7.31-7.35 (3H, m), 7.24-7.29 (2H, m), 3.32 (2H, t), 3.28 (3H, s), 3.24 (2H, t), 2.74-2.82 (2H, m), 2.54-2.64 (2H, m), 2.19-2.30 (1H, m), 1.92-2.03 (1H, m). LCMS (Method A) RT=3.81 min, M+H$^+$=471.16.

Example 11

7-(4-(1-aminocyclobutyl)phenyl)-N-methyl-8-phenyl-4,5-dihydro-2H-pyrazolo[3,4-f]quinolin-3-amine

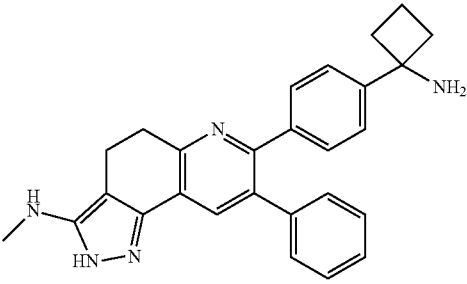 [SMILES: CNc1[nH]nc2c1CCc1nc(-c3ccc(C4(N)CCC4)cc3)c(-c3ccccc3)cc1-2]

Step 1: tert-butyl(1-(4-(3-(methylamino)-8-phenyl-4,5-dihydro-2H-pyrazolo[3,4-f]quinolin-7-yl)phenyl)cyclobutyl)carbamate To a solution of tert-butyl(1-(4-(6-(bis(methylthio)methylene)-5-oxo-3-phenyl-5,6,7,8-tetrahydroquinolin-2-yl)phenyl)cyclobutyl)carbamate (100 mg, 0.18 mmol) in ethanol (873 μl) was added methylamine (2M in THF, 87 μl, 0.18 mmol) and the mixture heated to 80° C. under a nitrogen atmosphere for 2 hours. Further methylamine (2M in THF, 873 μl, 1.746 mmol) was added and the mixture heated to 80° C. under a nitrogen atmosphere for 2 hours. Hydrazine monohydrate (25.4 μl, 0.52 mmol) was added and the mixture heated to 80° C. for 18 hours. The reaction mixture was concentrated to dryness under reduced pressure and purified via Biotage chromatography (silica, DCM: MeOH, gradient elution from 100:0 to 90:10) to give a colourless solid (47 mg, 52% yield). $^1$H-NMR (500 MHz, CDCl$_3$) δ 7.63 (1H, s), 7.32 (2H, d), 7.27 (2H, d), 7.16-7.22 (3H, m), 7.09-7.16 (2H, m), 5.06 (1H, br s), 3.10 (2H, t), 2.68 (3H, s), 2.22-2.60 (6H, br m), 1.97-2.09 (1H, m), 1.72-1.84 (1H, m), 1.03-1.53 (9H, br m). LCMS (Method A) RT=5.34 min, M+H$^+$=522.19.

Step 2: 7-(4-(1-aminocyclobutyl)phenyl)-N-methyl-8-phenyl-4,5-dihydro-2H-pyrazolo[3,4-f]quinolin-3-amine tert-butyl(1-(4-(3-(methylamino)-8-phenyl-4,5-dihydro-2H-pyrazolo[3,4-f]quinolin-7-yl)phenyl)cyclobutyl)carbamate (47 mg, 0.090 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (31 mg, 53% yield). $^1$H-NMR (500 MHz, CD$_3$OD) δ 8.08 (1H, s), 7.50 (2H, d), 7.44 (2H, d), 7.30-7.50 (3H, m), 7.23-7.27 (2H, m), 3.30 (2H, t), 2.98 (3H, s), 2.87 (2H, t), 2.73-2.81 (2H, m), 2.54-2.64 (2H, m), 2.19-2.31 (1H, m), 1.92-2.04 (1H, m). LCMS (Method A) RT=3.28 min, M+H$^+$=422.18.

Example 12

2-((7-(4-(1-aminocyclobutyl)phenyl)-8-phenyl-4,5-dihydro-2H-pyrazolo[3,4-f]quinolin-3-yl)amino)ethanol pressure and purified via Biotage chromatography (silica, DCM:MeOH, gradient elution from 100:0 to 90:10) to give a colourless solid (51 mg, 53% yield). $^1$H-NMR (500 MHz, CDCl$_3$) δ 7.67 (1H, s), 7.18-7.28 (4H, br m), 7.10-7.16 (3H, m), 7.01-7.08 (2H, m), 5.11 (1H, br s), 3.74 (2H, t), 3.35 (2H, t), 3.15 (2H, t), 2.66 (2H, t), 2.19-2.58 (4H, br m), 1.95-2.08 (1H, m), 1.69-1.81 (1H, m), 1.03-1.49 (9H, br m). LCMS (Method A) RT=5.20 min, M+H$^+$=552.24.

Step 2: 24(7-(4-(1-aminocyclobutyl)phenyl)-8-phenyl-4,5-dihydro-2H-pyrazolo[3,4-f]quinolin-3-yl)amino)ethanol tert-butyl(1-(4-(3-((2-hydroxyethyl)amino)-8-phenyl-4,5-dihydro-2H-pyrazolo[3,4-f]quinolin-7-yl)phenyl)cyclobutyl)carbamate (25 mg, 0.045 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (22 mg, 71% yield). $^1$H-NMR (500 MHz, CD$_3$OD) δ 8.06 (1H, s), 7.50 (2H, d), 7.44 (2H, d), 7.29-7.34 (3H, m), 7.22-7.28 (2H, m), 3.78 (2H, t), 3.41 (2H, t), 3.30 (2H, t), 2.90 (2H, t), 2.71-2.82 (2H, m), 2.54-2.66 (2H, m), 2.19-2.30 (1H, m), 1.91-2.03 (1H, m). LCMS (Method A) RT=3.30 min, M+H$^+$=452.17.

Example 13

1-(4-(3-morpholino-8-phenyl-4,5-dihydro-2H-pyrazolo[3,4-f]quinolin-7-yl)phenyl)cyclobutanamine

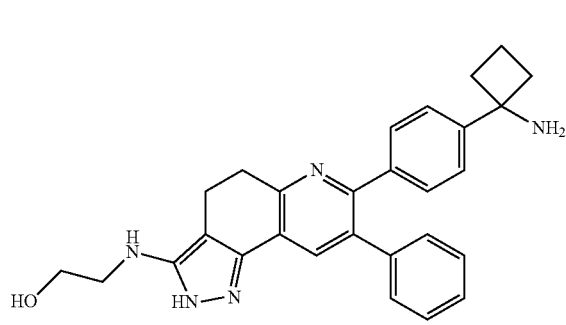 [SMILES: NC1(c2ccc(-c3nc4c(cc3-c3ccccc3)-c3n[nH]c(NCCO)c3CC4)cc2)CCC1]

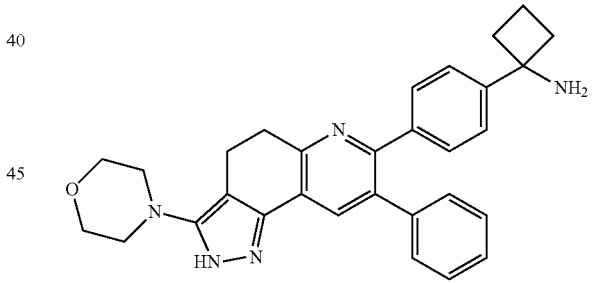

Step 1: tert-butyl(1-(4-(3-[(2-hydroxyethyl)amino)-8-phenyl-4,5-dihydro-2H-pyrazolo-3,4-f]quinolin-7-yl)phenyl)cyclobutyl)carbamate To a solution of tert-butyl(1-(4-(6-(bis(methylthio)methylene)-5-oxo-3-phenyl-5,6,7,8-tetrahydroquinolin-2-yl)phenyl)cyclobutyl)carbamate (100 mg, 0.18 mmol) in ethanol (873 μl) was added ethanolamine (10.6 μl, 0.18 mmol) and the mixture heated to 80° C. under a nitrogen atmosphere for 2 hours. Further ethanolamine (106 μl, 1.75 mmol) was added and the mixture heated to 80° C. under a nitrogen atmosphere for 18 hours. Hydrazine monohydrate (25.4 μl, 0.52 mmol) was added and the mixture heated to 80° C. for 3 hours. The reaction mixture was concentrated to dryness under reduced Step 1: tert-butyl(1-(4-(3-morpholino-8-phenyl-4,5-dihydro-2H-pyrazolo[3,4-f]quinolin-7-yl)phenyl)cyclobutyl)carbamate To a solution of tert-butyl(1-(4-(6-(bis(methylthio)methylene)-5-oxo-3-phenyl-5,6,7,8-tetrahydroquinolin-2-yl)phenyl)cyclobutyl)carbamate (100 mg, 0.18 mmol) in ethanol (873 μl) was added morpholine (76 μl, 0.87 mmol) and the mixture heated to 80° C. under a nitrogen atmosphere for 2 hours. Hydrazine monohydrate (12.7 μl, 0.26 mmol) was added and the mixture heated to 80° C. for 1 hour. Further hydrazine monohydrate (72 μl, 1.48 mmol) was added and the mixture heated to 80° C. for 18 hours. The reaction mixture was concentrated to dryness under reduced pressure and purified via Biotage chromatography (silica, cyclohexane:ethyl acetate, gradient elution from 92:2 to 100:0) to give a white solid (30 mg, 30% yield). ¹H-NMR (500 MHz, CDCl₃) δ 7.67 (1H, s), 7.31 (2H, d), 7.23-7.28 (2H, m), 7.18-7.24 (3H, m), 7.07-7.14 (2H, m), 4.95-5.44 (1H, br m), 3.82 (4H, t), 3.24 (2H, t), 3.21 (4H, t), 2.91 (2H, t), 2.19-2.64 (4H, br m), 1.97-2.09 (1H, m), 1.73-1.84 (1H, m), 1.10-1.46 (9H, br m). LCMS (Method A) RT=6.18 min, M+H⁺=578.24.

Step 2: 1-(4-(3-morpholino-8-phenyl-4,5-dihydro-2H-pyrazolo[3,4-f]quinolin-7-yl)phenyl)cyclobutanamine tert-butyl(1-(4-(3-morpholino-8-phenyl-4,5-dihydro-2H-pyrazolo[3,4-f]quinolin-7-yl)phenyl)cyclobutyl)carbamate (30 mg, 0.052 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (23 mg, 63% yield). ¹H-NMR (500 MHz, CD₃OD) δ 8.08 (1H, s), 7.49 (2H, d), 7.44 (2H, d), 7.29-7.33 (3H, m), 7.22-7.27 (2H, m), 3.86 (4H, t), 3.26 (2H, t), 3.22 (4H, t), 2.98 (2H, t), 2.73-2.82 (2H, m), 2.54-2.64 (2H, m), 2.19-2.30 (1H, m), 1.92-2.03 (1H, m). LCMS (Method A) RT=3.74 min, M+H⁺=478.23.

Example 14

7-(4-(1-aminocyclobutyl)phenyl)-2-methyl-8-phenyl-4,5-dihydro-3H-imidazo[4,5-f]quinolin-3-ol

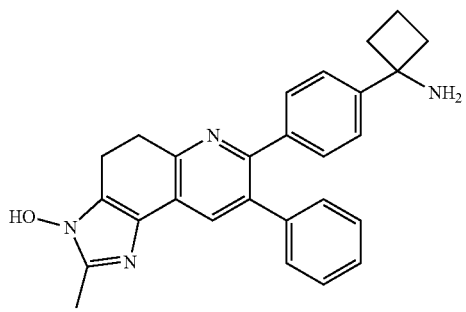 [SMILES: Cc1nc2c(n1O)CCc1nc(-c3ccc(C4(N)CCC4)cc3)c(-c3ccccc3)cc1-2]

Step 1: tert-butyl(1-(4-(6-(hydroxyimino)-5-oxo-3-phenyl-5,6,7,8-tetrahydroquinolin-2-yl)phenyl)cyclobutyl)carbamate To a solution of tert-butyl(1-(4-(5-oxo-3-phenyl-5,6,7,8-tetrahydroquinolin-2-yl)phenyl)cyclobutyl)carbamate (1.00 g, 2.134 mmol) in anhydrous THF (30 mL) was added dropwise potassium tert-butoxide (1M in THF, 2.56 ml, 2.56 mmol) over a period of 10 min to give a deep red solution. The reaction mixture was stirred at room temperature under a nitrogen atmosphere for 30 min. To this was added dropwise isopentyl nitrite (0.286 ml, 2.134 mmol) over a period of 5 min to give a red solution. The reaction mixture was stirred at 50° C. under a nitrogen atmosphere for 1 hour then allowed to cool to room temperature and concentrated to dryness under reduced pressure. The residue was redissolved in water (5 mL), acidified with 1M HCl solution (5 mL) and extracted into ethyl acetate (3×10 mL). The combined organic phases were washed with water (20 mL), brine (20 mL), dried over Na₂SO₄, filtered and concentrated to dryness under reduced pressure. The residue was purified via Biotage chromatography (silica, hexane:ethyl acetate, gradient elution from 88:12 to 0:100) to give the desired product as a brown solid (436 mg, 41% yield)). ¹H-NMR (500 MHz, CDCl₃) δ 8.40 (1H, s), 7.40 (2H, d), 7.32 (2H, d), 7.25-7.29 (3H, m), 7.18-7.22 (2H, m), 5.04 (1H, br s), 3.38 (2H, t), 3.29 (2H, t), 2.26-2.59 (4H, br m), 2.01-2.12 (1H, m), 1.76-1.86 (1H, m), 1.15-1.45 (9H, br m). LCMS (Method A) RT=6.74 min, M+H⁺=498.13.

Step 2: tert-butyl(1-(4-(3-hydroxy-2-methyl-8-phenyl-4,5-dihydro-3H-imidazo[4,5-f]quinolin-7-yl)phenyl)cyclobutyl)carbamate To a solution of tert-butyl(1-(4-(6-(hydroxyimino)-5-oxo-3-phenyl-5,6,7,8-tetrahydroquinolin-2-yl)phenyl)cyclobutyl)carbamate (300 mg, 0.603 mmol) in ethanol (3.0 mL) was added acetaldehyde (68.1 µl, 1.206 mmol) followed by ammonium hydroxide (329 µl, 2.53 mmol). The reaction mixture was heated at 80° C. under a nitrogen atmosphere for 2 hours, then allowed to cool to room temperature and concentrated to dryness under reduced pressure and dried to give the crude product as a brown solid (306 mg, 97% yield).

A 50 mg portion of this was further purified by Biotage chromatography (silica, DCM:MeOH, gradient elution from 100:0 to 50:50) to give the desired product as a brown solid (10 mg). ¹H-NMR (500 MHz, CDCl₃) δ 7.70 (1H, s), 7.15-7.24 (7H, m), 7.09-7.14 (2H, br m), 3.19 (2H, t), 2.91 (2H, t), 2.20-2.52 (4H, br m), 2.30 (3H, s), 1.93-2.06 (1H, m), 1.69-1.79 (1H, m), 1.06-1.45 (9H, br m). LCMS (Method A) RT=5.00 min, M+H⁺=523.19.

Step 3: 7-(4-(1-aminocyclobutyl)phenyl)-2-methyl-8-phenyl-4,5-dihydro-3H-imidazo[4,5-f]quinolin-3-ol tert-butyl(1-(4-(3-hydroxy-2-methyl-8-phenyl-4,5-dihydro-3H-imidazo[4,5-f]quinolin-7-yl)phenyl)cyclobutyl)carbamate (10 mg, 0.019 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as a pale brown solid (10 mg, 80% yield). ¹H-NMR (500 MHz, CD₃OD) δ 7.92 (1H, s), 7.48 (2H, d), 7.43 (2H, d), 7.30-7.34 (3H, m), 7.22-7.26 (2H, m), 3.42 (2H, t), 3.18 (2H, t), 2.72-2.81 (2H, m), 2.63 (3H, s), 2.54-2.64 (2H, m), 2.18-2.29 (1H, m), 1.91-2.02 (1H, m). LCMS (Method A) RT=3.14 min, M+H⁺=423.12.

Example 15

1-(4-(2-methyl-8-phenyl-4,5-dihydro-3H-imidazo[4,5-f]quinolin-7-yl)phenyl)cyclobutanamine

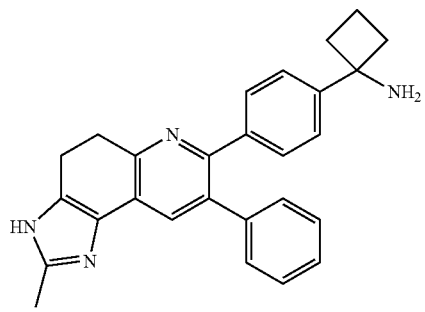 [SMILES: Cc1nc2c([nH]1)CCc1nc(-c3ccc(C4(N)CCC4)cc3)c(-c3ccccc3)cc1-2]

Step 1: tert-butyl(1-(4-(2-methyl-8-phenyl-4,5-dihydro-3H-imidazo[4,5-f]quinolin-7-yl)phenyl)cyclobutyl)carbamate To a solution of tert-butyl(1-(4-(3-hydroxy-2-methyl-8-phenyl-4,5-dihydro-3H-imidazo[4,5-f]quinolin-7-yl)phenyl)cyclobutyl)carbamate (276 mg, 0.528 mmol) in anhydrous DMF (1.4 mL) was added triethyl phosphite (181 μl, 1.056 mmol) and heated to 100° C. under a nitrogen atmosphere overnight. The reaction mixture was allowed to cool to room temperature, diluted with 50:50 water:brine (10 mL) and extracted into ethyl acetate (3×5 mL). The combined organic phases were washed with 50:50 water:brine (2×10 mL), brine (10 mL) dried over $Na_2SO_4$, filtered and concentrated to dryness under reduced pressure. The residue was purified via Biotage chromatography (silica, DCM:MeOH, gradient elution from 100:0 to 90:10) to give the desired product as a pale brown solid (100 mg, 37% yield). $^1$H-NMR (500 MHz, $CDCl_3$) δ 7.74 (1H, s), 7.28 (2H, d), 7.23 (2H, d), 7.13-7.17 (3H, m), 7.06-7.11 (2H, m), 5.09 (1H, br s), 3.25 (2H, t), 2.92 (2H, t), 2.16-2.59 (4H, br m), 2.41 (3H, s), 1.95-2.08 (1H, m), 1.70-1.82 (1H, m), 1.05-1.47 (9H, br m). LCMS (Method A) RT=4.66 min, M+H$^+$=507.20.

Step 2: 1-(4-(2-methyl-8-phenyl-4,5-dihydro-3H-imidazo[4,5-f]quinolin-7-yl)phenyl)cyclobutanamine tert-butyl(1-(4-(2-methyl-8-phenyl-4,5-dihydro-3H-imidazo[4,5-f]quinolin-7-yl)phenyl)cyclobutyl)carbamate (25 mg, 0.049 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and freeze-dried to give the desired product as an off-white solid (23 mg, 74% yield). $^1$H-NMR (500 MHz, $CD_3OD$) δ 7.90 (1H, s), 7.49 (2H, d), 7.44 (2H, d), 7.31-7.35 (3H, m), 7.23-7.27 (2H, m), 3.44 (2H, t), 3.20 (2H, t), 2.73-2.81 (2H, m), 2.72 (3H, s), 2.55-2.65 (2H, m), 2.19-2.30 (1H, m), 1.92-2.03 (1H, m). LCMS (Method A) RT=3.02 min, M+H$^+$=407.14.

Example 16

1-(4-(9-phenyl-5,6-dihydropyrido[2,3-h]quinazolin-8-yl)phenyl)-cyclobutanamine

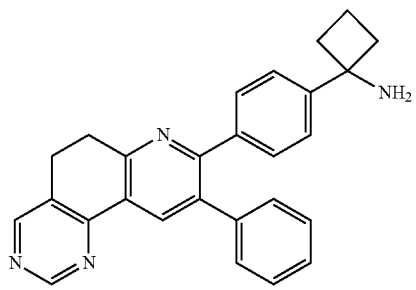 [SMILES: NC1(c2ccc(-c3nc4c(cc3-c3ccccc3)-c3ncncc3CC4)cc2)CCC1]

Step 1: tert-butyl(1-(4-(9-phenyl-5,6-dihydropyrido[2,3-h]quinazolin-8-yl)phenyl)cyclobutyl)carbamate To a solution of tert-butyl 1-(4-(6-((dimethylamino)methylene)-5-oxo-3-phenyl-5,6,7,8-tetrahydronaphthalen-2-yl)phenyl)cyclobutyl)carbamate (50 mg, 0.09 mmol) in anhydrous ethanol (1000 μL) was added sodium ethoxide solution (21% in ethanol, 150 μL, 0.38 mmol) and formamidine acetate (20 mg, 0.19 mmol). The reaction mixture was heated to 80° C. under a nitrogen atmosphere for 2 hours. It was concentrated to dryness under reduced pressure, purified by Biotage chromatography (silica, hexane:ethyl acetate, gradient elution from 95:5 to 60:40) and slurried in diethyl ether (1 mL) to give the desired product as an off-white solid (12 mg, 26% yield). $^1$H NMR (500 MHz, $CH_3OD$) 9.03 (s, 1H), 8.66 (s, 1H), 8.59 (s, 1H), 7.31 (bs, 4H), 7.25 (dd, 3H), 7.21 (m, 2H), 3.23 (m, 2H), 3.16 (m, 2H), 2.31-2.45 (m, 4H), 1.92-1.97 (m, 1H), 1.72-1.74 (m, 1H), 1.2-1.5 (br s, 9H). LCMS (Method A): $R_T$=7.64 min, M+H$^+$=505.

Step 2: 1-(4-(9-phenyl-5,6-dihydropyrido[2,3-h]quinazolin-8-yl)phenyl)cyclobutanamine Tert-butyl (1-(4-(9-phenyl-5,6-dihydropyrido[2,3-h]quinazolin-8-yl)phenyl)cyclobutyl)carbamate (12 mg, 0.023 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (8 mg, 70% yield). $^1$H NMR (500 MHz, $CH_3OD$) 9.09 (s, 1H), 8.74 (s, 1H), 8.67 (s, 1H), 7.52 (d, 2H), 7.43 (d, 2H), 7.32 (m, 3H), 7.26 (m, 2H), 3.22 (m, 2H), 2.75 (m, 2H), 2.59 (m, 2H), 2.23 (m, 1H), 1.98 (m, 1H). LCMS (Method A): $R_T$=4.26 min, M+2H$^+$=406.

Example 17

8-(4-(9-phenyl-5,6-dihydropyrido[2,3-h]quinazolin-2-amine

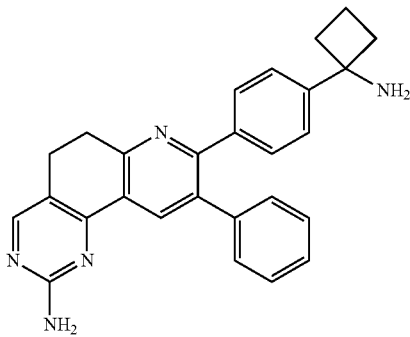 [SMILES: Nc1ncc2c(n1)-c1cc(-c3ccccc3)c(-c3ccc(C4(N)CCC4)cc3)nc1CC2]

Step 1: tert-butyl(1-(4-(2-amino-9-phenyl-5,6-dihydropyrido[2,3-h]quinazolin-8-yl)phenyl)cyclobutyl)carbamate To a solution of tert-butyl 1-(4-(6-((dimethylamino)methylene)-5-oxo-3-phenyl-5,6,7,8-tetrahydronaphthalen-2-yl)phenyl)cyclobutyl)carbamate (45 mg, 0.085 mmol) in anhydrous ethanol (1500 μL) was added sodium ethoxide solution (21% in ethanol, 130 pt, 0.34 mmol) and guanidine nitrate (22 mg, 0.17 mmol). The reaction mixture was heated to 80° C.

under a nitrogen atmosphere for one hour. It was concentrated to dryness under reduced pressure, purified by Biotage chromatography (silica, dichloromethane: methanol, gradient elution from 99:1 to 90:10) and slurried in diethyl ether (1 mL) to give the desired product as an off-white solid (10 mg, 23% yield). $^1$H NMR (500 MHz, d$_6$-DMSO) 8.36 (s, 1H), 8.25 (s, 1H), 7.31 (m, 5H), 7.25 (m 4H), 6.56 (bs, 1H), 3.11 (t, 2H), 2.91 (t, 2H), 2.33 (br m, 4H), 1.93-2.04 (m, 1H), 1.70-1.82 (m, 1H), 1.1-1.41 (br s, 9H). LCMS (Method A): R$_T$=6.23 min, M+H$^+$=520.

Step 2: 8-(4-(9-phenyl-5,6-dihydropyrido[2,3-h]
quinazolin-2-amine

Tert-butyl (1-(4-(2-amino-9-phenyl-5,6-dihydropyrido[2,3-h]quinazolin-8-yl)phenyl)cyclobutyl)carbamate (10 mg, 0.019 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed under reduced pressure and dried to give the desired product as an off-white solid (2 mg, 20% yield). $^1$H NMR (500 MHz, d$_6$-DMSO) 8.04 (br s, 2H), 8.31 (s, 1H), 8.23 (s, 1H), 7.40 (d, 2H), 7.35 (d, 2H), 7.29 (m, 3H), 7.20 (m, 2H), 3.13 (t, 2H), 2.94 (t, 2H), 2.56 (m, 4H), 2.07-2.19 (br m, 1H), 1.74-1.85 (br m, 1H). LCMS (Method A): R$_T$=3.58 min, M+H$^+$=420.

Example 18

2-(4-(1-aminocyclobutyl)phenyl)-7,7-dimethyl-3-phenyl-7,8-dihydroquinolin-5(6H)-one

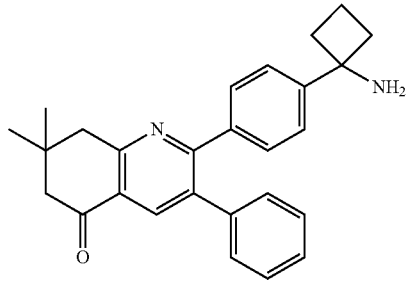 [SMILES: CC1(C)CC(=O)c2cc(-c3ccccc3)c(-c3ccc(C4(N)CCC4)cc3)nc2C1]

Step 1: tert-butyl(1-(4-(7,7-dimethyl-5-oxo-3-phenyl-5,6,7,8-tetrahydroquinolin-2-yl)phenyl)cyclobutyl)carbamate To a solution of tert-butyl(1-(4-(3-(dimethylamino)-2-phenylacryloyl)phenyl)cyclobutyl)carbamate (166 mg, 0.40 mmol) in acetic acid (1 mL) was added molecular sieves (10 mg) and 3-amino-5,5-dimethylcyclohex-2-enone (82 mg, 0.59 mmol) under nitrogen. The resulting mixture was heated at 100° C. for 2 h. After cooled down to room temperature, the mixture was partitioned between water (10 mL) and dichloromethane (10 mL). The layers were separated and the aqueous phase extracted into dichloromethane (2×10 mL). The combined organic phases were washed with saturated NaHCO$_3$ solution (20 mL), dried over Na$_2$SO$_4$, filtered and concentrated to dryness under reduced pressure. The resulting residue was purified by Biotage silica gel chromatography (gradient 0 to 20% EtOAc in hexane) to give the title compound (80 mg, 41%). $^1$H NMR (500 MHz, CDCl$_3$): 8.27 (1H, s), 7.37 (2H, d), 7.30 (2H, d), 7.25-7.24 (3H, m), 7.19-7.17 (2H, m), 5.06 (1H, br s), 3.13 (2H, s), 2.59 (2H, s), 2.55-2.25 (4H, m), 2.09-2.01 (1H, m), 1.82-1.77 (1H, m), 1.44-1.15 (9H, br), 1.17 (6H, s).

Step 2: 2-(4-(1-aminocyclobutyl)phenyl)-7,7-dimethyl-3-phenyl-7,8-dihydroquinolin-5(6H)-one Following the procedure for 2-(4-(1-aminocyclobutyl)phenyl)-3-phenyl-7,8-dihydroquinolin-5(6H)-one, tert-butyl (1-(4-(7,7-dimethyl-5-oxo-3-phenyl-5,6,7,8-tetrahydroquinolin-2-yl)phenyl)cyclobutyl)carbamate (30 mg, 0.06 mmol) was reacted to afford the title compound as a white solid (27 mg, 87%). LCMS (Method A): R$_T$=4.48 min, M-NH$_2$=380. $^1$H NMR (500 MHz, MeOD): 8.26 (1H, s), 7.50 (2H, d), 7.43 (2H, d), 7.31-7.29 (3H, m), 7.21-7.19 (2H, m), 3.15 (2H, s), 2.78-2.72 (2H, m), 2.66 (2H, s), 2.60-2.54 (2H, m), 2.27-2.18 (1H, m), 2.00-1.91 (1H, m), 1.17 (6H, s).

Example 19

1-(4-(4,4-dimethyl-8-phenyl-4,5-dihydro-2H-pyrazolo[3,4-f]quinolin-7-yl)phenyl)cyclobutanamine

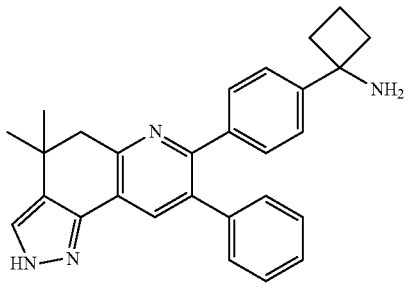 [SMILES: CC1(C)Cc2nc(-c3ccc(C4(N)CCC4)cc3)c(-c3ccccc3)cc2-c2n[nH]cc21]

Step 1: tert-butyl(1-(4-(6-((dimethylamino)methylene)-7,7-dimethyl-5-oxo-3phenyl-5,6,7,8-tetrahydroquinolin-2-yl)phenyl)cyclobutyl)carbamate Tert-butyl (1-(4-(7,7-dimethyl-5-oxo-3-phenyl-5,6,7,8-tetrahydroquinolin-2-yl)phenyl)cyclobutyl)carbamate (1 g, 2 mmol) was dissolved in 10 ml of anhydrous N,N-dimethylfomamide dimethylformamide dimethyl acetate. The resulting mixture was heated to 100° C. under a nitrogen atmosphere for 48 hours. TLC and LC-MS analysis showed complete consumption of the starting material. The reaction mixture was concentrated to dryness under reduced pressure. The crude residue was slurried in n-hexane (10 ml) for 1 hour. The suspension was filtered and the solid was dried until constant weigh to give the desired product as a bright yellow solid (420 mg, 76% yield). LCMS (Method A): R$_T$=8.51 min, M+H$^+$=552; R$_T$=8.81 min, M+H$^+$=525 (tert-butyl(1-(4-(6-(hydroxymethylene)-7,7-dimethyl-5-oxo-3-phenyl-5,6,7,8-tetrahydroquinolin-2-yl)phenyl)cyclobutyl)carbamate.

Step 2: tert-butyl(1-(4-(4,4-dimethyl-8-phenyl-4,5-dihydro-2H-pyrazolo[3,4-f]quinolin-7-yl)phenyl)cyclobutyl)carbamate To a solution of tert-butyl(1-(4-(6-((dimethylamino)methylene)-7,7-dimethyl-5-oxo-3-phenyl-5,6,7,8-tetrahydroquinolin-2-yl)phenyl)cyclobutyl)carbamate (180 mg, 0.33 mmol) in anhydrous ethanol (4 mL) was added hydrazine hydrate (48 μL, 1 mmol). The reaction mixture was stirred at room temperature under a nitrogen atmosphere for 2 hours. The reaction mixture was concentrated to dryness under reduced pressure, purified by Biotage chromatography (silica, hexane:ethyl acetate, gradient elution from 99:1 to 60:40) and PREP HPLC (Method A) to give the desired product as a white solid (8 mg, 5% yield). $^1$H NMR (500 MHz, CDCl$_3$) 8.12 (s, 1H), 7.27-7.48 (br m, 5H), 7.25-7.18 (br m, 5H), 5.03 (br s, 1H), 3.16 (s, 2H), 2.23-2.68 (br m, 4H), 1.97-2.12 (m, 1H), 1.75-1.88 (m, 1H), 1.11-1.57 (br s, 9H+6H). LCMS (Method A): $R_T$=6.62 min, M+H$^+$=521.

Step 3: 1-(4-(4,4-dimethyl-8-phenyl-4,5-dihydro-2H-pyrazolo[3,4-f]quinolin-7-yl)phenyl)cyclobutan-amine tert-butyl(1-(4-(4,4-dimethyl-8-phenyl-4,5-dihydro-2H-pyrazolo[3,4-f]quinolin-7-yl)phenyl)cyclobutyl)carbamate (8 mg, 0.015 mmol) was dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (1 mL) and after settling the supernatant solvent removed by pipette. This was repeated three times. The remaining solvent was removed under reduced pressure and dried to give the desired product as an off-white solid (4 mg, 50% yield). $^1$H NMR (500 MHz, CH$_3$OD) 8.18 (s, 1H), 7.63 (s, 1H), 7.47 (d, 2H), 7.41 (d, 2H), 7.19-7.33 (br m, 5H), 3.08 (s, 2H), 2.68-2.79 (br m, 2H), 2.51-2.64 (br m, 2H), 2.15-2.30 (br m, 1H), 1.87-2.01 (br m, 1H), 1.35 (s, 6H). LCMS (Method A): $R_T$=3.03 min, M+H$^+$=421.

Example 20

2-(4-(1-aminocyclobutyl)phenyl)-3-phenyl-6,7,8,9-tetrahydro-5H-cyclohepta[b]pyridin-5-one

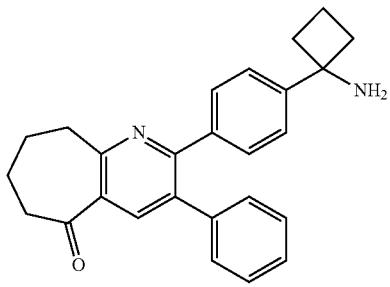 [SMILES: NC1(c2ccc(-c3nc4c(cc3-c3ccccc3)C(=O)CCCC4)cc2)CCC1]

Step 1: tert-butyl(1-(4-(5-oxo-3-phenyl-6,7,8,9-tetrahydro-5H-cyclohepta[b]pyridin-2-yl)phenyl)cyclobutyl)carbamate To a solution of tert-butyl(1-(4-(3-(dimethylamino)-2-phenylacryloyl)phenyl)cyclobutyl)carbamate (119 mg, 0.28 mmol) in acetic acid (1 mL) was added molecular sieves (10 mg) and cycloheptane-1,3-dione (36 μL, 0.42 mmol) under nitrogen. The resulting mixture was heated at 100° C. for 2 h. After cooled down to room temperature, the mixture was partitioned between water (10 mL) and dichloromethane (10 mL). The layers were separated and the aqueous phase extracted into dichloromethane (2×10 mL). The combined organic phases were washed with saturated NaHCO$_3$ solution (20 mL), brine (20 mL), dried over Na$_2$SO$_4$, filtered and concentrated to dryness under reduced pressure. The resulting residue was purified by Biotage silica gel chromatography (gradient 0 to 20% EtOAc in hexane) to give the title compound (32 mg, 24%). $^1$H NMR (500 MHz, CDCl$_3$): 8.09 (1H, s), 7.38 (2H, d), 7.30 (2H,d), 7.25-7.24 (3H, m), 7.19-7.17 (2H, m), 5.04 (1H, br s), 3.29 (2H,t), 2.87 (2H, t), 2.60-2.25 (4H, m), 2.07-2.01 (3H, m), 1.99-1.94 (2H, m), 1.84-1.75 (1H, m), 1.42-1.15 (9H, br).

Step 2: 2-(4-(1-aminocyclobutyl)phenyl)-3-phenyl-6,7,8,9-tetrahydro-5H-cyclohepta[b]pyridin-5-one Following the procedure for 2-(4-(1-aminocyclobutyl)phenyl)-3-phenyl-7,8-dihydroquinolin-5(6H)-one, tert-butyl (1-(4-(5-oxo-3-phenyl-6,7,8,9-tetrahydro-5H-cyclohepta[b]pyridin-2-yl)phenyl)cyclobutyl)carbamate (14 mg, 0.03 mmol) was reacted to afford the title compound as a white solid (14 mg, 100%). LCMS (Method A): $R_T$=4.26 min, M-NH$_2$=366. $^1$H NMR (500 MHz, MeOD): 8.06 (1H, s), 7.50 (2H, d), 7.42 (2H, d), 7.29-7.28 (3H, m), 7.20-7.18 (2H, m), 3.30 (2H, t), 2.89 (2H, t), 2.78-2.72 (2H, m), 2.59-2.54 (2H, m), 2.25-2.19 (1H, m), 2.06-2.01 (2H, m), 1.98-1.92 (3H, m).

Example 21

1-(4-(9-phenyl-2,4,5,6-tetrahydropyrazolo[3',4':3,4]cyclohepta[1,2-b]pyridin-8-yl)phenyl)cyclobutan-amine

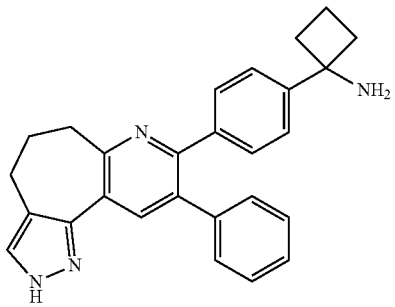 [SMILES: NC1(c2ccc(-c3nc4c(cc3-c3ccccc3)-c3n[nH]cc3CCC4)cc2)CCC1]

Step 1: tert-butyl(1-(4-(6-((dimethylamino)methylene)-5-oxo-3-phenyl-6,7,8,9-tetrahydro-5H-cyclohepta[b]pyridin-2-yl)phenyl)cyclobutyl)carbamate Tert-butyl (1-(4-(5-oxo-3-phenyl-6,7,8,9-tetrahydro-5H-cyclohepta[b]pyridine-2-yl)phenyl)cyclobutyl)carbamate (270 mg, 0.56 mmol) was dissolved in 3 ml of anhydrous N,N-dimethylformamide dimethyl acetate. The resulting mixture was heated to 100° C. under a nitrogen atmosphere for 18 hours. TLC and LC-MS analysis showed complete consumption of the starting material. The reaction mixture was concentrated to dryness under reduced pressure. The crude residue was slurried in n-hexane (5 ml) for 1 hour. The suspension was filtered and the solid was dried until constant weigh to give the desired product as a bright yellow solid (190 mg, 63% yield). LCMS (Method A): $R_T$ 6.55 min, M+H$^+$=538; $R_T$=8.43 min, M+H$^+$=511 (tert-butyl(1-(4-(6-(hydroxymethylene)-5-oxo-3-phenyl-6,7,8,9-tetrahydro-5H-cyclohepta[b]pyridin-2-yl)cyclobutyl)carbamate.

Step 2: tert-butyl(1-(4-(9-phenyl-2,4,5,6-tetrahydropyrazolo[3',': 3,4]cyclohepta[1,2-b]pyridin-8-yl)phenyl)cyclobutyl)carbamate To a solution of tert-butyl(1-(4-(6-((dimethylamino)methylene)-5-oxo-3-phenyl-6,7,8,9-tetrahydro-5H-cyclohepta[b]pyridin-2-yl)phenyl)cyclobutyl)carbamate (90 mg, 0.17 mmol) in anhydrous ethanol (2 mL) was added hydrazine hydrate (25 μL, 0.5 mmol). The reaction mixture was stirred at room temperature under a nitrogen atmosphere for 18 hours. The reaction mixture was concentrated to dryness under reduced pressure, purified by Biotage chromatography (silica, hexane:ethyl acetate, gradient elution from 99:1 to 60:40) and preparative HPLC (Method G, gradient 5 to 95% 0.1% FA/ACN in 0.1% FA/H$_2$O, 20 minutes run) to give the desired product as a white solid (50 mg, 58% yield). $^1$H NMR (500 MHz, CDCl$_3$) 7.49 (s, 1H), 7.38 (d, 2H), 7.29 (d, 2H), 7.21-7.25 (br m, 5H+1H), 3.25 (m, 2H), 2.94 (t, 2H), 2.53-2.61 (br m, 1H), 2.42-2.52 (m, 2H), 2.31-2.41 (br m, 1H), 2.14-2.21 (m, 2H), 1.98-2.10 (m, 1H), 1.74-1.85 (m, 1H), 1.30-1.43 (br s, 9H). LCMS (Method A): R$_T$=6.09 min, M+H$^+$=507.

Step 3: 1-(4-(9-phenyl-2,4,5,6-tetrahydropyrazolo[3',4':3,4]cyclohepta[1,2-b]pyridin-8-yl)phenyl)cyclobutanamine Tert-butyl (1-(4-(9-phenyl-2,4,5,6-tetrahydropyrazolo[3',': 3,4]cyclohepta[1,2-b]pyridin-8-yl)phenyl)cyclobutyl)carbamate (10 mg, 0.019 mmol) was dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (1 mL) and after settling the supernatant solvent removed by pipette. This was repeated three times. The remaining solvent was removed under reduced pressure and dried to give the desired product as an off-white solid (2 mg, 20% yield). $^1$H NMR (500 MHz, CH$_3$OD) 8.69 (s, 1H), 7.66 (s, 1H), 7.56 (d, 2H), 7.2 (d, 2H), 7.34 (m, 3H), 7.29 (m, 2H), 3.47-3.53 (m, 1H), 3.03 (m, 2H), 2.74-2.82 (br m, 2H), 2.56-2.67 (br m, 2H), 2.19-2.34 (br m, 3H), 1.91-2.03 (m, 1H). LCMS (Method A): R$_T$=3.03 min, M+H$^+$=407.

Example 22

2-(4-(1-aminocyclobutyl)phenyl)-3-phenyl-7,8-dihydro-1,6-naphthyridin-5(6H)-one

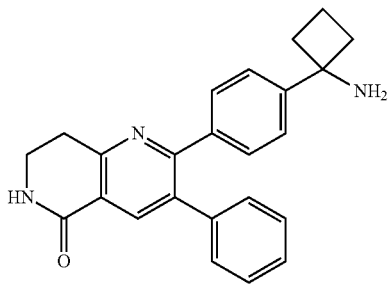 [SMILES: NC1(c2ccc(-c3nc4c(cc3-c3ccccc3)C(=O)NCC4)cc2)CCC1]

Step 1: tert-butyl(1-(4-(5-oxo-3-phenyl-5,6,7,8-tetrahydro-1,6-naphthyridin-2-yl)phenyl)cyclobutyl)carbamate To a solution of tert-butyl(1-(4-(3-(dimethylamino)-2-phenylacryloyl)phenyl)cyclobutyl)carbamate (952 mg, 2.27 mmol) in acetic acid (10 mL) was added molecular sieves (100 mg), ammonium acetate (524 mg, 6.80 mmol) and piperidine-2,4-dione (385 mg, 3.40 mmol) under nitrogen. The resulting mixture was heated at 100° C. for 2 h. After cooled down to room temperature, the mixture was partitioned between water (100 mL) and dichloromethane (100 mL). The layers were separated and the aqueous phase extracted into dichloromethane (2×50 mL). The combined organic phases were washed with saturated NaHCO$_3$ solution (100 mL), dried over Na$_2$SO$_4$, filtered and concentrated to dryness under reduced pressure. The resulting residue was purified by Biotage silica gel chromatography (gradient 0 to 100% EtOAc in hexane) to give the title compound as a yellow solid (353 mg, 33%). $^1$H NMR (500 MHz, MeOD): 8.28 (1H, s), 7.38-7.34 (4H, m), 7.32-7.29 (3H, m), 7.23-7.21 (2H, m), 3.69 (2H, t), 3.25 (2H, t), 2.51-2.40 (4H, m), 2.13-2.05 (1H, m), 1.91-1.84 (1H, m), 1.44-1.18 (9H, br).

Step 2: 2-(4-(1-aminocyclobutyl)phenyl)-3-phenyl-7,8-dihydro-1,6-naphthyridin-5(6H)-one Following the procedure for 2-(4-(1-aminocyclobutyl)phenyl)-3-phenyl-7,8-dihydroquinolin-5(6H)-one, tert-butyl (1-(4-(5-oxo-3-phenyl-5,6,7,8-tetrahydro-1,6-naphthyridin-2-yl)phenyl)cyclobutyl)carbamate (10 mg, 0.021 mmol) was reacted to afford the title compound (7 mg, 69%). LCMS (Method A): R$_T$=3.62 min, M+H$^+$=370. $^1$H NMR (500 MHz, MeOD) 8.30 (1H, s), 7.51 (2H, d), 7.45 (2H, d), 7.31 (3H, m), 7.22 (2H, m), 3.70 (2H, t), 3.27 (2H, t), 2.85-2.70 (2H, m), 2.65-2.50 (2H, m), 2.30-2.20 (1H, m), 2.05-1.90 (1H, m).

Example 23

2-(4-(1-aminocyclobutyl)phenyl)-6-methyl-3-phenyl-7,8-dihydro-1,6-naphthyridin-5(6H)-one

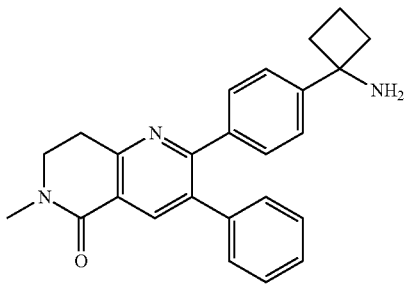 [SMILES: CN1CCc2nc(-c3ccc(C4(N)CCC4)cc3)c(-c3ccccc3)cc2C1=O]

Step 1: tert-butyl(1-(4-(6-methyl-5-oxo-3-phenyl-5,6,7,8-tetrahydro-1,6-naphthyridin-2-yl)phenyl)cyclobutyl)carbamate To a solution of tert-butyl(1-(4-(5-oxo-3-phenyl-5,6,7,8-tetrahydro-1,6-naphthyridin-2-yl)phenyl)cyclobutyl)carbamate (30 mg, 0.06 mmol) in dry DMF (1 mL) was added sodium hydride (3 mg, 0.07 mmol) at 0° C. under nitrogen. After 1 h at 0° C., iodomethane (17 μL, 0.19 mmol) was added and the resulting mixture was stirred for an additional 10 min at 0° C. A saturated solution of NH$_4$Cl was added and the mixture was extracted with dichloromethane (3×) using a phase separator (Isolute® SPE). The combined organic phases were concentrated to dryness under reduced pressure. The resulting residue was purified by silica gel chromatography (gradient 0 to 50% EtOAc in hexane) to give the title compound (22 mg, 71%). $^1$H NMR (500 MHz, CDCl$_3$): 8.35 (1H, s), 7.34 (2H, d), 7.29 (2H,d), 7.24-7.22 (3H, m), 7.19-7.17 (2H, m), 5.06 (1H, br s), 3.70 (2H, t), 3.29 (2H, t), 3.19 (3H, s), 2.54-2.30 (4H, m), 2.08-2.00 (1H, m), 1.83-1.74 (1H, m), 1.44-1.18 (9H, br).

Step 2: 2-(4-(1-aminocyclobutyl)phenyl)-3-phenyl-7,8-dihydro-1,6-naphthyridin-5(6H)-one Following the procedure for 2-(4-(1-aminocyclobutyl)phenyl)-3-phenyl-7,8-dihydroquinolin-5(6H)-one, tert-butyl (1-(4-(6-methyl-5-oxo-3-phenyl-5,6,7,8-tetrahydro-1,6-naphthyridin-2-yl)phenyl)cyclobutyl)carbamate (29 mg, 0.06 mmol) was reacted to afford the title compound (32 mg, 87%). LCMS (Method A): R$_T$=3.76 min, M-NH$_2$=367. $^1$H NMR (500 MHz, MeOD): 8.29 (1H, S), 7.49 (2H, d), 7.42 (2H, d), 7.30-7.29 (3H, m), 7.21-7.19 (m, 2H), 3.80 (2H, t), 3.30 (2H, t), 3.20 (3H, s), 2.78-2.72 (m, 2H), 2.60-2.54 (m, 2H), 2.27-2.18 (m, 1H), 2.00-1.91 (m, 1H).

Example 24

2-(2-(4-(1-aminocyclobutyl)phenyl)-5-oxo-3-phenyl-7,8-dihydro-1,6-naphthyridin-6(5H)-yl)acetonitrile

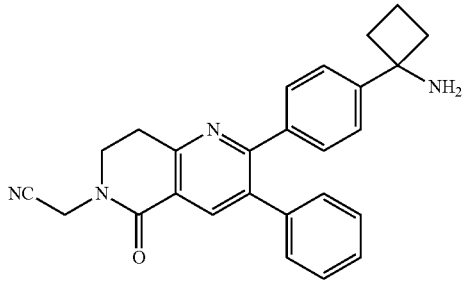 [SMILES: N#CCN1CCc2nc(-c3ccc(C4(N)CCC4)cc3)c(-c3ccccc3)cc2C1=O]

Step 1: tert-butyl(1-(4-(6-(cyanomethyl)-5-oxo-3-phenyl-5,6,7,8-tetrahydro-1,6-naphthyridin-2-yl)phenyl)cyclobutyl)carbamate To a solution of tert-butyl(1-(4-(5-oxo-3-phenyl-5,6,7,8-tetrahydro-1,6-naphthyridin-2-yl)phenyl)cyclobutyl)carbamate (31 mg, 0.07 mmol) in dry DMF (1 mL) was added sodium hydride (3 mg, 0.07 mmol) at 0° C. under nitrogen. After 1 h at 0° C., 2-bromoacetonitrile (14 µL, 0.20 mmol) was added and the resulting mixture was stirred for an additional 30 min at 0° C. A saturated solution of NH$_4$Cl was added and the mixture was extracted with dichloromethane (3×) using a phase separator (Isolute® SPE). The combined organic phases were concentrated to dryness under reduced pressure. The resulting residue was purified by silica gel chromatography (gradient 0 to 40% EtOAc in hexane) to give the title compound (10 mg, 29%). $^1$H NMR (500 MHz, CDCl$_3$): 8.36 (1H, s), 7.35 (2H,d), 7.30 (2H, d), 7.27-7.26 (3H, m), 7120-7.18 (2H, m), 5.05 (1H, br s), 4.59 (2H, s), 3.86 (2H, t), 3.40 (2H, t), 2.55-2.25 (4H, m), 2.10-2.02 (1H, m), 1.85-1.76 (1H, m), 1.44-1.18 (9H, br).

Step 2: 2-(2-(4-(1-aminocyclobutyl)phenyl)-5-oxo-3-phenyl-7,8-dihydro-1,6-naphthyridin-6(5H)-yl)acetonitrile Following the procedure for 2-(4-(1-aminocyclobutyl)phenyl)-3-phenyl-7,8-dihydroquinolin-5(6H)-one, tert-butyl (1-(4-(6-(cyanomethyl)-5-oxo-3-phenyl-5,6,7,8-tetrahydro-1,6-naphthyridin-2-yl)phenyl)cyclobutyl)carbamate (17 mg, 0.03 mmol) was reacted to afford the title compound (15 mg, 71%). LCMS (Method A): R$_T$=3.80 min, M-NH$_2$=392. $^1$H NMR (500 MHz, MeOD): 8.33 (1H, S), 7.50 (2H, d), 7.42 (2H, d), 7.31-7.29 (3H, m), 7.22-7.20 (m, 2H), 4.66 (2H, s), 3.92 (2H, t), 3.38 (2H, t), 2.78-2.72 (m, 2H), 2.60-2.54 (m, 2H), 2.27-2.18 (m, 1H), 2.00-1.91 (m, 1H).

Example 25

2-(4-(1-aminocyclobutyl)phenyl)-6-(2-dimethylamino)ethyl)-3-phenyl-7,8-dihydro-1,6-naphthyridin-5(6H)-one

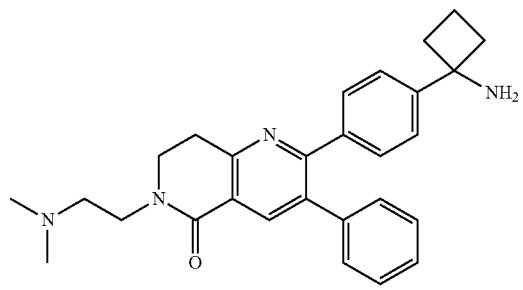 [SMILES: CN(C)CCN1CCc2nc(-c3ccc(C4(N)CCC4)cc3)c(-c3ccccc3)cc2C1=O]

Step 1: tert-butyl(1-(4-(6-(2-(dimethylamino)ethyl)-5-oxo-3-phenyl-5,6,7,8-tetrahydro-1,6-naphthyridin-2-yl)phenyl)cyclobutyl)carbamate To a solution of tert-butyl(1-(4-(5-oxo-3-phenyl-5,6,7,8-tetrahydro-1,6-naphthyridin-2-yl)phenyl)cyclobutyl)carbamate (25 mg, 0.05 mmol) in dry DMF (1 mL) was added sodium hydride (5 mg, 0.106 mmol) at 0° C. under nitrogen. After 1 h at 0° C., a solution of 2-chloro-N,N-dimethylethanamine hydrochloride (9 mg, 0.064 mmol) and potassium carbonate (9 mg, 0.064) in 1 mL of DMF was added and the resulting mixture was stirred for one hour at 40° C. The reaction mixture was cooled to 0° C. and a saturated solution of NH$_4$Cl was added while stirring, keeping the temperature below 10° C. The resulting mixture was extracted with dichloromethane (3×) using a phase separator (Isolute® SPE). The combined organic phases were concentrated to dryness under reduced pressure. The resulting residue was purified by PREP HPLC (method G) to give the desired product as a white solid (5 mg, 17% yield). $^1$H NMR (500 MHz, CDCl$_3$): 8.35 (1H, s), 7.34 (2H, d), 7.29 (2H, d), 7.23-7.25 (3H, m), 7.17-7.20 (2H, m), 5.01 (1H, s), 3.77 (4H, m), 3.28 (2H, t), 2.63 (2H, t), 2.47 (2H+1H, m), 2.35 (6H, s), 2.24-2.32 (2H, m), 1.98-2.12 (1H, m), 1.67-1.89 (9H, br s).

Step 2: 2-(4-(1-aminocyclobutyl)phenyl)-6-(2-dimethylamino)ethyl)-3-phenyl-7,8-dihydro-1,6-naphthyridin-5(6H)-one Tert-butyl (1-(4-(6-(2-(dimethylamino)ethyl)-5-oxo-3-phenyl-5,6,7,8-tetrahydro-1,6-naphthyridin-2-yl)phenyl)cyclobutyl)carbamate (5 mg, 0.01 mmol) dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (1 mL) and after settling the supernatant solvent removed by pipette. This was repeated three times. The remaining solvent was removed under reduced pressure and dried to give the desired product as an off-white solid (1.66 mg, 35% yield). $^1$H NMR (500 MHz, CH$_3$OD) 8.22 (s, 1H), 7.50 (d, 2H), 7.39 (d, 2H), 7.33 (d, 2H), 7.18-7.22 (m, 3H), 7.08-7.13 (m, 2H), 3.90 (t, 2H), 3.76 (t, 2H), 3.39 (t, 2H), 3.24 (t, 2H), 2.94 (s, 6H), 2.60-2.70 (br m, 2H), 2.43-2.52 (br m, 2H), 2.09-2.19 (br m, 1H), 1.80-1.95 (br m, 1H). LCMS (Method A): $R_T$=3.03 min, M+H$^+$=441.

Example 26

8-(4-(1-aminocyclobutyl)phenyl)-9-phenyl-5,6-dihydro-[1,2,4]triazolo[3,4][1,6]naphthyridin-3(2H)-one

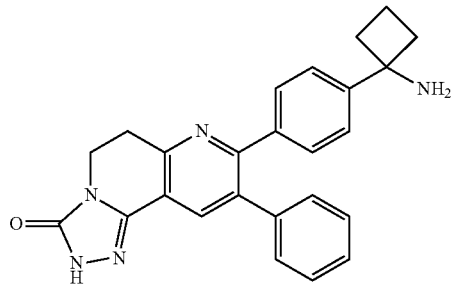 [SMILES: NC1(c2ccc(-c3nc4c(cc3-c3ccccc3)-c3n[nH]c(=O)n3CC4)cc2)CCC1]

Step 1: tert-butyl(1-(4-(3-phenyl-5-thioxo-5,6,7,8-tetrahydro-1,6-naphthyridin-2-yl)phenyl)cyclobutyl) carbamate To a solution of tert-butyl(1-(4-(5-oxo-3-phenyl-5,6,7,8-tetrahydro-1,6-naphthyridin-2-yl)phenyl)cyclobutyl)carbamate (223 mg, 0.47 mmol) in toluene (15 mL) was added lawesson's reagent (192 mg, 0.47 mmol) under nitrogen. The resulting mixture was heated under reflux for 2 h. After cooled down to room temperature, the mixture was concentrated to dryness under reduced pressure. The resulting residue was purified by Biotage silica gel chromatography (gradient 0 to 1% MeOH in dichloromethane) to give the title compound as a yellow solid (231 mg, quantitative). $^1$H NMR (500 MHz, MeOD): 8.76 (1H, s), 7.37-7.33 (4H, m), 7.31-7.28 (3H, m), 7.22-7.20 (2H, m), 3.69 (2H, t), 3.25 (2H, t), 2.49-2.39 (4H, m), 2.15-2.05 (1H, m), 1.91-1.80 (1H, m), 1.45-1.15 (9H, br).

Step 2: tert-butyl(1-(4-(3-oxo-9-phenyl-2,3,5,6-tetrahydro-[1,2,4]triazolo[3,4-f][1,6]naphthyridin-8-yl) phenyl)cyclobutyl)carbamate To a solution of tert-butyl(1-(4-(3-phenyl-5-thioxo-5,6,7,8-tetrahydro-1,6-naphthyridin-2-yl)phenyl)cyclobutyl)carbamate (55 mg, 0.113 mmol) in THF (7 mL) was added ethyl carbazate (23.6 mg, 0.226 mmol) and mercury acetate (54.1 mg, 0.17 mmol) under nitrogen. The resulting mixture was stirred at r.t. for 2 h. The mixture was concentrated to dryness under reduced pressure and partitioned between DCM (15 ml) and water (15 ml). The organic phase was separated and concentrated to dryness under reduced pressure. The resulting residue was suspended in toluene (7 ml). The resulting mixture was heated under reflux for 3 h. After cooled down to room temperature, the mixture was concentrated to dryness under reduced pressure. The resulting residue was purified by Biotage silica gel chromatography (gradient 0 to 4% MeOH in dichloromethane) to give tert-butyl(1-(4-(3-oxo-9-phenyl-2,3,5,6-tetrahydro-[1,2,4]triazolo[3,4-f][1,6]naphthyridin-8-yl)phenyl)cyclobutyl)carbamate (32 mg, 56%). LCMS (Method A): $R_T$=6.29 min, M+1=510. $^1$H NMR (500 MHz, CDCl$_3$): 9.83 (1H,S), 8.10 (1H, s), 7.29 (2H, d), 7.22 (2H, d), 7.19-7.18 (3H, m), 7.13-7.11 (2H, m), 5.1 (1H, br), 4.01 (2H, t), 3.36 (2H, t), 2.43-2.28 (4H, m), 2.02-1.97 (1H, m), 1.76-1.70 (1H, m), 1.30-1.14 (9H, br).

Step 3: 8(4-(1-aminocyclobutyl)phenyl)-9-phenyl-5,6-dihydro-[1,2,4]triazolo[3,4-f][1,6]naphthyridin-3 (2H)-one Following the procedure for 2-(4-(1-aminocyclobutyl)phenyl)-3-phenyl-7,8-dihydroquinolin-5(6H)-one, tert-butyl (1-(4-(3-oxo-9-phenyl-2,3,5,6-tetrahydro-[1,2,4]triazolo[3,4-f][1,6]naphthyridin-8-yl)phenyl)cyclobutyl)carbamate (10 mg, 0.019 mmol) was reacted to afford the title compound (6 mg, 58%). LCMS (Method A): $R_T$=3.51 min, M+2=411.2. $^1$H NMR (500 MHz, MeOD): 8.23 (1H, S), 7.52 (2H, d), 7.43 (2H, d), 7.34-7.32 (3H, m), 7.26-7.24 (2H, m), 4.09 (2H, t), 3.46 (2H, t), 2.81-2.75 (2H, m), 2.62-2.56 (2H, m), 2.28-2.22 (1H, m), 2.01-1.95 (1H, m).

Example 27

1-(4-(6-ethyl-3-phenyl-5,6,7,8-tetrahydro-1,6-naphthyridin-2-yl)phenyl)cyclobutanamine

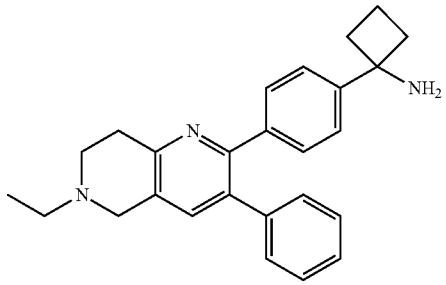 [SMILES: CCN1CCc2nc(-c3ccc(C4(N)CCC4)cc3)c(-c3ccccc3)cc2C1]

Step 1: tert-butyl(1-(4-(6-ethyl-3-phenyl-5,6,7,8-tetrahydro-1,6-naphthyridin-2-yl)phenyl)cyclobutyl) carbamate To a solution of tert-butyl(1-(4-(3-phenyl-5-thioxo-5,6,7,8-tetrahydro-1,6-naphthyridin-2-yl)phenyl)cyclobutyl)carbamate (41 mg, 0.08 mmol) in dry ethanol (1 mL) was added Raney Nickel (1 mL) under nitrogen. The resulting mixture was heated under reflux for 4 h. After cooled down to room temperature, the mixture was filtered on celite (rinse few times with ethanol) and concentrated to dryness under reduced pressure to give the title compound (28 mg, 74%). $^1$H NMR (500 MHz, CDCl$_3$): 7.29 (1H, s), 7.22-7.18 (4H, m), 7.15-7.14 (3H, m), 7.07-7.06 (2H, m), 4.98 (1H, br s), 3.64 (2H, S), 3.09 (2H, t), 2.83 (2H, t), 2.58 (2H, q), 2.50-2.20 (4H, m), 2.00-1.91 (1H, m), 1.74-1.66 (1H, m), 1.40-1.10 (9H, br), 1.15 (3H, t).

Step 2: 1-(4-(6-ethyl-3-phenyl-5,6,7,8-tetrahydro-1,6-naphthyridin-2-yl)phenyl)cyclobutanamine Following the procedure for 2-(4-(1-aminocyclobutyl)phenyl)-3-phenyl-7,8-dihydroquinolin-5(6H)-one, tert-butyl (1-(4-(6-ethyl-3-phenyl-5,6,7,8-tetrahydro-1,6-naphthyridin-2-yl)phenyl)cyclobutyl)carbamate (14 mg, 0.03 mmol) was reacted to afford the title compound (18 mg, quantitative). LCMS (Method A): $R_T$=0.44 min, M-NH$_2$=367. $^1$H NMR (500 MHz, MeOD) 7.76 (1H, s), 7.45 (2H, d), 7.42 (2H, d), 7.30-7.29 (3H, m), 7.19-7.18 (2H, m), 3.47 (2H, q), 3.46 (2H, t), 3.39 (2H, br s), 3.32 (2H, m), 2.77-2.71 (2H, m), 2.60-2.54 (2H, m), 2.27-2.18 (1H, m), 1.99-1.90 (1H, m), 1.50 (3H, t).

Example 28

1-(4-(9-phenyl-5,6-dihydro-[1,2,4]triazolo[3,4-f][1,6]naphthyridin-8-yl)phenyl)cyclobutanamine

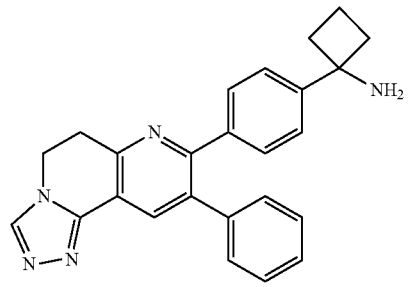 [SMILES: NC1(c2ccc(-c3nc4c(cc3-c3ccccc3)-c3nncn3CC4)cc2)CCC1]

Step 1: tert-butyl(1-(4-(5-hydrazono-3-phenyl-5,6,7,8-tetrahydro-1,6-naphthyridin-2-yl)phenyl)cyclobutyl)carbamate To a solution of tert-butyl(1-(4-(3-phenyl-5-thioxo-5,6,7,8-tetrahydro-1,6-naphthyridin-2-yl)phenyl)cyclobutyl)carbamate (127 mg, 0.26 mmol) in THF (2 mL) was added hydrazine.H$_2$O (63 μL, 1.31 mmol) and mercuric acetate (125 mg, 0.39 mmol) to give a black solution under nitrogen. The resulting mixture was stirred at room temperature for 2 h. After cooled down to room temperature, the mixture was filtered on celite (rinse with dichloromethane) and concentrated to dryness under reduced pressure. The resulting black yellow oil was used directly in the following step without any further purification. LCMS (Method A): $R_T$=4.77 min, M+H$^+$=484.

Step 2: tert-butyl(1-(4-(9-phenyl-5,6-dihydro-[1,2,4]triazolo[3,4-f][1,6]naphthyridin-8-yl)phenyl)cyclobutyl)carbamate A solution of tert-butyl(1-(4-(5-hydrazono-3-phenyl-5,6,7,8-tetrahydro-1,6-naphthyridin-2-yl)phenyl)cyclobutyl)carbamate (40 mg, 0.08 mmol) in triethyl orthoformate (1 mL) was heated at 150° C. for 1.5 h under microwave irradiation. The resulting reaction mixture was concentrated to dryness under reduced pressure and purified by preparative HPLC (method G, gradient 5 to 95% 0.1% FA/ACN in 0.1% FA/H$_2$O) to give the title compound (9 mg, 22%). $^1$H NMR (500 MHz, CDCl$_3$): 8.47 (1H, s), 8.29 (1H, s), 7.37 (2H, d), 7.31 (2H, d), 7.28-7.26 (3H, m), 7.23-7.21 (2H, m), 5.07 (1H, br s), 4.42 (2H, t), 3.50 (2H, t), 2.55-2.25 (4H, m), 2.10-2.02 (1H, m), 1.85-1.76 (1H, m), 1.45-1.20 (9H, br).

Step 3: 1-(4-(9-phenyl-5,6-dihydro-[1,2,4]triazolo[3,4-f][1,6]naphthyridin-8-yl)phenyl)cyclobutanamine Following the procedure for 2-(4-(1-aminocyclobutyl)phenyl)-3-phenyl-7,8-dihydroquinolin-5(6H)-one, tert-butyl (1-(4-(9-phenyl-5,6-dihydro-[1,2,4]triazolo[3,4-f][1,6]naphthyridin-8-yl)phenyl)cyclobutyl)carbamate (9 mg, 0.02 mmol) was reacted to afford the title compound (10 mg, quantitative). LCMS (Method A): $R_T$=3.53 min, M-NH$_2$=377. $^1$H NMR (500 MHz, MeOD) 8.70 (1H, s), 8.41 (1H, s), 7.52 (2H, d), 7.43 (2H, d), 7.33-7.31 (3H, m), 7.29-7.27 (2H, m), 4.57 (2H, t), 3.51 (2H, t), 2.79-2.73 (2H, m), 2.60-2.54 (2H, m), 2.27-2.20 (1H, m), 1.99-1.92 (1H, m).

Example 29

1-(4-(3-(1-methyl-1H-imidazol-4-yl)-9-phenyl-5,6-dihydro-[1,2,4]triazolo[3,4-f][1,6]naphthyridin-8-yl)phenyl)cyclobutanamine

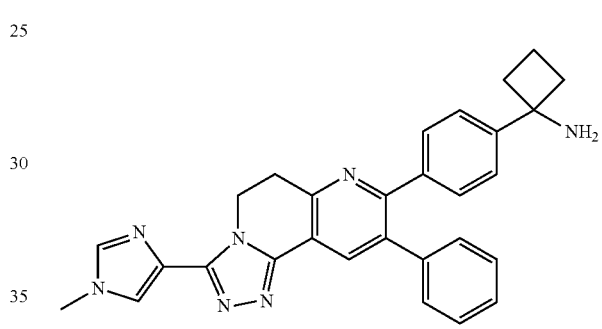

Step 1: tert-butyl(1-(4-(3-(1-methyl-1H-imidazol-4-yl)-9-phenyl-5,6-dihydro-[1,2,4]triazolo[3,4-f][1,6]naphthyridin-8-yl)phenyl)cyclobutyl)carbamate To a solution of tert-butyl(1-(4-(5-hydrazono-3-phenyl-5,6,7,8-tetrahydro-1,6-naphthyridin-2-yl)phenyl)cyclobutyl)carbamate (22 mg, 0.04 mmol) in dry DMF (1 mL) was added EDCI (11 mg, 0.06 mmol), HOBt.H$_2$O (8 mg, 0.06 mmol) and 1-methyl-1H-imidazole-4-carboxylic acid (8 mg, 0.06 mmol) under nitrogen. The reaction mixture was heated at 60° C. overnight. After cooled down to room temperature, the mixture was partitioned between saturated NaHCO$_3$ solution and ethyl acetate. The layers were separated and the organic phase washed with water and brine, dried over Na$_2$SO$_4$, filtered and concentrated to dryness under reduced pressure. The resulting residue was purified by preparative HPLC (method G, gradient 5 to 95% 0.1% FA/ACN in 0.1% FA/H$_2$O) to give the title compound (1 mg, 5%). $^1$H NMR (500 MHz, CDCl$_3$): 8.49 (1H, s), 7.74 (1H, s), 7.54 (1H, s), 7.38 (2H, d), 7.31 (2H, d), 7.28-7.23 (5H, m), 5.01 (1H, br s), 4.94 (2H, t), 3.81 (3H, s), 3.49 (2H, t), 2.60-2.30 (4H, m), 2.10-2.01 (1H, m), 1.85-1.76 (1H, m), 1.45-1.20 (9H, br).

Step 2: 1-(4-(3-(1-methyl-1H-imidazol-4-yl)-9-phenyl-5,6-dihydro-[1,2,4]triazolo[3,4-f][1,6]naphthyridin-8-yl)phenyl)cyclobutanamine Following the procedure for 2-(4-(1-aminocyclobutyl)phenyl)-3-phenyl-7,8-dihydroquinolin-5(6H)-one, tert-butyl (1-(4-(3-(1-methyl-1H-imidazol-4-yl)-9-phenyl-5,6-dihydro-[1,2,4]triazolo[3,4-f][1,6]naphthyridin-8-yl)phenyl)cyclobutyl)carbamate (9 mg, 0.02 mmol) was reacted to afford the title compound (10 mg, quantitative). LCMS (Method A): $R_T$=3.53 min, M-NH$_2$=377. $^1$H NMR (500 MHz, MeOD): 8.43 (1H, s), 7.99 (1H, br s), 7.91 (1H, br s), 7.52 (2H, d), 7.44 (2H, d), 7.33-7.27 (5H, m), 3.89 (3H, s), 3.54 (2H, t), 3.32 (2H, t), 2.79-2.73 (2H, m), 2.61-2.55 (2H, m), 2.27-2.20 (1H, m), 2.00-1.92 (1H, m).

Example 30

6-(4-(1-aminocyclobutyl)phenyl)-7-phenyl-1H-pyrido[2,3-b][1,4]oxazin-2(3H)-one

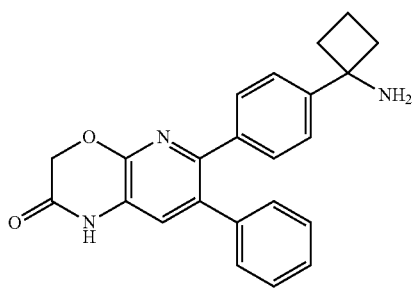

Step 1: tert-butyl(1-(4-(5-cyano-6-hydroxy-3-phenylpyridin-2-yl)phenyl)cyclobutyl)carbamate To a suspension of sodium hydride (3.58 g, 0.089 mol) in DMF (150 ml) at 0° C. was added a solution of 2-cyanoacetamide (3.48 g, 0.041 mol) and (E)-tert-butyl(1-(4-(3-(dimethylamino)-2-phenylacryloyl)phenyl)cyclobutyl)carbamate (15 g, 0.0357 mol) in methanol (5.5 ml) and DMF (150 ml). The resulting mixture was heated at 40° C. for 16 h. After cooled down to room temperature, the mixture was added to a solution of acetic (50 ml) in water (300 ml) slowly. The resulting precipitate was filtered and the filter cake was partitioned between water (250 ml) and dichloromethane (150 ml). The layers were separated and the aqueous phase extracted into dichloromethane (150 ml). The combined organic phases were washed with water (200 ml) and brine (150 ml), dried over Na$_2$SO$_4$, filtered and concentrated to dryness under reduced pressure to give the title compound as a yellow solid (14.6 g, 93%). LCMS (Method A): $R_T$=6.59 min, M+1=442. $^1$H NMR (500 MHz, CDCl$_3$): 7.89 (1H, s), 7.37-7.32 (2H, m), 7.22-7.16 (5H, m), 7.03-6.98 (2H, m), 2.50-2.37 (4H, m), 2.06-1.97 (1H, m), 1.82-1.77 (1H, m), 1.45-1.05 (9H, br).

Step 2: tert-butyl(1-(4-(5-carbamoyl-6-hydroxy-3-phenylpyridin-2-yl)phenyl)cyclobutyl)carbamate To a suspension of tert-butyl(1-(4-(5-cyano-6-hydroxy-3-phenylpyridin-2-yl)phenyl)cyclobutyl)carbamate (14.6 g, 3.58 g, 0.033 mol) in ethanol (112 ml) and water (112 ml) at room temperature was added sodium hydroxide solution (6M, 54.4 ml) and hydrogenperoxide (30%, 21.9 ml). The resulting mixture was heated at 50° C. for 16 h. After cooled down to 0° C., the mixture was added acetic acid to adjust pH=4. The resulting precipitate was filtered and the filter cake was dried to give the title compound as white solid (10.8 g, 72%). LCMS (Method A): $R_T$=5.88 min, M+1=460. $^1$H NMR (500 MHz, DMSO-d$_6$): 9.65 (1H, br), 8.10 (1H, s), 7.25-7.05 (7H, m), 6.98 (2H, m), 2.45-2.25 (4H, m), 2.0-1.95 (1H, m), 1.79-1.75 (1H, m), 1.3-1.0 (9H-1, br).

Step 3: tert-butyl(1-(4-(5-amino-6-hydroxy-3-phenylpyridin-2-1/1)phenyl)cyclobutyl)carbamate To a solution of bromine (5.99 g, 0.037 mol) in water (350 ml) was added a solution of sodium hydroxide (15.02 g, 0.37 mol) in water (350 ml). The resulting solution was stirred at 0° C. for 10 min. To this solution was added tert-butyl(1-(4-(5-carbamoyl-6-hydroxy-3-phenylpyridin-2-yl)phenyl)cyclobutyl)carbamate (10.8 g, 0.0235 mol). The resulting mixture was heated at 65° C. for 24 h. After cooled down to room temperature, the mixture was extracted with ethyl acetate (200 ml). The layers were separated and the aqueous phase extracted into ethyl acetate (2×200 ml). The combined organic phases were washed with water (400 ml) and brine (300 ml), dried over Na$_2$SO$_4$, filtered and concentrated to dryness under reduced pressure. The resulting residue was purified by Biotage silica gel chromatography (gradient 0 to 5% methanol in DCM) to give the title compound (1.8 g, 18%). LCMS (Method A): $R_T$=6.13 min, M+1=432. $^1$H NMR (500 MHz, CDCl$_3$): 7.45-6.9 (10H, m), 7.37 (2H, d), 5.0 (1H, br), 2.4-2.1 (4H, m), 2.09-1.95 (1H, m), 1.85-1.7 (1H, m), 1.4-1.0 (9H, br).

Step 4: tert-butyl(1-(4-(2-oxo-7-phenyl-2,3-dihydro-1H-pyrido[2,3-b][1,4]oxazin-6-yl)phenyl)cyclobutyl)carbamate To a solution of tert-butyl(1-(4-(5-amino-6-hydroxy-3-phenylpyridin-2-yl)phenyl)cyclobutyl)carbamate (1.8 g, 4.17 mmol), DIPEA (3.63 ml, 20 mmol) in DCM (100 ml) at 0° C. was added a solution of chloroacetyl chloride (0.465 ml) in DCM (20 ml). The resulting mixture was stirred at room temperature for 16 h. The reaction mixture was concentrated to dryness under reduced pressure. To the residue was added MIBK (120 ml) and saturated sodium bicarbonate (120 ml). The resulting mixture was heated at 115° C. for 16 h. After cooled down to room temperature, the MIBK was removed under reduced pressure. The residue was extracted with ethyl acetate (75 ml). The layers were separated and the aqueous phase extracted into ethyl acetate (2×50 ml). The combined organic phases were washed with water (150 ml) and brine (150 ml), dried over Na$_2$SO$_4$, filtered and concentrated to dryness under reduced pressure. The resulting residue was purified by Biotage silica gel chromatography (gradient 0 to 2% methanol in DCM) to give the title compound (0.82 g, 42%). LCMS (Method A): $R_T$=6.55 min, M+1=472. $^1$H NMR (500 MHz, CDCl$_3$): 7.3-7.0 (10H, m), 4.96 (1H, br), 4.82 (2H, s), 2.55-2.25 (4H, m), 2.1-1.9 (1H, m), 1.8-1.65 (1H, m), 1.35-1.1 (9H, br).

Step 5: 6-(4-(1-aminocyclobutyl)phenyl)-7-phenyl-1H-pyrido[2,3-b][1,4]oxazin-2(3H)-one Following the procedure for 2-(4-(1-aminocyclobutyl)phenyl)-3-phenyl-7,8-dihydroquinolin-5(6H)-one, tert-butyl (1-(4-(2-oxo-7-phenyl-2,3-dihydro-1H-pyrido[2,3-b][1,4]oxazin-6-yl)phenyl)cyclobutyl)carbamate (8 mg, 0.017 mmol) was reacted to afford the title compound (6 mg, 73%). LCMS (Method A): $R_T$=3.59 min, M+1=373. $^1$H NMR (500 MHz, MeOD): 7.40 (2H, d), 7.37 (2H, d), 7.33 (1H, s), 7.32-

7.28 (3H, m), 7.19-7.17 (2H, m), 4.93 (2H, s), 2.78-2.72 (2H, m), 2.60-2.54 (2H, m), 2.27-2.19 (1H, m), 2.00-1.91 (1H, m).

Example 31

6-(4-(1-aminocyclobutyl)phenyl)-1-methyl-7-phenyl-1H-pyrido[2,3-b][1,4]oxazin-2(3H)-one

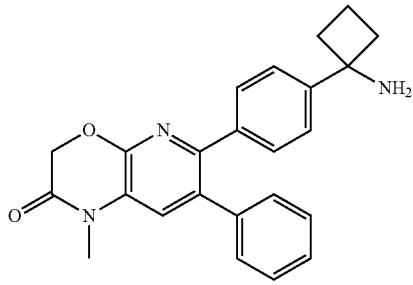 [SMILES: CN1C(=O)COc2nc(-c3ccc(C4(N)CCC4)cc3)c(-c3ccccc3)cc21]

Step 1: tert-butyl(1-(4-(1-methyl-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (60 mg, 0.13 mmol) in dry DMF (1 mL) was added sodium hydride (6 mg, 0.14 mmol) at 0° C. under nitrogen. After 1 h at 0° C., iodomethane (9 µL, 0.14 mmol) was added and the resulting mixture was stirred for an additional 10 min at 0° C. A saturated solution of NH₄Cl was added and the mixture was extracted with dichloromethane (3×) using a phase separator (Isolute® SPE). The combined organic phases were concentrated to dryness under reduced pressure. The resulting residue was purified by Biotage silica gel chromatography (gradient 0 to 30% EtOAc in cyclohexane) to give the title compound as a white solid (38 mg, 60%). $^1$H NMR (500 MHz, CDCl₃): 7.31-7.24 (8H, m), 7.21-7.19 (2H, m), 5.01 (1H, br s), 4.90 (2H, s), 3.39 (3H, s), 2.55-2.25 (4H, m), 2.09-2.01 (1H, m), 1.84-1.76 (1H, m), 1.44-1.15 (9H, br).

Step 2: 6-(4-(1-aminocyclobutyl)phenyl)-1-methyl-7-phenyl-1H-pyrido[2,3-b][1,4]oxazin-2(3H)-one Following the procedure for 2-(4-(1-aminocyclobutyl)phenyl)-3-phenyl-7,8-dihydroquinolin-5(6H)-one, tert-butyl (1-(4-(1-methyl-2-oxo-7-phenyl-2,3-dihydro-1H-pyrido[2,3-b][1,4]oxazin-6-yl)phenyl)cyclobutyl)carbamate (37 mg, 0.08 mmol) was reacted to afford the title compound (25 mg, 78%). LCMS (Method A): $R_T$=3.90 min, M+2H⁺=387. $^1$H NMR (500 MHz, MeOD): 7.54 (1H, S), 7.40 (2H, d), 7.37 (2H, d), 7.29-7.27 (3H, m), 7.23-7.21 (m, 2H), 4.95 (2H, s), 3.42 (3H, s), 2.77-2.71 (m, 2H), 2.59-2.53 (m, 2H), 2.26-2.17 (m, 1H), 1.99-1.90 (m, 1H).

Example 32

6-(4-(1-aminocyclobutyl)phenyl)-7-phenyl-1-(prop-2-yn-1-yl)-1H-pyrido[2,3-b][1,4]oxazin-2(3H)-one

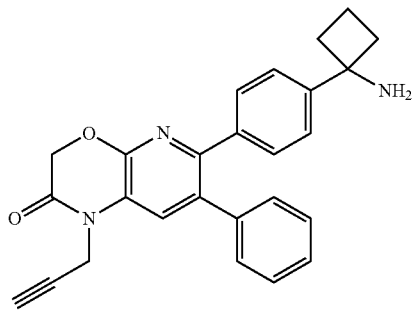 [SMILES: C#CCN1C(=O)COc2nc(-c3ccc(C4(N)CCC4)cc3)c(-c3ccccc3)cc21]

Step 1: tert-butyl(1-(4-(2-oxo-7-phenyl-1-(prop-2-yn-1-yl)-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (23 mg, 0.05 mmol) in dry DMF (1 mL) was added sodium hydride (3 mg, 0.05 mmol) at 0° C. under nitrogen. After 1 h at 0° C., propargyl bromide (16 µL, 0.15 mmol) was added and the resulting mixture was stirred for an additional 1 h at 0° C. A saturated solution of NH₄Cl was added and the mixture was extracted with dichloromethane (3×) using a phase separator (Isolute® SPE). The combined organic phases were concentrated to dryness under reduced pressure. The resulting residue was purified by silica gel chromatography (gradient 0 to 30% EtOAc in cyclohexane) to give the title compound (17 mg, 68%). $^1$H NMR (500 MHz, CDCl₃): 7.50 (1H, s), 7.31-7.24 (7H, m), 7.22-7.20 (2H,m), 5.01 (1H, br s), 4.92 (2H, s), 4.73 (2H, d), 2.55-2.25 (4H, m), 2.32 (1H, t), 2.09-2.01 (1H, m), 1.85-1.76 (1H, m), 1.44-1.15 (9H, br).

Step 2: 6-(4-(1-aminocyclobutyl)phenyl)-7-phenyl-1-(prop-2-yn-1-yl)-1H-pyrido[2,3-b][1,4]oxazin-2 (3H)-one Following the procedure for 2-(4-(1-aminocyclobutyl)phenyl)-3-phenyl-7,8-dihydroquinolin-5(6H)-one tert-butyl (1-(4-(2-oxo-7-phenyl-1-(prop-2-yn-1-yl)-2,3-dihydro-1H-pyrido[2,3-b][1,4]oxazin-6-yl)phenyl)cyclobutyl)carbamate (6 mg, 0.01 mmol) was reacted to afford the title compound (3 mg, 40%). LCMS (Method A): $R_T$=4.12 min, M+2H⁺=411. $^1$H NMR (500 MHz, MeOD): 7.69 (1H,S), 7.41 (2H, d), 7.38 (2H, d), 7.30-7.29 (3H, m), 7.23-7.21 (m, 2H), 4.98 (2H, s), 4.85 (2H, s), 2.80 (1H, t), 2.77-2.71 (m, 2H), 2.59-2.53 (m, 2H), 2.26-2.17 (m, 1H), 1.97-1.92 (m, 1H).

Example 33

2-(6-(4-(1-aminocyclobutyl)phenyl)-2-oxo-7-phenyl-2,3-dihydro-1H-pyrido[2,3-b][1,4]oxazin-1-yl)acetonitrile

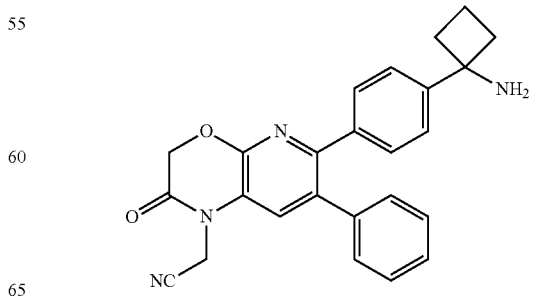

Step 1: tea-butyl (1-(4-(1-(cyanomethyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (14 mg, 0.03 mmol) in dry DMF (1 mL) was added sodium hydride (2 mg, 0.05 mmol) at 0° C. under nitrogen. After 1 h at 0° C., 2-bromoacetonitrile (7 μL, 0.09 mmol) was added and the resulting mixture was stirred for an additional 4 h at room temperature. Water was added and the mixture was extracted with ethyl acetate (3×). The combined organic phases were dried over $Na_2SO_4$, filtered and concentrated to dryness under reduced pressure. The resulting residue was purified by silica gel chromatography (gradient 0 to 40% EtOAc in hexane) to give the title compound (6 mg, 40%). $^1$H NMR (500 MHz, $CDCl_3$): 7.36 (1H, s), 7.30-7.26 (7H, m), 7.22-7.20 (2H, m), 5.01 (1H, br s), 4.96 (2H, s), 4.88 (2H, s), 2.55-2.25 (4H, m), 2.10-2.02 (1H, m), 1.85-1.76 (1H, m), 1.44-1.15 (9H, br).

Step 2: 2-(6-(4(1-aminocyclobutyl)phenyl)-2-oxo-7-phenyl-2,3-dihydro-1H-pyrido[2,3-b][1,4]oxazin-1-yl)acetonitrile Following the procedure for 2-(4-(1-aminocyclobutyl) phenyl)-3-phenyl-7,8-dihydroquinolin-5(6H)-one, tert-butyl (1-(4-(1-(cyanomethyl)-2-oxo-7-phenyl-2,3-dihydro-1H-pyrido[2,3-b][1,4]oxazin-6-yl)phenyl)cyclobutyl)carbamate (6 mg, 0.02 mmol) was reacted to afford the title compound (6 mg, quantitative). LCMS (Method A): $R_T$=3.95 min, M+2H$^+$=412. $^1$H NMR (500 MHz, MeOD): 7.69 (1H,S), 7.43 (2H, d), 7.38 (2H, d), 7.31-7.30 (3H, m), 7.25-7.24 (m, 2H), 5.13 (2H, s), 5.03 (2H, s), 2.77-2.72 (m, 2H), 2.59-2.53 (m, 2H), 2.26-2.17 (m, 1H), 1.99-1.92 (m, 1H).

Example 34

6-(4-(1-aminocyclobutyl)phenyl)-1-(2-(dimethylamino)ethyl)-7-phenyl-1H-pyrido[2,3-b][1,4]oxazin-2(3H)-one

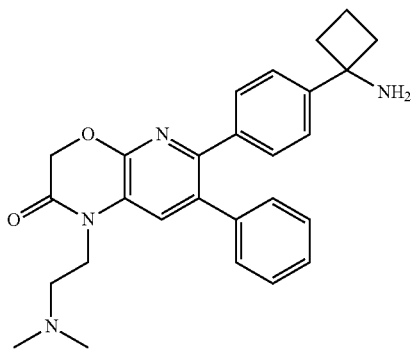 [SMILES: CN(C)CCN1C(=O)COc2nc(-c3ccc(C4(N)CCC4)cc3)c(-c3ccccc3)cc21]

Step 1: tert-butyl(1-(4-(1-(2-(dimethylamino)ethyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (19 mg, 0.04 mmol) in dry DMF (1 mL) was added sodium hydride (8 mg, 0.18 mmol) at 0° C. under nitrogen. After 1 h at 0° C., 2-chloro-N,N-dimethylethanamine.hydrochloride (18 mg, 0.12 mmol) was added and the resulting mixture was stirred for an additional 5 h at 40° C. Water was added and the mixture was extracted with ethyl acetate (3×). The combined organic phases were dried over $Na_2SO_4$, filtered and concentrated to dryness under reduced pressure. The resulting residue was purified by silica gel chromatography (gradient 0 to 3% MeOH in dichloromethane) to give the title compound (7 mg, 32%). $^1$H NMR (500 MHz, $CDCl_3$): 7.38 (1H, s), 7.31-7.24 (7H,m), 7.20-7.18 (2H,m), 5.01 (1H, br s), 4.88 (2H, s), 4.08 (2H,t), 2.60 (2H, t), 2.55-2.25 (4H, m), 2.33 (6H, s), 2.09-2.01 (1H, m), 1.85-1.76 (1H, m), 1.44-1.15 (9H, br).

Step 2: 6-(4-(1-aminocyclobutyl)phenyl)-1-(2-(dimethylamino)ethyl)-7-phenyl-1H-pyrido[2,3-b][1,4]oxazin-2(3H)-one Following the procedure 2-(4-(1-aminocyclobutyl)phenyl)-3-phenyl-7,8-dihydroquinolin-5(6H)-one, tert-butyl(1-(4-(1-(2-(dimethylamino)ethyl)-2-oxo-7-phenyl-2,3-dihydro-1H-pyrido[2,3-b][1,4]oxazin-6-yl)phenyl)cyclobutyl) carbamate (7 mg, 0.01 mmol) was reacted to afford the title compound (7 mg, quantitative). LCMS (Method A): $R_T$=2.92 min, M+H$^+$=443. $^1$H NMR (500 MHz, MeOD): 7.63 (1H, S), 7.41 (2H, d), 7.38 (2H, d), 7.31-7.29 (3H, m), 7.25-7.23 (m, 2H), 5.00 (2H, s), 4.45 (2H, t), 3.48 (2H, t), 3.02 (6H, s), 2.77-2.72 (m, 2H), 2.59-2.53 (m, 2H), 2.25-2.19 (m, 1H), 1.99-1.92 (m, 1H).

Example 35

2-(6-(4-(1-aminocyclobutyl)phenyl)-2-oxo-7-phenyl-2,3-dihydro-1H-pyrido[2,3-b][1,4]oxazin-1-yl)acetamide

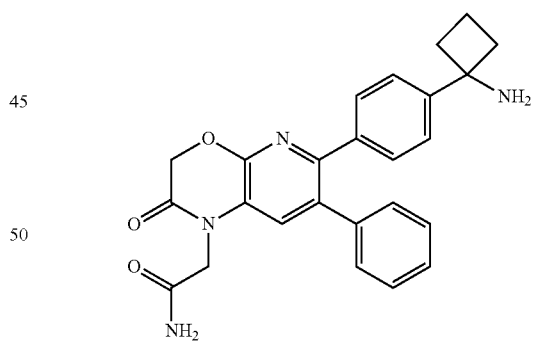

Step 1: tert-butyl(1-(4-(1-(2-amino-2-oxoethyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (19 mg, 0.04 mmol) in dry DMF (1 mL) was added potassium carbonate (12 mg, 0.08 mmol) and 2-chloroacetamide (12 mg, 0.12 mmol) at room temperature under nitrogen. The reaction mixture was stirred overnight at room temperature and concentrated to dryness under reduced pressure.

The resulting residue was purified by silica gel chromatography (gradient 0 to 80% AcOEt in hexane) to give the title compound (14 mg, 67%). $^1$H NMR (500 MHz, CDCl$_3$): 7.32 (1H, s), 7.28-7.23 (7H,m), 7.16-7.14 (2H,m), 6.22 (1H, br s), 5.65 (1H, br s), 5.09 (1H, br s), 4.94 (2H, s), 4.52 (2H,s), 2.55-2.25 (4H, m), 2.09-2.01 (1H, m), 1.85-1.76 (1H, m), 1.44-1.15 (9H, br).

Step 2: 2-(6-(4-(1-aminocyclobutyl)phenyl)-2-oxo-7-phenyl-2,3-dihydro-1H-pyrido[2,3-b][1,4]oxazin-1-yl)acetamide Following the procedure for 2-(4-(1-aminocyclobutyl)phenyl)-3-phenyl-7,8-dihydroquinolin-5(6H)-one, tert-butyl (1-(4-(1-(2-amino-2-oxoethyl)-2-oxo-7-phenyl-2,3-dihydro-1H-pyrido[2,3-b][1,4]oxazin-6-yl)phenyl)cyclobutyl)carbamate (10 mg, 0.02 mmol) was reacted to afford the title compound (10 mg, quantitative). LCMS (Method A): R$_T$=3.43 min, M-NH$_2$=412. $^1$H NMR (500 MHz, MeOD): 7.39 (2H, d), 7.36 (2H, d), 7.34 (1H,S), 7.28-7.26 (3H, m), 7.18-7.17 (m, 2H), 5.01 (2H, s), 4.72 (2H, s), 2.76-2.70 (m, 2H), 2.57-2.51 (m, 2H), 2.25-2.16 (m, 1H), 1.98-1.89 (m, 1H).

Example 36

6-(4-(1-aminocyclobutyl)phenyl)-1-(2-oxopropyl)-7-phenyl-1H-pyrido[2,3-b][1,4]oxazin-2(3H)-one

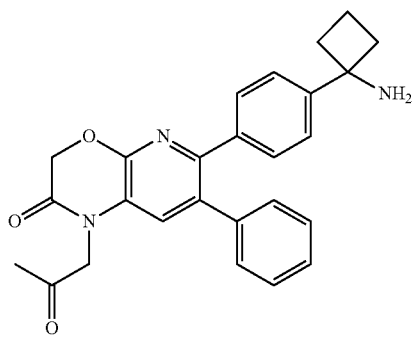 [SMILES: CC(=O)CN1C(=O)COc2nc(-c3ccc(C4(N)CCC4)cc3)c(-c3ccccc3)cc21]

Step 1: tert-butyl(1-(4-(1-(2-oxo-1-(2-oxopropyl)-7-phenyl-2,3-dihydro-1H-pyrido[2,3-b][1,4]oxazin-6-yl)phenyl)cyclobutyl)carbamate To a solution of tert-butyl(1-(4-(2-oxo-1-(2-oxopropyl)-7-phenyl-2,3-dihydro-1H-pyrido[2,3-b][1,4]oxazin-6-yl)phenyl)cyclobutyl)carbamate (60 mg, 0.13 mmol) in dry DMF (2.5 mL) was added sodium hydride (5 mg, 0.14 mmol) at 0° C. under nitrogen. After 1 h at 0° C., chloroacetone (11 □L, 0.14 mmol) was added and the resulting mixture was stirred for two hours at 0° C. A saturated solution of NH$_4$Cl was added while stirring, keeping the temperature below 10° C. The resulting mixture was extracted with dichloromethane (3×) using a phase separator (Isolute® SPE). The combined organic phases were concentrated to dryness under reduced pressure. The resulting residue was purified by Biotage chromatography (silica, hexane:ethyl acetate, gradient elution from 100:0 to 55:45) to give the desired product as a white solid (41 mg, 60% yield). $^1$H NMR (500 MHz, CDCl$_3$): 7.12-7.28 (9H, m), 6.82 (1H,S), 4.95 (2H, s), 4.54 (2H, s), 2.36-2.52 (4H, m), 2.23 (3H, s), 1.98-2.12 (1H, m), 1.69-1.75 (1H, m), 1.47 (9H, br s). $^1$H NMR (Method A): R$_T$=6.87 min, M+H$^+$=528.

Step 2: 6-(4-(1-aminocyclobutyl)phenyl)-1-(2-oxopropyl)-7-phenyl-1H-pyrido[2,3-b][1,4]oxazin-2(3H)-one Tert-butyl (1-(4-(1-(2-oxo-1-(2-oxopropyl)-7-phenyl-2,3-dihydro-1H-pyrido[2,3-b][1,4]oxazin-6-yl)phenyl)cyclobutyl)carbamate (5 mg, 0.009 mmol) was dissolved in TFA (0.5 mL) and stirred for 30 seconds. The solution was immediately concentrated to dryness under reduced pressure. The residue was dissolved in diethyl ether (~1 mL) and concentrated to dryness under reduced pressure three times. The residue was then slurried in diethyl ether (0.5 mL) and after settling the supernatant solvent removed by pipette. This was repeated three times. The remaining solvent was removed under reduced pressure and dried to give the desired product as an off-white solid (2.2 mg, 46% yield). $^1$H NMR (500 MHz, CH$_3$OD) 7.15-7.50 (m, 10H), 5.01 (s, 2H), 4.98 (s, 2H), 2.71-2.81 (m, 2H), 2.53-2.63 (m, 2H), 2.30 (s, 3H), 2.18-2.27 (br m, 1H), 1.92-2.03 (br m, 1H). LCMS (Method A): R$_T$=3.03 min, M+H$^+$=428.

Example 37

1-(4-(7-phenyl-2,3-dihydro-1H-pyrido[2,3-b][1,4]oxazin-6-yl)phenyl)cyclobutanamine

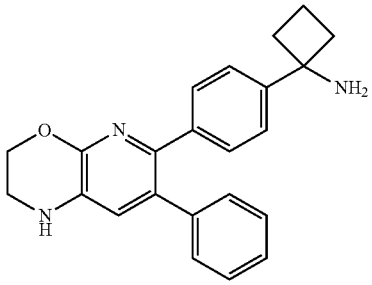 [SMILES: NC1(c2ccc(-c3nc4c(cc3-c3ccccc3)NCCO4)cc2)CCC1]

Step 1: tert-butyl(1-(4-(7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (143 mg, 0.42 mmol) in dry THF (4 mL) was added boron trifluoride diethyl etherate (91 μL, 0.73 mmol) and sodium borohydride (27 mg, 0.73 mmol) at 0° C. under nitrogen. The resulting mixture was stirred for 4 h at 0° C. AcOEt (5 mL) and a saturated solution of NaHCO$_3$ (10 mL) were added. The aqueous phase was extracted with dichloromethane (3×) using a phase separator (Isolute® SPE). The combined organic phases were concentrated to dryness under reduced pressure. The resulting residue was purified by Biotage silica gel chromatography (gradient 0 to 2% MeOH in DCM) to give the title compound as a white solid (66 mg, 48%). $^1$H NMR (500 MHz, CDCl$_3$): 7.21-7.26 (7H, m), 7.14-7.12 (2H,m), 6.97 (1H, s), 4.48 (2H, t), 3.48 (2H, br s), 2.55-2.25 (4H, m), 2.06-1.98 (1H, m), 1.82-1.73 (1H, m), 1.44-1.15 (9H, br).

Step 2: 1-(4-(7-phenyl-2,3-dihydro-1H-pyrido[2,3-b][1,4]oxazin-6-yl)phenyl)cyclobutanamine Following the procedure for 2-(4-(1-aminocyclobutyl)phenyl)-3-phenyl-7,8-dihydroquinolin-5(6H)-one, tert-butyl (1-(4-(7-phenyl-2,3-dihydro-1H-pyrido[2,3-b][1,4]oxazin-6-yl)phenyl)cyclobutyl)carbamate (15 mg, 0.03 mmol) was reacted to afford the title compound (15 mg, quantitative). LCMS (Method A): $R_T$=3.80 min, M-NH$_2$=341. $^1$H NMR (500 MHz, MeOD): 7.31 (4H, s), 7.22-7.21 (3H, m), 7.12-7.11 (2H, m), 7.01 (1H, s), 4.45 (2H, t), 3.45 (2H, t), 2.75-2.70 (m, 2H), 2.56-2.50 (m, 2H), 2.24-2.15 (m, 1H), 1.97-1.88 (m, 1H).

Example 38

7-(4-(1-aminocyclobutyl)phenyl)-8-phenyl-2,4-dihydro-1H-pyrido[2,3-b][1,2,4]triazolo[4,3-d][1,4]oxazin-1-one

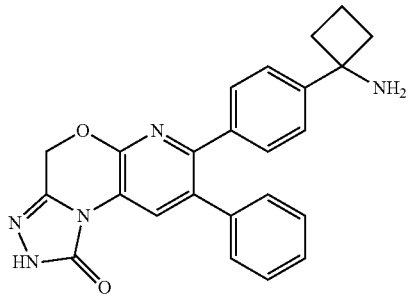 [SMILES: NC1(c2ccc(-c3nc4c(cc3-c3ccccc3)-n3c(n[nH]c3=O)CO4)cc2)CCC1]

Step 1: tert-butyl(1-(4-(7-phenyl-2-thioxo-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (211 mg, 0.45 mmol) in toluene (15 mL) was added lawesson's reagent (181 mg, 0.45 mmol) under nitrogen. The resulting mixture was heated under reflux for 2 h. After cooled down to room temperature, the mixture was concentrated to dryness under reduced pressure. The resulting residue was purified by Biotage silica gel chromatography (gradient 0 to 5% MeOH in dichloromethane) to give the title compound as a yellow solid (124 mg, 57%). $^1$H NMR (500 MHz, CDCl$_3$): 9.47 (1H, br s), 7.30-7.24 (7H, m), 7.18 (1H, s), 7.16-7.14 (2H, m), 5.17 (2H, s), 5.04 (1H, br s), 2.55-2.25 (4H, m), 2.10-2.01 (1H, m), 1.85-1.76 (1H, m), 1.44-1.15 (9H, br).

Step 2: Ethyl 2-(6-(4-(1-(tert-butoxycarbonylamino)cyclobutyl)phenyl)-7-phenyl-1H-pyrido[2,3-b][1,4]oxazin-2(3H)-ylidene)hydrazinecarboxylate To a solution of tert-butyl(1-(4-(7-phenyl-2-thioxo-2,3-dihydro-1H-pyrido[2,3-b][1,4]oxazin-6-yl)phenyl)cyclobutyl)carbamate (20 mg, 0.04 mmol) in dry THF (1 mL) was added ethyl hydrazinecarboxylate (21 mg, 0.20 mmol) and mercuric acetate (21 mg, 0.06 mmol) under nitrogen. The reaction mixture was stirred for 2 h at room temperature, filtered on celite and concentrated to dryness under reduced pressure to give the title compound which was used without purification in the next step.

Step 3: tert-butyl(1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate A solution of Ethyl 2-(6-(4-(1-(tert-butoxycarbonylamino)cyclobutyl)phenyl)-7-phenyl-1H-pyrido[2,3-b][1,4]oxazin-2(3H)-ylidene)hydrazinecarboxylate (24 mg, 0.04 mmol) in dry DMF (1 mL) was heated at 200° C. for 10 min under microwave irradiation. The reaction mixture was diluted with dichloromethane, filtered on celite and concentrated to dryness under reduced pressure. The resulting residue was purified by preparative HPLC (method G, gradient 5 to 95% 0.1% FA/ACN in 0.1% FA/H$_2$O) to give the title compound (7 mg, 32%). $^1$H NMR (500 MHz, CDCl$_3$): 9.18 (1H, br s), 8.54 (1H, s), 7.32 (2H, d), 7.28-7.26 (5H,m), 7.22-7.20 (2H,m), 5.32 (2H, s), 5.07 (1H, br s), 2.55-2.25 (4H, m), 2.10-2.03 (1H, m), 1.86-1.78 (1H, m), 1.44-1.15 (9H, br).

Step 4: 7-(4-(1-aminocyclobutyl)phenyl)-8-phenyl-2,4-dihydro-1H-pyrido[2,3-b][1,2,4]triazolo[4,3-d][1,4]oxazin-1-one Following the procedure for 2-(4-(1-aminocyclobutyl)phenyl)-3-phenyl-7,8-dihydroquinolin-5(6H)-one, tert-butyl (1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate (7 mg, 0.01 mmol) was reacted to afford the title compound (7 mg, quantitative). LCMS (Method A): $R_T$=3.54 min, M+2H$^+$=413. $^1$H NMR (500 MHz, MeOD): 8.56 (1H, s), 7.44 (2H, d), 7.38 (2H, d), 7.30-7.29 (3H, m), 7.23-7.21 (m, 2H), 5.41 (2H, s), 2.78-2.72 (m, 2H), 2.59-2.53 (m, 2H), 2.25-2.18 (m, 1H), 1.99-1.91 (m, 1H).

Example 39

1-(4-(8-phenyl-4H-pyrido[2,3-b][1,2,4]triazolo[4,3-d][1,4]oxazin-7-yl)phenyl)cyclobutanamine

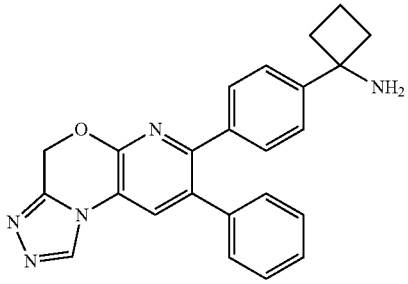 [SMILES: NC1(c2ccc(-c3nc4c(cc3-c3ccccc3)-n3cnnc3CO4)cc2)CCC1]

Step 1: tert-butyl(1-(4-(2-hydrazono-7-phenyl-2,3-dihydro-1H-pyrido[2,3-b][1,4]oxazin-6-yl)phenyl)cyclobutyl)carbamate To a solution of tert-butyl(1-(4-(7-phenyl-2-thioxo-2,3-dihydro-1H-pyrido[2,3-b][1,4]oxazin-6-yl)phenyl)cyclobutyl)carbamate (20 mg, 0.04 mmol) in THF (2 mL) was added hydrazine.H$_2$O (10 μL, 0.20 mmol) under nitrogen. The resulting mixture was stirred at room temperature for 1.5 h.

After cooled down to room temperature, the mixture was concentrated to dryness under reduced pressure to give the title compound which was used directly in the next step without any purification.

Step 2: tert-butyl(1-(4-(8-phenyl-4H-pyrido[2,3-b][1,2,4]triazolo[4,3-d][1,4]oxazin-7-yl)phenyl)cyclobutyl)carbamate A solution of tert-butyl(1-(4-(2-hydrazono-7-phenyl-2,3-dihydro-1H-pyrido[2,3-b][1,4]oxazin-6-yl)phenyl)cyclobutyl)carbamate (20 mg, 0.04 mmol) in triethyl orthoformate (1 mL) was heated at 150° C. for 10 min under microwave irradiation. The reaction mixture was concentrated to dryness under reduced pressure. The resulting residue was purified by silica gel chromatography (gradient 0 to 2% MeOH in dichloromethane) to give the title compound (3 mg, 15%). $^1$H NMR (500 MHz, CDCl$_3$): 8.68 (1H, s), 7.75 (1H, s), 7.34-7.26 (7H, m), 7.22-7.20 (2H,m), 5.70 (2H, s), 5.02 (1H, br s), 2.55-2.25 (4H, m), 2.10-2.03 (1H, m), 1.86-1.78 (1H, m), 1.44-1.15 (9H, br).

Step 3: 1-(4-(8-phenyl-4H-pyrido[2,3-b][1,2,4]triazolo[4,3-d][1,4]oxazin-7-yl)phenyl)cyclobutanamine Following the procedure 2-(4-(1-aminocyclobutyl)phenyl)-3-phenyl-7,8-dihydroquinolin-5(6H)-one tert-butyl(1-(4-(8-phenyl-4H-pyrido[2,3-b][1,2,4]triazolo[4,3-d][1,4]oxazin-7-yl)phenyl)cyclobutyl)carbamate (2 mg, 0.004 mmol) was reacted to afford the title compound (2 mg, quantitative). LCMS (Method A): R$_T$=3.60 min, M+2H$^+$=397. $^1$H NMR (500 MHz, MeOD): 9.31 (1H, s), 8.30 (1H, s), 7.44 (2H, d), 7.38 (2H, d), 7.32-7.31 (3H, m), 7.27-7.25 (m, 2H), 5.77 (2H, s), 2.78-2.72 (m, 2H), 2.59-2.53 (m, 2H), 2.25-2.18 (m, 1H), 1.99-1.91 (m, 1H).

Example 40

1-(4-(1-methyl-7-phenyl-2,3-dihydro-1H-pyrido[2,3-b][1,4]oxazin-6-yl)phenyl)cyclobutanamine

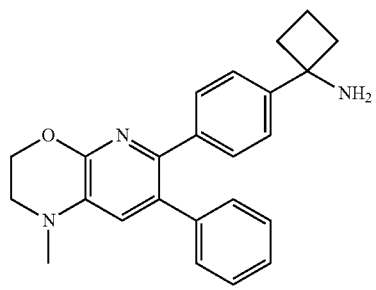 [SMILES: CN1CCOc2nc(-c3ccc(C4(N)CCC4)cc3)c(-c3ccccc3)cc21]

Step 1: tert-butyl(1-(4-(1-methyl-7-phenyl-2,3-dihydro-1H-pyrido[2,3-b][1,4]oxazin-6-yl)phenyl)cyclobutyl)carbamate To a solution of tert-butyl(1-(4-(7-phenyl-2,3-dihydro-1H-pyrido[2,3-b][1,4]oxazin-6-yl)phenyl)cyclobutyl)carbamate (20 mg, 0.04 mmol) in dry DMF (1 ml) at 0° C. was added sodium hydride (2 mg, 0.05 mmol) and methyl iodide (5 μl, 0.05 mmol) under nitrogen. The resulting mixture was stirred for 30 minutes at 0° C. A saturated solution of NH$_4$Cl was added and the mixture was extracted with DCM (3×10 ml). The combined organic phases were dried over Na$_2$SO$_4$ and concentrated to dryness under reduced pressure. The resulting residue was purified by Biotage silica gel chromatography (gradient 0 to 20% EtOAc in cyclohexane) to give the title compound (8 mg, 44%). $^1$H NMR (500 MHz, CDCl$_3$): 7.39-7.19 (9H, m), 6.85 (1H, s), 4.51-4.50 (2H, d), 3.45-3.43 (2H, d), 2.80-2.70 (2H, m), 2.61-2.51 (4H, m), 2.01-1.88 (1H, m), 2.00 (3H, s), 1.40-1.10 (9H, br).

Step 2: 1-(4-(1-methyl-7-phenyl-2,3-dihydro-1H-pyrido[2,3-b][1,4]oxazin-6-yl)phenyl)cyclobutanamine Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, 2-((1r,3r)-1-(4-(1-ethyl-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione (21 mg, 0.04 mmol) was reacted to afford the title compound (3 mg, quantitative). LCMS (Method A): R$_T$=4.21 min, M+1=355. $^1$H NMR (500 MHz, MeOD): 7.36-7.32 (4H, m), 7.29-7.20 (3H, m), 7.19-7.15 (2H, m), 7.00 (1H, s), 4.45 (2H, d), 3.45 (2H, d), 2.88 (3H, s), 2.75-2.70 (2H, m), 2.61-2.51 (2H, m), 2.28-2.17 (1H, m), 2.01-1.88 (1H, m).

Example 41

1-(6-(4-(1-aminocyclobutyl)phenyl)-7-phenyl-2,3-dihydro-1H-pyrido[2,3-b][1,4]oxazin-1-yl)ethanone

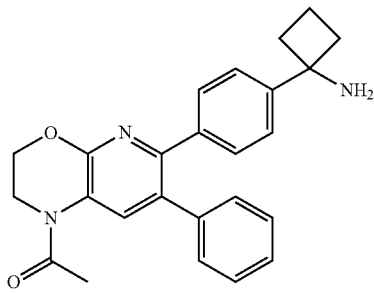 [SMILES: CC(=O)N1CCOc2nc(-c3ccc(C4(N)CCC4)cc3)c(-c3ccccc3)cc21]

Step 1: tert-butyl(1-(4-(1-acetyl-7-phenyl-2,3-dihydro-1H-pyrido[2,3-b][1,4]oxazin-6-yl)phenyl)cyclobutyl)carbamate To a solution of tert-butyl(1-(4-(7-phenyl-2,3-dihydro-1H-pyrido[2,3-b][1,4]oxazin-6-yl)phenyl)cyclobutyl)carbamate (22 mg, 0.05 mmol) in dry DCM (1 ml) was added triethyl amine (10 μl, 0.07 mmol) and acetyl chloride (5 μl, 0.07 mmol) under nitrogen. The resulting mixture was stirred for 1 h at room temperature. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 80% EtOAc in cyclohexane) to give the title compound (20 mg, 83%). $^1$H NMR (500 MHz, CDCl$_3$): 8.50 (1H, br s), 7.25 (2H, d), 7.19-7.17 (5H, m), 7.11-7.10 (2H,m), 4.95 (1H, s), 4.43 (2H, t), 3.94 (2H, br s), 2.55-2.25 (7H, m), 2.06-1.98 (1H, m), 1.82-1.73 (1H, m), 1.44-1.15 (9H, br).

Step 2: 1-(6-(4-(1-aminocyclobutyl)phenyl)-7-phenyl-2,3-dihydro-1H-pyrido[2,3-b][1,4]oxazin-1-yl)ethanone Tert-butyl (1-(4-(1-acetyl-7-phenyl-2,3-dihydro-1H-pyrido[2,3-b][1,4]oxazin-6-yl)phenyl)cyclobutyl)carbamate (20 mg, 0.04 mmol) was dissolved in 2M HCl in Et₂O (1 ml). The resulting mixture was stirred overnight at room temperature and evaporated under reduced pressure. The deprotected compound was taken back twice into diethyl ether. The remaining solvent was removed under reduced pressure and dried to afford the title compound (21 mg, quantitative). LCMS (Method A): R$_T$=3.87 min, M-16=383. ¹H NMR (500 MHz, MeOD): 8.70 (1H, br s), 7.44-7.43 (4H,m), 7.30-7.28 (3H, m), 7.21-7.19 (2H, m), 4.63 (2H, t), 4.11 (2H, t), 2.75-2.70 (2H, m), 2.56-2.50 (2H, m), 2.42 (3H, s), 2.24-2.15 (1H, m), 1.97-1.88 (1H, m).

Example 42

1-((1H-imidazol-2-yl)methyl)-6-(4-(1-aminocyclobutyl)phenyl)-7-phenyl-1H-pyrido[2,3-b][1,4]oxazin-2(3H)-one

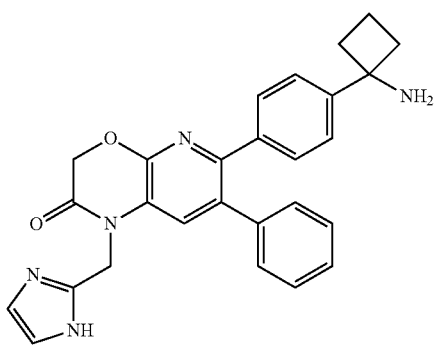 [SMILES: NC1(c2ccc(-c3nc4c(cc3-c3ccccc3)N(Cc3ncc[nH]3)C(=O)CO4)cc2)CCC1]

Step 1: tert-butyl(1-(4-(1-((1H-imidazol-2-yl)methyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (26 mg, 0.05 mmol) in dry DMF (1 ml) was added sodium hydride (5 mg, 0.13 mmol) at 0° C. under nitrogen. After 1 hour at 0° C., 2-(chloromethyl)-1H-imidazole.HCl (10 mg, 0.07 mmol) was added and the resulting mixture was stirred for an additional 1 h at room temperature. A saturated solution of NaHCO₃ was added and the mixture was extracted with dichloromethane (3×10 ml) using a phase separator (Isolute® SPE). The combined organic phases were concentrated to dryness under reduced pressure. The resulting residue was purified by preparative HPLC (method G, gradient 5 to 95% 0.1% FA/ACN in 0.1% FA/H₂O) to give the title compound (5 mg, 17%). ¹H NMR (500 MHz, CDCl₃): 7.83 (1H, s), 7.22-7.15 (7H,m), 7.14-7.13 (2H,m), 6.94 (2H,s), 6.22 (1H, br s), 5.14 (2H, s), 4.98 (1H, br s), 4.83 (2H, s), 2.52-2.20 (4H, m), 2.00-1.95 (1H, m), 1.75-1.70 (1H, m), 1.44-1.15 (9H, br).

Step 2: 1-((1H-imidazol-2-yl)methyl)-6-(4-(1-aminocyclobutyl)phenyl)-7-phenyl-1H-pyrido[2,3-b][1,4]oxazin-2(3H)-one Tert-butyl (1-(4-(1-((1H-imidazol-2-yl)methyl)-2-oxo-7-phenyl-2,3-dihydro-1H-pyrido[2,3-b][1,4]oxazin-6-yl)phenyl)cyclobutyl)carbamate (5 mg, 0.001 mmol) was dissolved in TFA (1 ml). The resulting mixture was stirred for 30 seconds at room temperature and evaporated under reduced pressure. The deprotected compound was taken back twice into diethyl ether and the solid formed was washed twice with DCM. The remaining solvent was removed under reduced pressure and dried to afford the title compound (5 mg, quantitative). LCMS (Method A): R$_T$=2.80 min, M-NH₂=435. ¹H NMR (500 MHz, MeOD): 7.44 (1H, s), 7.41 (2H, s), 7.31-7.26 (4H,m), 7.18-7.16 (3H,m), 7.06-7.05 (2H, m), 5.44 (2H, s), 4.97 (2H, s), 2.66-2.60 (2H, m), 2.49-2.43 (2H, m), 2.14-2.10 (1H, m), 1.89-1.82 (1H, m).

Example 43

2-(6-(4-(1-aminocyclobutyl)phenyl)-7-phenyl-2,3-dihydro-1H-pyrido[2,3-b][1,4]oxazin-1-yl)acetonitrile Example 44

2-(6-(4-(1-aminocyclobutyl)phenyl)-7-phenyl-2,3-dihydro-1H-pyrido[2,3-b][1,4]oxazin-1-yl)acetamide

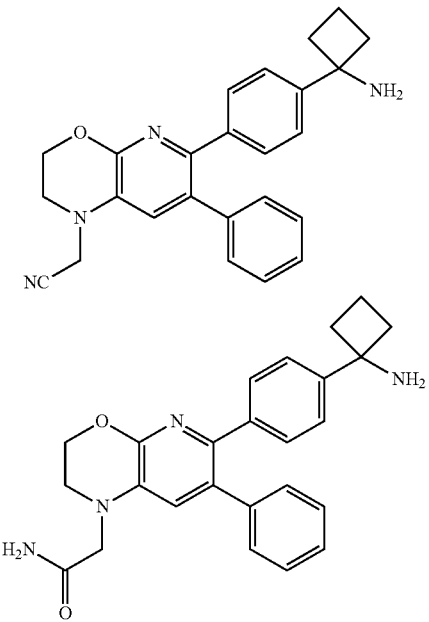

Step 1: tea-butyl (1-(4-(1-(cyanomethyl)-7-phenyl-2,3-dihydro-1H-pyrido[2,3-b][1,4]oxazin-6-yl)phenyl)cyclobutyl)carbamate To a solution of tert-butyl(1-(4-(7-phenyl-2,3-dihydro-1H-pyrido[2,3-b][1,4]oxazin-6-yl)phenyl)cyclobutyl)carbamate (24 mg, 0.05 mmol) in dry DMF (1 ml) was added potassium carbonate (93 mg, 1.57 mmol) and bromoacetonitrile (110 μl, 1.57 mmol) under nitrogen. The resulting mixture was stirred for 4 hours at 80 C. A saturated solution of NaHCO₃ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 60% EtOAc in cyclohexane) to give the title compound (5 mg, 19%). $^1$H NMR (500 MHz, CDCl$_3$): 7.22-7.11 (9H, m), 6.93 (1H, s), 4.92 (1H, s), 4.51-4.49 (2H, m), 4.15 (2H, s), 3.39-3.37 (2H, m), 2.55-2.25 (4H, m), 1.99-1.94 (1H, m), 1.75-1.63 (1H, m), 1.44-1.15 (9H, br).

Step 2: 2-(6-(4-(1-aminocyclobutyl)phenyl)-7-phenyl-2,3-dihydro-1H-pyrido[2,3-b][1,4]oxazin-1-yl)acetonitrile 2-(6-(4-(1-aminocyclobutyl)phenyl)-7-phenyl-2,3-dihydro-1H-pyrido[2,3-b][1,4]oxazin-1-yl)acetamide Following the procedure for 1-(6-(4-(1-aminocyclobutyl)phenyl)-7-phenyl-2,3-dihydro-1H-pyrido[2,3-b][1,4]oxazin-1-yl)ethanone, 1-((1H-imidazol-2-yl)ethyl)-6-(4-(1-aminocyclobutyl)phenyl)-7-phenyl-1H-pyrido[2,3-b][1,4]oxazin-2(3H)-one, tert-butyl(1-(4-(1-(cyanomethyl)-7-phenyl-2,3-dihydro-1H-pyrido[2,3-b][1,4]oxazin-6-yl)phenyl)cyclobutyl)carbamate (5 mg, 0.01 mmol) was reacted to afford the two title compounds (1 mg, 25% and 2 mg, 41%). LCMS: R$_T$=3.99 min, M-16=380. $^1$H NMR (500 MHz, MeOD): 7.20-7.13 (8H, m), 7.09-7.07 (2H, m), 4.46 (2H, t), 3.54 (2H, s), 3.22 (2H, t), 2.46-2.40 (2H, m), 2.17-2.11 (2H, m), 1.97-1.94 (1H, m), 1.66-1.62 (1H, m). LCMS (Method A): R$_T$=3.99 min, M-16=398. $^1$H NMR (500 MHz, D$_2$O): 8.39 (2H, s), 7.27-7.22 (7H, m), 7.11-7.09 (2H, m), 6.89 (1H, s), 4.78 (2H, s), 4.48 (2H, t), 4.00 (2H, s), 3.50 (2H, t), 2.65-2.60 (2H, m), 2.53-2.47 (2H, m), 2.09-2.05 (1H, m), 1.86-1.79 (1H, m).

Example 45

6-(4-(1-aminocyclobutyl)phenyl)-7-phenyl-1-(pyridin-4-ylmethyl)-1H-pyrido[2,3-b][1,4]oxazin-2(3H)-one

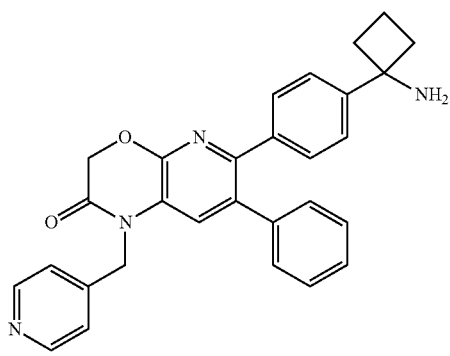 [SMILES: NC1(c2ccc(-c3nc4c(cc3-c3ccccc3)N(Cc3ccncc3)C(=O)CO4)cc2)CCC1]

Step 1: tert-butyl(1-(4-(2-oxo-7-phenyl-1-(pyridin-4-ylmethyl)-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (35 mg, 0.07 mmol) in dry DMF (1 ml) was added sodium hydride (7 mg, 0.18 mmol) and 4-(bromomethyl)pyridine.HBr (23 mg, 0.09 mmol) under nitrogen. The resulting mixture was stirred for 1 hour at room temperature. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 80% EtOAc in cyclohexane) to give the title compound (21 mg, 50%). $^1$H NMR (500 MHz, CDCl$_3$): 8.54 (2H,s), 7.19-7.12 (9H,m), 6.97 (1H,S), 6.93-6.91 (2H,m), 5.11 (2H, s), 4.98 (1H, br s), 4.95 (2H, s), 2.52-2.20 (4H, m), 2.00-1.95 (1H, m), 1.75-1.70 (1H, m), 1.44-1.15 (9H, br).

Step 2: 6-(4-(1-aminocyclobutyl)phenyl)-7-phenyl-1-(pyridin-4-ylmethyl)-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-7-phenyl-1-(pyridin-4-ylmethyl)-2,3-dihydro-1H-pyrido[2,3-b][1,4]oxazin-6-yl)phenyl)cyclobutyl)carbamate (21 mg, 0.04 mmol) was reacted to afford the title compound (26 mg, quantitative). LCMS (Method A): R$_T$=3.25 min, M+1=464. $^1$H NMR (500 MHz, MeOD): 8.57 (2H, s), 7.67 (2H, s), 7.28-7.24 (4H, m), 7.23 (1H, s), 7.14-7.10 (3H, m), 6.96-6.94 (2H, m), 5.37 (2H, s), 5.03 (2H, s), 2.66-2.60 (2H, m), 2.49-2.43 (2H, m), 2.14-2.10 (1H, m), 1.89-1.82 (1H, m).

Example 46

6-(4-(1-aminocyclobutyl)phenyl)-7-phenyl-1-(pyridin-3-ylmethyl)-1H-pyrido[2,3-b][1,4]oxazin-2(3H)-one

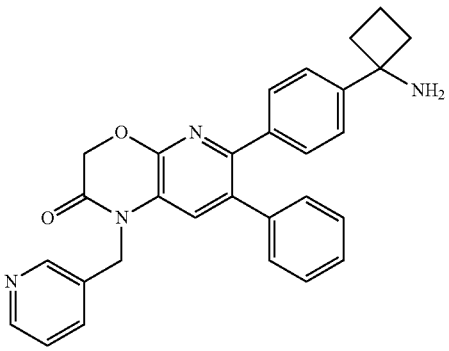 [SMILES: NC1(c2ccc(-c3nc4c(cc3-c3ccccc3)N(Cc3cccnc3)C(=O)CO4)cc2)CCC1]

Step 1: tert-butyl(1-(4-(2-oxo-7-phenyl-1-(pyridin-3-ylmethyl)-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (51 mg, 0.11 mmol) in dry DMF (1 ml) was added sodium hydride (11 mg, 0.26 mmol) and 3-(bromomethyl)pyridine.HBr (33 mg, 0.13 mmol) under nitrogen. The resulting mixture was stirred for 1 hour at room temperature. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 80% EtOAc in cyclohexane) to give the title compound (23 mg, 38%). $^1$H NMR (500 MHz, CDCl$_3$): 8.60-8.50 (2H, br s), 7.60 (2H, d), 7.28 (1H, s), 7.19-7.15 (6H, m), 7.12 (1H, s), 6.97 (2H, d), 5.13 (2H, s), 4.93 (3H, s), 2.52-2.20 (4H, m), 2.00-1.95 (1H, m), 1.75-1.70 (1H, m), 1.44-1.15 (9H, br).

Step 2: 6-(4-(1-aminocyclobutyl)phenyl)-7-phenyl-1-(pyridin-3-ylmethyl)-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-7-phenyl-1-(pyridin-3-ylmethyl)-2,3-dihydro-1H-pyrido[2,3-b][1,4]oxazin-6-yl)phenyl)cyclobutyl)carbamate (23 mg, 0.04 mmol) was reacted to afford the title compound (27 mg, quantitative). LCMS (Method A): $R_T$=3.48 min, M+1=464. $^1$H NMR (500 MHz, MeOD): 8.75 (1H, br s), 8.60 (1H, br s), 8.12 (1H, d), 7.67 (1H, s), 7.49 (1H, s), 7.40-7.36 (4H, m), 7.28-7.24 (3H, m), 7.09 (2H, d), 5.42 (2H, s), 5.12 (2H, s), 2.77-2.72 (2H, m), 2.59-2.53 (2H, m), 2.25-2.21 (1H, m), 1.98-1.94 (1H, m).

Example 47

1-(4-(1-ethyl-8-phenyl-4H-pyrido[2,3-b][1,2,4]triazolo[4,3-d][1,4]oxazin-7-yl)phenyl)cyclobutanamine

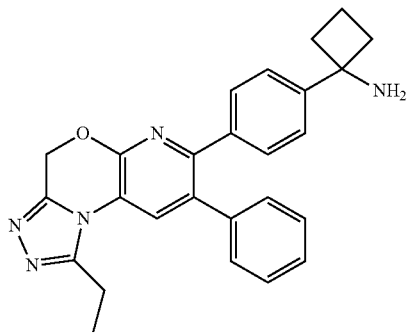 [SMILES: CCc1nnc2n1-c1cc(-c3ccccc3)c(-c3ccc(C4(N)CCC4)cc3)nc1OC2]

Step 1: tert-butyl(1-(4-(7-phenyl-2-thioxo-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6yl)phenyl)cyclobutyl)carbamate (5 g, 10.60 mmol) in toluene (380 ml) was added Lawesson's reagent (4.29 g, 10.60 mmol). The resulting mixture was heated under reflux for 5 hours. After it was cooled down to room temperature, the mixture was concentrated to dryness under reduced pressure. The resulting residue was dissolved in the minimum amount of dichloromethane (500 ml) and treated with diisopropyl ether (800 ml). A yellow solid crushed out. It was filtered and dried until constant weight (4.7 g, 91%). LCMS (Method D): $R_T$=1.526 min, M+1=488.

Step 2: (E)-tert-butyl(1-(4-(2-hydrazono-7-phenyl-2,3-dihydro-1H-pyrido[2,3-b][1,4]oxazin-6-yl)phenyl)cyclobutyl)carbamate To a solution of tert-butyl(1-(4-(7-phenyl-2-thioxo-2,3-dihydro-1H-pyrido[2,3-b][1,4]oxazin-6-yl)phenyl)cyclobutyl)carbamate (2 g, 2.05 mmol) in THF (350 mL) was added hydrazine monohydrate (645 µl, 20.51 mmol) to give a yellow solution. The resulting mixture was stirred at room temperature for 2 hours. The mixture was filtered to remove insoluble black particles and concentrated to dryness under reduced pressure. The resulting yellow solid was used directly in the following step as crude without any further purification. LCMS (Method D): $R_T$=1.04 min, M+1=486.

Step 3: tert-butyl(1-(4-(9-phenyl-5,6-dihydro-[1,2,4]triazolo[3,4-f][1,6]naphthyridin-8-yl)phenyl)cyclobutyl)carbamate A solution of (E)-tert-butyl(1-(4-(2-hydrazono-7-phenyl-2,3-dihydro-1H-pyrido[2,3-b][1,4]oxazin-6-yl)phenyl)cyclobutyl)carbamate (50 mg, 0.103 mmol) in triethyl orthopropionate (1 ml) was heated to 150° C. for 15 minutes under microwave irradiation. The resulting reaction mixture was concentrated to dryness under reduced pressure and purified by Biotage silica gel chromatography (gradient 0% to 100% ethyl acetate in n-hexanes) to give the title compound (30 mg, 55%). LCMS (Method D): $R_T$=1.43 min, M+1=524. $^1$H NMR (500 MHz, CDCl$_3$): 7.80 (1H, s), 7.27-7.26 (5H, m), 7.22 (2H, d), 7.15 (2H, m), 5.56 (2H, s), 3.22 (2H, q), 2.50-2.33 (4H, m), 2.07-1.94 (1H, m), 1.81-1.68 (1H, m), 1.52 (3H, t), 1.38-1.11 (9H, br).

Step 4: 1-(4-(1-ethyl-8-phenyl-4H-pyrido[2,3-b][1,2,4]triazolo[4,3-d][1,4]oxazin-7-yl)phenyl)cyclobutanamine Tert-butyl (1-(4-(9-phenyl-5,6-dihydro-[1,2,4]triazolo[3,4-f][1,6]naphthyridin-8-yl)phenyl)cyclobutyl)carbamate (30 mg, 0.057 mmol) was dissolved in TFA (2 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and the residue was dried to give the desired product as an off-white solid (15 mg, 61% yield). LCMS (Method A) RT=3.78 min, M+1=425. $^1$H-NMR (500 MHz, CD$_3$OD) δ 8.10 (1H, s), 7.49 (2H, d), 7.35 (3H, m), 7.29 (4H, m), 5.66 (2H, s), 3.26 (2H, t), 2.84-2.71 (2H, m), 2.64-2.54 (2H, m), 2.31-2.14 (1H, m), 2.04-1.93 (1H, m), 1.51 (3H, t).

Example 48

6-(4-(1-aminocyclobutyl)phenyl)-1-(cyclobutylmethyl)-7-phenyl-1H-pyrido[2,3-b][1,4]oxazin-2(3H)-one

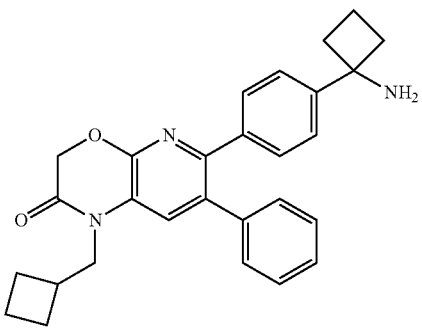 [SMILES: NC1(c2ccc(-c3nc4c(cc3-c3ccccc3)N(CC3CCC3)C(=O)CO4)cc2)CCC1]

Step 1: tert-butyl 1-(4-(1-(cyclobutylmethyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (44 mg, 0.09 mmol) in dry DMF (1 ml) was added sodium hydride (9 mg, 0.22 mmol) and (bromomethyl)cyclobutane (130, 0.11 mmol) under nitrogen. The resulting mixture was stirred for 1 h at 80 C. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 40% EtOAc in cyclohexane) to give the title compound (8 mg, 16%). $^1$H NMR (500 MHz, CDCl$_3$): 7.23-7.17 (8H, m), 7.13-7.11 (2H, m), 4.95 (1H, s), 4.80 (2H, s), 3.96 (2H, d), 2.68-2.64 (1H, m), 2.52-2.20 (4H, m), 2.00-1.95 (3H, m), 1.86-1.50 (5H, m), 1.44-1.15 (9H, br).

Step 2: 6-(4-(1-aminocyclobutyl)phenyl)-1-(cyclobutylmethyl)-7-phenyl-1H-pyrido[2,3-b][1,4]oxazin-2(3H)-one Following the procedure for 14(1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-(cyclobutylmethyl)-2-oxo-7-phenyl-2,3-dihydro-1H-pyrido[2,3-b][1,4]oxazin-6-yl)phenyl)cyclobutyl)carbamate (8 mg, 0.02 mmol) was reacted to afford the title compound (8 mg, 97%). LCMS (Method A): R$_T$=4.65 min, M-16=423. $^1$H NMR (500 MHz, MeOD): 7.56 (1H,s), 7.42-7.37 (4H,m), 7.32-7.30 (3H, m), 7.23-7.21 (2H, m), 4.97 (1H, s), 4.59 (2H, s), 4.14 (2H, d), 2.80-2.72 (3H, m), 2.59-2.53 (2H, m), 2.24-2.20 (1H, m), 2.10-2.06 (2H, m), 1.98-1.87 (5H, m).

Example 49 ethyl 2-(6-(4-(1-aminocyclobutyl)phenyl)-2-oxo-7-phenyl-2,3-dihydro-1H-pyrido[2,3-b][1,4]oxazin-1-yl)acetate

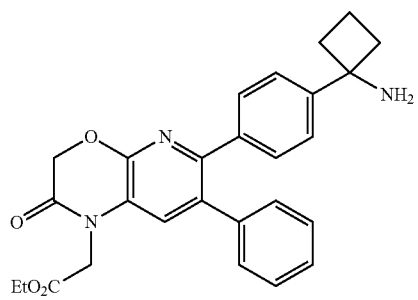 [SMILES: CCOC(=O)CN1C(=O)COc2nc(-c3ccc(C4(N)CCC4)cc3)c(-c3ccccc3)cc21]

Step 1: ethyl 2-(6-(4-(1-(tert-butoxycarbonylamino)cyclobutyl)phenyl)-2-oxo-7-phenyl-2,3-dihydro-1H-pyrido[2,3-b][1,4]oxazin-1-yl)acetate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol) in anhydrous N,N-dimethylformamide (1 mL) to give a red solution, then cooled to 0° C. under a nitrogen atmosphere. Sodium hydride, 60% in oil (6.4 mg, 0.159 mmol) was added and the mixture stirred at 0° C. for 15 minutes. Ethyl 2-bromoacetate (0.035 mL, 0.318 mmol) was added and the mixture stirred at 0° C. for 30 minutes, allowed to warm to room temperature then stirred for one hour. The reaction mixture was quenched by the addition of saturated ammonium chloride solution (5 mL) and extracted into ethyl acetate (3×3 mL). The organic phase was washed with 50:50 water:brine (2×5 mL) then brine (5 mL), dried over Na$_2$SO$_4$, filtered and concentrated to dryness under reduced pressure. The residue was purified by Biotage chromatography (cyclohexane:ethyl acetate, gradient elution from 88:12 to 0:100) to give the desired product as an off-white solid (22 mg, 39% yield). $^1$H-NMR (500 MHz, CDCl$_3$) δ 7.13-7.28 (8H, m), 7.37-7.43 (2H, m), 5.24 (1H, br s), 5.18 (2H, s), 4.89 (2H, s), 4.49 (2H, q), 2.40-2.90 (4H, m), 2.21-2.35 (1H, m), 1.90-2.10 (1H, m), 1.20-1.75 (9H, br m), 1.53 (3H, t). LCMS (Method A) RT=7.20 min, M+H$^+$=558.13.

Step 2: ethyl 2-(6-(4-(1-aminocyclobutyl)phenyl)-2-oxo-7-phenyl-2,3-dihydro-1H-pyrido[2,3-b][1,4]oxazin-1-yl)acetate Ethyl 2-(6-(4-(1-(tert-butoxycarbonylamino)cyclobutyl)phenyl)-2-oxo-7-phenyl-2,3-dihydro-1H-pyrido[2,3-b][1,4]oxazin-1-yl)acetate (22 mg, 0.039 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (22 mg, 98% yield).

$^1$H-NMR (500 MHz, MeOD) δ 7.37-7.48 (5H, m), 7.25-7.37 (3H, m), 7.15-7.25 (2H, m), 5.01 (2H, s), 4.85 (2H, s), 4.26 (2H, q), 2.70-2.83 (2H, m), 2.48-2.62 (2H, m), 2.15-2.30 (1H, m), 1.90-2.05 (1H, m), 1.28 (3H, t). LCMS (Method A) RT=4.08 min, M+2H$^+$=459.20.

Example 50

7-(4-(1-aminocyclobutyl)phenyl)-8-phenyl-4H-pyrido[2,3-b][1,2,4]triazolo[4,3-d][1,4]oxazin-1-amine

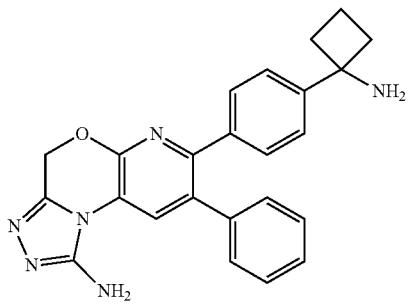 [SMILES: Nc1nnc2n1-c1cc(-c3ccccc3)c(-c3ccc(C4(N)CCC4)cc3)nc1OC2]

Step 1: tert-butyl(1-(4-(1-amino-8-phenyl-4H-pyrido[2,3-b][1,2,4]triazolo[3,4-d][1,4]oxazin-7-yl)phenyl)cyclobutyl)carbamate A solution of (E)-tert-butyl(1-(4-(2-hydrazono-7-phenyl-2,3-dihydro-1H-pyrido[2,3-b][1,4]oxazin-6-yl)phenyl)cyclobutyl)carbamate (50 mg, 0.103 mmol), cyanogen bromide (33 mg, 0.309 mmol) and sodium carbonate (22 mg, 0.206 mmol) in a mixture of ethanol (1 ml) and 1,4-dioxane (1 ml) was stirred at room temperature for one hour. The resulting reaction mixture was concentrated to dryness under reduced pressure and purified by Biotage silica gel chromatography (gradient 100% to 94:6 dichloromethane in methanol) to give the title compound (15 mg, 30%). LCMS (Method A): $R_T$=5.73 min, M+1=511. $^1$H NMR (500 MHz, CDCl$_3$): 7.80 (1H, s), 7.36-7.28 (7H, m), 7.23-7.19 (2H, m), 5.48 (2H, s), 2.56-2.41 (4H, m), 2.13-2.02 (1H, m), 1.89-1.77 (1H, m), 1.46-1.21 (9H, bs).

Step 2: 7-(4-(1-aminocyclobutyl)phenyl)-8-phenyl-4H-pyrido[2,3-b][1,2,4]triazolo[4,3-d][1,4]oxazin-1-amine Tert-butyl (1-(4-(1-amino-8-phenyl-4H-pyrido[2,3-b][1,2,4]triazolo[3,4-d][1,4]oxazin-7-yl)phenyl)cyclobutyl)carbamate (15 mg, 0.029 mmol) was dissolved in TFA (2 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and the residue was dried to give the desired product as an off-white solid (10 mg, 80% yield). LCMS (Method A) RT=3.40 min, M+1=412. $^1$H-NMR (500 MHz, CD$_3$OD) δ 8.21 (1H, s), 7.41-7.36 (2H, d), 7.35-7.30 (2H, d), 7.27-7.19 (5H, m), 5.44 (2H, s), 2.72-2.62 (2H, m), 2.53-2.43 (2H, m), 2.20-2.09 (1H, m), 1.92-1.82 (1H, m).

Example 51

6-(4-(1-aminocyclobutyl)phenyl)-1-(2-methoxyethyl)-7-phenyl-1H-pyrido[2,3-b][1,4]oxazin-2(3H)-one

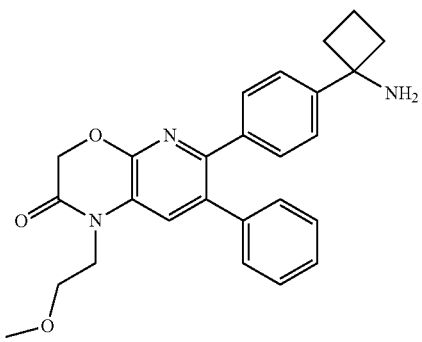 [SMILES: COCCN1C(=O)COc2nc(-c3ccc(C4(N)CCC4)cc3)c(-c3ccccc3)cc21]

Step 1: tert-butyl(1-(4-(1-(2-methoxyethyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl) carbamate (48 mg, 0.10 mmol) in dry DMF (1 mL) was added sodium hydride (16 mg, 0.41 mmol) and 1-bromo-2-methoxyethane (28 mg, 0.20 mmol) under nitrogen. The resulting mixture was stirred for 2 hours at 80° C. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 40% EtOAc in cyclohexane) to give the title compound (10 mg, 18%). $^1$H NMR (500 MHz, CDCl$_3$): 7.49 (1H, s), 7.23-7.17 (7H, m), 7.12-7.11 (2H, m), 4.95 (1H, s), 4.82 (2H, s), 4.05 (2H, t), 3.61 (2H, t), 3.29 (3H, s), 2.52-2.20 (4H, m), 2.00-1.95 (1H, m), 1.79-1.65 (1H, m), 1.40-1.10 (9H, br).

Step 2: 6-(4-(1-aminocyclobutyl)phenyl)-1-(2-methoxyethyl)-7-phenyl-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-(2-methoxyethyl)-2-oxo-7-phenyl-2,3-dihydro-1H-pyrido[2,3-b][1,4]oxazin-6-yl)phenyl)cyclobutyl)carbamate (10 mg, 0.02 mmol) was reacted to afford the title compound (7 mg, 68%). LCMS (Method D): $R_T$=4.11 min, M-16=423. $^1$H NMR (500 MHz, MeOD): 7.77 (1H,S), 7.43-7.38 (4H,m), 7.33-7.28 (3H, m), 7.23-7.21 (2H, m), 4.96 (2H, s), 4.24-4.22 (2H, t), 3.72-3.70 (2H, t), 3.36 (3H, s), 2.77-2.72 (2H, m), 2.59-2.53 (2H, m), 2.25-2.21 (1H, m), 1.98-1.94 (1H, m).

Example 52

6-(4-(1-aminocyclobutyl)phenyl)-1-ethyl-7-phenyl-1H-pyrido[2,3-b][1,4]oxazin-2(3H)-one

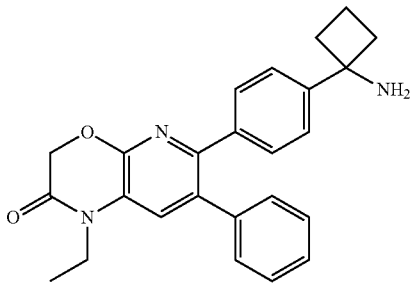 [SMILES: CCN1C(=O)COc2nc(-c3ccc(C4(N)CCC4)cc3)c(-c3ccccc3)cc21]

Step 1: tert-butyl 1-(4-(1-ethyl-2-oxo-7-phenyl-2,3-dihydro-1H-pyrido[2,3-b][1,4]oxazin-6-yl)phenyl) cyclobutylcarbamate In a 15 mL reaction tube was added tert-butyl 1-(4-(2-oxo-7-phenyl-2,3-dihydro-1H-pyrido[2,3-b][1,4]oxazin-6-yl) phenyl)cyclobutylcarbamate (50 mg, 0.106 mmol) in anhydrous N,N-dimethylformamide (1 mL) to give a yellow solution, then cooled to 0° C. under a nitrogen atmosphere. Sodium hydride, 60% in oil (10 mg, 0.254 mmol) was added and the mixture stirred at 0° C. for 15 minutes. Iodoethane (10 μl, 0.127 mmol) was added and the mixture stirred at 0° C. for 30 minutes, allowed to warm to room temperature then stirred for one hour. Further sodium hydride, 60% in oil (10.18 mg, 0.254 mmol) was added and the reaction mixture was heated to 40° C. under a nitrogen atmosphere for one hour. Further iodoethane (10 μl, 0.127 mmol) was added and the mixture stirred at room temperature for 30 minutes. The reaction mixture was quenched by the addition of saturated sodium bicarbonate solution (5 mL) and extracted into ethyl acetate (3×5 mL). The organic phase was washed with 50:50 water:brine (2×10 mL) then brine (10 mL), dried over $Na_2SO_4$, filtered and concentrated to dryness under reduced pressure. The residue was purified by Biotage chromatography (cyclohexane:ethyl acetate, gradient elution from 88:12 to 0:100) to give the desired product as a pale yellow solid (7 mg, 13% yield). $^1$H-NMR (500 MHz, $CDCl_3$) δ 7.10-7.28 (10H, m), 4.93 (1H, br s), 4.81 (2H, s), 3.94 (2H, q), 2.10-2.55 (4H, m), 1.90-2.08 (1H, m), 1.65-1.80 (1H, m), 1.00-1.40 (9H, br m), 1.14 (3H, t). LCMS (Method A) RT=7.29 min, $M+H^+$=500.12.

Step 2: 6-(4-(1-aminocyclobutyl)phenyl)-1-ethyl-7-phenyl-1H-pyrido[2,3-b][1,4]oxazin-2(3H)-one tert-Butyl 1-(4-(1-ethyl-2-oxo-7-phenyl-2,3-dihydro-1H-pyrido[2,3-b][1,4]oxazin-6-yl)phenyl)cyclobutylcarbamate (7 mg, 0.014 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (6 mg, 83% yield). $^1$H-NMR (500 MHz, MeOD) δ 7.57 (1H, s), 7.42 (2H, d), 7.38 (2H, d), 7.28-7.35 (3H, m), 7.20-7.28 (2H, m), 4.95 (2H, s), 4.10 (2H, q), 2.68-2.85 (2H, m), 2.50-2.65 (2H, m), 2.15-2.30 (1H, m), 1.90-2.05 (1H, m), 1.30 (3H, t). LCMS (Method A) RT=4.04 min, $M+2H^4$=401.18.

Example 53

1-((1H-imidazol-5-yl)methyl)-6-(4-(1-aminocyclobutyl)phenyl)-7-phenyl-1H-pyrido[2,3-b][1,4]oxazin-2(3H)-one

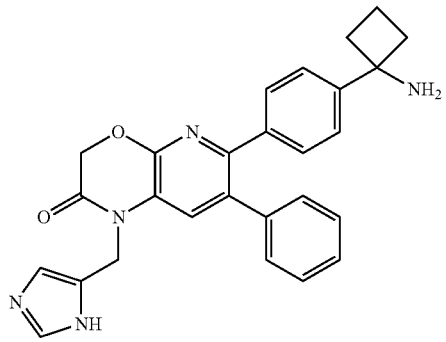 [SMILES: NC1(c2ccc(-c3nc4c(cc3-c3ccccc3)N(Cc3cnc[nH]3)C(=O)CO4)cc2)CCC1]

Step 1: tert-butyl(1-(4-(1-((1H-imidazol-5-yl)methyl)-2-oxo-7-phenyl-2,3-dihydro-1H-pyrido[2,3-b][1,4]oxazin-6-yl)phenyl)cyclobutyl)carbamate In a round bottom flask was added tert-butyl 1-(4-(2-oxo-7-phenyl-2,3-dihydro-1H-pyrido[2,3-b][1,4]oxazin-6-yl) phenyl)cyclobutylcarbamate (150 mg, 0.318 mmol) in DMF (Volume: 8 ml) to give a brown solution. sodium hydride (30.5 mg, 0.763 mmol) and 5-(chloromethyl)-1H-imidazole hydrochloride salt (58.4 mg, 0.501 mmol) was added. The resulting mixture was stirred at room temperature for 2 h. further sodium hydride (15.2 mg) and imidazole (29 mg) were added and the resulting mixture stirred for another hour. The reaction mixture was concentrated to dryness. The residue was partitioned between ethyl acetate (35 ml) and water (30 ml). The organic phase was separated and washed with water (2×25 ml), brine and concentrated. The residue was purified by column (biotage 25 g) to give product (14 mg). LCMS (Method A) RT=4.58 min, $M+H^+$=552.1.

Step 2: 1-((1H-imidazol-5-yl)methyl)-6-(4-(1-aminocyclobutyl)phenyl)-7-phenyl-1H-pyrido[2,3-b][1,4]oxazin-2(3H)-one tert-butyl(1-(4-(1-((1H-imidazol-5-yl)methyl)-2-oxo-7-phenyl-2,3-dihydro-1H-pyrido[2,3-b][1,4]oxazin-6-yl)phenyl)cyclobutyl)carbamate (12 mg, 0.022 mmol) was dissolved in TFA (1 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound (7.5 mg). $^1$H-NMR (500 MHz, MeOD) δ 8.81 (1H, s), 7.62 (2H, br), 7.39-7.41 (m, 4H), 7.28-7.30 (3H, m), 7.16-7.18 (2H, m), 5.39 (2H, s), 5.07 (2H, s), 2.7-2.8 (2H, m), 2.55-2.65 (2H, m), 2.2-2.3 (1H, m), 1.9-2.05 (1H, m), LCMS (Method A) RT=2.83 min, $M+H^+$=453.1.

Example 54

2-(6-(4-(1-aminocyclobutyl)phenyl)-2-oxo-7-phenyl-2,3-dihydro-1H-pyrido[2,3-b][1,4]oxazin-1-yl)propanenitrile

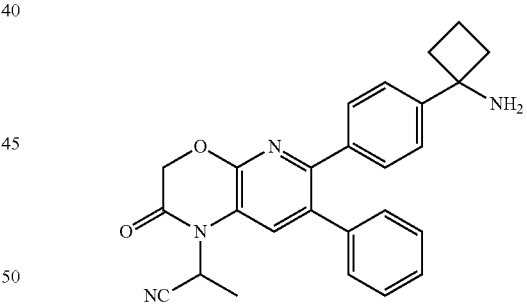

Step 1: tert-butyl(1-(4-(1-(1-cyanoethyl)-2-oxo-7-phenyl-2,3-dihydro-1H-pyrido[2,3-b][1,4]oxazin-6-yl)phenyl)cyclobutyl)carbamate In a 50 ml round bottom flask was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol) in DMF (Volume: 4 ml) to give a brown solution. sodium hydride (10.18 mg, 0.254 mmol) and 2-bromopropanenitrile (17.05 mg, 0.127 mmol) were added. The reaction mixture was stirred at 50 degree for 1 h then room temperature overnight. The reaction mixture was partitioned between DCM (20 ml) and water (20 ml). The organic phase was separated and concentrated. The residue was purified by column (biotage, 25 g) eluted with ethyl acetate/cyclohexane (0-50%) to give product (19 mg). LCMS (Method A): $R_T$=7.14 min, M+H$^+$=525.0.

Step 2: 2-(6-(4-(1-aminocyclobutyl)phenyl)-2-oxo-7-phenyl-2,3-dihydro-1H-pyrido[2,3-b][1,4]oxazin-1-yl)propanenitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(1-cyanoethyl)-2-oxo-7-phenyl-2,3-dihydro-1H-pyrido[2,3-b][1,4]oxazin-6-yl)phenyl)cyclobutyl)carbamate (7 mg, 0.013 mmol) was reacted to afford the title compound (5.5 mg). $^1$H NMR (500 MHz, CH$_3$OD) 7.77 (1H, s), 7.44 (2H, d), 7.40 (2H, d), 7.30-7.34 (3H, m), 7.25-7.28 (2H, m), 6.03 (1H, q), 4.99 (2H, s), 2.7-2.85 (2H, m), 2.55-2.65 (2H, m), 2.2-2.3 (1H, m), 1.9-2.1 (1H, m), 1.81 (3H, d), LCMS (Method A): $R_T$=4.11 min, M+H$^+$=426.1.

Example 55

6-(4-(1-aminocyclobutyl)phenyl)-1-(cyclopropylmethyl)-7-phenyl-1H-pyrido[2,3-b][1,4]oxazin-2(3H)-one

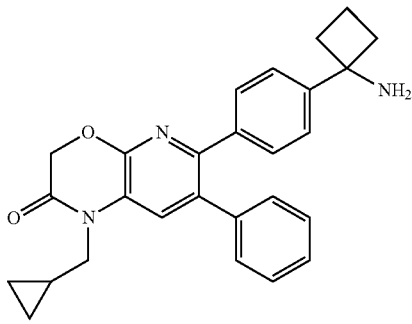 [SMILES: NC1(c2ccc(-c3nc4c(cc3-c3ccccc3)N(CC3CC3)C(=O)CO4)cc2)CCC1]

Step 1: tert-butyl 1-(4-(1-(cyclopropylmethyl)-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol), potassium carbonate (44 mg, 0.318 mmol) and (bromomethyl)cyclopropane (0.031 mL, 0.318 mmol) in anhydrous N,N-dimethylformamide (1 mL) to give an orange suspension. The reaction mixture was stirred at 80° C. for one hour. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane: ethyl acetate, gradient elution from 90:10 to 20:80) to give the desired product as an off-white solid (40 mg, 72% yield). $^1$H-NMR (500 MHz, CDCl$_3$) δ 7.32 (1H, s), 7.10-7.28 (9H, m), 4.98 (1H, br s), 4.82 (2H, s), 3.79 (2H, d), 2.05-2.60 (4H, m), 1.90-2.05 (1H, m), 1.65-1.79 (1H, m), 1.00-1.45 (10H, br m), 0.45-0.57 (2H, m), 0.35-0.45 (2H, m). LCMS (Method A) RT=7.79 min, M+H$^+$=526.18.

Step 2: 6-(4-(1-aminocyclobutyl)phenyl)-1-(cyclopropylmethyl)-7-phenyl-1H-pyrido[2,3-b][1,4]oxazin-2(3H)-one tert-Butyl 1-(4-(1-(cyclopropylmethyl)-2-oxo-7-phenyl-2,3-dihydro-1H-pyrido[2,3-b][1,4]oxazin-6-yl)phenyl)cyclobutylcarbamate (40 mg, 0.076 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (30 mg, 73% yield).
$^1$H-NMR (500 MHz, MeOD) δ 7.67 (1H, s), 7.43 (2H, d), 7.40 (2H, d), 7.28-7.36 (3H, m), 7.20-7.25 (2H, m), 4.96 (2H, s), 3.98 (2H, d), 2.70-2.80 (2H, m), 2.52-2.63 (2H, m), 2.18-2.30 (1H, m), 1.90-2.03 (1H, m), 1.17-1.30 (1H, m), 0.55-0.65 (2H, m), 0.42-0.50 (2H, m). LCMS (Method A) RT=4.44 min, M+2H$^+$=427.20.

Example 56

6-(4-(1-aminocyclobutyl)phenyl)-7-phenyl-1-(pyridin-2-ylmethyl)-1H-pyrido[2,3-b][1,4]oxazin-2(3H)-one

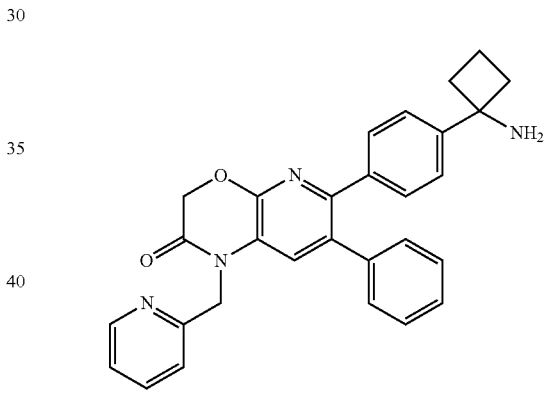

Step 1: tert-butyl(1-(4-(2-oxo-7-phenyl-1-(pyridin-2-ylmethyl)-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (75 mg, 0.16 mmol) in dry DMF (1 mL) was added sodium hydride (15 mg, 0.38 mmol) and 2-(bromomethyl)pyridine.HBr (48 mg, 0.19 mmol) under nitrogen. The resulting mixture was stirred for 1 hour at room temperature. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 40% EtOAc in cyclohexane) to give the title compound (11 mg, 12%). $^1$H NMR (500 MHz, CDCl$_3$): 8.49 (1H, d), 7.63 (1H, t), 7.42 (1H, s), 7.27 (1H, d), 7.19-7.13 (8H, m), 7.01-6.98 (2H, d), 5.23 (2H, s), 4.92 (2H, s), 4.91 (1H, s), 2.52-2.20 (4H, m), 2.00-1.95 (1H, m), 1.75-1.70 (1H, m), 1.44-1.15 (9H, br).

Step 2: 6-(4-(1-aminocyclobutyl)phenyl)-7-phenyl-1-(pyridin-2-yl)methyl)-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-7-phenyl-1-(pyridin-2-ylmethyl)-2,3-dihydro-1H-pyrido[2,3-b][1,4]oxazin-6-yl)phenyl)cyclobutyl)carbamate (16 mg, 0.03 mmol) was reacted to afford the title compound (17 mg, 87%). LCMS (Method A): $R_T$=4.11 min, M-16=446. $^1$H NMR (500 MHz, MeOD): 8.54 (1H, d), 7.91-7.87 (1H, t), 7.53 (1H, d), 7.42-7.35 (6H, m), 7.26-7.21 (3H, m), 7.04 (2H, d), 5.39 (2H, s), 5.11 (2H, s), 2.77-2.72 (2H, m), 2.59-2.53 (2H, m), 2.25-2.21 (1H, m), 1.98-1.94 (1H, m).

Example 57

6-(4-(1-aminocyclobutyl)phenyl)-1-isopropyl-7-phenyl-1H-pyrido[2,3-b][1,4]oxazin-2(3H)-one

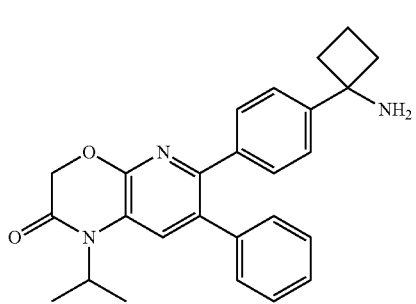 [SMILES: CC(C)N1C(=O)COc2nc(-c3ccc(C4(N)CCC4)cc3)c(-c3ccccc3)cc21]

Step 1: tert-butyl 1-(4-(1-isopropyl-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (25 mg, 0.053 mmol), potassium carbonate (22 mg, 0.159 mmol) and 2-iodopropane (16 µl, 0.159 mmol) in anhydrous N,N-dimethylformamide (500 µl) to give an orange suspension. The reaction mixture was stirred at 80° C. for one hour. The reaction mixture was allowed to cool to room temperature, diluted with saturated sodium bicarbonate solution (5 ml) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane:ethyl acetate, gradient elution from 90:10 to 20:80) to give the desired product as an off-white solid (13 mg, 48% yield). $^1$H-NMR (500 MHz, CDCl$_3$) δ 7.37 (1H, s), 7.10-7.28 (9H, m), 4.95 (1H, br s), 4.65-4.77 (3H, m), 2.05-2.60 (4H, m), 1.92-2.06 (1H, m), 1.65-1.80 (1H, m), 1.50 (6H, d), 1.00-1.45 (9H, br m). LCMS (Method A) RT=7.73 min, M+H$^+$=514.15.

Step 2: 6-(4-(1-aminocyclobutyl)phenyl)-1-isopropyl-7-phenyl-1H-pyrido[2,3-b][1,4]oxazin-2(3H)-one tert-Butyl 1-(4-(1-isopropyl-2-oxo-7-phenyl-2,3-dihydro-1H-pyrido[2,3-b][1,4]oxazin-6-yl)phenyl)cyclobutylcarbamate (7 mg, 0.014 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (7 mg, 97% yield). $^1$H-NMR (500 MHz, MeOD) δ 7.64 (1H, s), 7.41 (2H, d), 7.36 (2H, d), 7.26-7.32 (3H, m), 7.19-7.26 (2H, m), 4.80 (2H, s), 4.75 (1H, sep), 2.68-2.80 (2H, m), 2.50-2.62 (2H, m), 2.13-2.29 (1H, m), 1.89-2.00 (1H, m), 1.48 (6H, d). LCMS (Method A) RT=4.20 min, M+2H$^+$=415.19.

Example 58

6-(4-(1-aminocyclobutyl)phenyl)-1-cyclopentyl-7-phenyl-1H-pyrido[2,3-b][1,4]oxazin-2(3H)-one

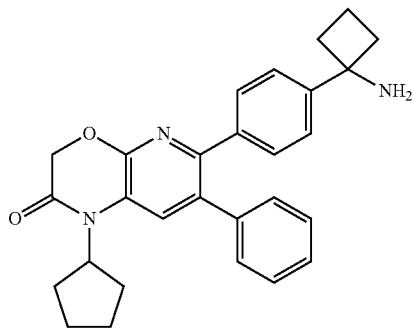 [SMILES: NC1(c2ccc(-c3nc4c(cc3-c3ccccc3)N(C3CCCC3)C(=O)CO4)cc2)CCC1]

Step 1: tert-butyl 1-(4-(1-cyclopentyl-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol), potassium carbonate (44 mg, 0.318 mmol) and bromocyclopentane (0.034 mL, 0.318 mmol) in anhydrous N,N-dimethylformamide (1 mL) to give an orange suspension. The reaction mixture was stirred at 80° C. for one hour. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane: ethyl acetate, gradient elution from 90:10 to 20:80) to give the desired product as an off-white solid (12 mg, 21% yield). $^1$H-NMR (500 MHz, CDCl$_3$) δ 7.32 (1H, s), 7.17-7.28 (7H, m), 7.10-717 (2H, m), 4.94 (1H, br s), 4.83 (1H, quin), 4.72 (2H, s), 2.05-2.60 (6H, m), 1.83-2.03 (5H, m), 1.54-1.82 (3H, m), 1.00-1.45 (9H, br m). LCMS (Method A) RT=8.25 min, M+H$^+$=540.19.

Step 2: 6-(4-(1-aminocyclobutyl)phenyl)-1-cyclopentyl-7-phenyl-1H-pyrido[2,3-b][1,4]oxazin-2(3H)-one tert-Butyl 1-(4-(1-cyclopentyl-2-oxo-7-phenyl-2,3-dihydro-1H-pyrido[2,3-b][1,4]oxazin-6-yl)phenyl)cyclobutylcarbamate (12 mg, 0.022 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (6 mg, 49% yield). $^1$H-NMR (500 MHz, MeOD) δ 7.60 (1H, s), 7.40 (2H, d), 7.36 (2H, d), 7.25-7.36 (3H, m), 7.18-7.25 (2H, m), 4.91 (1H, quin), 4.84 (2H, s), 2.66-2.31 (2H, m), 2.47-2.61 (2H, m), 2.12-2.31 (3H, m), 1.83-2.12 (5H, m), 1.63-1.81 (2H, m). LCMS (Method A) RT=4.55 min, M+2H$^+$=441.19.

Example 59

6-(4-(1-aminocyclobutyl)phenyl)-7-phenyl-1-(thiazol-4-ylmethyl)-1H-pyrido[2,3-b][1,4]oxazin-2(3H)-one

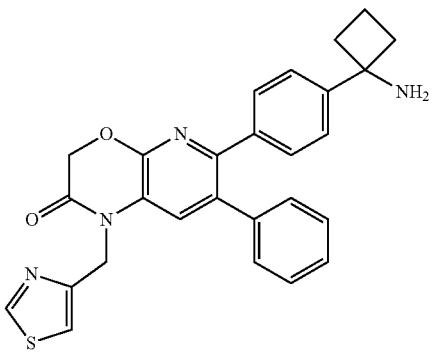 [SMILES: NC1(c2ccc(-c3nc4c(cc3-c3ccccc3)N(Cc3cscn3)C(=O)CO4)cc2)CCC1]

Step 1: tert-butyl 1-(4-(2-oxo-7-phenyl-1-(thiazol-4-ylmethyl)-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol), potassium carbonate (59 mg, 0.424 mmol) and 4-(chloromethyl)thiazole HCl salt (54 mg, 0.318 mmol) in anhydrous N,N-dimethylformamide (1 mL) to give an orange suspension. The reaction mixture was stirred at 80° C. for one hour. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane: ethyl acetate, gradient elution from 90:10 to 0:100) to give the desired product as an off-white solid (54 mg, 90% yield). $^1$H-NMR (500 MHz, CDCl$_3$) δ 8.70 (1H, s), 7.61 (1H, s), 7.28 (1H, s), 7.12-7.27 (7H, m), 7.03-7.12 (2H, m), 5.23 (2H, s), 4.99 (1H, br s), 4.86 (2H, s), 2.10-2.60 (4H, m), 2.41-2.06 (1H, m), 1.65-1.79 (1H, m), 1.00-1.45 (9H, br m). LCMS (Method A) RT=7.11 min, M+H$^+$=569.14.

Step 2: 6-(4-(1-aminocyclobutyl)phenyl)-7-phenyl-1-(thiazol-4-ylmethyl)-1H-pyrido[2,3-b][1,4]oxazin-2(3H)-one tert-Butyl 1-(4-(2-oxo-7-phenyl-1-(thiazol-4-ylmethyl)-2,3-dihydro-1H-pyrido[2,3-b][1,4]oxazin-6-yl)phenyl)cyclobutylcarbamate (54 mg, 0.095 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (30 mg, 54% yield). $^1$H-NMR (500 MHz, MeOD) δ 8.97 (1H, s), 7.63 (1H, s), 7.60 (1H, s), 7.32-7.41 (4H, m), 7.20-7.29 (3H, m), 7.05-7.15 (2H, m), 5.39 (2H, s), 5.03 (2H, s), 2.66-2.88 (2H, m), 2.47-2.38 (2H, m), 2.13-2.28 (1H, m), 1.85-1.98 (1H, m). LCMS (Method A) RT=3.81 min, M+2H$^+$=470.18.

Example 60

6-(4-(1-aminocyclobutyl)phenyl)-7-phenyl-1-(2,2,2-trifluoroethyl)-1H-pyrido[2,3-b][1,4]oxazin-2(3H)-one

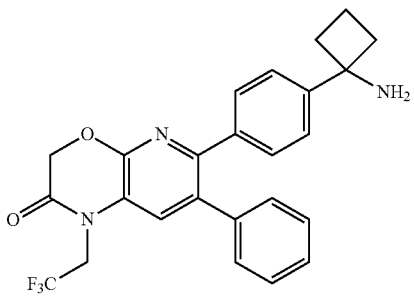 [SMILES: NC1(c2ccc(-c3nc4c(cc3-c3ccccc3)N(CC(F)(F)F)C(=O)CO4)cc2)CCC1]

Step 1: tert-butyl 1-(4-(2-oxo-7-phenyl-1-(2,2,2-trifluoroethyl)-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol), potassium carbonate (44 mg, 0.318 mmol) and 2-bromo-1,1,1-trifluoroethane (0.193 mL, 2.121 mmol) in anhydrous N,N-dimethylformamide (1 mL) to give an orange suspension. The reaction mixture was stirred at 80° C. for one hour. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane: ethyl acetate, gradient elution from 90:10 to 20:80) to give the desired product as an off-white solid (31 mg, 53% yield). $^1$H-NMR (500 MHz, CDCl$_3$) δ 7.38 (1H, s), 7.25-7.37 (7H, m), 7.17-7.23 (2H, m), 5.05 (1H, br s), 4.97 (2H, s), 4.63 (2H, q), 2.20-2.58 (4H, m), 2.00-2.15 (1H, m), 1.75-1.88 (1H, m), 1.10-1.50 (9H, br m). LCMS (Method A) RT=7.65 min, M+H$^+$=554.05.

Step 2: 6-(4-(1-aminocyclobutyl)phenyl)-7-phenyl-1-(2,2,2-trifluoroethyl)-1H-pyrido[2,3-b][1,4]oxazin-2(3H)-one tert-Butyl 1-(4-(2-oxo-7-phenyl-1-(2,2,2-trifluoroethyl)-2,3-dihydro-1H-pyrido[2,3-b][1,4]oxazin-6-yl)phenyl)cyclobutylcarbamate (31 mg, 0.056 mmol) was dissolved in TEA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (6 mg, 19% yield).

$^1$H-NMR (500 MHz, MeOD) δ 7.74 (1H, s), 7.41 (2H, d), 7.37 (2H, d), 7.25-7.33 (3H, m), 7.17-7.25 (2H, m), 5.01 (2H, s), 4.90 (2H, q), 2.65-2.82 (2H, m), 2.50-2.63 (2H, m), 2.13-2.30 (1H, m), 1.85-2.02 (1H, m). LCMS (Method A) RT=4.22 min, M+2H$^+$=455.19.

Example 61

6-(4-(1-aminocyclobutyl)phenyl)-1-cyclobutyl-7-phenyl-1H-pyrido[2,3-b][1,4]oxazin-2(3H)-one

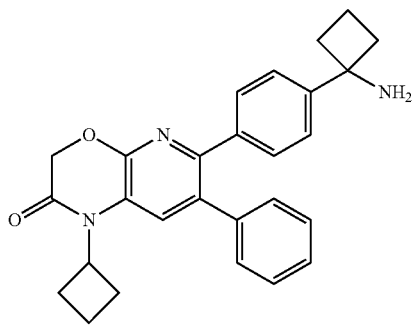 [SMILES: NC1(c2ccc(-c3nc4c(cc3-c3ccccc3)N(C3CCC3)C(=O)CO4)cc2)CCC1]

Step 1: tert-butyl 1-(4-(1-cyclobutyl-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (50 mg, 0.106 mmol), potassium carbonate (44 mg, 0.318 mmol) and bromocyclobutane (0.030 mL, 0.318 mmol) in anhydrous N,N-dimethylformamide (1 mL) to give an orange suspension. The reaction mixture was stirred at 80° C. for one hour, then 100° C. for 2 hours. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane:ethyl acetate, gradient elution from 90:10 to 20:80) to give the desired product as an off-white solid (15 mg, 27% yield). $^1$H-NMR (500 MHz, CDCl$_3$) δ 7.25-7.37 (8H, m), 7.16-7.25 (2H, m), 5.03 (1H, br s), 4.78 (2H, s), 4.53 (1H, quin), 2.30-2.67 (8H, m), 2.02-2.14 (1H, m), 1.76-1.97 (3H, m), 1.10-1.50 (9H, br m). LCMS (Method A) RT=7.76 min, M+H$^+$=526.16.

Step 2: 6-(4-(1-aminocyclobutyl)phenyl)-1-cyclobutyl-7-phenyl-1H-pyrido[2,3-b][1,4]oxazin-2(3H)-one tert-Butyl 1-(4-(1-cyclobutyl-2-oxo-7-phenyl-2,3-dihydro-1H-pyrido[2,3-b][1,4]oxazin-6-yl)phenyl)cyclobutyl-carbamate (31 mg, 0.059 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (11 mg, 35% yield). $^1$H-NMR (500 MHz, MeOD) δ 7.35-7.58 (5H, m), 7.25-7.35 (3H, m), 7.10-7.25 (2H, m), 4.80 (2H, s), 4.59 (1H, quin), 2.65-2.83 (2H, m), 2.40-2.65 (6H, m), 2.13-2.29 (1H, m), 1.79-2.02 (3H, m). LCMS (Method A) RT=4.58 min, M+2H$^+$=427.21.

Example 62

3-(6-(4-(1-aminocyclobutyl)phenyl)-2-oxo-7-phenyl-2,3-dihydro-1H-Pyrido[2,3-b][1,4]oxazin-1-yl)propanenitrile

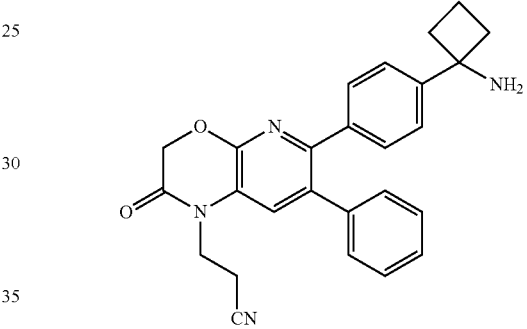

Step 1: tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate A mixture of tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol), 3-bromopropanenitrile (85 mg, 0.636 mmol) and potassium carbonate (88 mg) in DMF (4 ml) was heated at 80 degree for 16 h.

The reaction mixture was partitioned between dichloromethane (20 ml) and water (20 ml). The organic phase was separated using phase separator and concentrated. The crude product was purified by column (biotage, 25 g) eluted with ethyl acetate/cyclohexane to afford product (45 mg). $^1$H NMR (500 MHz, CDCl$_3$): 7.39 (1H, s), 7.16-7.39 (9H, m), 5.1 (1H, br), 4.91 (2H, s), 4.25 (2H, t), 2.83 (2H, t), 2.3-2.5 (4H, m), 2.04-2.09 (1H, m), 1.79-1.84 (1H, m), 1.27-1.36 (9H, br).

Step 2: 3-(6-(4-(1-aminocyclobutyl)phenyl)-2-oxo-7-phenyl-2,3-dihydro-1H-pyrido[2,3-b][1,4]oxazin-1-yl)propanenitrile tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate (15 mg, 0.029 mmol) was dissolved in TFA (0.5 mL) and stirred for 30 seconds. The solution was immediately concentrated to dryness under reduced pressure. The residue was dissolved in diethyl ether (1 mL) and concentrated to dryness under reduced pressure three times. The residue was then slurried in diethyl ether (0.5 mL) and after settling the supernatant solvent removed by pipette. This was repeated three times. The remaining solvent was removed under reduced pressure and dried to give the desired product as an off-white solid (12 mg). $^1$H NMR (500 MHz, CH$_3$OD) 7.77 (1H, s), 7.43 (2H, d), 7.39 (2H, d), 7.3 (3H, m), 7.27 (2H, m), 4.99 (2H, s), 4.37 (2H, t), 2.94 (2H, t), 2.73-2.79 (2H, m), 2.55-2.61 (2H, m), 2.2-2.27 (1H, m), 1.93-1.99 (1H, m). LCMS (Method A): R$_T$=3.73 min, M+H$^+$=425.

Example 63

1-(4-(1-methyl-8-phenyl-4H-pyrido[2,3-b][1,2,4]triazolo[4,3-d][1,4]oxazin-7-yl)phenyl)cyclobutan-amine

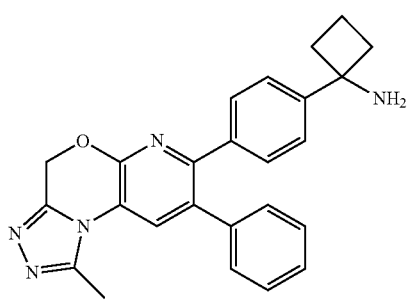 [SMILES: Cc1nnc2n1-c1cc(-c3ccccc3)c(-c3ccc(C4(N)CCC4)cc3)nc1OC2]

Step 1: Tert-butyl (1-(4-(1-methyl-8-phenyl-4H-pyrido[2,3-b][1,2,4]triazolo[4,3-d][1,4]oxazin-7-yl)phenyl)cyclobutyl)carbamate A solution of (E)-tert-butyl(1-(4-(2-hydrazono-7-phenyl-2,3-dihydro-1H-pyrido[2,3-b][1,4]oxazin-6-yl)phenyl)cyclobutyl)carbamate (50 mg, 0.103 mmol) in 1,1,1-trimethoxyethane (1 ml) was heated to 150° C. for 15 minutes under microwave irradiation. The resulting reaction mixture was concentrated to dryness under reduced pressure and purified by Biotage silica gel chromatography (gradient 0% to 100% ethyl acetate in n-hexanes) to give the title compound (24 mg, 47%). LCMS (Method A): R$_T$=6.71 min, M+1=510. $^1$H NMR (500 MHz, CDCl$_3$): 7.84 (1H, s), 7.37-7.33 (5H, m), 7.30-7.27 (2H, m), 7.24-7.19 (2H, m), 5.59 (2H, s), 2.87 (3H, s), 2.54-2.40 (4H, m), 2.13-2.02 (1H, m), 1.87-1.78 (1H, m), 1.45-1.27 (9H, br s).

Step 2: 1-(4-(1-methyl-8-phenyl-4H-pyrido[2,3-b][1,2,4]triazolo[4,3-d][1,4]oxazin-7-yl)phenyl)cyclobutanamine Tert-butyl (1-(4-(1-methyl-8-phenyl-4H-pyrido[2,3-b][1,2,4]triazolo[4,3-d][1,4]oxazin-7-yl)phenyl)cyclobutyl)carbamate (11 mg, 0.022 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent removed by pipette. This was repeated three times. The residue was then slurred in n-hexanes (2 ml) and after settling the supernatant solvent removed by pipette. This was repeated three times. The remaining solvent was removed under reduced pressure and the residue was dried to give the desired product as an off-white solid (5 mg, 55% yield). LCMS (Method A): RT=3.71 min, M+1=411. $^1$H-NMR (500 MHz, CD$_3$OD) δ 8.11 (1H, s), 7.49-7.44 (2H, d), 7.42-7.37 (2H, d), 7.35-7.30 (3H, m), 7.29-7.25 (2H, m), 5.63 (2H, s), 2.84 (3H, s), 2.80-2.70 (2H, m), 2.61-2.51 (2H, m), 2.28-2.17 (1H, m), 2.01-1.88 (1H, m).

Example 64

4-(6-(4-(1-aminocyclobutyl)phenyl)-2-oxo-7-phenyl-2,3-dihydro-1H-pyrido[2,3-b][1,4]oxazin-1-yl)butanenitrile

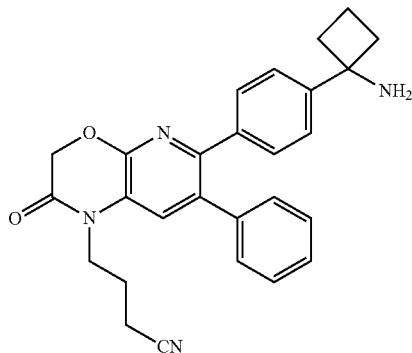 [SMILES: N#CCCCN1C(=O)COc2nc(-c3ccc(C4(N)CCC4)cc3)c(-c3ccccc3)cc21]

Step 1: tert-butyl(1-(4-(1-(3-cyanopropyl)-2-oxo-7-phenyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 4-bromobutanenitrile (94 mg, 0.636 mmol) to afford the title compound (68 mg. $^1$H NMR (500 MHz, CDCl$_3$): 7.20-7.32 (10H, m), 5.1 (1H, br), 4.90 (2H, s), 4.11 (2H, m), 2.44-2.50 (6H, m), 2.05-2.13 (3H, m), 1.79-1.84 (1H, m), 1.27-1.36 (9H, br).

Step 2: 4-(6-(4-(1-aminocyclobutyl)phenyl)-2-oxo-7-phenyl-2,3-dihydro-1H-pyrido[2,3-b][1,4]oxazin-1-yl)butanenitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(3-cyanopropyl)-2-oxo-7-phenyl-2,3-dihydro-1H-pyrido[2,3-b][1,4]oxazin-6-yl)phenyl)cyclobutyl)carbamate (35 mg, 0.065 mmol) was reacted to afford the title compound (28 mg). $^1$H NMR (500 MHz, CH$_3$OD) 7.62 (1H, s), 7.41 (2H, d), 7.39 (2H, d), 7.3 (3H, m), 7.25 (2H, m), 4.98 (2H, s), 4.19 (2H, t), 2.73-2.79 (2H, m), 2.55-2.61 (4H, m), 2.22-2.25 (1H, m), 2.10-2.25 (2H, m), 1.95-1.99 (1H, m). LCMS (Method A): R$_T$=4.01 min, M+H$^+$=440.2.

Example 65

6-(4-(1-aminocyclobutyl)phenyl)-7-phenyl-1-(tetrahydro-2H-pyran-4-yl)-1H-pyrido[2,3-b][1,4]oxazin-2(3H)-one

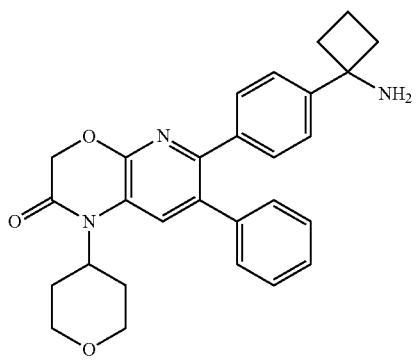 [SMILES: NC1(c2ccc(-c3nc4c(cc3-c3ccccc3)N(C3CCOCC3)C(=O)CO4)cc2)CCC1]

Step 1: tert-butyl(1-(4-(6-hydroxy-3-phenyl-5-((tetrahydro-2H-pyran-4-yl)amino)pyridin-2-yl)phenyl) cyclobutyl)carbamate To a solution of tert-butyl(1-(4-(5-amino-6-hydroxy-3-phenylpyridin-2-yl)phenyl)cyclobutyl)carbamate (200 mg, 0.46 mmol) in dry DCE (2 ml) was added dihydro-2H-pyran-4(3H)-one (88 mg, 0.88 mmol), AcOH (0.16 ml, 2.78 mmol), sodium triacetoxyborohydride (275 mg, 1.30 mmol) under nitrogen. The resulting mixture was stirred for 3 h at room temperature. A saturated solution of NaHCO$_3$ was added and the mixture was extracted with AcOEt (3×10 ml). The combined organic phases were dried over Na$_2$SO$_4$ and concentrated to dryness under reduced pressure. The resulting residue was used in the next step without any purification.

Step 2: tert-butyl(1-(4-(2-oxo-7-phenyl-1-(tetrahydro-2H-pyran-4-yl)-2,3-dihydro-1H-pyrido[2,3-b][1,4]oxazin-6-yl)phenyl)cyclobutyl)carbamate To a solution of tert-butyl(1-(4-(6-hydroxy-3-phenyl-5-((tetrahydro-2H-pyran-4-yl)amino)pyridin-2-yl)phenyl)cyclobutyl)carbamate (240 mg, 0.46 mmol) in dry THF (11 mL) was added N,N-diisopropylethylamine (0.41 mL, 2.32 mmol). 2-chloroacetyl chloride (0.19 mL, 2.32 mmol) was added dropwise at 0 C. The resulting mixture was stirred overnight at room temperature. A saturated solution of NaHCO$_3$ (8 mL) was added and the mixture was stirred under reflux for 2 hours. After allowing to cool to room temperature, the organic phase was separated and the aqueous phase extracted with AcOEt (3×10 ml). The combined organic phases were dried over Na$_2$SO$_4$ and concentrated to dryness under reduced pressure. The resulting residue was purified by Biotage silica gel chromatography (gradient 0 to 50% EtOAc in cyclohexane) to give the title compound (154 mg, 59%). $^1$H NMR (500 MHz, CDCl$_3$): 7.45 (1H, s), 7.24-7.22 (5H, m), 7.19-7.17 (2H, m), 7.14-7.12 (2H, m), 4.94 (1H, s), 4.71 (2H, s), 4.60-4.55 (1H, m), 4.07-4.03 (2H, m), 3.45 (2H, t), 2.63-2.54 (2H, m), 2.52-2.20 (4H, m), 2.00-1.95 (1H, m), 1.79-1.65 (3H, m), 1.40-1.10 (9H, br).

Step 3: 6-(4-(1-aminocyclobutyl)phenyl)-7-phenyl-1-(tetrahydro-2H-pyran-41)-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-7-phenyl-1-(tetrahydro-2H-pyran-4-yl)-2,3-dihydro-1H-pyrido[2,3-b][1,4]oxazin-6-yl)phenyl)cyclobutyl)carbamate (55 mg, 0.10 mmol) was reacted to afford the title compound (53 mg, 93%). LCMS (Method A): R$_T$=4.19 min, M+1=457. $^1$H NMR (500 MHz, MeOD): 7.76 (1H, S), 7.44-7.38 (4H, m), 7.33-7.31 (3H, m), 7.27-7.25 (2H, m), 4.90 (2H, s), 4.59-4.53 (1H, m), 4.09-4.06 (2H, m), 3.60 (2H, t), 2.80-2.72 (4H, m), 2.59-2.53 (2H, m), 2.25-2.21 (1H, m), 1.98-1.94 (1H, m), 1.81-1.79 (2H, m).

Example 66

5-(6-(4-(1-aminocyclobutyl)phenyl)-2-oxo-7-phenyl-2,3-dihydro-1H-pyrido[2,3-b][1,4]oxazin-1-yl)pentanenitrile

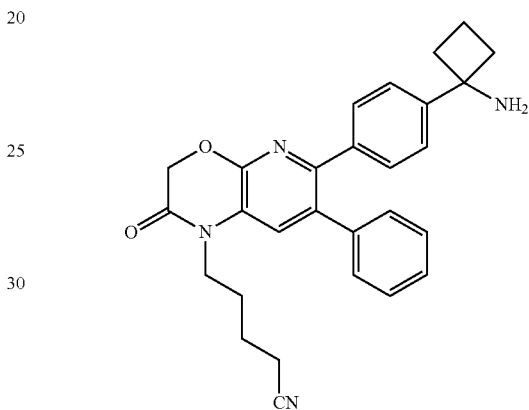

Step 1: tert-butyl(1-(4-(1-(4-cyanobutyl)-2-oxo-7-phenyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 5-bromopentanenitrile (103 mg, 0.636 mmol) to afford the title compound (82 mg. $^1$H NMR (500 MHz, CDCl$_3$): 7.20-7.33 (10H, m), 5.03 (1H, br), 4.91 (2H, s), 4.05 (2H, t), 2.45-2.51 (6H, m), 2.05-2.10 (1H, m), 1.88-1.94 (2H, m), 1.67-1.85 (3H, m), 1.27-1.38 (9H, br).

Step 2: 5-(6-(4-(1-aminocyclobutyl)phenyl)-2-oxo-7-phenyl-2,3-dihydro-1H-pyrido[2,3-b][1,4]oxazin-1-yl)pentanenitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(4-cyanobutyl)-2-oxo-7-phenyl-2,3-dihydro-1H-pyrido[2,3-b][1,4]oxazin-6-yl)phenyl)cyclobutyl)carbamate (25 mg, 0.045 mmol) was reacted to afford the title compound (14.5 mg). $^1$H NMR (500 MHz, CH$_3$OD) 7.60 (1H, s), 7.42 (2H, d), 7.39 (2H, d), 7.31 (3H, m), 7.25 (2H, m), 4.97 (2H, s), 4.11 (2H, t), 2.73-2.79 (2H, m), 2.54-2.61 (4H, m), 2.22-2.25 (1H, m), 1.95-1.97 (1H, m), 1.84-1.89 (2H, m), 1.74-1.78 (2H, m). LCMS (Method A): R$_T$=4.19 min, M+H$^+$=453.5.

Example 67

1-allyl-6-(4-(1-aminocyclobutyl)phenyl)-7-phenyl-1H-pyrido[2,3-b][1,4]oxazin-2(3H)-one

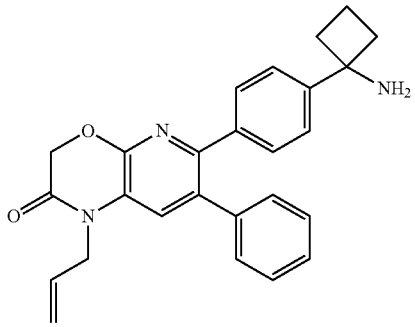 [SMILES: C=CCN1C(=O)COc2nc(-c3ccc(C4(N)CCC4)cc3)c(-c3ccccc3)cc21]

Step 1: tert-butyl 1-(4-(1-allyl-2-oxo-7-phenyl-2,3-dihydro-1H-pyrido[2,3-b][1,4]oxazin-6-yl)phenyl)cyclobutylcarbamate In a sealed tube was added tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) in DMF to give a brown solution. bromocyclopropane (76.9652 mg, 0.636 mmol) and potassium carbonate were added. The reaction mixture was heated at 80 degree for 16 h. The reaction mixture was then heated under microwave 100 degree for 2 h and 130 degree for 8 h. The reaction mixture was partitioned between dichloromethane (20 ml) and water (20 ml). The organic phase was separated using phase separator and concentrated. The crude product was purified by column (biotage, 25 g) eluted with ethyl acetate/cyclohexane to afford product (12 mg). $^1$H NMR (500 MHz, CDCl$_3$) 7.17-7.23 (m, 8H), 7.07-7.10 (m, 2H), 5.77-5.84 (m, 1H), 5.18-5.24 (m, 2H), 4.51 (d, 2H), 2.2-2.5 (m, 4H), 1.9-2.0 (m, 1H), 1.69-1.79 (m, 1H), 1.1-1.35 (br, 9H). LCMS (Method A): R$_T$=7.9 min, M+H$^+$=512.17.

Step 2: 1-allyl-6-(4-(1-aminocyclobutyl)phenyl)-7-phenyl-1H-pyrido[2,3-b][1,4]oxazin-2(3H)-one to a round bottomed flask containing tert-butyl 1-(4-(1-allyl-2-oxo-7-phenyl-2,3-dihydro-1H-pyrido[2,3-b][1,4]oxazin-6-yl)phenyl)cyclobutylcarbamate (6.5 mg, 0.013 mmol) was added trifluoroacetic acid (0.5 ml). The resulting solution was stirred for 60 seconds then concentrated to dryness under reduced pressure. The residue was dissolved in diethyl ether (1 ml) and concentrated to dryness three times to give the trifluoroacetic acid salt of the product (3.55 mg) (3.55 mg). $^1$H NMR (500 MHz, CD$_3$OD) 7.49 (s, 1H), 7.38-7.43 (m, 4H), 7.29-7.30 (m, 3H), 7.18-7.20 (m, 2H), 5.9-6.0 (m, 1H), 5.25-5.35 (m, 2H), 5.01 (s, 2H), 4.68 (d, 2H), 2.7-2.8 (m, 2H), 2.55-2.65 (m, 2H), 2.21-2.27 (m, 1H), 1.9-2.0 (m, 1H), LCMS (Method A): R$_T$=4.38 min, M+H$^+$=413.18.

Example 68

6-(4-(1-aminocyclobutyl)phenyl)-1-(2-hydroxyethyl)-7-phenyl-1H-pyrido[2,3-b][1,4]oxazin-2(3H)-one

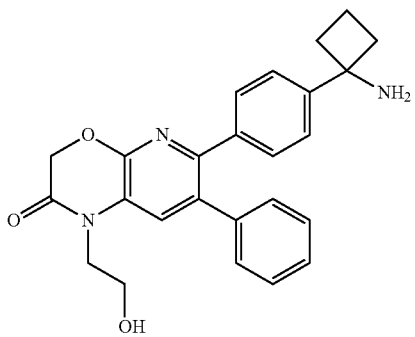 [SMILES: NC1(c2ccc(-c3nc4c(cc3-c3ccccc3)N(CCO)C(=O)CO4)cc2)CCC1]

Step 1 tert-butyl(1-(4-(1-(2-hydroxyethyl)-2-oxo-7-phenyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 2-bromoethanol (80 mg, 0.636 mmol) to afford the title compound (75 mg. $^1$H NMR (500 MHz, CDCl$_3$): 7.47 (s, 1H), 7.23-7.29 (m, 7H), 7.16-7.19 (m, 2H), 5.04 (br, 1H), 4.89 (s, 2H), 4.12 (m, 2H), 3.94 (m, 2H), 2.37-2.48 (m, 4H), 2.37 (t, 1H), 2.05 (m, 1H), 1.81 (m, 1H), 1.2-1.43 (br, 9H).

Step 2: 6-(4-(1-aminocyclobutyl)phenyl)-1-(2-hydroxyethyl)-7-phenyl-1H-pyrido[2,3-b][1,4]oxazin-2(3H)-one to a round bottomed flask containing tert-butyl 1-(4-(1-(2-hydroxyethyl)-2-oxo-7-phenyl-2,3-dihydro-1H-pyrido[2,3-b][1,4]oxazin-6-yl)phenyl)cyclobutylcarbamate (25 mg, 0.048 mmol) was added dichloromethane (2.5 ml) followed with hydrochloric acid (2.5 ml, 2M in diethyl ether). The resulting solution was stirred for 16 h. The precipitate was filtered and washed with ether (2×10 ml) and dried to afford the product (15.5 mg). $^1$H NMR (500 MHz, CH$_3$OD) 7.78 (s, 1H), 7.42 (d, 2H), 7.38 (d, 2H), 7.30 (m, 3H), 7.22 (m, 2H), 4.96 (s, 2H), 4.16 (t, 2H), 3.86 (t, 2H), 2.73-2.79 (m, 2H), 2.54-2.60 (m, 2H), 2.21-2.26 (m, 1H), 1.94-1.99 (m, 1H). LCMS (Method D): R$_T$=1.99 min, M+H$^+$=416.2.

Example 69

1-(4-(8-phenyl-1-propyl-4H-pyrido[2,3-b][1,2,4]triazolo[4,3-d][1,4]oxazin-7-yl)phenyl)cyclobutanamine

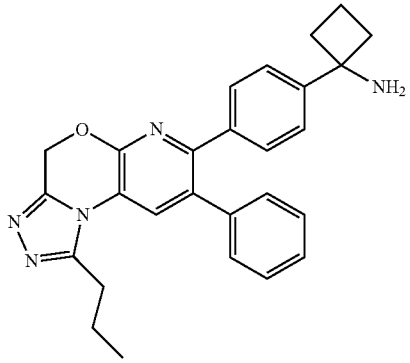 [SMILES: CCCc1nnc2n1-c1cc(-c3ccccc3)c(-c3ccc(C4(N)CCC4)cc3)nc1OC2]

Step 1: Tert-butyl (1-(4-(8-phenyl-1-propyl-4H-pyrido[2,3-b][1,2,4]triazolo[4,3-d][1,4]oxazin-7-yl)phenyl)cyclobutyl)carbamate A solution of (E)-tert-butyl(1-(4-(2-hydrazono-7-phenyl-2,3-dihydro-1H-pyrido[2,3-b][1,4]oxazin-6-yl)phenyl)cyclobutyl)carbamate (60 mg, 0.124 mmol) in 1,1,1-trimethoxybutane (1 ml) was heated to 150° C. for 15 minutes under microwave irradiation. The resulting reaction mixture was concentrated to dryness under reduced pressure and purified by Biotage silica gel chromatography (gradient 0% to 100% ethyl acetate in n-hexanes) to give the title compound (30 mg, 45%). LCMS (Method A): R$_T$=7.34 min, M+1=538. $^1$H NMR (500 MHz, CDCl$_3$): 7.80 (1H, s), 7.36-7.32 (5H, m), 7.31-7.27 (2H, m), 7.23-7.19 (2H, m), 5.57 (2H, s), 3.08 (2H, t), 2.55-2.40 (4H, m), 2.15-2.03 (1H, m), 2.00 (2H, q), 1.89-1.77 (1H, m), 1.41-1.29 (9H, br), 1.12 (3H, t).

Step 2: 1-(4-(8-phenyl-1-propyl-4H-pyrido[2,3-b][1,2,4]triazolo[4,3-d][1,4]oxazin-7-yl)phenyl)cyclobutanamine Tert-butyl (1-(4-(8-phenyl-1-propyl-4H-pyrido[2,3-b][1,2,4]triazolo[4,3-d][1,4]oxazin-7-yl)phenyl)cyclobutyl)carbamate (39 mg, 0.073 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure three times. The residue was then slurred in diethyl ether (2 ml) and after settling the supernatant solvent removed by pipette. This was repeated three times. The residue was then slurred in n-hexane (2 ml) and after settling the supernatant solvent removed by pipette. This was repeated three times. The remaining solvent was removed under reduced pressure and the residue was dried to give the desired product as an off-white solid (10 mg, 30% yield). LCMS (Method A): RT=3.85 min, M+1=439. $^1$H-NMR (500 MHz, CD$_3$OD) δ 8.09 (1H, s), 7.50 (2H, d), 7.43 (2H, d), 7.37-7.34 (3H, m), 7.31-7.27 (2H, m), 5.66 (2H, s), 3.2 (2H, t), 2.83-2.71 (2H, m), 2.64-2.54 (2H, m), 2.32-2.19 (1H, m), 2.02-1.90 (1H, m+2H, t), 1.16-1.09 (3H, t).

Example 70

1-(4-(1-(methylsulfonyl)-7-phenyl-2,3-dihydro-1H-pyrido[2,3-b][1,4]oxazin-6-yl)phenyl)cyclobutanamine

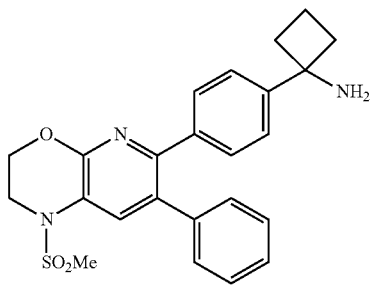 [SMILES: CS(=O)(=O)N1CCOc2nc(-c3ccc(C4(N)CCC4)cc3)c(-c3ccccc3)cc21]

Step 1: tert-butyl(1-(4-(1-(methylsulfonyl)-7-phenyl-2,3-dihydro-1H-pyrido[2,3-b][1,4]oxazin-6-yl)phenyl)cyclobutyl)carbamate To a solution of tert-butyl(1-(4-(7-phenyl-2,3-dihydro-1H-pyrido[2,3-b][1,4]oxazin-6-yl)phenyl)cyclobutyl)carbamate (50 mg, 0.11 mmol) in dry DCM (1 ml) was added triethyl amine (46 µl, 0.33 mmol) and methanesulfonyl chloride (26 µl, 0.33 mmol) under nitrogen. The resulting mixture was stirred for 1 hour at room temperature. A saturated solution of NaHCO$_3$ was added and the mixture was extracted with dichloromethane (3×10 ml) using a phase separator (Isolute® SPE). The combined organic phases were concentrated to dryness under reduced pressure. The resulting residue was purified by Biotage silica gel chromatography (gradient 0 to 50% EtOAc in cyclohexane) to give the title compound (45 mg, 77%). $^1$H NMR (500 MHz, CDCl$_3$): 8.00 (1H, s), 7.25 (2H, d), 7.19-7.17 (5H, m), 7.11-7.10 (2H, m), 4.95 (1H, s), 4.43 (2H, t), 3.90 (2H, t), 2.55-2.25 (7H, m), 2.06-1.98 (1H, m), 1.82-1.73 (1H, m), 1.44-1.15 (9H, br).

Step 2: 1-(4-(1-(methylsulfonyl)-7-phenyl-2,3-dihydro-1H-pyrido[2,3-b][1,4]oxazin-6-yl)phenyl)cyclobutanamine Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-(methylsulfonyl)-7-phenyl-2,3-dihydro-1H-pyrido[2,3-b][1,4]oxazin-6-yl)phenyl)cyclobutyl)carbamate (45 mg, 0.08 mmol) was reacted to afford the title compound (44 mg, 95%). LCMS (Method A): R$_T$=2.34 min, M+1=437. $^1$H NMR (500 MHz, MeOD): 8.15 (1H, s), 7.43-7.38 (4H,m), 7.30-7.28 (3H, m), 7.21-7.19 (2H, m), 4.57 (2H, t), 4.01 (2H, t), 3.19 (3H, s), 2.79-2.73 (2H, m), 2.60-2.54 (2H, m), 2.24-2.21 (1H, m), 1.99-1.94 (1H, m).

Example 71

6-(4-(1-aminocyclobutyl)phenyl)-3-(2-hydroxyethyl)-7-phenyl-1H-pyrido[2,3-b][1,4]oxazin-2(3H)-one

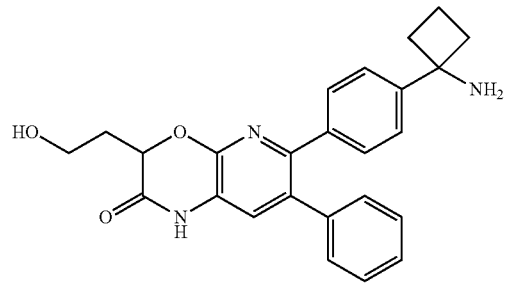 [SMILES: NC1(c2ccc(-c3nc4c(cc3-c3ccccc3)NC(=O)C(CCO)O4)cc2)CCC1]

Step 1: tert-butyl(1-(4-(3-(2-hydroxyethyl)-2-oxo-7-phenyl-2,3-dihydro-1H-pyrido[2,3-b][1,4]oxazin-6-yl)phenyl)cyclobutyl)carbamate In a 100 mL round bottom flask was added tert-butyl 1-(4-(5-amino-6-oxo-3-phenyl-1,6-dihydropyridin-2-yl)phenyl)cyclobutylcarbamate (0.5 g, 1.159 mmol) in THF (Volume: 25 ml) to give a red suspension followed with the addition of DIPEA (1.0 ml). 2,4-dibromobutanol chloride (0.735 g, 2.78 mmol) in THF (5 ml) was added in drop wise at 0 degree. The resulted mixture was stirred at room temperature for 20 hours. The reaction mixture was transferred to a 250 ml round bottom flask and sodium bicarbonate saturated solution (40 ml) and sodium bicarbonate (1 g) was added. The resulted mixture was heated to reflux for 24 h. The reaction mixture was cooled down to room temperature. The organic phase was separated. The aqueous phase was extracted with ethyl acetate (45 ml). The organic phases were combined and washed with water (30 mlX2), brine (25 ml) then concentrated at reduced pressure. The residue was suspended in DCM (10 ml). The precipitate was collected by filtration and washed with DCM (5 ml) to afford crude product which was purified by biotage column (25 g silicon) to afford tert-butyl 1-(4-(3-(2-hydroxyethyl)-2-oxo-7-phenyl-2,3-dihydro-1H-pyrido[2,3-b][1,4]oxazin-6-yl)phenyl)cyclobutylcarbamate (45 mg) and tert-butyl 1-(4-(7-phenyl-3,3a-dihydro-2H-furo[2,3-e]pyrido[2,3-b][1,4]oxazin-6-yl)phenyl)cyclobutylcarbamate (0.35 g). $^1$H NMR (500 MHz, CD$_3$OD): 7.50 (s, 1H), 7.31 (m, 2H), 7.26 (m, 5H), 7.16 (m, 2H), 5.38 (dd, 1H), 4.72 (t, 1H), 4.55 (m, 1H), 2.92 (m, 1H), 2.67 (m, 1H), 2.43-2.47 (m, 4H), 2.07 (m, 1H), 1.85 (m, 1H), 1.23-1.39 (br, 9H).

LCMS (Method A): $R_T$=6.89 min, M+H$^+$=498.12. A solution of tert-butyl 1-(4-(7-phenyl-3,3a-dihydro-2H-furo[2,3-e]pyrido[2,3-b][1,4]oxazin-6-yl)phenyl)cyclobutylcarbamate (0.35 g, 0.703 mmol) in DCM (15 ml) and acetic acid (10 ml) was stirred at room temp for 48 h. The reaction mixture was concentrated and portioned between ethyl acetate (40 ml) and water (30 ml). The separated organic phase was washed with water (2×25 ml), brine and concentrated to give product 0.36 g (45 mg). $^1$H NMR (500 MHz, CD$_3$OD): 7.23-7.31 (m, 8H), 7.16 (m, 2H), 5.05 (dd, 1H), 3.91 (m, 1H), 3.85 (m, 1H), 2.45 (m, 4H), 2.26 (m, 1H), 2.15 (m, 1H), 2.07 (m, 1H), 1.86 (m, 1H), 1.23-1.39 (br, 9H). LCMS (Method A): $R_T$=5.92 min, M+H$^+$=516.04.

Step 2: 6-(4-(1-aminocyclobutyl)phenyl)-3-(2-hydroxyethyl)-7-phenyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(4-cyanobutyl)-2-oxo-7-phenyl-2,3-dihydro-1H-pyrido[2,3-b][1,4]oxazin-6-yl)phenyl)cyclobutyl)carbamate (15 mg, 0.029 mmol) was reacted to afford the title compound (8.5 mg). $^1$H NMR (500 MHz, CD$_3$OD): 7.28-7.42 (m, 8H), 7.18 (m, 2H), 5.08 (dd, 1H), 3.84-3.93 (m, 2H), 2.73-2.79 (m, 2H), 2.55-2.61 (m, 2H), 2.25-2.29 (m, 2H), 2.15-2.24 (m, 1H), 1.95-1.97 (m, 1H). LCMS (Method A): $R_T$=3.49 min, M+H$^+$=416.18.

Example 72

6-(4-(1-aminocyclobutyl)phenyl)-4-methyl-7-phenyl-3,4-dihydropyrido[2,3-b]pyrazin-2(1H)-one

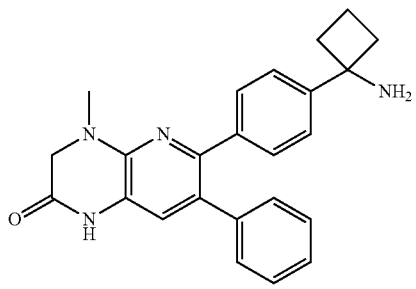 [SMILES: CN1CC(=O)Nc2cc(-c3ccccc3)c(-c3ccc(C4(N)CCC4)cc3)nc21]

Step 1: methyl 24(6-(4-(1-((tert-butoxycarbonyl)amino)cyclobutyl)phenyl)-3-nitro-5-phenylpyridin-2-yl)(methyl)amino)acetate In a microwave vial were added tert-butyl(1-(4-(6-chloro-5-nitro-3-phenylpyridin-2-yl)phenyl)cyclobutyl)carbamate (200 mg, 0.417 mmol), methyl 2-(methylamino)acetate hydrochloride (58 mg, 0.417 mmol) and triethylamine (58 μl, 0.417 mmol) in methanol (2 ml). The solution was heated to 80° C. under microwave irradiation for 1 hour. The reaction mixture was concentrated to dryness under reduced pressure and purified by Biotage chromatography (cyclohexane:ethyl acetate, gradient elution from 100:0 to 0:100) to afford the title compound (103 mg, 65%). $^1$H NMR (500 MHz, CDCl$_3$): 8.29 (1H, s), 7.25-7.38 (7H, m), 7.15-7.23 (2H, m), 5.05 (1H, br s), 4.39 (2H, s), 3.83 (3H, s), 3.11 (3H, s), 2.25-2.65 (4H, m), 2.05-2.20 (1H, m), 1.80-1.95 (1H, m), 1.10-1.50 (9H, br).

Step 2: tert-butyl(1-(4-(4-methyl-2-oxo-7-phenyl-1,2,3,4-tetrahydropyrido[2,3-b]pyrazin-6-yl)phenyl)cyclobutyl)carbamate In a glass autoclave were added methyl 2-((6-(4-(1-((tert-butoxycarbonyl)amino)cyclobutyl)phenyl)-3-nitro-5-phenylpyridin-2-yl)(methyl)amino)acetate (800 mg, 1.46 mmol) and 10% palladium on carbon (300 mg, 0.28 mmol) in THF (100 ml). The solution was hydrogenated at room temperature under 1.5 atm hydrogen for 20 hours. The reaction mixture was filtered through celite, then concentrated to dryness under reduced pressure. The residue was purified by Biotage chromatography (cyclohexane:ethyl acetate, gradient elution from 100:0 to 0:100) to afford the title compound (270 mg, 38%). $^1$H NMR (500 MHz, CDCl$_3$): 7.35 (2H, d), 7.20-7.33 (5H, m), 7.15 (2H, d), 6.98 (1H, s), 5.05 (1H, br s), 4.11 (2H, s), 3.18 (3H, s), 2.20-2.70 (4H, br m), 2.00-2.14 (1H, m), 1.77-1.87 (1H, m), 1.10-1.50 (9H, br).

Step 3: 6-(4-(1-aminocyclobutyl)phenyl)-4-methyl-7-phenyl-3,4-dihydropyrido[2,3-b]pyrazin-2(1H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl 1-(4-(4-methyl-2-oxo-7-phenyl-1,2,3,4-tetrahydropyrido[2,3-b]pyrazin-6-yl)phenyl)cyclobutylcarbamate (29 mg, 0.060 mmol) was reacted to afford the title compound (29 mg, 97%). LCMS (Method A): $R_T$=3.69 min, M+2H$^+$=386. $^1$H NMR (500 MHz, MeOD): 7.44 (2H, d), 7.32 (2H, d), 7.20-7.28 (3H, m), 7.12 (2H, d), 7.02 (1H, s), 4.08 (2H, s), 3.11 (3H, s), 2.70-2.80 (2H, m), 2.50-2.63 (2H, m), 2.13-2.27 (1H, m), 1.88-2.02 (1H, m).

Example 73

6-(4-(1-aminocyclobutyl)phenyl)-1-methyl-7-phenyl-1H-pyrido[3,2-e][1,3,4]oxathiazine 2,2-dioxide

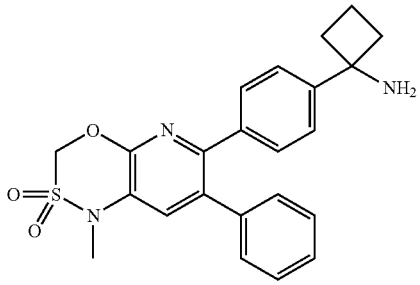 [SMILES: CN1c2cc(-c3ccccc3)c(-c3ccc(C4(N)CCC4)cc3)nc2OCS1(=O)=O]

Step 1: tert-butyl(1-(4-(2,2-dioxido-7-phenyl-1H-pyrido[3,2-e][1,3,4]oxathiazin-6-yl)phenyl)cyclobutyl)carbamate In a 40 mL reaction tube was added tert-butyl 1-(4-(5-amino-6-oxo-3-phenyl-1,6-dihydropyridin-2-yl)phenyl)cyclobutylcarbamate (500 mg, 1.159 mmol) in anhydrous pyridine (5 mL) to give a yellow solution. After stirring at room temperature for 15 minutes, chloromethanesulfonyl chloride (126 μl, 1.390 mmol) was added and the resulting solution stirred at room temperature for 3 hours. The reaction mixture was concentrated to dryness under reduced pressure and redissolved in anhydrous methanol (5 mL), followed by the addition of potassium carbonate (641 mg, 4.63 mmol) and heating to 60° C. overnight. The reaction mixture was allowed to cool to room temperature and concentrated to dryness under reduced pressure. The residue was redissolved in ethyl acetate (5 mL) and washed with 50:50 water:brine (2×5 mL), dried over $Na_2SO_4$, filtered and concentrated to dryness under reduced pressure to give a brown oil. This was purified by Biotage chromatography (cyclohexane:ethyl acetate:dichloromethane:methanol, gradient elution from 80:10:10:0 to 0:90:10:0 then to 0:90:10) to give the desired product as an off-white solid (330 mg, 56% yield). $^1$H-NMR (500 MHz, $d_6$-Acetone) δ 7.35 (1H, s), 7.23-7.32 (7H, m), 7.16-7.32 (2H, m), 5.39 (2H, s), 2.30-2.60 (4H, m), 2.00-2.12 (1H, m), 1.75-1.88 (1H, m), 1.05-1.40 (9H, br m). LCMS (Method A) RT=6.68 min, M+H$^+$=508.01.

Step 2: tert-butyl(1-(4-(1-methyl-2,2-dioxido-7-phenyl-1H-pyrido[3,2-e][1,3,4]oxathiazin-6-yl)phenyl)cyclobutyl)carbamate In a 15 mL reaction tube was added tert-butyl(1-(4-(2,2-dioxido-7-phenyl-1H-pyrido[3,2-e][1,3,4]oxathiazin-6-yl)phenyl)cyclobutyl)carbamate (50 mg, 0.099 mmol), potassium carbonate (41 mg, 0.296 mmol) and iodomethane (7.5 μL, 0.118 mmol) in anhydrous N,N-dimethylformamide (1 mL) to give an orange suspension. The reaction mixture was stirred at room temperature for 2 hours, then diluted with saturated sodium bicarbonate solution (5 mL) and extracted into dichloromethane (3×3 mL). The combined organic phases were dried over $Na_2SO_4$, filtered and concentrated to dryness under reduced pressure to give a yellow oil. This was purified by Biotage chromatography (cyclohexane:ethyl acetate, gradient elution from 90:10 to 20:80) to give the desired product as a colourless oil (50 mg, 97% yield). $^1$H-NMR (500 MHz, CDCl$_3$) δ 7.24-7.47 (8H, m), 7.16-7.23 (2H, m), 5.23 (2H, s), 5.05 (1H, br s), 3.36 (3H, s), 2.20-2.65 (4H, m), 2.01-2.15 (1H, m), 1.77-1.90 (1H, m), 1.10-1.50 (9H, br m). LCMS (Method A) RT=7.16 min, M+H$^+$=522.01.

Step 3: 6-(4-(1-aminocyclobutyl)phenyl)-1-methyl-7-phenyl-1H-pyrido[3,2-e][1,3,4]oxathiazine 2,2-dioxide tert-Butyl (1-(4-(1-methyl-2,2-dioxido-7-phenyl-1H-pyrido[3,2-e][1,3,4]oxathiazin-6-yl)phenyl)cyclobutyl)carbamate (50 mg, 0.096 mmol) was dissolved in TFA (3 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as an off-white solid (32 mg, 62% yield). $^1$H-NMR (500 MHz, MeOD) δ 7.58 (1H, s), 7.41 (2H, d), 7.37 (2H, d), 7.25-7.33 (3H, m), 7.17-7.25 (2H, m), 5.45 (2H, s), 3.35 (3H, s), 2.66-2.78 (2H, m), 2.46-2.57 (2H, m), 2.12-2.25 (1H, m), 1.85-1.97 (1H, m). LCMS (Method A) RT=3.98 min, M+2H$^+$=423.13.

Example 74

6-(4-(1-aminocyclobutyl)phenyl)-7-phenyl-1-(pyridin-3-yl)-1H-pyrido[3,2-e][1,3,4]oxathiazine 2,2-dioxide

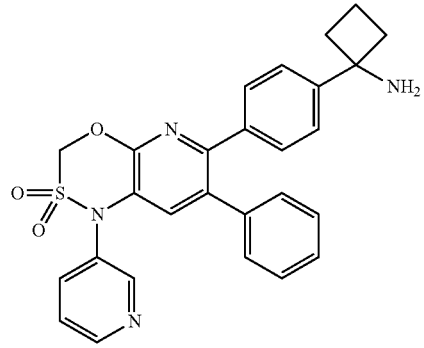 [SMILES: NC1(c2ccc(-c3nc4c(cc3-c3ccccc3)N(c3cccnc3)S(=O)(=O)CO4)cc2)CCC1]

Step 1: tert-butyl(1-(4-(2,2-dioxido-7-phenyl-1-(pyridin-3-yl)-1H-pyrido[3,2-e][1,3,4]oxathiazin-6-yl)phenyl)cyclobutyl)carbamate In a 15 mL reaction tube was added tert-butyl (1-(4-(2,2-dioxido-7-phenyl-1H-pyrido[3,2-e][1,3,4]oxathiazin-6-yl)phenyl)cyclobutyl)carbamate (50 mg, 0.099 mmol), pyridin-3-ylboronic acid (24 mg, 0.197 mmol), copper(II)acetate (27 mg, 0.148 mmol) and 5 Å molecular sieves (30 mg) in anhydrous dichloromethane (1 ml). To this was added anhydrous pyridine (16 μl, 0.197 mmol) and the resulting black suspension stirred at room temperature under air for 24 hours. Further pyridine (1 mL) was added and the resulting black solution stirred at room temperature for 24 hours. Further pyridin-3-ylboronic acid (24 mg, 0.197 mmol) and copper (II)acetate (27 mg, 0.148 mmol) were added and the mixture stirred at room temperature for 72 hours. The reaction mixture was concentrated to dryness under reduced pressure and the residue purified by Biotage chromatography (cyclohexane:ethyl acetate, gradient elution from 88:12 to 0:100) to give the desired product as an off-white solid (40 mg 70% yield). $^1$H-NMR (500 MHz, CDCl$_3$) δ 8.67-8.76 (2H, m), 7.89 (1H, d), 7.54 (1H, dd), 7.20-7.35 (7H, m), 7.06 (2H, d), 7.03 (1H, s), 5.38 (2H, s), 5.07 (1H, br s), 2.20-2.60 (4H, m), 2.00-2.15 (1H, m), 1.78-1.90 (1H, m), 1.10-1.50 (9H, br s). LCMS (Method A) RT=6.98 min, M+H$^+$=584.99.

Step 2: 6-(4-(1-aminocyclobutyl)phenyl)-7-phenyl-1-(pyridin-3-yl)-1H-pyrido[3,2-e][1,3,4]oxathiazine 2,2-dioxide tert-Butyl (1-(4-(2,2-dioxido-7-phenyl-1-(pyridin-3-yl)-1H-pyrido[3,2-e][1,3,4]oxathiazin-6-yl)phenyl)cyclobutyl)carbamate (40 mg, 0.068 mmol) was dissolved in TFA (3 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as an off-white solid (23 mg, 56% yield). $^1$H-NMR (500 MHz, MeOD) δ 8.70 (1H, d), 8.65 (1H, dd), 8.00 (1H, dd), 7.61 (1H, dd), 7.44 (2H, d), 7.38 (2H, d), 7.17-7.25 (3H, m), 7.09 (1H, s), 7.06 (2H, d), 5.67 (2H, s), 2.68-2.77 (2H, m), 2.50-2.59 (2H, m), 2.14-2.25 (1H, m), 1.87-2.00 (1H, m). LCMS (Method A) RT=4.00 min, M+2H$^+$=486.07.

Example 75

6-(4-(1-aminocyclobutyl)phenyl)-7-phenyl-1-(pyridin-3-yl)-1H-pyrido[2,3-b][1,4]oxazin-2(3H)-one

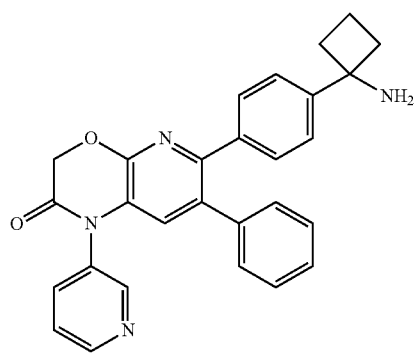 [SMILES: NC1(c2ccc(-c3nc4c(cc3-c3ccccc3)N(c3cccnc3)C(=O)CO4)cc2)CCC1]

Step 1: tert-butyl 1-(4-(2-oxo-7-phenyl-1-(pyridin-3-yl)-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol), pyridin-3-ylboronic acid (52 mg, 0.424 mmol), copper(II)acetate (58 mg, 0.318 mmol) and 5 Å molecular sieves (60 mg) in anhydrous dichloromethane (2 ml). To this was added anhydrous pyridine (34 µl, 0.424 mmol) and the resulting blue suspension stirred at room temperature under air for 24 hours. Further pyridine (1 mL) was added and the resulting deep blue solution stirred at room temperature for 24 hours. Further pyridin-3-ylboronic acid (52 mg, 0.424 mmol) and copper(II) acetate (58 mg, 0.318 mmol) were added and the mixture stirred at room temperature for 72 hours. The reaction mixture was concentrated to dryness under reduced pressure and the residue purified by Biotage chromatography (cyclohexane:ethyl acetate, gradient elution from 88:12 to 0:100) to give the desired product as an off-white solid (32 mg 28% yield). $^1$H-NMR (500 MHz, CDCl$_3$) δ 8.50-8.80 (2H, br m), 7.71 (1H, d), 7.50 (1H, br s), 7.09-7.26 (7H, m), 6.92-7.02 (2H, d), 6.71 (1H, s), 5.00 (3H, s), 2.10-2.55 (4H, m), 1.92-2.05 (1H, m), 1.66-1.80 (1H, m), 1.00-1.45 (9H, br m). LCMS (Method A) RT=6.61 min, M+H$^+$=549.09.

Step 2: 6-(4-(1-aminocyclobutyl)phenyl)-7-phenyl-1-(pyridin-3-yl)-1H-pyrido[2,3-b][1,4]oxazin-2(3H)-one tert-Butyl 1-(4-(2-oxo-7-phenyl-1-(pyridin-3-yl)-2,3-dihydro-1H-pyrido[2,3-b][1,4]oxazin-6-yl)phenyl)cyclobutylcarbamate (30 mg, 0.055 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (15 mg, 49% yield). $^1$H-NMR (500 MHz, MeOD) δ 8.62-8.77 (2H, m), 7.98 (1H, d), 7.68 (1H, dd), 7.36 (2H, d), 7.39 (2H, d), 7.15-7.24 (3H, m), 6.97-7.05 (2H, m), 6.77 (1H, s), 5.14 (2H, s), 2.66-2.77 (2H, m), 2.46-2.58 (2H, m), 2.13-2.25 (1H, m), 1.86-1.97 (1H, m). LCMS (Method A) RT=3.71 min, M+2H$^+$=450.20.

Example 76

2-(6-(4-(1-aminocyclobutyl)phenyl)-2,2-dioxido-7-phenyl-1H-pyrido[3,2-e][1,3,4]oxathiazin-1-yl)acetonitrile

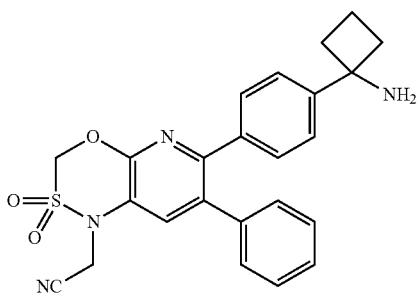 [SMILES: N#CCN1c2cc(-c3ccccc3)c(-c3ccc(C4(N)CCC4)cc3)nc2OCS1(=O)=O]

Step 1: tert-butyl(1-(4-(1-(cyanomethyl)-2,2-dioxido-7-phenyl-1H-pyrido[3,2-e][1,3,4]oxathiazin-6-yl)phenyl)cyclobutyl)carbamate In a 15 mL reaction tube was added tert-butyl(1-(4-(2,2-dioxido-7-phenyl-1H-pyrido[3,2-e][1,3,4]oxathiazin-6-yl)phenyl)cyclobutyl)carbamate (50 mg, 0.099 mmol), potassium carbonate (41 mg, 0.296 mmol) and 2-bromoacetonitrile (0.021 mL, 0.296 mmol) in anhydrous N,N-dimethylformamide (1 mL) to give a yellow suspension. The reaction mixture was stirred at room temperature for one hour. The reaction mixture was allowed to cool to room temperature, diluted with saturated sodium bicarbonate solution (5 mL) and extracted into dichloromethane (3×3 mL). The combined organic phases were dried over Na$_2$SO$_4$, filtered and concentrated to dryness under reduced pressure to give a yellow oil. This was purified by Biotage chromatography (cyclohexane:ethyl acetate, gradient elution from 90:10 to 20:80) to give the desired product as a colourless oil (32 mg, 59% yield). $^1$H-NMR (500 MHz, CDCl$_3$) δ 8.04 (1H, s), 7.25-7.38 (7H, m), 7.17-7.25 (2H, m), 5.32 (2H, s), 5.05 (1H, br s), 4.73 (2H, s), 2.20-2.65 (4H, m), 2.00-2.18 (1H, m), 1.77-1.90 (1H, m), 1.05-1.55 (9H, br m). LCMS (Method D) RT=1.60 min, M+H$^+$=547.10.

Step 2: 2-(6-(4-(1-aminocyclobutyl)phenyl)-2,2-dioxido-7-phenyl-1H-pyrido[3,2-e][1,3,4]oxathiazin-1-yl)acetonitrile tert-Butyl (1-(4-(1-(cyanomethyl)-2,2-dioxido-7-phenyl-1H-pyrido[3,2-e][1,3,4]oxathiazin-6-yl)phenyl)cyclobutyl)carbamate (32 mg, 0.059 mmol) was dissolved in TFA (3 mL)

and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as an off-white solid (16 mg, 49% yield). $^1$H-NMR (500 MHz, MeOD) δ 7.83 (1H, s), 7.44 (2H, d), 7.39 (2H, d), 7.26-7.35 (3H, m), 7.20-7.26 (2H, m), 5.53 (2H, s), 5.01 (2H, s), 2.68-2.78 (2H, m), 2.50-2.60 (2H, m), 2.14-2.27 (1H, m), 1.87-1.99 (1H, m). LCMS (Method A) RT=4.00 min, M+2H$^+$=448.12.

Example 77

6-(4-(1-aminocyclobutyl)phenyl)-3-(2-hydroxy-ethyl)-1-methyl-7-phenyl-1H-pyrido[2,3-b][1,4]oxazin-2(3H)-one

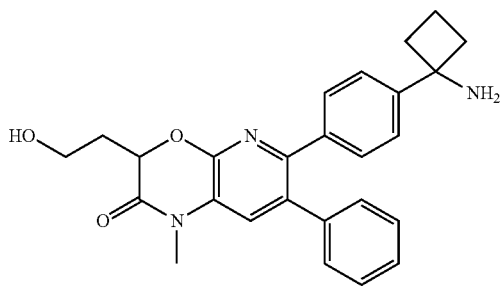 [SMILES: CN1C(=O)C(CCO)Oc2nc(-c3ccc(C4(N)CCC4)cc3)c(-c3ccccc3)cc21]

Step 1: tert-butyl(1-(4-(3-(2-hydroxyethyl)-1-methyl-2-oxo-7-phenyl-2,3-dihydro-1H-pyrido[2,3-b][1,4]oxazin-6-yl)phenyl)cyclobutyl)carbamate A solution of tert-butyl 1-(4-(3-(2-hydroxyethyl)-2-oxo-7-phenyl-2,3-dihydro-1H-pyrido[2,3-b][1,4]oxazin-6-yl)phenyl)cyclobutylcarbamate (40 mg, 0.078 mmol) in DMF(1 ml) was added potassium carbonate (32 mg) and methyl iodide (13.2 mg, 0.093 mml) were added. The reaction mixture was stirred at room temperature for 4 h.

The reaction mixture was partitioned between dichloromethane (20 ml) and water (20 ml). The organic phase was separated using phase separator and concentrated. The crude product was purified by column (biotage, column size: 25 g) eluted with ethyl acetate/cyclohexane to afford product (18 mg) $^1$H NMR (500 MHz, CDCl$_3$): 7.25-7.30 (m, 8H), 7.19 (m, 2H), 5.04 (dd, 1H), 5.01 (br, 1H), 3.95 (m, 2H), 3.40 (s, 3H), 2.45 (m, 4H), 2.45 (m, 2H), 2.02 (m, 1H), 1.79 (m, 1H), 1.15-1.35 (m, 9H).

Step 2: 6-(4-(1-aminocyclobutyl)phenyl)-3-(2-hydroxyethyl)-1-methyl-7-phenyl-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(3-(2-hydroxyethyl)-1-methyl-2-oxo-7-phenyl-2,3-dihydro-1H-pyrido[2,3-b][1,4]oxazin-6-yl)phenyl)cyclobutyl)carbamate (12.5 mg, 0.024 mmol) was reacted to afford the title compound (5.5 mg). $^1$H NMR (500 MHz, CH$_3$OD) 7.64 (s, 1H), 7.41 (m, 4H), 7.28 (m, 3H), 7.18 (m, 2H), 5.09 (dd, 1H), 3.80-3.92 (m, 2H), 3.41 (s, 1H), 2.72 (m, 2H), 2.54 (m, 2H), 2.24 (m, 2H), 2.13 (m, 1H), 1.94 (m, 1H). LCMS (Method A): R$_T$=3.76 min, M+H$^+$=413.16.

Example 78

2-(6-(4-(1-aminocyclobutyl))phenyl)-3-(2-hydroxyethyl)-2-oxo-7-phenyl-2,3-dihydro-1H-pyrido-[2,3-b][1,4]oxazin-1-yl)acetonitrile

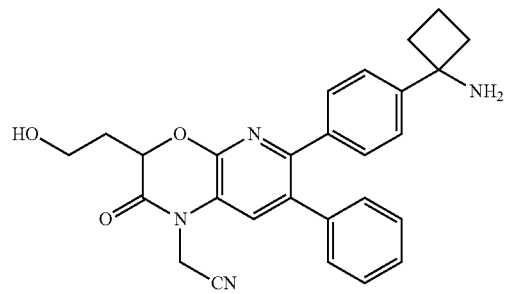 [SMILES: N#CCN1C(=O)C(CCO)Oc2nc(-c3ccc(C4(N)CCC4)cc3)c(-c3ccccc3)cc21]

Step 1: tert-butyl(1-(4-(1-(cyanomethyl)-3-(2-hydroxyethyl)-2-oxo-7-phenyl-2,3-dihydro-1H-pyrido[2,3-b][1,4]oxazin-6-yl)phenyl)cyclobutyl)carbamate A solution of tert-butyl 1-(4-(3-(2-hydroxyethyl)-2-oxo-7-phenyl-2,3-dihydro-1H-pyrido[2,3-b][1,4]oxazin-6-yl)phenyl)cyclobutylcarbamate (51 mg, 0.099 mmol) in DMF(2 ml) was added potassium carbonate (41 mg) and 2-bromoacetonitrile (35.5 mg, 0.297 mmol). The reaction mixture was stirred at 50 degree for 3 h.

The reaction mixture was partitioned between dichloromethane (20 ml) and water (20 ml). The organic phase was separated using phase separator and concentrated. The crude product was purified by column (biotage, column size: 25 g) eluted with ethyl acetate/cyclohexane to afford product (18 mg). LCMS (Method A): R$_T$=6.45 min, M+H: 555.0

Step 2: 2-(6-(4-(1-aminocyclobutyl)phenyl)-3-(2-hydroxyethyl)-2-oxo-7-phenyl-2,3-dihydro-1H-pyrido[2,3-b][1,4]oxazin-1-yl)acetonitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(cyanomethyl)-3-(2-hydroxyethyl)-2-oxo-7-phenyl-2,3-dihydro-1H-pyrido[2,3-b][1,4]oxazin-6-yl)phenyl)cyclobutyl)carbamate (15 mg, 0.027 mmol) was reacted to afford the title compound (7.5 mg). $^1$H NMR (500 MHz, CH$_3$OD) 7.67 (s, 1H), 7.41 (d, 2H), 7.38 (d, 2H), 7.30 (m, 3H), 7.24 (m, 2H), 5.18 (dd, 1H), 5.11 (s, 2H), 3.81-3.89 (m, 2H), 2.71-2.77 (m, 2H), 2.52-2.58

(m, 2H), 2.27-2.30 (m, 1H), 2.16-2.23 (m, 2H), 1.93-2.10 (m, 1H). LCMS (Method A): R$_T$=3.78 min, M+H$^+$=456.2.

Example 79

7-(4-((1r,3r)-1-amino-3-hydroxy-3-methylcyclobutyl)phenyl)-8-phenyl-2,4-dihydro-1H-pyrido[2,3-b][1,2,4]triazolo[4,3-d][1,4]oxazin-1-one

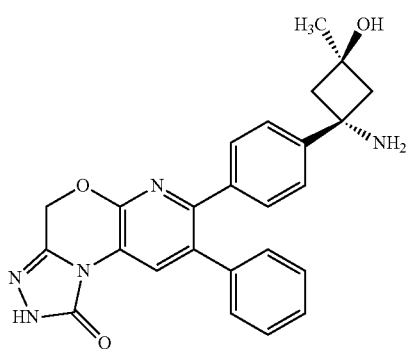 [SMILES: C[C@]1(O)C[C@@](N)(c2ccc(-c3nc4c(cc3-c3ccccc3)-n3c(n[nH]c3=O)CO4)cc2)C1]

Step 1: 2-((1r,3r)-3-hydroxy-3-methyl-(4-(1-oxo-8-phenyl-2,4-dihydro-1H-pyrido[2,3-b][1,2,4]triazolo[4,3-d][1,4]oxazin-7-yl)phenyl)cyclobutyl)isoindoline-1,3-dione In a 15 mL round-bottomed flask was 7-bromo-8-phenyl-2,4-dihydro-1H-pyrido[2,3-b][1,2,4]triazolo[4,3-d][1,4]oxazin-1-one (30 mg, 0.087 mmol), 2-((1r,3r)-1-(4-(5,5-dimethyl-1,3,2-dioxaborinan-2-yl)phenyl)-3-hydroxy-3-methylcyclobutyl)isoindoline-1,3-dione (30.4 mg, 0.072 mmol), and cesium carbonate (118 mg, 0.362 mmol) in 1,4-dioxane (1.55 ml) and water (0.5 ml) to give a yellow solution. The reaction mixture was degassed for 15 minutes, following by the addition of PdCl$_2$(dppf)-CH$_2$Cl$_2$ adduct (20 mg) and degassing for further 15 minutes. The reaction mixture was heated to 50° C. overnight under nitrogen atmosphere.

The reaction mixture was allowed to cool to room temperature and water was added (7 ml). The reaction mixture was extracted using ethyl acetate (10 ml×3). The combined organic layers were concentrated under reduced pressure.

The crude residue was purified by Biotage silica gel chromatography (gradient 0% to 100% ethyl acetate in n-hexanes) to give the title compound (5 mg, 12%). LCMS (Method D): RT 1.167 min, M+1=572. $^1$H NMR (500 MHz, CD$_3$OD): 8.53 (1H, s), 7.84-7.78 (4H, m), 7.71-7.64 (2H, m), 7.51-7.45 (3H, m), 7.30-7.22 (4H, m), 5.38 (2H, s), 3.50-3.45 (2H, m), 3.36 (3H, s), 3.02-2.96 (2H, m).

Step 2: 7-(4-((1r,3r)-1-amino-3-hydroxy-3-methylcyclobutyl)phenyl)-8-phenyl-2,4-dihydro-1H-pyrido[2,3-b][1,2,4]triazolo[4,3-d][1,4]oxazin-1-one In a 10 ml microwave vial was 2-((1r,3r)-3-hydroxy-3-methyl-1-(4-(1-oxo-8-phenyl-2,4-dihydro-1H-pyrido[2,3-b][1,2,4]triazolo[4,3-d][1,4]oxazin-7-yl)phenyl)cyclobutyl)isoindoline-1,3-dione (5 mg, 8.75 µmol), hydrazine monohydrate (2.75 µl, 0.087 mmol) in 1,4-dioxane (0.3 ml) and ethanol (0.1 ml) to give a colourless solution. The reaction mixture was heated to 120° C. for one hour.

The reaction mixture was cooled to room temperature and filtered to remove the solid. This was washed thoroughly with ethanol. The filtrates were combined and concentrated under reduced pressure.

The crude residue (5 mg) was purified by preparatory HPLC. The combined product fractions were concentrated to dryness under reduced pressure to give an off-white solid as the title compound (3 mg, 78%). LCMS (Method D) RT=0.578 min, M+1=442.
$^1$H-NMR (500 MHz, CD$_3$OD) δ 8.43 (1H, s), 7.27-7.17 (7H, m), 7.15-7.10 (2H, m), 5.29 (2H, s), 2.59-2.52 (2H+3H, m), 2.32-2.24 (2H, m).

Example 80

6-(4-(1-aminocyclobutyl)phenyl)-3-methyl-7-phenyl-1H-pyrido[2,3-b][1,4]oxazin-2(3H)-one

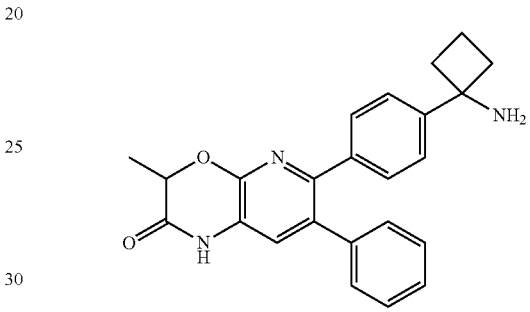

Step 1: tert-butyl(1-(4-(3-methyl-2-oxo-7-phenyl-2,3-dihydro-1H-pyrido[2,3-b][1,4]oxazin-6-yl)phenyl)cyclobutyl)carbamate A solution of tert-butyl 1-(4-(5-amino-6-oxo-3-phenyl-1,6-dihydropyridin-2-yl)phenyl)cyclobutylcarbamate (0.5 g, 1.159 mmol) in THF (Volume: 20 ml) was added DIPEA (1.01 ml) followed by the addition of 2-chloropropanoyl chloride (0.235 g, 1.854 mmol) in THF (5 ml) in dropwise at 0 degree over 1 h. The resulted mixture was stirred at r.t. over night. Sodium bicarbonate saturated solution (30 ml) was added. The resulted mixture was heated to reflux for 16 h. The reaction mixture was cooled down to room temperature. The organic phase was separated. The aqueous phase was extracted with ethyl acetate (40 ml). The organic phase was combined and washed with water (30 mlX2), brine (25 ml) then concentrated at reduced pressure. The residue was suspended in DCM (10 ml). The precipitate was collected by filtration and washed with DCM (5 ml) to afford product (439 mg). $^1$H NMR (500 MHz, CD$_3$OD): 7.20-7.29 (m, 8H), 7.13-7.15 (m, 2H), 4.98 (q, 1H), 2.41-2.47 (m, 4H), 2.05 (m, 1H), 1.86 (m, 1H), 1.64 (d, 3H), 1.21-1.36 (br, 9H).

Step 2: 6-(4-(1-aminocyclobutyl)phenyl)-3-methyl-7-phenyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(3-methyl-2-oxo-7-phenyl-2,3-dihydro-1H-pyrido[2,3-b][1,4]oxazin-6-yl)phenyl)cyclobutyl)carbamate (25 mg, 0.051 mmol) was reacted to afford the title compound (18.5 mg). $^1$H NMR (500 MHz, CD$_3$OD): 7.37-7.42 (m, 4H), 7.34 (s, 1H), 7.28-7.30 (m, 3H), 7.18-7.20 (m, 2H), 5.03 (q, 1H), 2.73-2.79 (m, 2H), 2.56-2.60 (m, 2H), 2.20-2.26 (m, 1H), 1.96-1.99 (m, 1H), 1.65 (d, 3H). LCMS (Method D): R$_T$=0.73 min, M+H$^+$=386.2

Example 81

2-(6-(4-(1-aminocyclobutyl)phenyl)-3-methyl-2-oxo-7-phenyl-2,3-dihydro-1H-pyrido[2,3-b][1,4]oxazin-1-yl)acetonitrile

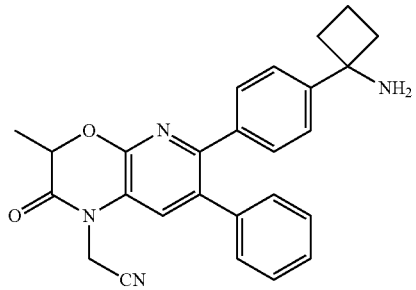 [SMILES: CC1Oc2nc(-c3ccc(C4(N)CCC4)cc3)c(-c3ccccc3)cc2N(CC#N)C1=O]

Step 1: tert-butyl(1-(4-(1-(cyanomethyl)-3-methyl-2-oxo-7-phenyl-2,3-dihydro-1H-pyrido[2,3-b][1,4]oxazin-6-yl)phenyl)cyclobutyl)carbamate A solution of tert-butyl 1-(4-(3-methyl-2-oxo-7-phenyl-2,3-dihydro-1H-pyrido[2,3-b][1,4]oxazin-6-yl)phenyl)cyclobutylcarbamate (50 mg, 0.103 mmol) in DMF (2 ml) was added potassium carbonate (42.7 mg) and 2-bromoacetonitrile (22 µl, 0.309 mmol). The reaction mixture was stirred at room temperature for 48 h then was diluted with ethyl acetate (20 ml). Washed with water, brine, and dried with Na2SO4, filtered and concentrated to give crude product which was purified by column (biotage, 25 g) eluted with ethyl acetate and cyclohexane to afford product (45 mg). $^1$H NMR (500 MHz, CDCl$_3$): 7.35 (s, 1H), 7.20-7.32 (m, 9H), 4.98 (q, 1H), 4.87 (dd, 2H), 2.44-2.49 (m, 4H), 2.06 (m, 1H), 1.80 (m, 1H), 1.75 (d, 3H), 1.24-1.36 (br, 9H).

Step 2: 2-(6-(4-(1-aminocyclobutyl)phenyl)-3-methyl-2-oxo-7-phenyl-2,3-dihydro-1H-pyrido[2,3-b][1,4]oxazin-1-yl)acetonitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(cyanomethyl)-3-methyl-2-oxo-7-phenyl-2,3-dihydro-1H-pyrido[2,3-b][1,4]oxazin-6-yl)phenyl)cyclobutyl)carbamate (25 mg, 0.048 mmol) was reacted to afford the title compound (20 mg). $^1$H NMR (500 MHz, CH$_3$OD) 7.71 (s, 1H), 7.45 (d, 2H), 7.39 (d, 2H), 7.32 (m, 3H), 7.26 (m, 2H), 5.14 (s, 2H), 5.10 (q, 1H), 2.74-2.80 (m, 2H), 2.55-2.61 (m, 2H), 2.22-2.26 (m, 1H), 1.96-1.99 (m, 1H), 1.71 (d, 3H). LCMS (Method D): R$_T$=0.81 min, M+H$^+$=425.2.

Example 82

6-(4-(1-aminocyclobutyl)phenyl)-1-(methylsulfonylmethyl)-7-phenyl-1H-pyrido[2,3-b][1,4]oxazin-2(3H)-one

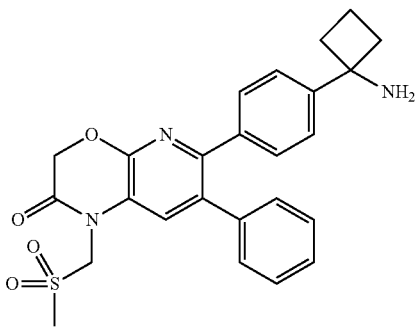 [SMILES: CS(=O)(=O)CN1C(=O)COc2nc(-c3ccc(C4(N)CCC4)cc3)c(-c3ccccc3)cc21]

Step 1: tert-butyl 1-(4-(1-(methylthiomethyl)-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (150 mg, 0.318 mmol), potassium carbonate (132 mg, 0.954 mmol) and chloromethyl methyl sulfide (0.079 mL, 0.954 mmol) in anhydrous N,N-dimethylformamide (2 mL) to give a yellow suspension. The reaction mixture was heated to 80° C. under a nitrogen atmosphere for 2 hours, then allowed to cool to room temperature, diluted with saturated sodium bicarbonate solution (10 mL) and extracted into dichloromethane (3×5 mL). The combined organic phases were dried over Na$_2$SO$_4$, filtered and concentrated to dryness under reduced pressure to give a yellow oil. This was purified by Biotage chromatography (cyclohexane:ethyl acetate, gradient elution from 90:10 to 80:20) to give the desired product as a white solid (75 mg, 44% yield). $^1$H-NMR (500 MHz, CDCl$_3$) δ 7.43 (1H, s), 7.23-7.35 (7H, m), 7.19-7.23 (2H, m), 5.09 (3H, br s), 4.94 (2H, s), 2.30-2.55 (4H, m), 2.26 (3H, s), 2.00-2.15 (1H, m), 1.75-1.90 (1H, m), 1.10-1.50 (9H, br s). LCMS (Method A) RT=7.42 min, M+H$^+$=532.14.

Step 2: tert-butyl 1-(4-(1-(methylsulfonylmethyl)-2-oxo-7-phenyl-2,3-dihydro-1H-pyrido[2,3-b][1,4]oxazin-6-yl)phenyl)cyclobutylcarbamate In a 15 mL reaction tube was added tert-butyl 1-(4-(1-(methylthiomethyl)-2-oxo-7-phenyl-2,3-dihydro-1H-pyrido[2,3-b][1,4]oxazin-6-yl)phenyl)cyclobutylcarbamate (50 mg, 0.094 mmol) in a mixture of methanol (1500 µl) and tetrahydrofuran (1500 µl) to give a yellow solution. To this was added dropwise a solution of oxone monopersulfate compound (463 mg, 0.752 mmol) in water (1500 µl) and the resulting suspension stirred at room temperature overnight. The reaction mixture was quenched by the careful addition of saturated sodium bicarbonate solution (3 mL) and extracted into ethyl acetate (3×5 mL). The combined organic phases were washed with saturated sodium bicarbonate solution (5 mL), brine (5 mL), dried over Na$_2$SO$_4$, filtered and concentrated to dryness under reduced pressure to give an off-white solid. This was purified by Biotage chromatography (cyclohexane:ethyl acetate, gradient elution from 88:12 to 0:100) to give the desired product as a white solid (30 mg, 57%). $^1$H-NMR (500 MHz, CDCl$_3$) δ 7.67 (1H, s), 7.25-7.34 (7H, m), 7.17-7.23 (2H, m), 5.21 (2H, br s), 5.08 (1H, br s), 4.99 (2H, s), 3.08 (3H, s), 2.20-2.60 (4H, m), 2.00-2.15 (1H, m), 1.75-1.90 (1H, m), 1.10-1.50 (9H, br m). LCMS (Method D) RT=1.44 min, M+H$^+$=564.00.

Step 3: 6-(4-(1-aminocyclobutyl)phenyl)-1-(methylsulfonylmethyl)-7-phenyl-1H-pyrido[2,3-b][1,4]oxazin-2(3H)-one tert-Butyl 1-(4-(1-(methylsulfonylmethyl)-2-oxo-7-phenyl-2,3-dihydro-1H-pyrido[2,3-b][1,4]oxazin-6-yl)phenyl)cyclobutylcarbamate (28 mg, 0.050 mmol) was dissolved in TFA (2 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed under reduced pressure and freeze-dried over the weekend to give the desired product as an off-white solid (28 mg, 98% yield). $^1$H-NMR (500 MHz, MeOD) δ 7.78 (1H, s), 7.32 (2H, d), 7.28 (2H, d), 7.13-7.23 (3H, m), 7.08-7.13 (2H, m), 5.43 (2H, s), 5.01 (2H, s), 2.86 (3H, s), 2.58-2.70 (2H, m), 2.40-2.52 (2H, m), 2.03-2.17 (1H, m), 1.76-1.90 (1H, m). LCMS (Method D) RT=0.87 min, M+H$^+$=464.00.

Example 83

6-(4-(1-aminocyclobutyl)phenyl)-1-(1-methyl-1H-pyrazol-4-yl)-7-phenyl-1H-pyrido[2,3-b][1,4]oxazin-2(3H)-one

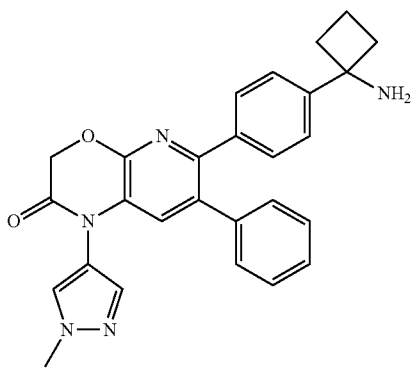 [SMILES: Cn1cc(N2C(=O)COc3nc(-c4ccc(C5(N)CCC5)cc4)c(-c4ccccc4)cc32)cn1]

Step 1: tert-butyl 1-(4-(1-(1-methyl-1H-pyrazol-4-yl)-2-oxo-7-phenyl-2,3-dihydro-1H-pyrido[2,3-b][1,4]oxazin-64)phenyl)cyclobutylcarbamate In a 15 mL reaction tube was added tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol), 1-methyl-4-(4,4,5,5-tetramethyl-1,3,2-dioxaborolan-2-yl)-1H-pyrazole (44 mg, 0.212 mmol), copper(II)acetate (58 mg, 0.318 mmol) and 5 Å molecular sieves (60 mg) in anhydrous dichloromethane (2 mL). To this was added anhydrous pyridine (1 mL, 12.36 mmol) and the resulting deep purple solution stirred at room temperature under air for 48 hours. Further 1-methyl-4-(4,4,5,5-tetramethyl-1,3,2-dioxaborolan-2-yl)-1H-pyrazole (44 mg, 0.212 mmol) and copper(II)acetate (58 mg, 0.318 mmol) were added and the reaction mixture stirred at room temperature for 72 hours, then heated to 40° C. overnight. To the reaction mixture was added further 1-methyl-4-(4,4,5,5-tetramethyl-1,3,2-dioxaborolan-2-yl)-1H-pyrazole (44 mg, 0.212 mmol) and copper(II)acetate (58 mg, 0.318 mmol) and heated at 40° C. for 6 days. The reaction mixture was allowed to cool to room temperature and concentrated to dryness under reduced pressure. The residue was purified by Biotage chromatography (cyclohexane:ethyl acetate, gradient elution from 88:12 to 0:100) to give the desired product as an off-white solid (30 mg, 51% yield). $^1$H-NMR (500 MHz, CDCl$_3$) δ 7.53 (1H, s), 7.49 (1H, s), 7.12-7.27 (7H, m), 6.98-7.08 (3H, m), 4.93 (2H, s), 3.90 (3H, s), 2.10-2.50 (4H, m), 1.92-2.04 (1H, m), 1.65-1.79 (1H, m), 1.00-1.45 (9H, br m). LCMS (Method D) RT=1.45 min, M+H$^+$=552.20.

Step 2: 6-(4-(1-aminocyclobutyl)phenyl)-1-(1-methyl-1H-pyrazol-4-yl)-7-phenyl-1H-pyrido[2,3-b][1,4]oxazin-2(3H)-one tert-Butyl 1-(4-(1-(1-methyl-1H-pyrazol-4-yl)-2-oxo-7-phenyl-2,3-dihydro-1H-pyrido[2,3-b][1,4]oxazin-6-yl)phenyl)cyclobutylcarbamate (30 mg, 0.054 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (29 mg, 94% yield). $^1$H-NMR (500 MHz, MeOD) δ 7.89 (1H, s), 7.62 (1H, s), 7.42-7.51 (4H, m), 7.40 (2H, d), 7.37 (2H, d), 7.18-7.27 (3H, m), 7.03-7.12 (3H, m), 5.06 (2H, s), 3.96 (3H, s), 2.66-2.78 (2H, m), 2.48-2.58 (2H, m), 2.13-2.26 (1H, m), 1.85-1.98 (1H, m). LCMS (Method D) RT=0.86 min, M+H$^+$=452.20.

Example 84

6-(4-(1-aminocyclobutyl)phenyl)-1,3-dimethyl-7-phenyl-1H-pyrido[2,3-b][1,4]oxazin-2(3H)-one

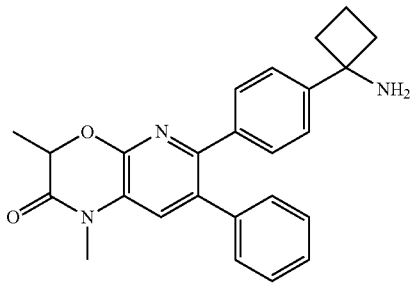 [SMILES: CC1Oc2nc(-c3ccc(C4(N)CCC4)cc3)c(-c3ccccc3)cc2N(C)C1=O]

Step 1: tert-butyl(1-(4-(1,3-dimethyl-2-oxo-7-phenyl-2,3-dihydro-1H-pyrido[2,3-b][1,4]oxazin-6-yl)phenyl)cyclobutyl)carbamate A solution of tert-butyl 1-(4-(3-methyl-2-oxo-7-phenyl-2,3-dihydro-1H-pyrido[2,3-b][1,4]oxazin-6-yl)phenyl)cyclobutylcarbamate (50 mg, 0.103 mmol) in DMF (2 ml) was added potassium carbonate (42.7 mg) and iodomethane (7.69 μl, 0.124 mmol). The reaction mixture was stirred at room temperature for 48 h then was diluted with ethyl acetate (20 ml). Washed with water, brine, and dried with Na2SO4, filtered and concentrated to give product 43 mg. $^1$H NMR (500 MHz, CDCl$_3$): 7.19-7.32 (m, 10H), 4.96 (q, 1H), 3.39 (s, 3H), 2.43-2.48 (m, 4H), 2.04 (m, 1H), 1.79 (m, 1H), 1.70 (d, 3H), 1.24-1.36 (m, 9H).

Step 2: 6-(4-(1-aminocyclobutyl)phenyl)-1,3-dimethyl-7-phenyl-1H-pyrido[2,3-b][1,4]oxazin-2(3H)one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1,3-dimethyl-2-oxo-7-phenyl-2,3-dihydro-1H-pyrido[2,3-b][1,4]oxazin-6-yl)phenyl)cyclobutyl)carbamate (40 mg, 0.08 mmol) was reacted to afford the title compound (34.5 mg). $^1$H NMR (500 MHz, CH$_3$OD) 7.56 (s, 1H), 7.42 (d, 2H), 7.38 (d,2H), 7.31 (m, 3H), 7.24 (m, 2H), 5.06 (q, 1H), 3.44 (s, 3H), 2.73-2.77

(m, 2H), 2.53-2.59 (m, 2H), 2.20-2.26 (m, 1H), 1.95-1.97 (m, 1H), 1.67 (d, 3H). LCMS (Method D): R$_T$=0.85 min, M+H$^+$=400.2.

Example 85

6-(4-(1-aminocyclobutyl)phenyl)-1-(2,2-difluoroethyl)-7-phenyl-1H-pyrido[2,3-b][1,4]oxazin-2(3H)-one

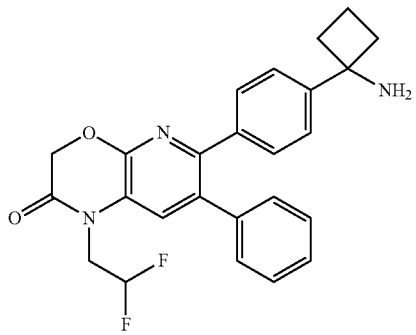 [SMILES: NC1(c2ccc(-c3nc4c(cc3-c3ccccc3)N(CC(F)F)C(=O)CO4)cc2)CCC1]

Step 1 tert-butyl(1-(4-(1-(2,2-difluoroethyl)-2-oxo-7-phenyl-2,3-dihydro-1H-pyrido[2,3-b][1,4]oxazin-6-yl)phenyl) cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 1,1-difluoro-2-iodoethane (122 mg, 0.636 mmol) to afford the title compound (85 mg. $^1$H NMR (500 MHz, CDCl$_3$): 7.42 (1H, s), 7.24-7.30 (7H, m), 7.17-7.19 (2H, m), 6.11 (1H, tt), 5.05 (1H, br), 4.92 (s, 2H), 4.28 (dt, 2H), 2.44-2.49 (m, 4H), 2.05 (m, 1H), 1.81 (m, 1H), 1.2-1.43 (br, 9H).

Step 2: 6-(4-(1-aminocyclobutyl)phenyl)-1-(2,2-difluoroethyl)-7-phenyl-1H-pyrido[2,3-b][1,4]oxazin-2(3H)-one Following the procedure for 3-(6-(4-(1-aminocyclobutyl) phenyl)-2-oxo-7-phenyl-2,3-dihydro-1H-pyrido[2,3-b][1,4] oxazin-1-yl)propanenitrile, tert-butyl(1-(4-(1-(2,2-difluoroethyl)-2-oxo-7-phenyl-2,3-dihydro-1H-pyrido[2,3-b][1,4] oxazin-6-yl)phenyl)cyclobutyl)carbamate (20 mg, 0.037 mmol) was reacted to afford the title compound (16 mg). $^1$H NMR (500 MHz, CH$_3$OD) 7.71 (s, 1H), 7.42 (d, 2H), 7.38 (d, 2H), 7.31 (m, 3H), 7.22 (m, 2H), 6.21 (tt, 1H), 5.01 (s, 2H), 4.50 (dt, 2H), 2.73-2.78 (m, 2H), 2.54-2.59 (m, 2H), 2.21-2.25 (m, 1H), 1.93-1.99 (m, 1H). LCMS (Method D): R$_T$=0.84 min, M+H$^+$=436.

Example 86

6-(4-(1-aminocyclobutyl)phenyl)-1-(2-fluoroethyl)-7-phenyl-1H-pyrido[2,3-b][1,4]oxazin-2(3H)-one

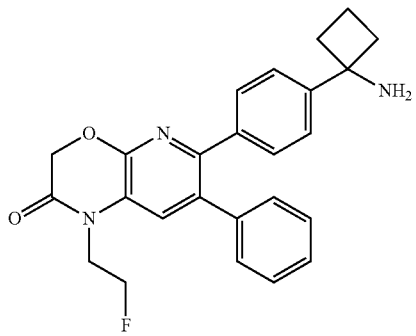 [SMILES: NC1(c2ccc(-c3nc4c(cc3-c3ccccc3)N(CCF)C(=O)CO4)cc2)CCC1]

Step 1 tert-butyl(1-(4-(1-(2-fluoroethyl)-2-oxo-7-phenyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 1-fluoro-2-iodoethane (111 mg, 0.636 mmol) to afford the title compound (85 mg. $^1$H NMR (500 MHz, CDCl$_3$): 7.45 (1H, s), 7.24-7.31 (7H, m), 7.17-7.20 (2H, m,), 5.01 (1H, s), 4.94 (2H, s), 4.80 (1H, t), 4.70 (1H, t), 4.27 (1H, t), 4.22 (1H, t), 2.44-2.49 (4H, m), 2.06 (1H, m), 1.86 (1H, m), 1.2-1.43 (9H, br).

Step 2: 6-(4-(1-aminocyclobutyl)phenyl)-1-(2-fluoroethyl)-7-phenyl-1H-pyrido[2,3-b][1,4]oxazin-2(3H)-one Following the procedure for 3-(6-(4-(1-aminocyclobutyl) phenyl)-2-oxo-7-phenyl-2,3-dihydro-1H-pyrido[2,3-b][1,4] oxazin-1-yl)propanenitrile, tert-butyl(1-(4-(1-(2-fluoroethyl)-2-oxo-7-phenyl-2,3-dihydro-1H-pyrido[2,3-b][1,4] oxazin-6-yl)phenyl)cyclobutyl)carbamate (60 mg, 0.116 mmol) was reacted to afford the title compound (50.5 mg). $^1$H NMR (500 MHz, CH$_3$OD) 7.69 (1H, s), 7.42 (2H, d), 7.38 (2H, d), 7.30 (3H, m), 7.22 (2H, m), 4.99 (2H, s), 4.80 (1H, t), 4.70 (1H, t), 4.40 (1H, t), 4.35 (1H, t), 2.73-2.79 (2H, m), 2.54-2.60 (2H, m), 2.20-2.25 (1H, m), 1.95-1.97 (1H, m). LCMS (Method D): R$_T$=0.83 min, M+H$^+$=418.

Example 87

6-(4-(1-aminocyclobutyl)phenyl)-7-phenyl-3,4-dihydropyrido[3,2-d]pyrimidin-2(1H)-one

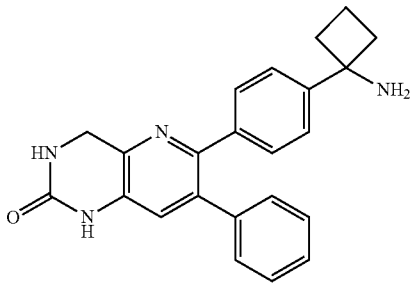 [SMILES: NC1(c2ccc(-c3nc4c(cc3-c3ccccc3)NC(=O)NC4)cc2)CCC1]

Step 1: tert-butyl(1-(4-(5-nitro-6-(nitromethyl)-3-phenylpyridin-2-yl)phenyl)cyclobutyl)carbamate To a solution of potassium tert-butoxide (468 mg, 4.17 mmol) in dry DMSO (20 ml) was slowly added nitromethane (225 ul, 4.17 mmol) under nitrogen. The resulting mixture was stirred for 15 min at room temperature before tert-butyl (1-(4-(6-chloro-5-nitro-3-phenylpyridin-2-yl)phenyl)cyclobutyl)carbamate (1 g, 2.08 mmol) was added. The resulting mixture was stirred for 1 hour at room temperature. A saturated solution of NH$_4$Cl was added and the mixture was extracted with AcOEt (3×50 ml). The combined organic phases were washed with water (3×20 ml), dried over Na$_2$SO$_4$ and concentrated to dryness under reduced pressure. The resulting residue was used directly without purification. $^1$H NMR (500 MHz, CDCl$_3$): 8.60 (1H, s), 7.44-7.35 (7H, m), 7.30-7.28 (2H, m), 6.21 (2H, s), 5.09 (1H, s), 2.52-2.20 (4H, m), 2.00-1.95 (1H, m), 1.79-1.65 (1H, m), 1.40-1.10 (9H, br).

Step 2: tert-butyl(1-(4-(5-amino-6-(aminomethyl)-3-phenylpyridin-2-yl)phenyl)cyclobutyl)carbamate To a solution of tert-butyl(1-(4-(5-nitro-6-(nitromethyl)-3-phenylpyridin-2-yl)phenyl)cyclobutyl)carbamate (74 mg, 0.15 mmol) in EtOH (50 mL) was added Raney Nickel (17 mg, 0.15 mmol). The resulting mixture was purged with nitrogen and with H$_2$ and then stirred under H$_2$ (1.5 bars) overnight at room temperature. The black mixture was filtered through celite, rinsed few times with EtOH (making sure that the cake remained wet at all times), dried over Na$_2$SO$_4$ and concentrated to dryness under reduced pressure. The resulting residue was used directly without purification.

Step 3: tert-butyl(1-(4-(2-oxo-7-phenyl-1,2,3,4-tetrahydropyrido[3,2-d]pyrimidin-6-yl)phenyl)cyclobutyl)carbamate To a solution of tert-butyl(1-(4-(5-amino-6-(aminomethyl)-3-phenylpyridin-2-yl)phenyl)cyclobutyl)carbamate (113 mg, 0.25 mmol) in dry THF (2 ml) was added CDI (41 mg, 0.25 mmol) under nitrogen. The resulting mixture was stirred for 1 h at 60 C and concentrated to dryness under reduced pressure. The resulting residue was purified by Biotage silica gel chromatography (gradient 0 to 5% MeOH in DCM) to give the title compound (71 mg, 59%). $^1$H NMR (500 MHz, CDCl$_3$): 8.91 (1H, br s), 7.19-7.11 (7H, m), 7.00-6.97 (3H, m), 5.73 (1H, s), 4.93 (1H, s), 4.65 (2H, s), 2.52-2.20 (4H, m), 2.00-1.95 (1H, m), 1.79-1.65 (1H, m), 1.40-1.10 (9H, br)

Step 4: 6-(4-(1-aminocyclobutyl)phenyl)-7-phenyl-3,4-dihydropyrido[3,2-d]pyrimidin-2(1H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-7-phenyl-1,2,3,4-tetrahydropyrido[3,2-d]pyrimidin-6-yl)phenyl)cyclobutyl)carbamate (12 mg, 0.03 mmol) was reacted to afford the title compound (12 mg, 97%). LCMS (Method D): R$_T$=0.684 min, M+1=371. $^1$H NMR (500 MHz, MeOD): 7.42-7.38 (4H, m), 7.31-7.28 (3H, m), 7.23 (1H, s), 7.21-7.18 (2H, m), 4.66 (2H, s), 2.81-2.75 (2H, m), 2.63-2.57 (2H, m), 2.26-2.24 (1H, m), 1.99-1.97 (1H, m).

Example 88

6-(4-(1-aminocyclobutyl)phenyl)-N-ethyl-7-phenyl-2,3-dihydro-1H-pyrido[2,3-b][1,4]oxazine-1-carboxamide

Step 1: Tert-butyl (1-(4-(ethylcarbamoyl)-7-phenyl-2,3-dihydro-1H-pyrido[2,3-b][1,4]oxazin-6-yl)phenyl)cyclobutyl)carbamate Tert-butyl 1-(4-(7-phenyl-2,3-dihydro-1H-pyrido-[2,3-b][1,4]oxazin-6-yl)phenyl)cyclobutyl)carbamate (50 mg, 0.109 mmol) and isocyanatoethane (40 mg ml, 0.546 mmol) in THF (1.5 mL) were heated to 50° C. for 24 hrs. The resulting reaction mixture was concentrated under reduced pressure. The obtained crude was purified by Biotage silica gel chromatography (gradient 100% to 80% n-hexane in ethyl acetate) to give the title compound (40 mg, 70%). $^1$H NMR (500 MHz, CDCl$_3$): 7.83 (1H, s), 7.33-7.29 (2H, d), 7.7-7.21 (4H, m), 7.18-7.13 (4H, m), 4.47 (2H, t), 3.93 (3H, t), 3.38 (2H, q), 2.53-2.38 (4H, m), 2.12-1.99 (1H, m), 1.96-1.86 (1H, m), 1.48-1.28 (9H, br), 1.29 (3H, t). LCMS (Method D): R$_T$=1.508 min, M+1=529.

Step 2: 6-(4-(1-aminocyclobutyl)phenyl)-N-ethyl-7-phenyl-2,3-dihydro-1H-pyrido[2,3-b][1,4]oxazine-1-carboxamide Tert-butyl (1-(4-(ethylcarbamoyl)-7-phenyl-2,3-dihydro-1H-pyrido[2,3-b][1,4]oxazin-6-yl)phenyl)cyclobutyl)carbamate (45 mg, 0.093 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and dried to give the desired product as an off-white solid (13 mg, 53% yield). $^1$H-NMR (500 MHz, CD$_3$OD) δ 8.24 (1H, s), 7.41 (2H, d), 7.38 (2H, d), 7.29-7.25 (3H, m), 7.23-7.18 (2H, m), 4.50 (2H, t), 3.89 (2H, t), 3.30 (2H, q), 2.81-2.71 (2H, m), 2.63-2.52 (2H, m), 2.29-2.19 (1H, m), 2.02-1.90 (1H, m), 1.21 (3H, t). LCMS (Method D) RT=0.779 min, M+1=429.

Example 89

6-(4-(1-aminocyclobutyl)phenyl)-1,3-dimethyl-7-phenyl-3,4-dihydropyrido[3,2-d]pyrimidin-2(1H)-one

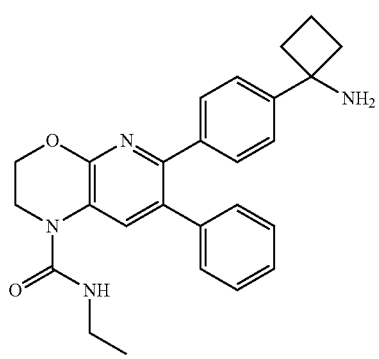 [SMILES: CCNC(=O)N1CCOc2nc(-c3ccc(C4(N)CCC4)cc3)c(-c3ccccc3)cc21]

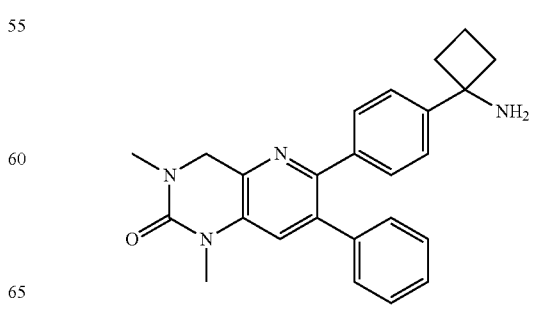

Step 1: tert-butyl(1-(4-(1,3-dimethyl-2-oxo-7-phenyl-1,2,3,4-tetrahydropyrido[3,2-d]pyrimidin-6-yl)phenyl)cyclobutyl)carbamate To a solution of tert-butyl(1-(4-(2-oxo-7-phenyl-1,2,3,4-tetrahydropyrido[3,2-d]pyrimidin-6-yl)phenyl)cyclobutyl)carbamate (46 mg, 0.10 mmol) in dry DMF (1 ml) at −78 C was added sodium hydride (3.9 mg, 0.10 mmol) and methyliodide (6.1 μl, 0.10 mmol) under nitrogen. The bath was removed and the resulting mixture was stirred for 1 h at room temperature. The mixture was cooled down to −78 C. Sodium hydride (3.9 mg, 0.10 mmol) and methyliodide (6.10, μl, 0.10 mmol) were added under nitrogen. The bath was removed and the resulting mixture was stirred for 1 h at room temperature. Water was added and the mixture was extracted with EtOAc (3×10 ml). The combined organic phases were dried over $Na_2SO_4$ and concentrated to dryness under reduced pressure. The resulting residue was purified by Biotage silica gel chromatography (gradient 0 to 50% EtOAc in cyclohexane) to give the title compound (30 mg, 61%). $^1$H NMR (500 MHz, $CDCl_3$): 7.20-7.19 (7H, m), 7.13-7.11 (2H, m), 7.02 (1H, s), 5.00 (1H, br s), 4.56 (2H, s), 3.27 (3H, s), 3.03 (3H, s), 2.52-2.20 (4H, m), 2.00-1.95 (1H, m), 1.79-1.65 (1H, m), 1.40-1.10 (9H, br)

Step 2: 6-(4-(1-aminocyclobutyl)phenyl)-1,3-dimethyl-7-phenyl-3,4-dihydropyrido[3,2-d]pyrimidin-2(1H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1,3-dimethyl-2-oxo-7-phenyl-1,2,3,4-tetrahydropyrido[3,2-d]pyrimidin-6-yl)phenyl)cyclobutyl)carbamate (30 mg, 0.06 mmol) was reacted to afford the title compound (28 mg, 91%). LCMS (Method D): $R_1$=0.798 min, M-$NH_2$=382. $^1$H NMR (500 MHz, MeOD): 7.45-7.39 (4H, m), 7.34 (1H, s), 7.32-7.30 (3H, m), 7.26-7.24 (2H, m), 4.67 (2H, s), 3.36 (3H, s), 3.11 (3H, s), 2.81-2.75 (2H, m), 2.63-2.57 (2H, m), 2.26-2.24 (1H, m), 1.99-1.97 (1H, m).

Example 90

6-(4-(1-Aminocyclobutyl)phenyl)-1-methyl-7-phenyl-1H-pyrido[2,3-b][1,4]oxazin-2(3H)-one O-methyl oxime

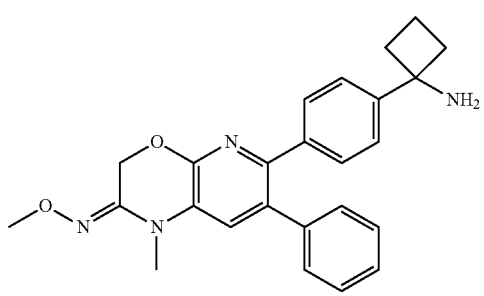 [SMILES: CO/N=C1\COc2nc(-c3ccc(C4(N)CCC4)cc3)c(-c3ccccc3)cc2N1C]

Step 1: tert-Butyl (1-(4-(2-(methoxyimino)-1-methyl-7-phenyl-2,3-dihydro-1H-pyrido[2,3-b][1,4]oxazin-6-yl)phenyl)cyclobutyl)carbamate In a round-bottomed flask was added tert-butyl 1-(4-(1-methyl-7-phenyl-2-thioxo-2,3-dihydro-1H-pyrido[2,3-b][1,4]oxazin-6-yl)phenyl)cyclobutylcarbamate (0.1 g, 0.199 mmol) and o-methylhydroxylamine hydrochloride (0.067 g, 0.797 mmol) in Pyridine (Volume: 2 ml). The resulting solution was stirring and heating at 70 degree for 18 h. The reaction mixture was concentrated to dryness and partitioned between ethyl acetate (20 ml) and water (20 ml). The organic phase was separated and washed with water (2×15 ml), brine (15 ml) concentrated to give the crude product which was purified by column (biotage, 25 g) eluted with ethyl acetate/cyclohexane (0-50%) to give product (21 mg) $^1$H NMR (500 MHz, $CDCl_3$) 7.20-7.29 (m, 9H), 7.10 (s, 1H), 5.19 (s, 2H), 4.95 (s, 1H), 3.81 (s, 3H), 3.31 (s, 3H), 2.2-2.6 (m, 4H), 1.95-2.15 (m, 1H), 1.75-1.85 (m, 1H), 1.2-1.4 (br, 9H).

Step 2: 6-(4-(1-Aminocyclobutyl)phenyl)-1-methyl-7-phenyl-1H-pyrido[2,3-b][1,4]oxazin-2(3H)-one O-methyl oxime to a round bottomed flask containing tert-butyl 1-(4-(2-(methoxyimino)-1-methyl-7-phenyl-2,3-dihydro-1H-pyrido[2,3-b][1,4]oxazin-6-yl)phenyl)cyclobutylcarbamate (28 mg, 0.054 mmol) was added trifluoroacetic acid (1 ml). The resulting solution was stirred for 60 seconds then concentrated to dryness under reduced pressure. The residue was dissolved in diethyl ether (1 ml) and concentrated to dryness three times to give the trifluoroacetic acid salt of the product (14.5 mg). $^1$H NMR (500 MHz, $CD_3OD$) 7.49 (s, 1H), 7.35-7.39 (m, 5H), 7.28-7.30 (m, 3H), 7.21-7.23 (m, 2H), 5.24 (s, 2H), 3.83 (s, 3H), 3.35 (s, 3H), 2.72-2.78 (m, 2H), 2.54-2.60 (m, 2H), 2.2-2.3 (m, 1H), 1.9-2.0 (m, 1H), LCMS (Method D): $R_T$=0.96 min, M+H$^+$=415.2.

Example 91

1-(4-(7-phenyl-1-(pyridin-3-yl)-2,3-dihydro-1H-pyrido[2,3-b][1,4]oxazin-6-yl)phenyl)cyclobutanamine

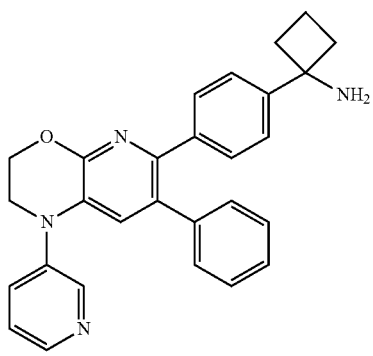 [SMILES: NC1(c2ccc(-c3nc4c(cc3-c3ccccc3)N(c3cccnc3)CCO4)cc2)CCC1]

Step 1: tert-butyl 1-(4-(7-phenyl-1-(pyridin-34)-2,3-dihydro-1H-pyrido[2,3-b][1,4]oxazin-6-yl)phenyl)cyclobutylcarbamate In a 15 mL reaction tube was added tert-butyl 1-(4-(2-oxo-7-phenyl-1-(pyridin-3-yl)-2,3-dihydro-1H-pyrido[2,3-b][1,4]oxazin-6-yl)phenyl)cyclobutylcarbamate (90 mg, 0.164 mmol) in anhydrous tetrahydrofuran (3 ml) to give a colourless solution. This was cooled to 0° C. followed by the addition of sodium borohydride (15 mg, 0.394 mmol) and boron trifluoride diethyl etherate (50 μl, 0.394 mmol). The reaction mixture was stirred at 0° C. under a nitrogen atmosphere for 3 hours then heated to 40° C. overnight. The reaction mixture was diluted with ethyl acetate (3 mL) and quenched by washing with saturated ammonium chloride solution (2×3 mL). The organic phase was dried over $Na_2SO_4$, filtered, concentrated to dryness under reduced pressure and purified by Biotage chromatography (cyclohexane:ethyl acetate, gradient elution from 88:12 to 0:100) then Biotage chromatography (dichloromethane:methanol, gradient elution from 99:1 to 90:10) then Biotage chromatography (dichloromethane: ethyl acetate, gradient elution from 88:12 to 0:100) to give the desired product as a yellow oil (30 mg, 34% yield). $^1$H-NMR (500 MHz, $CDCl_3$) δ 8.60 (1H, br s), 8.24 (1H, br s), 8.12 (1H, d), 7.65 (1H, br s), 7.36 (1H, s), 7.13-7.28 (7H, m), 7.02-7.08 (2H, m), 4.94 (1H, br s), 4.51 (2H, t), 3.86 (2H, t), 2.20-2.50 (4H, m), 1.95-2.05 (1H, m), 1.70-1.80 (1H, m), 1.00-1.38 (9H, br m). LCMS (Method D) RT=1.45 min, M+H$^+$=535.20.

Step 2: 1-(4-(7-phenyl-1-(pyridin-3-yl)-2,3-dihydro-1H-pyrido[2,3-b][1,4]oxazin-6-yl)phenyl)cyclobutanamine tert-Butyl 1-(4-(7-phenyl-1-(pyridin-3-yl)-2,3-dihydro-1H-pyrido[2,3-b][1,4]oxazin-6-yl)phenyl)cyclobutylcarbamate (10 mg, 0.019 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as an off-white solid (4 mg, 32% yield). $^1$H-NMR (500 MHz, MeOD) δ 8.57 (1H, br s), 8.28 (1H, br s), 7.80 (1H, d), 7.43 (1H, br s), 7.26 (2H, d), 7.24 (2H, d), 7.04-7.16 (4H, m), 6.90-7.00 (2H, m), 4.51 (2H, t), 3.80 (2H, t), 2.56-2.70 (2H, m), 2.37-2.52 (2H, m), 2.02-2.16 (1H, m), 1.74-1.90 (1H, m). LCMS (Method D) RT=0.77 min, M+H$^+$=435.20.

Example 92

1-(4-(1-bromo-8-phenyl-4H-pyrido[2,3-b][1,2,4]triazolo[4,3-d][1,4]oxazin-7-yl)phenyl)cyclobutanamine

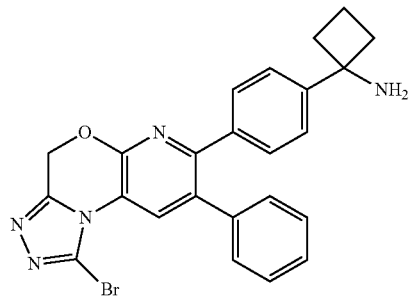 [SMILES: NC1(c2ccc(-c3nc4c(cc3-c3ccccc3)-n3c(Br)nnc3CO4)cc2)CCC1]

Step 1: tert-butyl(1-(4-(1-bromo-8-phenyl-4H-pyrido[2,3-b][1,2,4]triazolo[4,3-d][1,4]oxazin-7-yl)phenyl)cyclobutyl)carbamate A mixture of tert-butyl 1-(4-(8-phenyl-4H-pyrido[2,3-b][1,2,4]triazolo[4,3-d][1,4]oxazin-7-yl)phenyl)cyclobutyl-carbamate (200 mg, 0.404 mmol) and 1-bromopyrrolidine-2,5-dione (114.9275 mg, 0.646 mmol) in DCM (12 ml) and $CCl_4$ (18 ml) was heating at 50 degree for 24 h. The mixture was concentrated and the residue was partitioned between ethyl acetate (40 ml) and water (40 ml). The organic phase was separated and the aqueous phase was extracted with ethyl acetate (30 ml). The combined organic phase was washed with water (50 ml) brine (30 ml) and concentrated to give product 159 mg. $^1$H NMR (500 MHz, $CDCl_3$): 8.55 (s, 1H), 7.22-7.35 (m, 9H), 5.58 (s, 2H), 5.1 (br, 1H), 2.4-2.5 (m, 4H), 2.01-2.11 (m, 1H), 1.79-1.89 (m, 1H), 1.24-1.43 (br, 9H).

Step 2: 1-(4-(1-bromo-8-phenyl-4H-pyrido[2,3-b][1,2,4]triazolo[4,3-d][1,4]oxazin-7-yl)phenyl)cyclobutanamine Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(cyanomethyl)-3-(methoxymethyl)-2-oxo-7-phenyl-2,3-dihydro-1H-pyrido[2,3-b][1,4]oxazin-6-yl)phenyl)cyclobutyl)carbamate (18 mg, 0.031 mmol) was reacted to afford the title compound (4.5 mg). $^1$H NMR (500 MHz, $CH_3OD$) 8.71 (s, 1H), 7.50 (d, 2H), 7.43 (d, 2H), 7.34-7.36 (m, 3H), 7.28-7.31 (m, 2H), 5.70 (s, 2H), 2.76-2.80 (m, 2H), 2.57-2.61 (m, 2H), 2.2-2.27 (m, 1H), 1.9-2.0 (m, 1H), LCMS (Method D): $R_T$=0.774 min, M+=474.2, M+2=476.2

Example 93

(R)-2-(6-(4-(1-aminocyclobutyl)phenyl)-3-methyl-2-oxo-7-phenyl-2,3-dihydro-1H-pyrido[2,3-b][1,4]oxazin-1-yl)acetonitrile

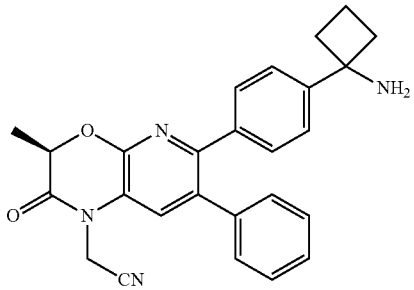 [SMILES: C[C@H]1Oc2nc(-c3ccc(C4(N)CCC4)cc3)c(-c3ccccc3)cc2N(CC#N)C1=O]

Step 1: (R) tert-butyl(1-(4-(1-(cyanomethyl)-3-methyl-2-oxo-7-phenyl-2,3-dihydro-1H-pyrido[2,3-b][1,4]oxazin-6-yl)phenyl)cyclobutyl)carbamate A solution of (R)-tert-butyl 1-(4-(3-methyl-2-oxo-7-phenyl-2,3-dihydro-1H-pyrido[2,3-b][1,4]oxazin-6-yl)phenyl)cyclobutylcarbamate (100 mg, 0.206 mmol) in DMF (2 ml) was added potassium carbonate (85 mg) and 2-bromoacetonitrile (44 μl, 0.618 mmol). The reaction mixture was stirred at room temperature for 48 h then was diluted with ethyl acetate (20 ml). Washed with water, brine, and dried with Na2SO4, filtered and concentrated to give crude product which was purified by column (biotage, 25 g) eluted with ethyl acetate and cyclohexane to afford product (55 mg). $^1$H NMR (500 MHz, $CDCl_3$): 7.35 (s, 1H), 7.20-7.32 (m, 9H), 4.98 (q, 1H), 4.87 (dd, 2H), 2.44-2.49 (m, 4H), 2.06 (m, 1H), 1.80 (m, 1H), 1.75 (d, 3H), 1.24-1.36 (br, 9H).

Step 2: (R)-2-(6-(4-(1-aminocyclobutyl)phenyl)-3-methyl-2-oxo-7-phenyl-2,3-dihydro-1H-pyrido[2,3-b][1,4]oxazin-1-yl)acetonitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, (R)-ten-butyl (1-(4-(1-(cyanomethyl)-3-methyl-2-oxo-7-phenyl-2,3-dihydro-1H-pyrido[2,3-b][1,4]oxazin-6-yl)phenyl)cyclobutyl)carbamate (41 mg, 0.078 mmol) was reacted to afford the title compound (22 mg). $^1$H NMR (500 MHz, CH$_3$OD) 7.71 (s, 1H), 7.45 (d, 2H), 7.39 (d, 2H), 7.32 (m, 3H), 7.26 (m, 2H), 5.14 (s, 2H), 5.10 (q, 1H), 2.74-2.80 (m, 2H), 2.55-2.61 (m, 2H), 2.22-2.26 (m, 1H), 1.96-1.99 (m, 1H), 1.71 (d, 3H). LCMS (Method D): R$_T$=0.81 min, M+H$^+$=425.2.

Example 94

(R)-6-(4-(1-aminocyclobutyl)phenyl)-1,3-dimethyl-7phenyl-1H-pyrido[2,3-b][1,4]oxazin-2(3H)-one

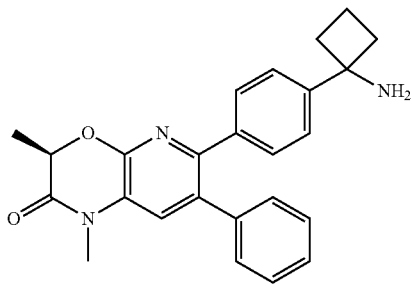 [SMILES: C[C@H]1Oc2nc(-c3ccc(C4(N)CCC4)cc3)c(-c3ccccc3)cc2N(C)C1=O]

Step 1: (R)-tert-butyl(1-(4-(3-methyl-2-oxo-7-phenyl-2,3-dihydro-1H-pyrido[2,3-b][1,4]oxazin-6-yl)phenyl)cyclobutyl)carbamate (S)-2-Chloropropanoic acid (0.20 g, 1.854 mmol) in a round-bottomed flask was mixed with thionyl chloride (0.149 ml, 2.039 mmol). A drop of DMF was added and the mixture was stirred for 0.5 h at room temperature then 80 degree for 2 h. The resulted light yellow liquid was diluted with THF (5 ml).

At 0 degree, in a 100 mL round-bottomed flask was tert-butyl 1-(4-(5-amino-6-oxo-3-phenyl-1,6-dihydropyridin-2-yl)phenyl)cyclobutylcarbamate (0.5 g, 1.159 mmol) and N-ethyl-N-isopropylpropan-2-amine (1.015 ml, 5.79 mmol) in THF (25 ml) to give a yellow suspension. The above acid chloride in THF solution was added in dropwise to the suspension in 30 min. The reaction mixture was stirred at room temperature for 16 h. The reaction mixture was transferred to a 250 ml round bottom flask. Sodium bicarbonate saturated solution (30 ml) and sodium bicarbonate (1 g) were added. The resulted mixture was heated to reflux for 24 h. The reaction mixture was cooled down to room temperature. The organic phase was separated. The aqueous phase was extracted with ethyl acetate (40 ml). The organic phase was combined and washed with water (30 mlX2), brine (25 ml) then concentrated at reduced pressure. The residue was suspended in DCM (10 ml). The precipitate was collected by filtration and washed with DCM (5 ml) to afford product 0.23 g. $^1$H NMR (500 MHz, CD$_3$OD): 7.20-7.32 (m, 8H), 7.13-7.15 (m, 2H), 4.98 (q, 1H), 2.41-2.47 (m, 4H), 2.05 (m, 1H), 1.86 (m, 1H), 1.64 (d, 3H), 1.21-1.36 (br, 9H).

Step 2: (R)-tert-butyl(1-(4-(1,3-dimethyl-2-oxo-7-phenyl-2,3-dihydro-1H-pyrido[2,3-b][1,4]oxazin-6-yl)phenyl)cyclobutyl)carbamate A solution of (R)-tert-butyl 1-(4-(3-methyl-2-oxo-7-phenyl-2,3-dihydro-1H-pyrido[2,3-b][1,4]oxazin-6-yl)phenyl)cyclobutylcarbamate (100 mg, 0.206 mmol) in DMF (2 ml) was added potassium carbonate (85 mg) and iodomethane (15p1, 0.247 mmol). The reaction mixture was stirred at room temperature for 16 h then was diluted with ethyl acetate (20 ml). Washed with water, brine, and dried with Na2SO4, filtered and concentrated to give crude product which was purified by column (Biotage, size: 25 g) eluted with ethyl acetate/cyclohexane (0-50%) to afford product (33 mg). $^1$H NMR (500 MHz, CDCl$_3$): 7.19-7.32 (m, 10H), 4.96 (q, 1H), 3.39 (s, 3H), 2.43-2.48 (m, 4H), 2.04 (m, 1H), 1.80 (m, 1H), 1.70 (d, 3H), 1.24-1.36 (m, 9H).

Step 3: 6-(4-(1-aminocyclobutyl)phenyl)-1,3-dimethyl-7=phenyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, (R)-tert-butyl(1-(4-(1,3-dimethyl-2-oxo-7-phenyl-2,3-dihydro-1H-pyrido[2,3-b][1,4]oxazin-6-yl)phenyl)cyclobutyl)carbamate (16 mg, 0.032 mmol) was reacted to afford the title compound (6.5 mg). $^1$H NMR (500 MHz, CH$_3$OD) 7.56 (s, 1H), 7.42 (d, 2H), 7.38 (d, 2H), 7.31 (m, 3H), 7.24 (m, 2H), 5.06 (q, 1H), 3.44 (s, 3H), 2.73-2.77 (m, 2H), 2.53-2.59 (m, 2H), 2.20-2.26 (m, 1H), 1.95-1.97 (m, 1H), 1.67 (d, 3H). LCMS (Method D): R$_T$=0.85 min, M+H$^+$=400.2.

Example 95

2-(6-(4-(1-aminocyclobutyl)phenyl)-3-(methoxymethyl)-2-oxo-7-phenyl-2,3-dihydro-1H-pyrido[2,3-b][1,4]oxazin-1-yl)acetonitrile

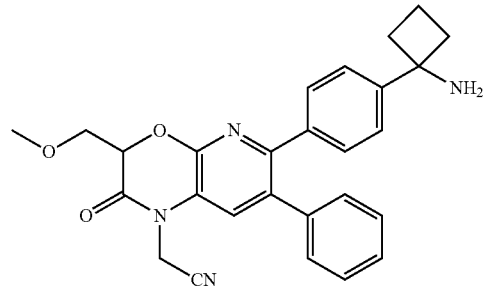 [SMILES: COCC1Oc2nc(-c3ccc(C4(N)CCC4)cc3)c(-c3ccccc3)cc2N(CC#N)C1=O]

Step 1: tert-butyl(1-(4-(1-(cyanomethyl)-3-(methoxymethyl)-2-oxo-7-phenyl-2,3-dihydro-1H-pyrido[2,3-b][1,4]oxazin-6-yl)phenyl)cyclobutyl)carbamate A solution of tert-butyl(1-(4-(3-(methoxymethyl)-2-oxo-7-phenyl-2,3-dihydro-1H-pyrido[2,3-b][1,4]oxazin-6-yl)phenyl)cyclobutyl)carbamate (60 mg, 0.116 mmol) in DMF (2 ml) was added potassium carbonate (48 mg) and 2-bromoacetonitrile (41.9 mg, 0.349 mmol). The reaction mixture was stirred at room temperature for 16 h then was diluted with ethyl acetate (20 ml). Washed with water, brine, and dried with $Na_2SO_4$, filtered and concentrated to give crude product which was purified by column (biotage, 25 g) eluted with ethyl acetate and cyclohexane to afford product (35 mg). $^1$H NMR (500 MHz, $CDCl_3$): 7.20-7.33 (m, 10H), 5.10 (t, 1H), 4.97 (s, 1H), 4.82 (dd, 2H), 4.03 (dd, 2H), 3.36 (s, 3H), 2.44-2.50 (m, 4H), 2.06 (m, 1H), 1.80 (m, 1H), 1.24-1.36 (br, 9H).

Step 2: 2-(6-(4-(1-aminocyclobutyl)phenyl)-3-(methoxymethyl)-2-oxo-7-phenyl-2,3-dihydro-1H-pyrido[2,3-b][1,4]oxazin-1-yl)acetonitrile Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(cyanomethyl)-3-(methoxymethyl)-2-oxo-7-phenyl-2,3-dihydro-1H-pyrido[2,3-b][1,4]oxazin-6-yl)phenyl)cyclobutyl)carbamate (35 mg, 0.063 mmol) was reacted to afford the title compound (18.5 mg). $^1$H NMR (500 MHz, $CH_3OD$) 7.63 (s, 1H), 7.45 (d, 2H), 7.39 (d,2H), 7.32 (m, 3H), 7.26 (m, 2H), 5.28 (t, 1H), 5.16 (dd, 2H), 4.01 (dd, 2H), 2.74-2.79 (m, 2H), 2.55-2.61 (m, 2H), 2.22-2.26 (m, 1H), 1.96-1.99 (m, 1H). LCMS (Method D): $R_T$=0.78 min, M+H$^+$=456.2.

Example 96

6-(4-(1-aminocyclobutyl)phenyl)-3-(methoxymethyl)-1-methyl-7-phenyl-1H-pyrido[2,3-b][1,4]oxazin-2(3H)-one

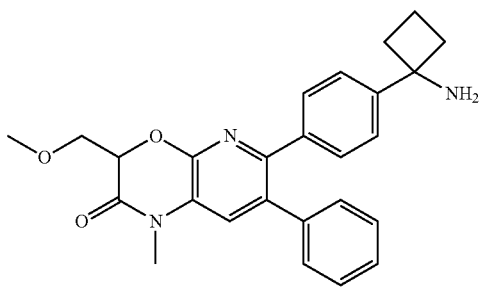 [SMILES: COCC1Oc2nc(-c3ccc(C4(N)CCC4)cc3)c(-c3ccccc3)cc2N(C)C1=O]

Step 1: tert-butyl(1-(4-(3-(methoxymethyl)-1-methyl-2-oxo-7-phenyl-2,3-dihydro-1H-pyrido[2,3-b][1,4]oxazin-6-yl)phenyl)cyclobutyl)carbamate 2-chloro-3-methoxypropanoic acid (0.257 g, 1.854 mmol) In a round-bottomed flask was mixed with thionyl chloride (0.149 ml, 2.039 mmol). A drop of DMF was added and the mixture was stirred for 0.5 h at room temperature then 80 degree for 2 h. The resulted light yellow liquid was diluted with THF (5 ml).

At 0 degree, in a 100 mL round-bottomed flask was tert-butyl 1-(4-(5-amino-6-oxo-3-phenyl-1,6-dihydropyridin-2-yl)phenyl)cyclobutylcarbamate (0.5 g, 1.159 mmol) and N-ethyl-N-isopropylpropan-2-amine (1.015 ml, 5.79 mmol) in THF (25 ml) to give a yellow suspension. The above acid chloride in THF solution was added in dropwise to the suspension in 30 min. The reaction mixture was stirred at room temperature for 16 h. The reaction mixture was transferred to a 250 ml round bottom flask. Sodium bicarbonate saturated solution (30 ml) and sodium bicarbonate (1 g) were added. The resulted mixture was heated to reflux for 24 hours. The reaction mixture was cooled down to room temperature. The organic phase was separated. The aqueous phase was extracted with ethyl acetate (40 ml). The organic phase was combined and washed with water (30 mlX2), brine (25 ml) then concentrated at reduced pressure. The residue was suspended in DCM (10 ml). The precipitate was collected by filtration and washed with DCM (5 ml) to afford product 0.26 g.). $^1$H NMR (500 MHz, $CDCl_3$): 8.11 (s, 1H), 7.23-7.31 (m, 6H), 7.15 (m, 2H), 7.07 (s, 1H), 5.06 (t, 1H), 5.01 (br, 1H), 4.08 (dd, 1H), 3.95 (dd, 1H), 3.39 (s, 3H), 2.41-2.47 (m, 4H), 2.05 (m, 1H), 1.80 (m, 1H), 1.21-1.36 (br, 9H).

Step 2: tert-butyl(1-(4-(3-(methoxymethyl)-1-methyl-2-oxo-7-phenyl-2,3-dihydro-1H-pyrido[2,3-b][1,4]oxazin-6-yl)phenyl)cyclobutyl)carbamate A solution of tert-butyl(1-(4-(3-(methoxymethyl)-1-methyl-2-oxo-7-phenyl-2,3-dihydro-1H-pyrido[2,3-b][1,4]oxazin-6-yl)phenyl)cyclobutyl)carbamate (60 mg, 0.116 mmol) in DMF (1 ml) was added potassium carbonate (48 mg) and iodomethane (8.7µl, 0.14 mmol). The reaction mixture was stirred at room temperature for 16 h then was diluted with ethyl acetate (20 ml). Washed with water, brine, and dried with $Na_2SO_4$, filtered and concentrated to give crude product which was purified by column (Biotage, size: 25 g) eluted with ethyl acetate/cyclohexane (0-50%) to afford product (27 mg). $^1$H NMR (500 MHz, $CDCl_3$): 7.19-7.32 (m, 10H), 5.05 (t, 1H), 4.97 (br, 1H), 4.06 (dd, 1H), 3.94 (dd, 1H), 3.40 (s, 3H), 3.37 (s, 3H), 2.43-2.48 (m, 4H), 2.04 (m, 1H), 1.79 (m, 1H), 1.24-1.36 (m, 9H).

Step 3: 6-(4-(1-aminocyclobutyl)phenyl)-3-(methoxymethyl)-1-methyl-7-phenyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(3-(methoxymethyl)-1-methyl-2-oxo-7-phenyl-2,3-dihydro-1H-pyrido[2,3-b][1,4]oxazin-6-yl)phenyl)cyclobutyl)carbamate (35 mg, 0.066 mmol) was reacted to afford the title compound (28 mg). $^1$H NMR (500 MHz, $CH_3OD$) 7.49 (s, 1H), 7.42 (d, 2H), 7.38 (d,2H), 7.31 (m, 3H), 7.25 (m, 2H), 5.19 (t, 1H), 4.02 (dd, 1H), 3.92 (dd, 1H), 3.44 (s, 3H), 2.74-2.79 (m, 2H), 2.56-2.60 (m, 2H), 2.21-2.26 (m, 1H), 1.94-1.99 (m, 1H). LCMS (Method D): $R_T$=0.79 min, M+H$^+$=430.2.

Example 97

6-(4-((1s,3s)-1-amino-3-hydroxycyclobutyl)phenyl)-1-methyl-7-phenyl-1H-pyrido[2,3-b][1,4]oxazin-2(3H)-one

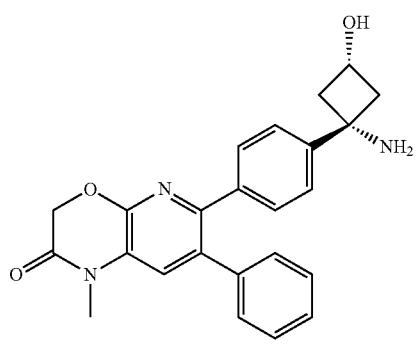 [SMILES: CN1C(=O)COc2nc(-c3ccc([C@]4(N)C[C@@H](O)C4)cc3)c(-c3ccccc3)cc21]

Step 1: tert-butyl(1s,3s)-3-hydroxy-1-(4-(4,4,5,5-tetramethyl-1,3,2-dioxaborolan-2-yl)phenyl)cyclobutylcarbamate In a 40 mL reaction tube was added tert-butyl(1s,3s)-1-(4-bromophenyl)-3-hydroxycyclobutylcarbamate (0.25 g, 0.731 mmol) in anhydrous tetrahydrofuran (14 ml) to give a colourless solution. This was degassed by bubbling nitrogen for 20 minutes, followed by the addition of [1,1'-bis(diphenylphosphino)ferrocene]dichloropalladium(II) dichloromethane adduct (60 mg, 0.073 mmol). After bubbling nitrogen for a further 15 minutes, potassium acetate (143 mg, 1.461 mmol) and bis(pinacolato)diboron (223 mg, 0.877 mmol) were added. The reaction mixture was heated to reflux overnight then concentrated to dryness under reduced pressure and purified by Biotage chromatography (cyclohexane:ethyl acetate, gradient elution from 88:12 to 0:100) to give the desired product as a colourless oil that solidified upon standing (240 mg, 84% yield). $^1$H-NMR (500 MHz, CDCl$_3$) δ 7.71 (2H, d), 7.44 (2H, d), 4.15 (1H, br s), 2.87-2.98 (2H, m), 2.27-2.44 (2H, m), 1.22-1.49 (21H, br m).

Step 2: tert-butyl(1s,3s)-3-hydroxy-1-(4-(1-methyl-2-oxo-7-phenyl-2,3-dihydro-1H-pyrido[2,3-b][1,4]oxazin-6-yl)phenyl)cyclobutylcarbamate In a 10 mL microwave tube was added 6-bromo-1-methyl-7-phenyl-1H-pyrido[2,3-b][1,4]oxazin-2(3H)-one (50 mg, 0.157 mmol), tert-butyl(1s,3s)-3-hydroxy-1-(4-(4,4,5,5-tetramethyl-1,3,2-dioxaborolan-2-yl)phenyl)cyclobutylcarbamate (73 mg, 0.188 mmol) and tert-butyl(1s,3s)-3-hydroxy-1-(4-(4,4,5,5-tetramethyl-1,3,2-dioxaborolan-2-yl)phenyl)cyclobutylcarbamate (73 mg, 0.188 mmol) in a mixture of 1,4-dioxane (3.6 mL) and water (1.2 mL) to give a yellow solution. This was degassed by bubbling nitrogen for 15 minutes, then heated to 100° C. under microwave irradiation for 15 minutes. The reaction mixture was diluted with water (10 mL) and extracted into ethyl acetate (3×5 mL). The combined organic phases were dried over Na$_2$SO$_4$, filtered and concentrated to dryness under reduced pressure to give a yellow oil. This was purified by Biotage chromatography (cyclohexane:ethyl acetate, gradient elution from 100:0 to 0:100) then Biotage chromatography (dichloromethane:methanol, gradient elution from 100:0 to 90:10) to give the desired product as a white solid (8 mg, 10% yield). $^1$H-NMR (500 MHz, CDCl$_3$) δ 7.18-7.36 (10H, m), 4.91 (3H, s), 4.06 (1H, br s), 3.40 (3H, s), 3.00 (2H, br s), 2.77 (2H, br s), 1.12-1.52 (9H, br m). LCMS (Method D) RT=1.19 min, M+H$^+$=502.20.

Step 3: 6-(4-((1s,3s)-1-amino-3-hydroxycyclobutyl)phenyl)-1-methyl-7-phenyl-1H-Pyrido[2,3-b][1,4]oxazin-2(3H)-one In a 10 mL round-bottomed flask was added tert-butyl(1s,3s)-3-hydroxy-1-(4-(1-methyl-2-oxo-7-phenyl-2,3-dihydro-1H-pyrido[2,3-b][1,4]oxazin-6-yl)phenyl)cyclobutylcarbamate (5 mg, 9.97 μmol) in 1,4-dioxane (1 mL) to give a colourless solution. To this was added dropwise 4M HCl in 1,4-dioxane (1 mL, 4.00 mmol) and the resulting solution stirred at room temperature for 6 hours. The reaction mixture was diluted by the dropwise addition of diethyl ether (2 mL) and stirred for 10 minutes to give a white precipitate. The layers were allowed to settle and the supernatant solution removed. The solid was washed twice more with diethyl ether (2 mL), allowing to settle and removing the supernatant solvent each time. The remaining solvent was removed by concentration to dryness under reduced pressure, then freeze-drying over the weekend to give the desired product as a white solid (4 mg, 92% yield). $^1$H-NMR (500 MHz, MeOD) δ 7.53 (1H, s), 7.38-7.45 (4H, m), 7.24-7.32 (3H, m), 7.18-7.24 (2H, m), 4.93 (2H, s), 4.05 (1H, quin), 3.42 (3H, s), 3.00-3.12 (2H, m), 2.37-2.48 (2H, m). LCMS (Method D) RT=0.71 min, M+H$^+$=402.20.

Example 98

1-(4-(1-(difluoromethyl)-8-phenyl-4H-pyrido[2,3-b][1,2,4]triazolo[4,3-d][1,4]oxazin-7-yl)phenyl)cyclobutanamine

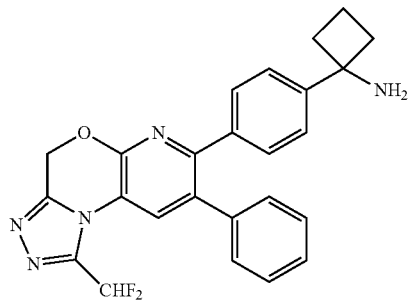

Step 1: (E)-Tert-butyl (1-(4-(2-(2-(2,2-difluoroacetyl)hydrazono)-7-phenyl-2,3-dihydro-1H-pyrido[2,3-b][1,4]oxazin-6-yl)phenyl)cyclobutyl)carbamate Ethyl 2,2-difluoroacetate (0.43 ml, 4.10 mmol) and hydrazine monohydrate were heated to 60° C. in N,N-dimethylformamide (1 ml) for 30 minutes to give a colourless solution. Tert-butyl (1-(4-(7-phenyl-2-thioxo-2,3-dihydro-1H-pyrido[2,3-b][1,4]oxazin-6-yl)phenyl)cyclobutyl)carbamate (100 mg, 0.205 mmol) was added to the previous solution at room temperature. The resulting mixture was heated to 70° C. for 20 hours. The reaction mixture was concentrated under reduced pressure and the crude material (100 mg, quantitative yield) was used for the next step without further purification. LCMS (Method D): R$_T$=1.37 min, M+1=564.

Step 2: Tert-butyl (1-(4-(1-(difluoromethyl)-8-phenyl-4H-pyrido[2,3-b][1,2,4]triazolo[4,3-d][1,4]oxazin-7-yl)phenyl)cyclobutyl)carbamate A solution of (E)-tert-butyl(1-(4-(2-(2-(2,2-difluoroacetyl)hydrazono)-7-phenyl-2,3-dihydro-1H-pyrido[2,3-b][1,4]oxazin-6-yl)phenyl)cyclobutyl)carbamate (80 mg, 0.142 mmol) in p-xylene (1 ml) was heated to 150° C. for 15 minutes under microwave irradiation. The resulting reaction mixture was concentrated to dryness under reduced pressure and purified by Biotage silica gel chromatography (gradient 0% to 2% methanol in dichloromethane) to give the title compound (15 mg, 20%). LCMS (Method D): R$_T$=1.529 min, M+1=546.

Step 3: 1-(4-(1-(difluoromethyl)-8-phenyl-4H-pyrido[2,3-b][1,2,4]triazolo[4,3-d][1,4]oxazin-7-yl)phenyl)cyclobutanamine Tert-butyl (1-(4-(1-(difluoromethyl)-8-phenyl-4H-pyrido[2,3-b][1,2,4]triazolo[4,3-d][1,4]oxazin-7-yl)phenyl)cyclobutyl)carbamate (15 mg, 0.073 mmol) was dissolved in TFA (1 mL) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent removed by pipette. This was repeated three times. The residue was then slurred in n-hexane (2 ml) and after settling the supernatant solvent removed by pipette. This was repeated three times. The remaining solvent was removed under reduced pressure and the residue was dried to give the desired product as an off-white solid (8 mg, 65% yield). LCMS (Method D): RT=0.803 min, M+1=446. $^1$H-NMR (500 MHz, CD$_3$OD) δ 8.20 (1H, s), 7.53-7.47 (3H, m), 7.46-7.41 (2H, m), 7.39-7.33 (3H, m), 7.30-7.23 (2H, m), 5.77 (2H, s), 2.83-2.70 (2H, m), 2.63-2.53 (2H, m), 2.30-2.19 (1H, m), 2.06-1.90 (1H, m).

Example 99

7-(4-(1-aminocyclobutyl)phenyl)-2-methyl-8-phenyl-2,4-dihydro-1H-pyrido[2,3-b][1,2,4]triazolo[4,3-d][1,4]oxazin-1-one

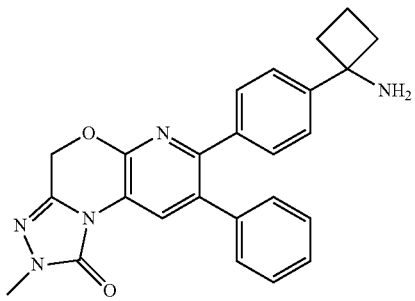 [SMILES: Cn1nc2n(c1=O)-c1cc(-c3ccccc3)c(-c3ccc(C4(N)CCC4)cc3)nc1OC2]

Step 1: tert-butyl(1-(4-(2-methyl-1-oxo-8-phenyl-2,4-dihydro-1H-pyrido[2,3-b][1,2,4]triazolo[4,3-d][1,4]oxazin-7-yl)phenyl)cyclobutyl)carbamate To a solution of tert-butyl(1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate (26 mg, 0.05 mmol) in dry DMF (1 ml) was added potassium carbonate (21 mg, 0.15 mmol) and methyliodide (10 μl, 0.15 mmol) under nitrogen. The resulting mixture was stirred overnight at room temperature. Water was added and the mixture was extracted with EtOAc (3×5 ml). The combined organic phases were dried over Na$_2$SO$_4$ and concentrated to dryness under reduced pressure. The resulting residue was purified by Biotage silica gel chromatography (gradient 0 to 40% EtOAc in cyclohexane) to give the title compound (22 mg, 82%). $^1$H NMR (500 MHz, CDCl$_3$): 8.50 (1H, s), 7.25 (2H, d), 7.20-7.19 (5H, m), 7.15-7.12 (2H, m), 5.21 (2H, s), 5.00 (1H, br s), 3.46 (3H, s), 2.55-2.25 (4H, m), 2.10-2.03 (1H, m), 1.86-1.78 (1H, m), 1.44-1.15 (9H, br).

Step 2: 7-(4-(1-aminocyclobutyl)phenyl)-2-methyl-8-phenyl-2,4-dihydro-1H-pyrido[2,3-b][1,2,4]triazolo[4,3-d][1,4]oxazin-1-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-methyl-1-oxo-8-phenyl-2,4-dihydro-1H-pyrido[2,3-b][1,2,4]triazolo[4,3-d][1,4]oxazin-7-yl)phenyl)cyclobutyl)carbamate (26 mg, 0.05 mmol) was reacted to afford the title compound (18 mg, 56%). LCMS (method D): R$_T$=0.764 min, M-NH$_2$=409. $^1$H NMR (500 MHz, MeOD): 8.56 (1H, s), 7.45 (2H, d), 7.41 (2H, d), 7.33-7.31 (3H, m), 7.24-7.23 (2H, m), 5.43 (2H, s), 3.53 (3H, s), 2.78-2.72 (2H, m), 2.59-2.53 (2H, m), 2.25-2.18 (1H, m), 1.99-1.91 (1H, m).

Example 100

1-(4-(8-phenyl-1-(trifluoromethyl)-4H-pyrido[2,3-b][1,2,4]triazolo[4,3-d][1,4]oxazin-7-yl)phenyl)cyclobutanamine

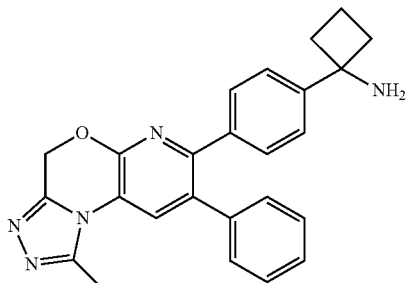

Step 1: Tert-butyl (1-(4-(8-phenyl-1-(trifluoromethyl)-4H-pyrido[2,3-b][1,2,4]triazolo[4,3-d][1,4]oxazin-7-yl)phenyl)cyclobutyl)carbamate A solution of tert-butyl(1-(4-(7-phenyl-2-thioxo-2,3-dihydro-1H-pyrido[2,3-b][1,4]oxazin-6-yl)phenyl)cyclobutyl)carbamate (70 mg, 0.144 mmol) and 2,2,2-trifluoroacetohydrazide (7.3 mg, 0.057 mmol) in p-xylene (1 ml) was heated to 150° C. for 30 minutes under microwave irradiation. The resulting reaction mixture was concentrated to dryness under reduced pressure and purified by Biotage silica gel chromatography (gradient 0% to 20% ethyl acetate in n-hexanes) to give the title compound (7 mg, 20%). LCMS (Method D): R$_T$=1.633 min, M+1=564. $^1$H NMR (500 MHz, CDCl$_3$): 7.96 (1H, s), 7.36-7.27 (7H, m), 7.21-7.17 (2H, m), 5.63 (2H, s), 2.55-2.40 (4H, m), 2.14-1.98 (1H, m), 1.88-1.78 (1H, m), 1.37-1.20 (9H, bs).

Step 2: 1-(4-(8-phenyl-1-(trifluoromethyl)-4H-pyrido[2,3-b][1,2,4]triazolo[4,3-d][1,4]oxazin-7-yl)phenyl)cyclobutanamine Tert-butyl (1-(4-(8-phenyl-1-(trifluoromethyl)-4H-pyrido[2,3-b][1,2,4]triazolo[4,3-d][1,4]oxazin-7-yl)phenyl)cyclobutyl)carbamate (7 mg, 0.012 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed 5.47 (2H, s), 5.01 (2H, s), 2.78-2.72 (m, 2H), 2.59-2.53 (m, 2H), 2.25-2.18 (m, 1H), 1.99-1.91 (m, 1H).

under reduced pressure and the residue was dried to give the desired product as an off-white solid (1.5 mg, 26% yield). LCMS (Method D): RT=0.877 min, M+1=465. $^1$H-NMR (500 MHz, CD$_3$OD) δ 8.02 (1H, s), 7.50 (2H, d), 7.43 (2H, d), 7.38-7.36 (3H, m), 7.25 (2H, m), 5.77 (2H, s), 2.75-2.69 (2H, m), 2.55-2.42 (2H, m), 2.29-2.17 (1H, m), 2.05-1.90 (1H, m).

Example 102

6-(4-(1-aminocyclobutyl)phenyl)-1-isobutyl-7-phenyl-1H-pyrido[2,3-b][1,4]oxazin-2(3H)-one

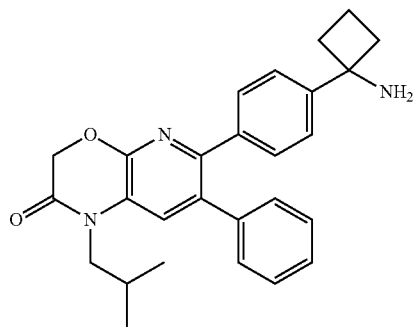

Example 101

2-(7-(4-(1-aminocyclobutyl)phenyl)-1-oxo-8-phenyl-1H-pyrido[2,3-b][1,2,4]triazolo[4,3-d][1,4]oxazin-2(4H)-yl)acetonitrile

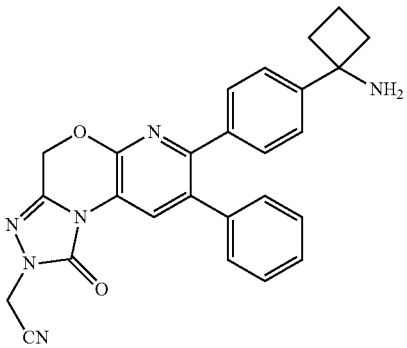 [SMILES: N#CCn1nc2n(c1=O)-c1cc(-c3ccccc3)c(-c3ccc(C4(N)CCC4)cc3)nc1OC2]

Step 1 tert-butyl(1-(4-(1-isobutyl-2-oxo-7-phenyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (100 mg, 0.212 mmol) was reacted with 1-bromo-2-methylpropane (87 mg, 0.636 mmol) to afford the title compound (78 mg). LCMS (method D) RT=1.73 min, M+H=528.2

Step 1: tert-butyl(1-(4-(2-(cyanomethyl)-1-oxo-8-phenyl-2,4-dihydro-1H-pyrido[2,3-b][1,2,4]triazolo[4,3-d][1,4]oxazin-7-yl)phenyl)cyclobutyl)carbamate To a solution of tert-butyl(1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate (70 mg, 0.14 mmol) in dry DMF (1 ml) was added potassium carbonate (57 mg, 0.41 mmol) and bromoacetonitrile (29 μl, 0.41 mmol) under nitrogen. The resulting mixture was stirred for 1 hour at room temperature. Water was added and the mixture was extracted with EtOAc (3×10 ml). The combined organic phases were dried over Na$_2$SO$_4$ and concentrated to dryness under reduced pressure. The resulting residue was purified by Biotage silica gel chromatography (gradient 0 to 35% EtOAc in cyclohexane) to give the title compound (45 mg, 60%). $^1$H NMR (500 MHz, CDCl$_3$): 8.43 (1H, s), 7.26-7.19 (7H,m), 7.14-7.12 (2H, m), 5.25 (2H, s), 4.96 (1H, br s), 4.72 (2H, s), 2.55-2.25 (4H, m), 2.10-2.03 (1H, m), 1.86-1.78 (1H, m), 1.44-1.15 (9H, br).

Step 2: 6-(4-(1-aminocyclobutyl)phenyl)-1-isobutyl-7-phenyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(2-oxo-7-phenyl-1-propyl-2,3-dihydro-1H-pyrido[2,3-b][1,4]oxazin-6-yl)phenyl)cyclobutyl)carbamate (50 mg, 0.078 mmol) was reacted to afford the title compound (34.5 mg). $^1$H NMR (500 MHz, CH$_3$OD) 7.57 (1H, s), 7.38-7.42 (4H, m), 7.30-32 (3H, m), 7.21-7.2 (2H, m), 4.97 (2H, s), 3.92 (2H, d), 2.73-2.79 (2H, m), 2.54-2.60 (2H, m), 2.22-2.25 (1H, m), 2.13-2.16 (1H, m), 1.95-1.99 (1H, m), 1.0 (6H, d). LCMS (method D) RT: 0.93, M+H$^+$=428.2.

Example 103

7-(4-(1-aminocyclobutyl)phenyl)-8-phenyl-2-(2,2,2-trifluoroethyl)-2,4-dihydro-1H-pyrido[2,3-b][1,2,4]triazolo[4,3-d][1,4]oxazin-1-one Step 2: 2-(7-(4-(1-aminocyclobutyl)phenyl)-1-oxo-8-phenyl-1H-pyrido[2,3-b][1,2,4]triazolo[4,3-d][1,4]oxazin-2(4H)-yl)acetonitrile Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-(cyanomethyl)-1-oxo-8-phenyl-2,4-dihydro-1H-pyrido[2,3-b][1,2,4]triazolo[4,3-d][1,4]oxazin-7-yl)phenyl)cyclobutyl)carbamate (45 mg, 0.08 mmol) was reacted to afford the title compound (34 mg, 61%). LCMS (Method D): R$_T$=0.777 min, M-NH$_2$=434. $^1$H NMR (500 MHz, MeOD): 8.54 (1H, s), 7.45 (2H, d), 7.41 (2H, d), 7.33-7.31 (3H, m), 7.24-7.23 (m, 2H),

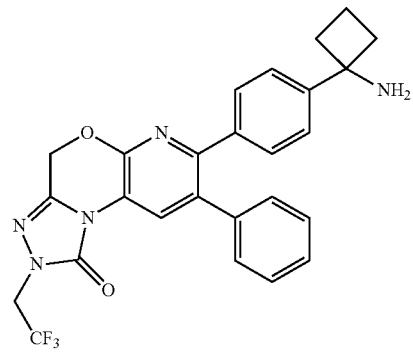 [SMILES: NC1(c2ccc(-c3nc4c(cc3-c3ccccc3)-n3c(nn(CC(F)(F)F)c3=O)CO4)cc2)CCC1]

Step 1: tert-butyl(1-(4-(1-oxo-8-phenyl-2-(2,2,2-trifluoroethyl)-2,4-dihydro-1H-pyrido[2,3-b][1,2,4]triazolo[4,3-d][1,4]oxazin-7-yl)phenyl)cyclobutyl)carbamate To a solution of tert-butyl(1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate (98 mg, 0.19 mmol) in dry DMF (2 ml) was added potassium carbonate (79 mg, 0.57 mmol) and 2-bromo-1,1,1-trifluoroethane (94 mg, 0.57 mmol) under nitrogen. The resulting mixture was stirred for 1 hour at 80° C. Water was added and the mixture was extracted with EtOAc (3×). The combined organic phases were dried over Na$_2$SO$_4$ and concentrated to dryness under reduced pressure. The resulting residue was purified by Biotage silica gel chromatography (gradient 0 to 27% EtOAc in cyclohexane) to give the title compound (45 mg, 40%). $^1$H NMR (500 MHz, CDCl$_3$): 8.47 (1H, s), 7.26-7.20 (7H,m), 7.14-7.12 (2H, m), 5.25 (2H, s), 4.96 (1H, br s), 4.38 (2H, q), 2.55-2.25 (4H, m), 2.10-2.03 (1H, m), 1.86-1.78 (1H, m), 1.44-1.15 (9H, br).

Step 2: 7-(4-(1-aminocyclobutyl)phenyl)-8-phenyl-2-(2,2,2-trifluoroethyl)-2,4-dihydro-1H-pyrido[2,3-b][1,2,4]triazolo[4,3-d][1,4]oxazin-1-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-oxo-8-phenyl-2-(2,2,2-trifluoroethyl)-2,4-dihydro-1H-pyrido[2,3-b][1,2,4]triazolo[4,3-d][1,4]oxazin-7-yl)phenyl)cyclobutyl)carbamate (45 mg, 0.08 mmol) was reacted to afford the title compound (34 mg, 61%). LCMS (Method D): R$_T$=0.923 min, M-NH$_2$=477. $^1$H NMR (500 MHz, MeOD): 8.43 (1H, s), 7.34-7.28 (4H, m), 7.21-7.20 (3H, m), 7.13-7.12 (2H, m), 5.34 (2H, s), 4.49 (2H, q), 2.70-2.62 (2H, m), 2.49-2.43 (2H, m), 2.15-2.08 (1H, m), 1.91-1.77 (1H, m).

Example 104

7-(4-(1-aminocyclobutyl)phenyl)-8-phenyl-4,5-dihydro-1H-pyrido[2,3-b][1,4]diazepin-2(3H)-one

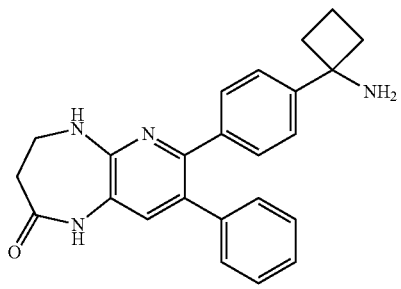 [SMILES: NC1(c2ccc(-c3nc4c(cc3-c3ccccc3)NC(=O)CCN4)cc2)CCC1]

Step 1: Ethyl 3-((6-(4-(1-((tert-butoxycarbonyl)amino)cyclobutyl)phenyl)-3-nitro-5-phenylpyridin-2-yl)amino)propanoate To a solution of tert-butyl(1-(4-(6-chloro-5-nitro-3-phenylpyridin-2-yl)phenyl)cyclobutyl)carbamate (1.03 g, 2.14 mmol) in EtOH (8 ml) was added triethylamine (1.49 ml, 10.72 mmol) and ethyl 3-aminopropanoate.HCl (1.65 g, 10.72 mmol) under nitrogen. The resulting mixture was stirred for 1.5 hours at 80° C. under microwave irradiation. Water was added and the mixture was extracted with AcOEt (3×15 ml). The combined organic phases were dried over Na$_2$SO$_4$ and concentrated to dryness under reduced pressure. The resulting residue was purified by Biotage silica gel chromatography (gradient 0 to 30% EtOAc in cyclohexane) to give the title compound (1.2 g, quantitative). $^1$H NMR (500 MHz, CDCl$_3$): 8.50 (1H, s), 8.38 (1H, s), 7.32 (2H, d), 7.23-7.18 (5H, m), 7.09-7.07 (2H, m), 5.00 (1H, br s), 4.12 (2H, q), 3.98 (2H, q), 2.71-2.68 (2H, t), 2.52-2.20 (4H, m), 2.00-1.95 (1H, m), 1.79-1.65 (1H, m), 1.40-1.10 (9H, br), 1.20 (3H, t).

Step 2: 34(6-(4-(1-(((tert-butoxycarbonyl)amino)cyclobutyl)phenyl)-3-nitro-5-phenylpyridin-2-yl)amino)propanoic acid To a solution of ethyl 3-((6-(4-(1-((tert-butoxycarbonyl)amino)cyclobutyl)phenyl)-3-nitro-5-phenylpyridin-2-yl)amino)propanoate (558 mg, 0.99 mmol) in THF (4 ml) was added 1M NaOH (4 ml, 4 mmol). The resulting mixture was stirred overnight at 50° C. The organic was separated and concentrated to dryness under reduced pressure. The resulting residue was used directly without purification.

Step 3: 34(3-amino-6-(4-(1-((tert-butoxycarbonyl)amino)cyclobutyl)phenyl)-5-phenylpyridin-2-yl)amino)propanoic acid To a solution of 34(6-(4-(1-((tert-butoxycarbonyl)amino)cyclobutyl)phenyl)-3-nitro-5-phenylpyridin-2-yl)amino)propanoic acid (200 mg, 0.38 mmol) in THF (100 mL) was added Pd/C (4 mg, 0.04 mmol). The resulting mixture was purged with nitrogen and with H$_2$ and then stirred under H$_2$ (2 bars) overnight at room temperature. The black mixture was filtered over celite, rinsed few times with THF (making sure the cake was wet at all times), dried over Na$_2$SO$_4$ and concentrated to dryness under reduced pressure. The resulting residue was used directly without purification.

Step 4: tert-butyl(1-(4-(2-oxo-8-phenyl-2,3,4,5-tetrahydro-1H-pyrido[2,3-b][1,4]diazepin-7-yl)phenyl)cyclobutyl)carbamate To a solution of 3-((3-amino-6-(4-(1-((tert-butoxycarbonyl)amino)cyclobutyl)phenyl)-5-phenylpyridin-2-yl)amino)propanoic acid (100 mg, 0.20 mmol) in dry DMF (1 ml) was added EDC (153 mg, 0.80 mmol) and HOBT (122 mg, 0.796 mmol) under nitrogen. The resulting mixture was stirred overnight at room temperature. Water was added and the mixture was extracted with EtOAc (3×10 ml). The combined organic phases were dried over Na$_2$SO$_4$ and concentrated to dryness under reduced pressure. The resulting residue was purified by Biotage silica gel chromatography (gradient 0 to 55% EtOAc in cyclohexane) to give the title compound (68 mg, 71%). $^1$H NMR (500 MHz, CDCl$_3$): 8.38 (1H, br s), 7.94 (1H, br s), 7.72-7.12 (8H, m), 7.01-6.99 (2H, m), 5.00 (1H, s), 3.68-3.66 (2H, m), 2.82-2.80 (2H, m), 2.52-2.20 (4H, m), 2.00-1.95 (1H, m), 1.79-1.65 (1H, m), 1.40-1.10 (9H, br)

Step 5: 7-(4-(1-aminocyclobutyl)phenyl)-8-phenyl-4,5-dihydro-1H-pyrido[2,3-b][1,4]diazepin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(2-oxo-8-phenyl-2,3,4,5-tetrahydro-1H-pyrido[2,3-b][1,4]diazepin-7-yl)phenyl)cyclobutyl)carbamate (27 mg, 0.06 mmol) was reacted to afford the title compound (25 mg, 73%). LCMS (Method D): $R_T$=0.644 min, M+1=385. $^1$H NMR (500 MHz, MeOD): 7.47-7.43 (5H, m), 7.27-7.25 (3H, m), 7.16-7.14 (2H, m), 3.78-3.76 (2H, m), 2.90-2.88 (2H, m), 2.79-2.73 (2H, m), 2.62-2.56 (2H, m), 2.26-2.22 (1H, m), 1.99-1.95 (1H, m).

Example 105

6-(4-(1-aminocyclobutyl)phenyl)-7-phenyl-1-propyl-1H-pyrido[2,3-b][1,4]oxazin-2(3H)-one

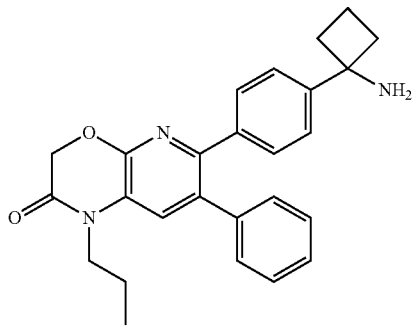 [SMILES: CCCN1C(=O)COc2nc(-c3ccc(C4(N)CCC4)cc3)c(-c3ccccc3)cc21]

Step 1 tert-butyl(1-(4-(2-oxo-7-phenyl-1-propyl-2,3-dihydro-1H-pyrido[2,3-b][1,4]oxazin-6-yl)phenyl)cyclobutyl)carbamate Following the procedure for tert-butyl(1-(4-(1-(2-cyanoethyl)-2-oxo-7-phenyl-2,3-dihydro-1H-pyrido[2,3-b][1,4]oxazin-6-yl)phenyl)cyclobutyl)carbamate, tert-butyl 1-(4-(2-oxo-7-phenyl-2,3-dihydro-1H-pyrido[2,3-b][1,4]oxazin-6-yl)phenyl)cyclobutylcarbamate (60 mg, 0.127 mmol) was reacted with 1-iodopropane (32.4 mg, 0.191 mmol) to afford the title compound (43 mg. $^1$H NMR (500 MHz, CD$_3$OD): 7.53 (1H, s), 7.21-7.32 (9H, m), 4.94 (2H, s), 4.02 (2H, t), 2.44-2.47 (4H, m), 2.05-2.10 (1H, m), 1.85-1.87 (1H, m), 1.73-1.77 (2H, m), 1.02-1.48 (9H, br), 1.01 (3H, t).

Step 2: 6-(4-(1-aminocyclobutyl)phenyl)-7-phenyl-1-propyl-1H-pyrido[2,3-b][1,4]oxazin-2(3H)-one Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(2-oxo-7-phenyl-1-propyl-2,3-dihydro-1H-pyrido[2,3-b][1,4]oxazin-6-yl)phenyl)cyclobutyl)carbamate (40 mg, 0.078 mmol) was reacted to afford the title compound (16.5 mg). $^1$H NMR (500 MHz, CH$_3$OD) 7.55 (1H, s), 7.41 (2H, d), 7.38 (2H, d), 7.32 (3H, m), 7.24 (2H, m), 4.96 (2H, s), 4.02 (2H, t), 2.73-2.78 (2H, m), 2.54-2.60 (2H, m), 2.20-2.28 (1H, m), 1.91-1.99 (1H, m), 1.71-1.79 (2H, m), 1.01 (3H, t). LCMS (Method D): $R_T$=0.79 min, M+H$^+$=414.2.

Example 106

6-(4-(1-aminocyclobutyl)phenyl)-1-(3-hydroxy-2-(hydroxymethyl)-2-methylpropyl)-7-phenyl-1H-pyrido[2,3-b][1,4]oxazin-2(3H)-one

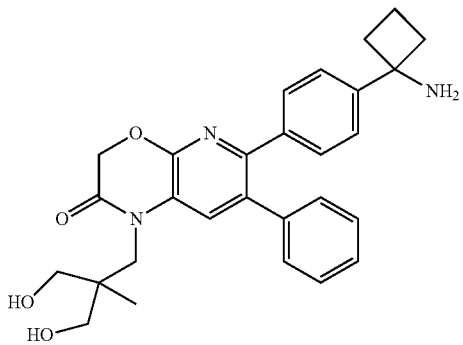 [SMILES: CC(CO)(CO)CN1C(=O)COc2nc(-c3ccc(C4(N)CCC4)cc3)c(-c3ccccc3)cc21]

Step 1: tert-butyl(1-(4-(1-((3-methyloxetan-3-yl)methyl)-2-oxo-7-phenyl-2,3-dihydro-1H-pyrido[2,3-b][1,4]oxazin-6-yl)phenyl)cyclobutyl)carbamate To a solution of tert-butyl(1-(4-(2-oxo-7-phenyl-2,3-dihydro-1H-pyrido[2,3-b][1,4]oxazin-6-yl)phenyl)cyclobutyl)carbamate (50 mg, 0.11 mmol) in dry DMF (1 mL) was added potassium carbonate (44 mg, 0.32 mmol) and 3-(chloromethyl)-3-methyloxetane (38 mg, 0.32 mmol) under nitrogen. The resulting mixture was stirred for 2.5 hours at 80° C. A saturated solution of NaHCO$_3$ was added and the mixture was extracted with AcOEt (3×). The combined organic phases were dried over Na$_2$SO$_4$ and concentrated to dryness under reduced pressure. The resulting residue was purified by Biotage silica gel chromatography (gradient 0 to 40% EtOAc in cyclohexane) to give the title compound (21 mg, 36%). $^1$H NMR (500 MHz, CDCl$_3$): 7.23-7.17 (8H, m), 7.09-7.07 (2H, m), 4.94 (2H, s), 4.83 (2H, s), 4.64 (2H, d), 4.23 (2H, d), 4.05 (2H, s), 2.52-2.20 (4H, m), 2.00-1.95 (1H, m), 1.79-1.65 (1H, m), 1.36 (3H, s), 1.40-1.10 (9H, br).

Step 2: 6-(4-(1-aminocyclobutyl)phenyl)-1-(3-hydroxy-2-(hydroxymethyl)-2-methylpropyl)-7-phenyl-1H-pyrido[2,3-b][1,4]oxazin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-((3-methyloxetan-3-yl)methyl)-2-oxo-7-phenyl-2,3-dihydro-1H-pyrido[2,3-b][1,4]oxazin-6-yl)phenyl)cyclobutyl)carbamate (16 mg, 0.03 mmol) was reacted to afford the title compound (16 mg, 79%). LCMS (Method D): $R_T$=0.721 min, M+1=474. $^1$H NMR (500 MHz, MeOD): 8.03 (1H,S), 7.44-7.38 (4H,m), 7.30-7.24 (5H, m), 4.96 (2H, s), 4.11 (2H, s), 3.47-3.41 (4H, m), 2.77-2.72 (2H, m), 2.59-2.53 (2H, m), 2.25-2.21 (1H, m), 1.98-1.94 (1H, m), 0.92 (3H, s).

Example 107

7-(4-(1-Aminocyclobutyl)phenyl)-8-phenyl-4H-pyrido[2,3-b][1,2,4]triazolo[4,3-d][1,4]oxazin-1-yl)phenyl)methanol

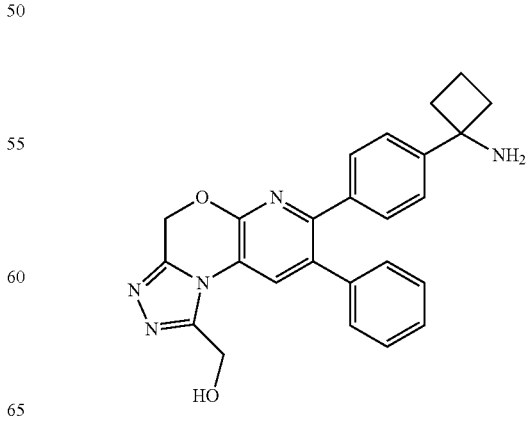

Step 1: 2-Hydroxyacetohydrazide

Ethyl glycolate (5 g, 0.047 mol) and hydrazine monohydrate (3.6 g, 0.071 mol) were heated to reflux for 15 hours. The reaction mixture was concentrated under reduced pressure and the residue was treated with toluene (3×50 ml) to azeotrope hydrazine in excess.

This was repeated three times. The crude residue was used for the next step without further purification.

Step 2: Tert-butyl (1-(4-(1-(hydroxymethyl)-8-phenyl-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (250 mg, 0.513 mmol) and 2-hydroxyacetohydrazide (230 mg, 2.56 mmol) in p-xylene (1.5 ml) was heated to 150° C. for 30 minutes under microwave irradiation. The resulting reaction mixture was concentrated to dryness under reduced pressure and purified by Biotage silica gel chromatography (gradient 0% to 20% ethyl acetate in n-hexanes) to give the title compound (40 mg, 15%). LCMS (Method D): $R_T$=1.297 min, M+1=526. $^1$H NMR (500 MHz, CDCl$_3$) δ 8.33 (1H, s), 7.37-7.32 (2H, m), 7.31-7.27 (5H, m), 7.25-7.20 (2H, m), 5.59 (2H, s), 5.06 (2H, bs), 5.02 (1H, bs), 2.53-2.43 (4H, m), 2.14-2.02 (1H, m), 1.88-1.76 (1H, m), 1.45-1.27 (9H, bs).

Step 3: 7-(4-(1-Aminocyclobutyl)phenyl)-8-phenyl-4H-pyrido[2,3-b][1,2,4]triazolo[4,3-d][1,4]oxazin-1-yl)phenyl)methanol Tert-butyl (1-(4-(1-(hydroxymethyl)-8-phenyl-4H-pyrido[2,3-b][1,2,4]triazolo[4,3-d][1,4]oxazin-7-yl)phenyl)cyclobutyl)carbamate (5 mg, 9.51 μmol) was dissolved in TFA (1 mL) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and dried to give the desired product as an off-white solid (2.5 mg, 60% yield). LCMS (Method D) RT=0.747 min, M+1=436. $^1$H-NMR (500 MHz, CD$_3$OD) δ 8.49 (1H, s), 7.42-7.36 (2H, d), 7.34-7.29 (2H, d), 7.26-7.20 (3H, m), 7.19-7.14 (2H, m), 5.60 (2H, s), 4.90 (2H, s), 2.72-2.61 (2H, m), 2.53-2.43 (2H, m), 2.20-2.08 (1H, m), 1.93-1.82 (1H, m), 2.01-1.92 (1H, m).

Example 108

6-(4-(1-aminocyclobutyl)phenyl)-1-methyl-7-phenyl-3,4-dihydropyrido[3,2-d]pyrimidin-2(1H)-one

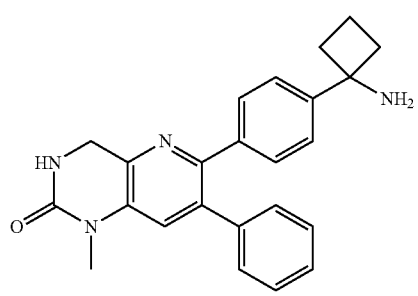 [SMILES: CN1C(=O)NCc2nc(-c3ccc(C4(N)CCC4)cc3)c(-c3ccccc3)cc21]

Step 1: tert-butyl 1-(4-(3-methyl-2-oxo-7-phenyl-1,2,3,4-tetrahydropyrido[2,3-b]pyrazin-6-yl)phenyl)cyclobutylcarbamate To a solution of tert-butyl(1-(4-(2-oxo-7-phenyl-1,2,3,4-tetrahydropyrido[3,2-d]pyrimidin-6-yl)phenyl)cyclobutyl)carbamate (71 mg, 0.15 mmol) in dry DMF (1 ml) was added potassium carbonate (21 mg, 0.15 mmol) and methyl iodide (9.4 μl, 0.15 mmol) under nitrogen. The resulting mixture was stirred overnight at room temperature. Potassium carbonate (42 mg, 0.30 mmol) and methyl iodide (18.8 μl, 0.30 mmol) were added under nitrogen. The resulting mixture was stirred for 1 hr at room temperature. Potassium carbonate (146 mg, 1.05 mmol) and methyl iodide (66 μl, 1.05 mmol) were added under nitrogen. The resulting mixture was stirred for 4 hr at 60° C. Saturated sodium bicarbonate solution was added and the mixture was extracted with ethyl acetate (3×10 ml). The combined organic phases were dried over Na$_2$SO$_4$ and concentrated to dryness under reduced pressure. The resulting residue was purified by Biotage silica gel chromatography (gradient 0 to 100% EtOAc in cyclohexane) to give the title compound (31 mg, 42%). LCMS (Method D): $R_T$=1.437 min, M+H$^+$=485. $^1$H NMR (500 MHz, CDCl$_3$): 7.25-7.38 (7H, m), 7.20-7.25 (2H, m), 7.16 (1H, s), 5.47 (1H, br s), 5.10 (1H, br s), 4.73 (2H, s), 3.35 (3H, s), 2.25-2.70 (4H, br m), 2.00-2.13 (1H, m), 1.75-1.85 (1H, m), 1.10-1.40 (9H, br).

Step 2: 6-(4-(1-aminocyclobutyl)phenyl)-1-methyl-7-phenyl-3,4-dihydropyrido[3,2-d]pyrimidin-2(1H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl 1-(4-(1-methyl-2-oxo-7-phenyl-1,2,3,4-tetrahydropyrido[3,2-d]pyrimidin-6-yl)phenyl)cyclobutylcarbamate (31 mg, 0.064 mmol) was reacted to afford the title compound (5 mg, 20%).

LCMS (Method D): $R_T$=0.763 min, M-NH$_2$=368. $^1$H NMR (500 MHz, MeOD): 7.20-7.40 (10H, m), 4.62 (2H, s), 3.30 (3H, s), 2.48-2.13 (2H, m), 2.20-2.35 (2H, m), 2.00-2.13 (1H, m), 1.70-1.80 (1H, m).

Example 109

6-(4-(1-aminocyclobutyl)phenyl)-1,3-bis(2-fluoroethyl)-7-phenyl-3,4-dihydropyrido[3,2-d]pyrimidin-2(1H)-one

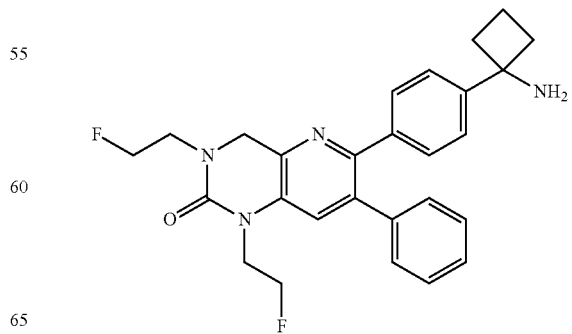

Step 1: tea-butyl (1-(4-(1,3-bis(2-fluoroethyl)-2-oxo-7-phenyl-1,2,3,4-tetrahydropyrido[3,2-d]pyrimidin-6-yl)phenyl)cyclobutyl)carbamate To a solution of tert-butyl(1-(4-(2-oxo-7-phenyl-1,2,3,4-tetrahydropyrido[3,2-d]pyrimidin-6-yl)phenyl)cyclobutyl)carbamate (41 mg, 0.09 mmol) in dry DMF (1 ml) at room temperature was added sodium hydride (3.5 mg, 0.09 mmol) and 1-fluoro-2-iodoethane (7.6 µl, 0.09 mmol) under nitrogen. The resulting mixture was stirred for 1 h at room temperature. Sodium hydride (3.5 mg, 0.09 mmol) and 1-fluoro-2-iodoethane (7.6 µl, 0.09 mmol) were added under nitrogen. The resulting mixture was stirred for 1 h at room temperature. Water was added and the mixture was extracted with EtOAc (3×5 ml). The combined organic phases were dried over $Na_2SO_4$ and concentrated to dryness under reduced pressure. The resulting residue was purified by Biotage silica gel chromatography (gradient 0 to 35% EtOAc in cyclohexane) to give the title compound (30 mg, 61%). $^1$H NMR (500 MHz, $CDCl_3$): 7.24 (1H, s), 7.20-7.17 (7H, m), 7.12-7.10 (2H, m), 4.96 (1H, br s), 4.74 (2H, s), 4.72 (2H, dt), 4.62 (2H, dt), 4.12 (2H, dt), 3.71 (2H, dt), 2.52-2.20 (4H, m), 2.00-1.95 (1H, m), 1.79-1.65 (1H, m), 1.40-1.10 (9H, br)

Step 2: 6-(4-(1-aminocyclobutyl)phenyl)-1,3-bis(2-fluoroethyl)-7-phenyl-3,4-dihydropyrido[3,2-d]pyrimidin-2(1H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1,3-bis(2-fluoroethyl)-2-oxo-7-phenyl-1,2,3,4-tetrahydropyrido[3,2-d]pyrimidin-6-yl)phenyl)cyclobutyl)carbamate (15 mg, 0.03 mmol) was reacted to afford the title compound (5 mg, 27%). LCMS (Method D): $R_T$=0.872 min, M-$NH_2$=446. $^1$H NMR (500 MHz, MeOD): 7.52 (1H, s), 7.45-7.39 (4H, m), 7.32-7.30 (3H, m), 7.24-7.22 (2H, m), 4.81-4.77 (4H, m), 4.68 (2H, dt), 4.28 (2H, dt), 3.83 (2H, dt), 2.81-2.75 (2H, m), 2.63-2.57 (2H, m), 2.26-2.24 (1H, m), 1.99-1.97 (1H, m).

Example 110

1-(4-(1-cyclopropyl-8-phenyl-4H-pyrido[2,3-b][1,2,4]triazolo[4,3-d][1,4]oxazin-7-yl)phenyl)cyclobutanamine

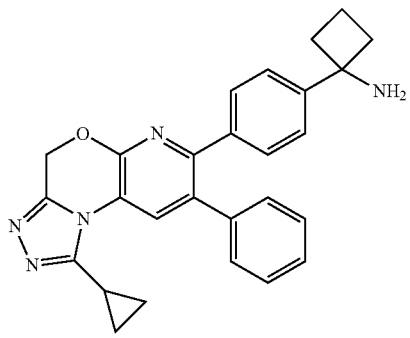 [SMILES: NC1(c2ccc(-c3nc4c(cc3-c3ccccc3)-n3c(nnc3C3CC3)CO4)cc2)CCC1]

Step 1: Tert-butyl (1-(4-(1-cyclopropyl-8-phenyl-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (150 mg, 0.308 mmol) and cyclopropanecarbohydrazide (41 mg, 0.410 mmol) in p-xylene (1.5 ml) was heated to 150° C. for 20 minutes under microwave irradiation. The resulting reaction mixture was concentrated to dryness under reduced pressure and purified by Biotage silica gel chromatography (gradient 0% to 20% ethyl acetate in n-hexanes) to give the title compound (36 mg, 32%). LCMS (Method D): $R_T$=1.457 min, M+1=536.
$^1$H NMR (500 MHz, $CDCl_3$): 8.24 (1H, s), 7.37-7.27 (7H, m), 7.24-7.19 (2H, m), 5.57 (2H, s), 2.55-2.40 (4H, m), 2.12-2.05 (1H, m), 1.87-1.78 (1H, m), 1.43-1.31 (9H, bs), 1.34-1.29 (3H, m), 1.23-1.17 (2H, m).

Step 2: 1-(4-(1-cyclopropyl-8-phenyl-4H-pyrido[2,3-b][1,2,4]triazolo[4,3-d][1,4]oxazin-7-yl)phenyl)cyclobutanamine Tert-butyl (1-(4-(1-cyclopropyl-8-phenyl-4H-pyrido[2,3-b][1,2,4]triazolo[4,3-d][1,4]oxazin-7-yl)phenyl)cyclobutyl)carbamate (36 mg, 0.012 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and the residue was dried to give the desired product as an off-white solid (24 mg, 82% yield). LCMS (Method D) RT=0.747 min, M+1=436. $^1$H-NMR (500 MHz, $CD_3OD$) δ 8.48 (1H, s), 7.53-7.47 (2H, m), 7.45-7.41 (2H, d), 7.38-7.33 (3H, m), 7.32-7.26 (2H, m), 5.66 (2H, s), 2.82-2.72 (2H, m), 2.63-2.55 (2H, m), 2.44-2.36 (1H, m), 2.30-2.19 (1H, m), 2.01-1.92 (1H, m), 1.28-1.17 (4H, overlapped ddd).

Example 111

7-(4-(1-aminocyclobutyl)phenyl)-1,5-dimethyl-8-phenyl-4,5-dihydro-1H-pyrido[2,3-b][1,4]diazepin-2(3H)-one

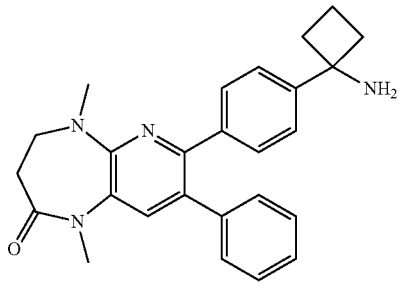

Step 1: tert-butyl(1-(4-(1,5-dimethyl-2-oxo-8-phenyl-2,3,4,5-tetrahydro-1H-pyrido[2,3-b][1,4]diazepin-7-yl)phenyl)cyclobutyl)carbamate To a solution of tert-butyl(1-(4-(2-oxo-8-phenyl-2,3,4,5-tetrahydro-1H-pyrido[2,3-b][1,4]diazepin-7-yl)phenyl)cyclobutyl)carbamate (41 mg, 0.09 mmol) in dry DMF (1 mL) was added potassium carbonate (117 mg, 0.85 mmol) and methyliodide (53 µl, 0.85 mmol) under nitrogen. The resulting mixture was stirred 1 hour at 80° C. Water was added and the mixture was extracted with EtOAc (3×15 ml). The combined organic phases were dried over Na$_2$SO$_4$ and concentrated to dryness under reduced pressure. The resulting residue was purified by Biotage silica gel chromatography (gradient 0 to 60% EtOAc in cyclohexane) to give the title compound (15 mg, 35%). $^1$H NMR (500 MHz, CDCl$_3$): 7.32-7.28 (3H, m), 7.21-7.18 (5H, m), 7.12-7.10 (2H, m), 4.94 (1H, br s), 3.65 (2H, t), 3.28 (3H, s), 2.96 (3H, s), 2.61-2.59 (2H, t), 2.55-2.25 (4H, m), 2.10-2.03 (1H, m), 1.86-1.78 (1H, m), 1.44-1.15 (9H, br).

Step 2: 7-(4-(1-aminocyclobutyl)phenyl)-1,5-dimethyl-8-phenyl-4,5-dihydro-1H-pyrido[2,3-b][1,4]diazepin-2(3H)-one Following the procedure for 1-((1H-imidazol-2-yl)methyl)-6-(4-(1-aminocyclobutyl)phenyl)-7-phenyl-1H-pyrido [2,3-b][1,4]oxazin-2(3H)-one, tert-butyl(1-(4-(1,5-dimethyl-2-oxo-8-phenyl-2,3,4,5-tetrahydro-1H-pyrido[2,3-b][1,4]diazepin-7-yl)phenyl)cyclobutyl)carbamate (15 mg, 0.03 mmol) was reacted to afford the title compound (12 mg, 64%). LCMS (Method D): R$_T$=0.880 min, M+1=413. $^1$H NMR (500 MHz, MeOD): 7.65 (1H, s), 7.53 (2H, d), 7.39 (2H, d), 7.31-7.28 (3H, m), 7.24-7.22 (2H, m), 3.73 (2H, t), 3.37 (3H, s), 3.02 (3H, s), 2.81-2.75 (2H, m), 2.68 (2H, t), 2.61-2.55 (2H, m), 2.25-2.18 (1H, m), 1.99-1.91 (1H, m).

Example 112

1-(4-(1-isopropyl-8-phenyl-4H-pyrido[2,3-b][1,2,4]triazolo[4,3-d][1,4]oxazin-7-yl)phenyl)cyclobutanamine

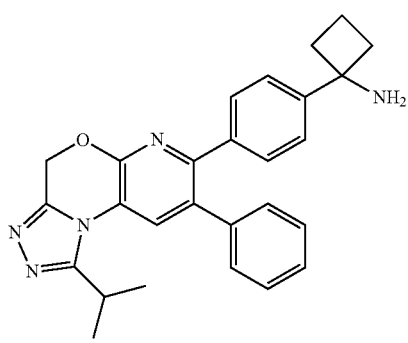 [SMILES: CC(C)c1nnc2n1-c1cc(-c3ccccc3)c(-c3ccc(C4(N)CCC4)cc3)nc1OC2]

Step 1: Isobutyrohydrazide

Ethylisobutyrate (5 g, 0.043 mol) and hydrazine monohydrate (3.2 g, 0.065 mol) were heated to reflux for 15 hours. The reaction mixture was concentrated under reduced pressure and the residue was treated with toluene(3×100 ml) to azeotrope hydrazine in excess. The crude residue was used for the next step without further purification.

Step 2: Tert-butyl (1-(4-(1-isopropyl-8-phenyl-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (150 mg, 0.308 mmol) and isobutyrohydrazide (28 mg, 0.308 mmol) in p-xylene (1.5 ml) was heated to 150° C. for 15 minutes under microwave irradiation. The resulting reaction mixture was concentrated to dryness under reduced pressure. The crude residue was purified by Biotage silica gel chromatography (gradient 0% to 20% ethyl acetate in n-hexanes) to give the title compound (28 mg, 17%). LCMS (Method D): R$_T$=1.497 min, M+1=538. $^1$H NMR (500 MHz, CDCl$_3$) δ 7.85 (1H, s), 7.36-7.31 (5H, m), 7.28 (2H, m), 7.24-7.19 (2H, m), 5.56 (2H, s), 3.46-3.36 (1H, m), 2.57-2.39 (4H, m), 2.13-2.02 (1H, m), 1.88-1.76 (1H, m), 1.57-1.53 (6H, d), 1.44-1.29 (9H, bs).

Step 3: 1-(4-(1-isopropyl-8-phenyl-4H-pyrido[2,3-b][1,2,4]triazolo[4,3-d][1,4]oxazin-7-yl)phenyl)cyclobutanamine Tert-butyl (1-(4-(1-isopropyl-8-phenyl-4H-pyrido[2,3-b][1,2,4]triazolo[4,3-d][1,4]oxazin-7-yl)phenyl)cyclobutyl)carbamate (24 mg, 0.045 mmol) was dissolved in TFA (1 ml) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurried in diethyl ether (2 ml) and after settling the supernatant solvent was removed by pipette. This was repeated three times. The residue was then slurried in n-hexanes (2 ml) and after settling the supernatant solvent was removed by pipette. This was repeated three times. The remaining solvent was removed under reduced pressure and dried to give the desired product as an off-white solid (18 mg, 92% yield). LCMS (Method D) RT=0.815 min, M+1=438. $^1$H-NMR (500 MHz, CD$_3$OD) δ 8.18 (1H, s), 7.52-7.47 (2H, m), 7.45-7.41 (2H, d), 7.38-7.34 (3H, m), 7.31-7.26 (2H, m), 5.64 (2H, s), 2.82-2.72 (2H, m), 2.63-2.54 (2H, m), 2.30-2.19 (1H, m), 2.02-1.92 (1H, m), 1.51 (6H, d).

Example 113

6-(4-((1r,3r)-1-amino-3-hydroxy-3-methylcyclobutyl)phenyl)-1-methyl-7-phenyl-1H-pyrido[2,3-b][1,4]oxazin-2(3H)-one

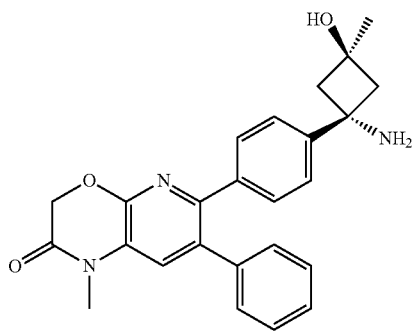 [SMILES: CN1C(=O)COc2nc(-c3ccc([C@]4(N)C[C@](C)(O)C4)cc3)c(-c3ccccc3)cc21]

Step 1: Ethyl 2-((5-bromo-3-nitropyridin-2-yl)oxy)acetate

To a suspension of sodium hydride (5.31 g, 133 mmol) in 1,4-dioxane (250 ml), ethyl glycolate (12.56 ml, 133 mmol) was added dropwise over a period of 30 minutes ensuring that the temperature was maintained below 30° C. The resulting thick suspension was stirred at room temperature for 15 minutes. In a separate 1 l round-bottomed flask was added 5-bromo-2-chloro-3-nitropyridine (21 g, 88 mmol) in 1,4-dioxane (150 ml) to give a brown solution. The suspension of sodium hydride and ethyl glycolate was added drop wise over a period of 30 minutes at 0° C. The resulting reaction mixture was heated to 80° C. overnight.

The reaction mixture was concentrated under reduced pressure and the crude residue was purified by Biotage silica chromatography (gradient 0% to 10% ethyl acetate in n-hexanes) to give the title compound (11.8 g, 44%). $^1$H NMR (500 MHz, CDCl$_3$): 8.48 (1H, s), 8.42 (1H, s), 5.07 (2H, s), 4.28-4.24 (2H, q), 1.31-1.28 (3H, t).

Step 2: Ethyl 2-((3-nitro-5-phenylpyridin-2-yl)oxy)acetate

In a 1 l round-bottomed flask was added ethyl 2-(5-bromo-3-nitropyridin-2-yloxy)acetate (18.33 g, 60.1 mmol), phenylboronic acid (10.99 g, 90 mmol), triphenylphosphine (4.73 g, 18.02 mmol) and cesium fluoride (45.6 g, 300 mmol) in 1,2-dimethoxyethane (300 ml) to give a yellow solution. The reaction mixture was degassed by bubbling nitrogen for 30 minutes. Palladium(II)acetate (2.023 g, 9.01 mmol) was added and the mixture was heated to 75° C. under a nitrogen atmosphere overnight. The reaction mixture was allowed to cool to room temperature and concentrated to dryness under reduced pressure to give a brown solid. This was re-dissolved in dichloromethane, filtered and concentrated to dryness under reduced pressure to give a brown solid The crude residue was purified via Biotage chromatography (gradient 5% to 60% ethyl acetate in n-hexanes) to give the title compound (6.9 g, 38%). $^1$H NMR (500 MHz, CDCl$_3$) δ 8.58 (1H, s), 8.56 (1H, s), 7.59-7.52 (2H, m), 7.48-7.46 (2H, m), 7.45-7.43 (1H, m), 5.13 (2H, s), 4.30-4.26 (2H, q), 1.33-1.30 (3H, t).

Step 3: 7-Phenyl-1H-pyrido[2,3-b][1,4]oxazin-2(3H)-one

In a 500 ml round-bottomed flask was added ethyl 2-(3-nitro-5-phenylpyridin-2-yloxy)acetate (4.6 g, 15.22 mmol) in hydrochloric acid, 37% (40 ml) to give a yellow suspension. The mixture was cooled to 0-5° C. followed by the portion wise addition of tin powder (9.94 g, 84 mmol). The addition proved to be exothermic. Caution should be taken while adding. The mixture was then stirred at room temperature for further 30 minutes until all foaming ceased. The reaction mixture was heated to 80° C. under a nitrogen atmosphere for 3 hours.

The reaction mixture cooled to room temperature and diluted with water (800 ml). The white precipitate was isolated by filtration, washed with water (100 ml) and sucked dry to give a white solid. The solid was azeotroped with toluene (3×30 ml) to give a white solid as the title compound (2.6 g, 77%). $^1$H NMR (500 MHz, (CD$_3$)$_2$SO) δ 10.41 (1H, s), 8.10 (1H, s), 7.59 (2H, d), 7.49-7.42 (2H, t), 7.39-7.38 (1H, d), 4.83 (2H, s).

Step 4: 6-bromo-7-phenyl-1H-pyrido[2,3-b][1,4]oxazin-2(3H)-one

In a 10 ml microwave vial was 7-phenyl-1H-pyrido[2,3-b][1,4]oxazin-2(3H)-one (50 mg, 0.221 mmol) and N-bromosuccinimide (78.6 mg, 0.441 mmol) in dimethylformamide (1 ml). The reaction mixture was heated to 80° C. under microwave irradiation for 30 minutes. The reaction mixture was cooled to room temperature and diluted with ethyl acetate (10 ml). The organic solution was washed with water (2×10 ml) and brine (2×10 ml). The organic phase was dried over anhydrous Na$_2$SO$_4$, filtered and concentrated under reduced pressure. The crude residue was purified via Biotage chromatography (gradient 0% to 5% methanol in dichloromethane) to give the title compound as a yellow solid (61 mg, 90%). $^1$H NMR (500 MHz, CD$_3$OD) δ 7.48-7.32 (5H, m), 7.12 (1H, s), 4.82 (2H, s).

Step 5: 2-((1r,3r)-3-hydroxy-3-methyl-1-(4-(1-methyl-2-oxo-7-phenyl-2,3-dihydro-1H-pyrido[2,3-b][1,4]oxazin-6-yl)phenyl)cyclobutyl)isoindoline-1,3-dione In a 10 mL microwave tube was added 6-bromo-1-methyl-7-phenyl-1H-pyrido[2,3-b][1,4]oxazin-2(3H)-one (32 mg, 0.100 mmol), 2-((1r,3r)-3-hydroxy-3-methyl-1-(4-(4,4,5,5-tetramethyl-1,3,2-dioxaborolan-2-yl)phenyl)cyclobutyl) isoindoline-1,3-dione (46 mg, 0.105 mmol) and sodium carbonate (21 mg, 0.201 mmol) in a mixture of 1,4-dioxane (3.50 mL) and water (1.20 mL) to give a colourless solution. This was degassed by bubbling nitrogen for 10 minutes followed by the addition of tetrakis(triphenylphosphine)palladium(0) (12 mg, 10.03 µmol). The reaction mixture was heated to 100° C. under microwave irradiation for 15 minutes. Additional 2-((1r,3r)-3-hydroxy-3-methyl-1-(4-(4,4,5,5-tetramethyl-1,3,2-dioxaborolan-2-yl)phenyl)cyclobutyl)isoindoline-1,3-dione (24 mg, 0.055 mmol) was added and the mixture heated to 100° C. under microwave irradiation for a further 15 minutes. The reaction mixture was diluted with ethyl acetate (12 mL), washed with water (10 mL), brine (10 mL), dried over Na$_2$SO$_4$, filtered and concentrated to dryness under reduced pressure to give a yellow oil. This was purified by Biotage chromatography (cyclohexane:ethyl acetate, gradient elution from 90:10 to 0:100) to give the desired product as an off-white solid (18 mg, 33% yield). $^1$H-NMR (500 MHz, CDCl$_3$) δ 7.74 (2H, dd), 7.66 (2H, dd), 7.51 (2H, d), 7.31 (2H, d), 7.22-7.29 (4H, m), 7.15-7.20 (2H, m), 4.87 (2H, s), 3.37 (3H, s), 3.32 (2H, d), 3.09 (2H, d), 1.40 (3H, s). LCMS (Method D) RT=1.30 min, M+H$^+$=546.00.

Step 6: 6-(4-((1r,3r)-1-amino-3-hydroxy-3-methylcyclobutyl)phenyl)-1-methyl-7-phenyl-1H-pyrido[2,3-b][1,4]oxazin-2(3H)-one In a 15 mL reaction tube was added 24(1r,3r)-3-hydroxy-3-methyl-1-(4-(1-methyl-2-oxo-7-phenyl-2,3-dihydro-1H-pyrido[2,3-b][1,4]oxazin-6-yl)phenyl)cyclobutyl)isoindoline-1,3-dione (18 mg, 0.033 mmol) and hydrazine monohydrate (8 µl, 0.165 mmol) in ethanol (1650 µl) to give a yellow solution. This was heated to 90° C. under a nitrogen atmosphere for 5 hours then allowed to cool to room temperature. Further hydrazine monohydrate (16 µl, 0.330 mmol) was added and the reaction mixture heated to 100° C. under microwave irradiation for 10 minutes, then to 120° C. under microwave irradiation for 20 minutes. Further hydrazine monohydrate (16 µl, 0.330 mmol) was added and the mixture heated to 120° C. under microwave irradiation for 60 minutes. The resulting precipitate was removed by filtration and washed well with ethanol. The combined filtrates were concentrated to dryness under reduced pressure to give a white solid. This was purified on an SCX catch-and-release column and freeze-dried to give the desired product as a white solid (10 mg, 73% yield). $^1$H-NMR (500 MHz, MeOD) δ 7.52 (1H, s), 7.20-7.35 (9H, m), 4.94 (2H, s), 3.42 (3H, s), 2.66 (2H, d), 2.39 (2H, d), 1.55 (3H, s). LCMS (Method D) RT=0.67 min, M+H⁺=416.20.

Example 114

7-(4-(1-aminocyclobutyl)phenyl)-1-methyl-8-phenyl-4,5-dihydro-1H-pyrido[2,3-b][1,4]diazepin-2(3H)-one

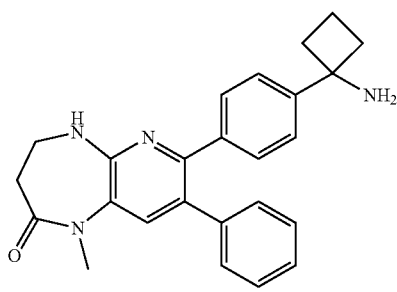 [SMILES: CN1C(=O)CCNc2nc(-c3ccc(C4(N)CCC4)cc3)c(-c3ccccc3)cc21]

Step 1: tert-butyl(1-(4-(1-methyl-2-oxo-8-phenyl-2,3,4,5-tetrahydro-1H-pyrido[2,3-b][1,4]diazepin-7-yl)phenyl)cyclobutyl)carbamate To a solution of tert-butyl(1-(4-(2-oxo-8-phenyl-2,3,4,5-tetrahydro-1H-pyrido[2,3-b][1,4]diazepin-7-yl)phenyl)cyclobutyl)carbamate (53 mg, 0.11 mmol) in dry DMF (1 ml) was added sodium hydride (4.4 mg, 0.11 mmol) and methyliodide (6.9 μl, 0.11 mmol) under nitrogen. The resulting mixture was stirred for 1 hour at room temperature. Water was added and the mixture was extracted with EtOAc (3×15 ml). The combined organic phases were dried over $Na_2SO_4$ and concentrated to dryness under reduced pressure. The resulting residue was purified by Biotage silica gel chromatography (gradient 0 to 57% EtOAc in cyclohexane) to give the title compound (21 mg, 38%). ¹H NMR (500 MHz, CDCl₃): 7.39 (1H, s), 7.27-7.23 (7H, m), 7.16-7.14 (2H, m), 5.04 (1H, s), 4.91 (1H, br s), 3.88 (2H, br s), 3.39 (3H, s), 2.74 (2H, t), 2.55-2.25 (4H, m), 2.10-2.03 (1H, m), 1.86-1.78 (1H, m), 1.44-1.15 (9H, br).

Step 2: 7-(4(1-aminocyclobutyl)phenyl)-1-methyl-8-phenyl-4,5-dihydro-1H-pyrido[2,3-b][1,4]diazepin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-methyl-2-oxo-8-phenyl-2,3,4,5-tetrahydro-1H-pyrido[2,3-b][1,4]diazepin-7-yl)phenyl)cyclobutyl)carbamate (21 mg, 0.04 mmol) was reacted to afford the title compound (19 mg, 72%). LCMS (Method D): $R_T$=0.806 min, M+1=399. ¹H NMR (500 MHz, MeOD): 7.65 (1H, s), 7.47 (2H, d), 7.41 (2H, d), 7.29-7.25 (3H, m), 7.20-7.19 (2H, m), 3.86-3.84 (4H, m), 3.41 (3H, s), 2.79-2.73 (4H, m), 2.61-2.55 (2H, m), 2.25-2.18 (1H, m), 1.99-1.91 (1H, m).

Example 115

1-(4-(1-isobutyl-8-phenyl-4H-pyrido[2,3-b][1,2,4]triazolo[4,3-d][1,4]oxazin-7-yl)phenyl)cyclobutanamine

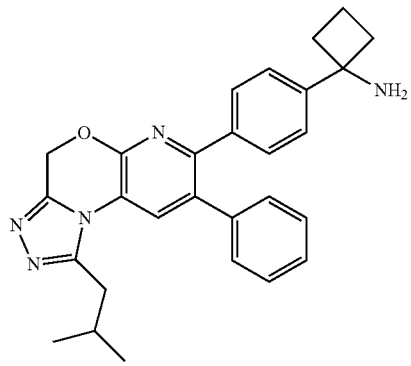 [SMILES: CC(C)Cc1nnc2n1-c1cc(-c3ccccc3)c(-c3ccc(C4(N)CCC4)cc3)nc1OC2]

Step 1: 3-Methylbutanehydrazide

Ethylvalerate (5 g, 0.038 mol) and hydrazine monohydrate (2.8 g, 0.057 mol) were heated to reflux for 15 hours. The reaction mixture was concentrated under reduced pressure and the residue was treated with toluene (100 ml×3) to azeotrope hydrazine in excess. This was repeated three times. The crude residue was used for the next step without further purification.

Step 2: Tert-butyl (1-(4-(1-isobutyl-8-phenyl-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (200 mg, 0.410 mmol) and 3-methylbutanehydrazide (47 mg, 0.410 mmol) in p-xylene (1.5 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in n-hexanes) to give the title compound (15 mg, 5%). LCMS (Method D): $R_T$=1.5687 min, M+1=552. ¹H NMR (500 MHz, CDCl₃): 7.80 (1H, s), 7.36-7.31 (5H, m), 7.30-7.27 (2H, m), 7.23-7.19 (2H, m), 5.57 (2H, s), 2.98 (2H, d), 2.54-2.41 (4H, m), 2.33-2.24 (1H, m), 2.13-2.01 (1H, m), 1.88-1.76 (1H, m), 1.44-1.26 (9H, bs), 1.11 (6H, d).

Step 3: 1-(4-(1-isobutyl-8-phenyl-4H-pyrido[2,3-b][1,2,4]triazolo[4,3-d][1,4]oxazin-7-yl)phenyl)cyclobutanamine Tert-butyl (1-(4-(1-isobutyl-8-phenyl-4H-pyrido[2,3-b][1,2,4]triazolo[4,3-d][1,4]oxazin-7-yl)phenyl)cyclobutyl)carbamate (7 mg, 0.013 mmol) was dissolved in dichloromethane (1 mL); TFA (1 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure three times. The residue was then slurred in diethyl ether (2 ml) and after settling the supernatant solvent removed by pipette. This was repeated three times. The residue was then slurred in n-hexanes (2 ml) and after settling the supernatant solvent was removed by pipette. This was repeated three times. The remaining solvent was removed under reduced pressure and dried to give the desired product as an off-white solid (4 mg, 68% yield). LCMS (Method D): RT=0.844 min, M+1=452. $^1$H-NMR (500 MHz, CD$_3$OD) δ 8.07 (1H, s), 7.52-7.45 (2H, d), 7.44-7.40 (2H, d), 7.38-7.33 (3H, m), 7.31-7.26 (2H, m), 5.66 (2H, s), 3.11 (2H, d), 2.81-2.68 (2H, m), 2.61-2.45 (2H, m), 2.32-2.17 (1H+1H, 2 m), 2.02-1.87 (1H, m), 1.10 (6H, d).

Example 116

7-(4-(1-aminocyclobutyl)phenyl)-N,N-dimethyl-8-phenyl-4H-pyrido[2,3-b][1,2,4]triazolo[4,3-d][1,4]oxazin-1-amine

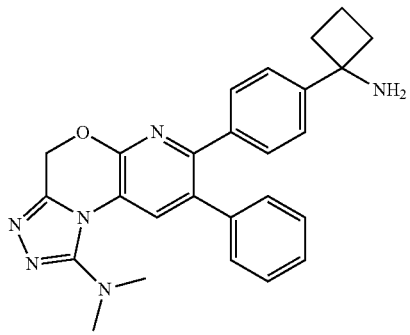 [SMILES: CN(C)c1nnc2n1-c1cc(-c3ccccc3)c(-c3ccc(C4(N)CCC4)cc3)nc1OC2]

Step 1: tert-butyl(1-(4-(1-(dimethylamino)-8-phenyl-4H-pyrido[2,3-b][1,2,4]triazolo[4,3-d][1,4]oxazin-7-yl)phenyl)cyclobutyl)carbamate A mixture of tert-butyl 1-(4-(1-bromo-8-phenyl-4H-pyrido[2,3-b][1,2,4]triazolo[4,3-d][1,4]oxazin-7-yl)phenyl)cyclobutylcarbamate (41 mg, 0.071 mmol), dimethylamine hydrochloride (58.2 mg, 0.714 mmol), and triethylamine (0.099 ml, 0.714 mmol) in NMP (1 ml) was heating at 130 degree for 50 min under microwave condition. The mixture was diluted with DCM (8 ml) and water (8 ml). The organic phase was washed with water (8 mlX3) and brine (5 ml). Concentrated and purified by column eluted with MeOH/DCM (0-4%) to give product (8 mg). $^1$H NMR (500 MHz, CDCl$_3$) 8.15 (s, 1H), 7.15-7.34 (m, 9H), 5.51 (s, 2H), 5.01 (s, 1H), 2.95 (s, 6H), 2.4-2.5 (m, 4H), 2.0-2.15 (m, 1H), 1.75-1.85 (m, 1H), 1.2-1.35 (m, 9H).

Step 2: 7-(4-(1-aminocyclobutyl)phenyl)-N,N-dimethyl-8-phenyl-4H-pyrido[2,3-b][1,2,4]triazolo[4,3-d][1,4]oxazin-1-amine Following the procedure for 3-(6-(4-(1-aminocyclobutyl)phenyl)-2-oxo-7-phenyl-2,3-dihydro-1H-pyrido[2,3-b][1,4]oxazin-1-yl)propanenitrile, tert-butyl(1-(4-(1-(cyanomethyl)-3-(methoxymethyl)-2-oxo-7-phenyl-2,3-dihydro-1H-pyrido[2,3-b][1,4]oxazin-6-yl)phenyl)cyclobutyl)carbamate (8 mg, 0.015 mmol) was reacted to afford the title compound (5.5 mg). $^1$H NMR (500 MHz, CH$_3$OD) 8.26 (s, 1H), 7.48 (d, 2H), 7.42 (d, 2H), 7.35 (m, 3H), 7.26 (m, 2H), 5.6 (s, 2H), 2.96 (s, 6H), 2.7-2.8 (m, 2H), 2.55-2.65 (m, 2H), 2.2-2.3 (m, 1H), 1.9-2.0 (m, 1H), LCMS (Method D): R$_T$=0.77 min, M+H$^+$ =439.2

Example 117

7-(4-(1-aminocyclobutyl)phenyl)-1-(2-fluoroethyl)-8-phenyl-4,5-dihydro-1H-pyrido[2,3-b][1,4]diazepin-2(3H)-one

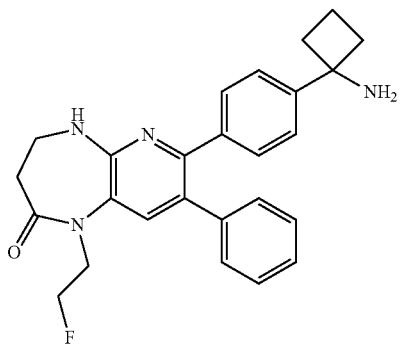 [SMILES: NC1(c2ccc(-c3nc4c(cc3-c3ccccc3)N(CCF)C(=O)CCN4)cc2)CCC1]

Step 1: tert-butyl(1-(4-(1-(2-fluoroethyl)-2-oxo-8-phenyl-2,3,4,5-tetrahydro-1H-pyrido[2,3-b][1,4]diazepin-7-yl)phenyl)cyclobutyl)carbamate To a solution of tert-butyl(1-(4-(2-oxo-8-phenyl-2,3,4,5-tetrahydro-1H-pyrido[2,3-b][1,4]diazepin-7-yl)phenyl)cyclobutyl)carbamate (101 mg, 0.21 mmol) in dry DMF (1 ml) was added sodium hydride (12 mg, 0.32 mmol) and 1-fluoro-2-iodoethane (27 μl, 0.32 mmol) under nitrogen. The resulting mixture was stirred for 1 hour at room temperature. Water was added and the mixture was extracted with EtOAc (3×10 ml). The combined organic phases were dried over Na$_2$SO$_4$ and concentrated to dryness under reduced pressure. The resulting residue was purified by Biotage silica gel chromatography (gradient 0 to 100% EtOAc in cyclohexane) to give the title compound (52 mg, 47%). $^1$H NMR (500 MHz, CDCl$_3$): 7.62 (1H, s), 7.31-7.22 (7H, m), 7.16-7.14 (2H, m), 5.01 (1H, s), 4.75 (1H, br s), 4.74 (2H, dt), 4.07 (2H, dt), 3.92-3.88 (2H, m), 2.73 (2H, t), 2.55-2.25 (4H, m), 2.10-2.03 (1H, m), 1.86-1.78 (1H, m), 1.44-1.15 (9H, br).

Step 2: 7-(4-(1-aminocyclobutyl)phenyl)-1-(2-fluoroethyl)-8-phenyl-4,5-dihydro-1H-pyrido[2,3-b][1,4]diazepin-2(3H)-one Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, tert-butyl(1-(4-(1-(2-fluoroethyl)-2-oxo-8-phenyl-2,3,4,5-tetrahydro-1H-pyrido[2,3-b][1,4]diazepin-7-yl)phenyl)cyclobutyl)carbamate (15 mg, 0.03 mmol) was reacted to afford the title compound (12 mg, 64%). LCMS (Method D): R$_T$=0.808 min, M+1=431. $^1$H NMR (500 MHz, MeOD): 7.76 (1H, s), 7.48 (2H, d), 7.41 (2H, d), 7.29-7.25 (3H, m), 7.20-7.18 (2H, m), 4.67 (2H, dt), 4.16 (2H, dt), 3.88-3.86 (2H, m), 2.79-2.73 (4H, m, 2.61-2.55 (2H, m), 2.25-2.18 (1H, m), 1.99-1.91 (1H, m).

Example 118

1-(4-(8-phenyl-1-(2,2,2-trifluoroethyl)-4H-pyrido[2,3-b][1,2,4]triazolo[4,3-d][1,4]oxazin-7-yl)phenyl)cyclobutanamine

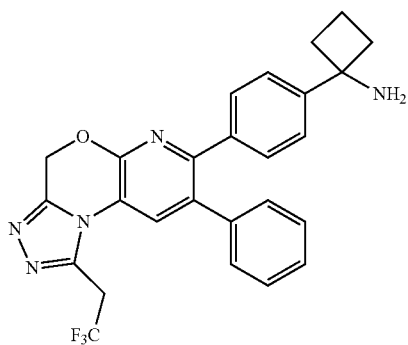 [SMILES: NC1(c2ccc(-c3nc4c(cc3-c3ccccc3)-n3c(nnc3CC(F)(F)F)CO4)cc2)CCC1]

Step 1: 3,3,3-Trifluoropropanehydrazide

Ethyl-3,3,3-trifluoropropanoate (2.5 g, 0.016 mol) and hydrazine monohydrate (1.2 g, 0.024 mol) were heated to reflux for 1 hour. The reaction mixture was concentrated under reduced pressure and the residue was treated with toluene (100 ml×3) to azeotrope hydrazine in excess.

The crude residue was used for the next step without further purification.

Step 2: Tert-butyl (1-(4-(8-phenyl-1-(2,2,2-trifluoroethyl)-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (250 mg, 0.513 mmol) and 3,3,3-trifluoropropanehydrazide (145 mg, 1.205 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in n-hexanes) to give the title compound (38 mg, 13%). LCMS (Method D): $R_T$=1.499 min, M+1=578. $^1$H NMR (500 MHz, CDCl$_3$): 7.84 (1H, s), 7.36-7.32 (5H, m), 7.31-7.28 (2H, m), 7.23-7.18 (2H, m), 5.60 (2H, s), 4.12 (2H, q), 2.52-2.42 (4H, m), 2.12-2.01 (1H, m), 1.87-1.78 (1H, m), 1.44-1.26 (9H, bs).

Step 3: 1-(4-(8-phenyl-1-(2,22-trifluoroethyl)-4H-pyrido[2,3-b][1,2,4]triazolo[4,3-d][1,4]oxazin-7-yl)phenyl)cyclobutanamine Tert-butyl (1-(4-(8-phenyl-1-(2,2,2-trifluoroethyl)-4H-pyrido[2,3-b][1,2,4]triazolo[4,3-d][1,4]oxazin-7-yl)phenyl)cyclobutyl)carbamate (25 mg, 0.043 mmol) was dissolved in dichloromethane (1 ml); TFA (1 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and dried to give the desired product as an off-white solid (16 mg, 77% yield). LCMS (Method D): RT=0.791 min, M+1=478. $^1$H-NMR (500 MHz, CD$_3$OD) δ 8.19 (1H, s), 7.52-7.48 (2H, d), 7.45-7.42 (2H, d), 7.38-7.34 (3H, m), 7.31-7.27 (2H, m), 5.69 (2H, s), 4.47 (2H, q), 2.82-2.73 (2H, m), 2.64-2.54 (2H, m), 2.31-2.19 (1H, m), 2.02-1.92 (1H, m).

Example 119

7-(4-(1-aminocyclobutyl)phenyl)-8-phenyl-4H-pyrido[2,3-b][1,2,4]triazolo[4,3-d][1,4]oxazine-1-carboxamide

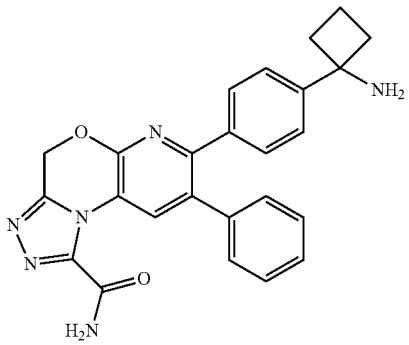 [SMILES: NC(=O)c1nnc2n1-c1cc(-c3ccccc3)c(-c3ccc(C4(N)CCC4)cc3)nc1OC2]

Step 1: Ethylhydrazine carboxylate

Diethyl oxalate (5 g, 0.042 mol) and hydrazine monohydrate (2.8 g, 0.057 mol) in ethanol (3 ml) were heated to reflux for 15 hour. The reaction mixture was concentrated under reduced pressure and the residue was treated with toluene (100 ml×3) to azeotrope hydrazine in excess. The crude residue was used for the next step without further purification.

Step 2: Ethyl 7-(4-(1-((tert-butoxycarbonyl)amino)cyclobutyl)phenyl)-8-phenyl-4H-pyrido[2,3-b][1,2,4]triazolo[4,3-d][1,4]oxazine-1-carboxylate A suspension of tert-butyl(1-(4-(7-phenyl-2-thioxo-2,3-dihydro-1H-pyrido[2,3-b][1,4]oxazin-6-yl)phenyl)cyclobutyl)carbamate (250 mg, 0.513 mmol) and ethylhydrazine carboxylate (271 mg, 2.05 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 30% ethyl acetate in n-hexanes) to give the title compound (38 mg, 13%). LCMS (Method D): $R_T$=1.531 min, M+1=568.

Step 3: Tert-butyl (1-(4-(1-carbamoyl-8-phenyl-4H-pyrido[2,3-b][1,2,4]triazolo[4,3-d][1,4]oxazin-7-yl)phenyl)cyclobutyl)carbamate A suspension of ethyl 7-(4-(1-((tert-butoxycarbonyl)amino)cyclobutyl)phenyl)-8-phenyl-4H-pyrido[2,3-b][1,2,4]triazolo[4,3-d][1,4]oxazine-1-carboxylate (70 mg, 0.123 mmol) and ammonium chloride (10 mg, 0.19 mmol) in ammonium hydroxide (1 ml) was heated to 100° C. for 10 minutes under microwave irradiation. The resulting reaction mixture was concentrated to dryness under reduced pressure and purified by Biotage silica gel chromatography (gradient 0% to 10% ethyl acetate in cyclohexane) to give the title compound (38 mg, 13%). LCMS (Method D): $R_T$=1.347 min, M+1=539. $^1$H-NMR (500 MHz, CD$_3$OD) δ 9.10 (1H, s), 7.47-7.40 (1H, bs), 7.40-7.37 (2H, d), 7.32-7.27 (6H, m), 5.59 (2H, s), 2.59-2.39 (4H, m), 2.14-2.01 (1H, m), 1.88-1.76 (1H, m), 1.44-1.33 (9H, bs).

Step 4: 7-(4-(1-aminocyclobutyl)phenyl)-8-phenyl-4H-pyrido[2,3-b][1,2,4]triazolo[4,3-d][1,4]oxazine-1-carboxamide Tert-butyl (1-(4-(1-carbamoyl-8-phenyl-4H-pyrido[2,3-b][1,2,4]triazolo[4,3-d][1,4]oxazin-7-yl)phenyl)cyclobutyl)carbamate (10 mg, 0.019 mmol) was dissolved in dichloromethane (0.5 ml); this solution was added to a scx-2 catch and release cartridge (1 g), precalibrated using methanol (15 ml) and dichloromethane (15 ml). After allowing to binding for 15 hours, the column was washed with methanol (6 ml) and then the product eluted with 7M ammonia in methanol (4 ml×2). The combined product fractions were concentrated to dryness under reduced pressure to give the desired product as a white solid (5 mg, 61% yield). LCMS (Method D) RT=0.695 min, M+1=440. $^1$H-NMR (500 MHz, CD$_3$OD) δ 8.80 (1H, s), 7.27-7.24 (4H, bs), 7.22-7.17 (3H, m), 7.16-7.13 (2H, m), 5.57 (2H, s), 2.49-2.38 (2H, m), 2.19-2.10 (2H, m), 2.03-1.92 (1H, m), 1.71-1.60 (1H, m).

Example 120

1-(4-(1-(fluoromethyl)-8-phenyl-4H-pyrido[2,3-b][1,2,4]triazolo[4,3-d][1,4]oxazin-7-yl)phenyl)cyclobutanamine

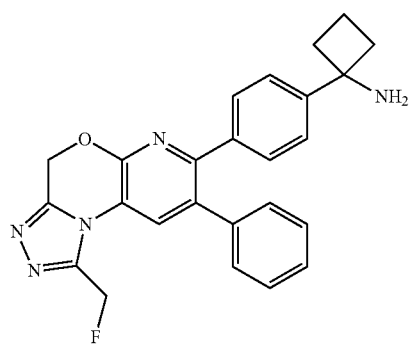 [SMILES: NC1(c2ccc(-c3nc4c(cc3-c3ccccc3)-n3c(CF)nnc3CO4)cc2)CCC1]

Step 1: Tert-butyl (1-(4-(1-(fluoromethyl)-8-phenyl-4H-pyrido[2,3-b][1,2,4]triazolo[4,3-d][1,4]oxazin-7-yl)phenyl)cyclobutyl)carbamate A solution of tert-butyl(1-(4-(1-(hydroxymethyl)-8-phenyl-4H-pyrido[2,3-b][1,2,4]triazolo[4,3-d][1,4]oxazin-7-yl)phenyl)cyclobutyl)carbamate (40 mg, 0.019 mmol), triethylamine (2.65 ml, 0.019 mmol) and DeoxoFluor® (50% in THF, 21.05 mg, 0.048 mmol) in dichloromethane (1 ml) was heated to 30° C. for 15 hours. The resulting reaction mixture was quenched with a saturated solution of sodium bicarbonate and extracted with dichloromethane (10 ml×3). The combined organic layers were concentrated to dryness under reduced pressure. The crude residue was purified by Biotage silica gel chromatography (gradient 0% to 20% ethyl acetate in cyclohexane) to give the title compound (38 mg, 13%). LCMS (Method D): $R_T$=1.439 min, M+1=528. $^1$H NMR (500 MHz, CDCl$_3$): 8.01 (1H, s), 7.37-7.27 (7H, m), 7.24-7.20 (2H, dd), 5.83 (2H, s), 5.73 (1H, s), 5.64 (1H, s), 2.54-2.41 (4H, m), 2.12-2.02 (1H, m), 1.88-1.76 (1H, m), 1.43-1.30 (9H, bs).

Step 2: 1-(4-(1-(fluoromethyl)-8-phenyl-4H-pyrido[2,3-b][1,2,4]triazolo[4,3-d][1,4]oxazin-7-yl)phenyl)cyclobutanamine Tert-butyl (1-(4-(1-(fluoromethyl)-8-phenyl-4H-pyrido[2,3-b][1,2,4]triazolo[4,3-d][1,4]oxazin-7-yl)phenyl)cyclobutyl)carbamate (3 mg, 5.69 μmol) was dissolved in dichloromethane (1 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and dried to give the desired product as an off-white solid (1.5 mg, 61% yield). LCMS (Method D) RT=0.774 min, M+1=428. $^1$H-NMR (500 MHz, CD$_3$OD) δ 8.03 (1H, s), 7.41-7.35 (2H, d), 7.34-7.29 (2H, d), 7.27-7.23 (3H, m), 7.21-7.15 (2H, m), 5.86 (1H, s), 5.75 (1H, s), 5.64 (2H, s), 2.71-2.58 (2H, m), 2.49-2.37 (2H, m), 2.18-2.07 (1H, m), 1.91-1.79 (1H, m).

Example 121

1-(4-(1-(2-methoxyethyl)-8-phenyl-4H-pyrido[2,3-b][1,2,4]triazolo[4,3-d][1,4]oxazin-7-yl)phenyl)cyclobutanamine

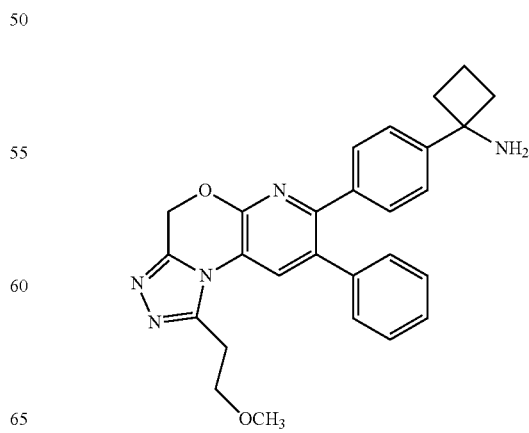

Step 1: Tert-butyl (1-(4-(1-(2-methoxyethyl)-8-phenyl-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (100 mg, 0.205 mmol) and 3-methoxypropanehydrazide (48 mg, 0.410 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in cyclohexane) to give the title compound (33 mg, 30%). LCMS (Method D): $R_T$=1.414 min, M+1=554. $^1$H NMR (500 MHz, CDCl$_3$) δ 8.16 (1H, s), 7.27-7.36 (7H, m), 7.23-7.18 (2H, m), 5.60 (2H, s), 3.99 (2H, t), 3.43 (3H, s), 3.38 (2H, t), 2.57-2.40 (4H, m), 2.12-2.01 (1H, m), 1.87-1.77 (1H, m), 1.49-1.27 (9H, bs).

Step 2: 1-(4-(1-(2-methoxyethyl)-8-phenyl-4H-pyrido[2,3-b][1,2,4]triazolo[4,3-d][1,4]oxazin-7-yl)phenyl)cyclobutanamine Tert-butyl (1-(4-(1-(2-methoxyethyl)-8-phenyl-4H-pyrido[2,3-b][1,2,4]triazolo[4,3-d][1,4]oxazin-7-yl)phenyl)cyclobutyl)carbamate (12 mg, 0.022 mmol) was dissolved in dichloromethane (0.5 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and dried to give the desired product as an off-white solid (5 mg, 50% yield). LCMS (Method D) RT=0.741 min, M+1=454. $^1$H-NMR (500 MHz, CD$_3$OD) δ 8.40 (1H, s), 7.52-7.47 (2H, d), 7.46-7.41 (2H, d), 7.38-7.34 (3H, m), 7.32-7.26 (2H, dd), 5.65 (2H, s), 3.94 (2H, t), 3.49 (2H, t), 3.35 (3H, s), 2.82-2.74 (2H, m), 2.63-2.54 (2H, m), 2.30-2.19 (1H, m), 2.04-1.93 (1H, m).

Example 122

1-(4-(8-phenyl-1-(pyridin-3-yl)-4H-pyrido[2,3-b][1,2,4]triazolo[4,3-d][1,4]oxazin-7-yl)phenyl)cyclobutanamine Step 1: Tert-butyl (1-(4-(8-phenyl-1-(pyridin-3-O-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (100 mg, 0.205 mmol) and nicotinic acid hydrazide (84 mg, 0.308 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in cyclohexane) to give the title compound (33 mg, 25%). LCMS (Method D): $R_T$=1.364 min, M+1=573. $^1$H NMR (500 MHz, CDCl$_3$): 9.00 (1H, d), 8.87 (1H, dd), 8.10 (1H, dt), 7.56 (1H, dd), 7.36-7.27 (5H, m), 7.24-7.17 (3H, m), 6.99-6.93 (2H, m), 5.67 (2H, s), 2.56-2.39 (4H, m), 2.13-2.01 (1H, m), 1.88-1.75 (1H, m), 1.49-1.26 (9H, bs).

Step 2: -(4-(8-phenyl-1-(pyridin-3-yl)-4H-pyrido[2,3-b][1,2,4]triazolo[4,3-d][1,4]oxazin-7-yl)phenyl)cyclobutanamine Tert-butyl (1-(4-(8-phenyl-1-(pyridin-2-yl)-4H-pyrido[2,3-b][1,2,4]triazolo[4,3-d][1,4]oxazin-7-yl)phenyl)cyclobutyl)carbamate (15 mg, 0.026 mmol) was dissolved in dichloromethane (1 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and dried to give the desired product as an off-white solid (8 mg, 56% yield). LCMS (Method A) RT=3.73 min, M+1=474. $^1$H NMR (500 MHz, CDCl$_3$): 8.99 (1H, d), 8.86 (1H, dd), 8.30 (1H, dt), 7.75 (1H, dd), 7.48 (2H, d), 7.42 (2H, d), 7.37 (1H, s), 7.31-7.20 (3H, m), 7.01 (2H, d), 5.78 (2H, s), 2.83-2.72 (2H, m), 2.63-2.54 (2H, m), 2.30-2.17 (1H, m), 2.05-1.90 (1H, m).

Example 123

1-(4-(8-phenyl-1-(pyridin-4-yl)-4H-pyrido[2,3-b][1,2,4]triazolo[4,3-d][1,4]oxazin-7-yl)phenyl)cyclobutanamine

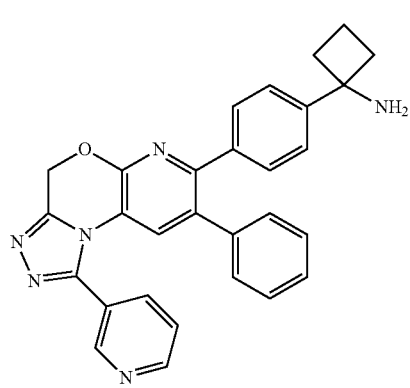 [SMILES: NC1(c2ccc(-c3nc4c(cc3-c3ccccc3)-n3c(nnc3-c3cccnc3)CO4)cc2)CCC1]

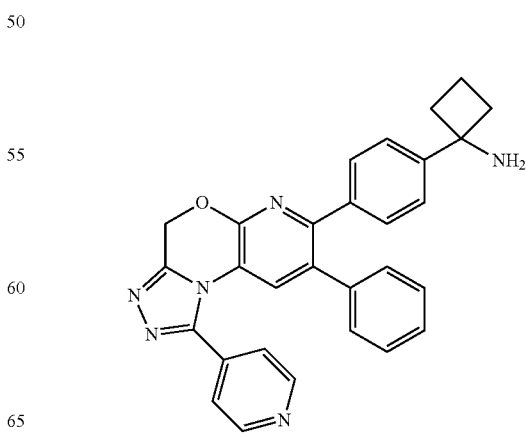

Step 1: Tert-butyl (1-(4-(8-phenyl-1-(pyridin-4-yl)-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (100 mg, 0.205 mmol) and isonicotinic acid hydrazide (127 mg, 0.923 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in n-hexanes) to give the title compound (14 mg, 12%), LCMS (Method A): $R_T$=6.28 min, M+1=573. $^1$H NMR (500 MHz, CDCl$_3$): 8.90 (2H, d), 7.70 (2H, d), 7.38 (1H, s), 7.36-7.32 (2H, d), 7.31-7.27 (2H, d), 7.25-7.18 (3H, m), 6.98-6.93 (2H, dd), 5.66 (2H, s), 2.55-2.41 (4H, m), 2.14-2.01 (1H, m), 1.88-1.78 (1H, m), 1.46-1.24 (9H, bs).

Step 2: 1-(4-(8-phenyl-1-(pyridin-4-yl)-4H-pyrido[2,3-b][1,2,4]triazolo[4,3-d][1,4]oxazin-7-yl)phenyl)cyclobutanamine Tert-butyl (1-(4-(8-phenyl-1-(pyridin-4-yl)-4H-pyrido[2,3-b][1,2,4]triazolo[4,3-d][1,4]oxazin-7-yl)phenyl)cyclobutyl)carbamate (14 mg, 0.024 mmol) was dissolved in dichloromethane (1 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure and dried to give the desired product as an off-white solid (10 mg, 87% yield). LCMS (Method A) RT=3.66 min, M+H$^+$=474. $^1$H NMR (500 MHz, CDCl$_3$): 8.77 (2H, d), 8.79 (2H, d), 7.41 (2H, d), 7.33 (1H, s), 7.32 (2H, d), 7.18-7.13 (3H, m), 6.96 (2H, dd), 5.66 (2H, s), 2.70-2.61 (2H, m), 2.52-2.43 (2H, m), 2.19-2.08 (1H, m), 1.92-1.82 (1H, m).

Example 124

6-(4-(1-aminocyclobutyl)phenyl)-1-methyl-7-(pyridin-3-0)-1H-pyrido[2,3-b][1,4]oxazin-2(3H)-one

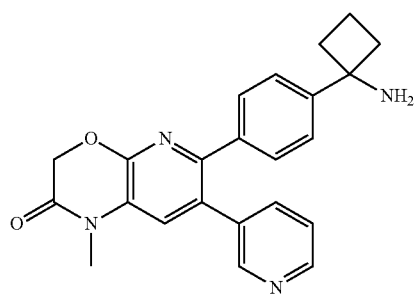 [SMILES: CN1C(=O)COc2nc(-c3ccc(C4(N)CCC4)cc3)c(-c3cccnc3)cc21]

Step 1: 6,7-dibromo-1H-pyrido[2,3-b][1,4]oxazin-2(3H)-one 7-bromo-1H-pyrido[2,3-b][1,4]oxazin-2(3H)-one (1.5 g, 6.55 mmol) and NBS (5.83, 32.7 mmol) were heated to 80° C. in DMF (30 ml) for 2 hours. The resulting reaction mixture was diluted with ethyl acetate (30 ml) and water (30 ml). The aqueous phase was extracted with fresh ethyl acetate (50 ml×3) and the combined organic layers were washed with brine (50 ml), dried on anhydrous Na$_2$SO$_4$, filtered and concentrated to dryness under reduced pressure to give the title compound (1.6 g, 79%). It was used for the next step without further purification. LCMS (Method D): $R_T$=0.91 min, M+1=309.

Step 2: 6,7-dibromo-1-methyl-1H-pyrido[2,3-b][1,4]oxazin-2(3H):one 6,7-Dibromo-1H-pyrido[2,3-b][1,4]oxazin-2(3H)-one (1.5 g mg, 4.88 mmol), potassium carbonate (2.02 g, 14.61 mmol) and methyl iodide (2.07, 14.61 mmol) were stirred in DMF (35 ml) at room temperature for one hour. The resulting reaction mixture was quenched with water (100 ml) and extracted with ethyl acetate (100 ml×3). The combined organic layers were washed with water (100 ml), brine (100 ml) and dried on anhydrous Na$_2$SO$_4$, filtered and concentrated to dryness under reduced pressure to give the title compound (1.3 g, 83%). It was used for the next step without further purification. LCMS (Method D) RT 1.053 min, M+1=322. $^1$H-NMR (500 MHz, CD$_3$OD) δ 7.41 (1H, s), 4.85 (2H, s), 3.35 (3H, s).

Step 3: Tert-butyl (1-(4-(trimethylstannyl)phenyl)cyclobutyl)carbamate

Tert-butyl (1-(4-bromophenyl)cyclobutyl)carbamate (5.45 g mg, 13.36 mmol) was dissolved in anhydrous toluene (250 ml). The solution was degassed by bubbling nitrogen for 15 minutes. Tetrakistriphenylphosphine palladium (0) (3.09 g, 2.67 mmol) was added and the resulting reaction mixture was degassed by bubbling nitrogen for 15 minutes. Hexamethylditin (6.57 g, 4.19 ml, 20.05 mmol) predissolved in anhydrous toluene (30 ml) was added to the previous mixture. The resulting reaction mixture was degassed by bubbling nitrogen for 10 minutes and heated to reflux for 2 hours. The reaction mixture was cooled down and filtered through celite, using fresh ethyl acetate to wash the cake. The filtrate was concentrated to dryness under reduced pressure. The obtained crude was purified by Biotage silica gel chromatography (gradient 0% to 90% ethyl acetate in n-hexanes; TLC stained with KMnO$_4$) to give the title compound (1.2 g, 22%). $^1$H NMR (500 MHz, CDCl$_3$): 7.53-7.36 (4H, m), 2.60-2.47 (4H, m), 2.13-2.03 (1H, m), 1.90-1.78 (1H, m), 1.47-1.27 (9H, br).

Step 4: Tert-butyl (1-(4-(7-bromo-1-methyl-2-oxo-2,3-dihydro-1H-pyrido[2,3-b][1,4]oxazin-6-yl)phenyl)cyclobutyl)carbamate 6,7-Dibromo-1-methyl-1H-pyrido[2,3-b][1,4]oxazin-2(3H)-one (0.628 g, 1.951 mmol) and tert-butyl 1-(4-(trimethylstannyl)phenyl)cyclobutylcarbamate (1.2 g, 2.93 mmol) was dissolved in DMF (10 ml) to give a yellow solution. The reaction mixture was degassed by bubbling nitrogen for 30 minutes.

Bis(dimethylphosphino)palladium(IV) chloride (0.137 g, 0.195 mmol) was added at room temperature. The resulting reaction was degassed and heated to 80° C.

The reaction mixture was quenched with water (80 ml); the aqueous phase was extracted with ethyl acetate (80 ml×3); the combined organic layers were washed with water (80 ml×2) and brine (80 ml×2). The organic layer was dried on anhydrous Na$_2$SO$_4$, filtered and concentrated to dryness under reduced pressure. The crude was purified by Biotage silica gel chromatography (gradient 0% to 70% ethyl acetate in n-hexanes) to give the title compound (400 mg, 42%). $^1$H NMR (500 MHz, CDCl$_3$): 7.73-7.56 (2H, m), 7.56-7.46 (3H, m), 4.88 (2H, s), 3.33 (3H, s), 2.68-2.49 (4H, m), 2.20-2.04 (1H, m), 1.94-1.80 (1H, m), 1.47-1.27 (9H, br s).

$^1$ This was a mixture of two regioisomers (7:3 in ratio).

Step 5: Tert-butyl (1-(4-(1-methyl-2-oxo-7-(pyridin-3-yl)-2,3-dihydro-1H-pyrido[2,3-b][1,4]oxazin-6-yl) phenyl)cyclobutyl)carbamate Tert-butyl (1-(4-(7-bromo-1-methyl-2-oxo-2,3-dihydro-1H-pyrido[2,3-b][1,4]oxazin-6-yl)phenyl)cyclobutyl)carbamate (57 mg, 0.117 mmol), pyridin-3-yl boronic acid (21.52 mg, 0.175 momol), triphenylphosphine (9.18 mg, 0.035 mmol), cesium fluoride (89 mg, 0.584 mmol) were dissolved in 1,2-dimethoxyethane (2 ml) to give an orange solution. The reaction mixture was degassed by bubbling nitrogen for 10 minutes. Palladium(II)acetate (3.93 mg, 0.018 mmol) was added at room temperature. The resulting reaction was degassed and heated to 80° C. for 18 hours. The reaction mixture was concentrated to dryness under reduced pressure. The crude was purified by preparatory HPLC to give the title compound (12 mg, 21%). LCMS (Method D) RT 1.158 min, M+1=487. $^1$H NMR (500 MHz, CDCl$_3$): 7.64-7.52 (1H, m), 7.37-7.21 (8H, m), 4.94 (2H, s), 3.43 (3H, s), 2.59-2.36 (4H, m), 2.15-2.01 (1H, m), 1.91-1.77 (1H, m), 1.47-1.20 (9H, br s).

Step 6: 6-(4-(1-aminocyclobutyl)phenyl)-1-methyl-7-(pyridin-3-yl)-1H-pyrido[2,3-b][1,4]oxazin-2(3H)-one Tert-butyl (1-(4-(1-methyl-2-oxo-7-(pyridin-3-yl)-2,3-dihydro-1H-pyrido[2,3-b][1,4]oxazin-6-yl)phenyl)cyclobutyl) carbamate (12 mg, 0.025 mmol) was dissolved in TFA (1 mL) and stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and dried to give the desired product as an off-white solid (14 mg, 78% yield). LCMS (Method D) RT=0.546 min, M+1=387. $^1$H-NMR (500 MHz, CD$_3$OD) δ 8.57-8.49 (1H, br s), 8.45-8.36 (1H, br s), 7.90 (1H, d), 7.67 (1H, s), 7.61-7.48 (2H, d), 7.48-7.36 (4H, m), 5.00 (2H, s), 3.45 (3H, s), 2.84-2.72 (2H, m), 2.65-2.54 (2H, m), 2.32-2.16 (1H, m), 2.06-1.90 (1H, m).

Example 125

6-(4-(1-aminocyclobutyl)phenyl)-1-methyl-7-(thiophen-3-yl)-1H-pyrido[2,3-b][1,4]oxazin-2(3H)-one

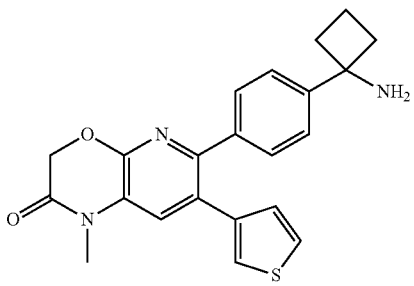 [SMILES: CN1C(=O)COc2nc(-c3ccc(C4(N)CCC4)cc3)c(-c3ccsc3)cc21]

Step 1: Tert-butyl (1-(4-(1-methyl-2-oxo-7-(thiophen-3-yl)-2,3-dihydro-1H-pyrido[2,3-b][1,4] oxazin-6-yl)phenyl)cyclobutyl)carbamate Tert-butyl (1-(4-(7-bromo-1-methyl-2-oxo-2,3-dihydro-1H-pyrido[2,3-b][1,4]oxazin-6-yl)phenyl)cyclobutyl)carbamate (70 mg, 0.143 mmol), thiophen-3-yl boronic acid (30 mg, 0.215 momol), triphenylphosphine (11 mg, 0.043 mmol), cesium fluoride (109 mg, 0.717 mmol) were dissolved in 1,2-dimethoxyethane (3 ml) to give an orange solution. The reaction mixture was degassed by bubbling nitrogen for 10 minutes.

Palladium(II)acetate (5 mg, 0.021 mmol) was added at room temperature. The resulting reaction was degassed and heated to 80° C. for 18 hours.

The reaction mixture was concentrated to dryness under reduced pressure. The crude was purified by Biotage silica gel chromatography (gradient 0% to 70% ethyl acetate in n-hexanes) to give the title compound as a mixture of two regioisomers (37 mg, 52%, 7:3). $^3$ $^1$H NMR (500 MHz, CDCl$_3$): 7.39-7.30 (5H, m), 7.24-7.20 (1H, dd), 7.15-7.12 (1H, dd), 6.82-6.78 (1H, dd), 4.81(2H, s), 3.39 (3H, s), 2.68-2.33 (4H, m), 2.15-2.05 (1H, m), 1.90-1.78 (1H, m), 1.47-1.20 (9H, br s). LCMS (Method D): RT 1.514 min, M+1=492.

$^3$ This was a mixture of two regioisomers (7:3 in ratio).

Step 2: 6-(4-(1-aminocyclobutyl)phenyl)-1-methyl-7-(thiophen-3-yl)-1H-pyrido[2,3-b][1,4]oxazin-2 (3H)-one Tert-butyl (1-(4-(1-methyl-2-oxo-7-(thiophen-3-yl)-2,3-dihydro-1H-pyrido[2,3-b][1,4]oxazin-6-yl)phenyl)cyclobutyl)carbamate (25 mg, 0.051 mmol) was dissolved in dichloromethane (0.5 ml); this solution was added to a scx-2 catch and release cartridge (5 g), precalibrated using methanol (15 ml) and dichloromethane (15 ml). After allowing binding for 12 hours, the column was washed with methanol (6 ml), then the product eluted with 7M ammonia in methanol (4×2 ml). The combined product fractions were concentrated to dryness under reduced pressure to give the desired product as a white solid (5.8 mg, 30% yield). LCMS (Method D): RT=0.777 min, M+1=393. $^1$H-NMR (500 MHz, CD$_3$OD) δ 7.35-7.29 (3H, m), 7.28-7.25 (1H, dd), 7.21-7.18 (1H, s), 7.17-7.14 (1H, dd), 7.07-7.03 (1H, dd), 6.71-6.67 (1H, dd), 4.80 (2H, s), 3.32 (3H, s), 2.51-2.37 (4H, m), 2.25-2.13 (1H, m).

Example 126

6-(4-(1-aminocyclobutyl)phenyl)-1-methyl-7-(thiophen-2-yl)-1H-pyrido[2,3-b][1,4]oxazin-2(3H)-one

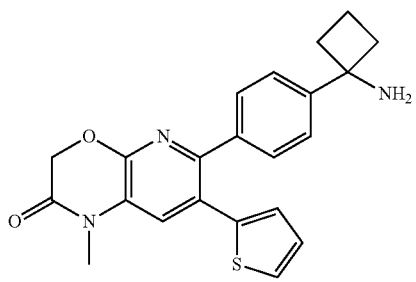 [SMILES: CN1C(=O)COc2nc(-c3ccc(C4(N)CCC4)cc3)c(-c3cccs3)cc21]

Step 1: Tert-butyl (1-(4-(1-methyl-2-oxo-7-(thiophen-2-yl)-2,3-dihydro-1H-pyrido[2,3-b][1,4]oxazin-6-yl)phenyl)cyclobutyl)carbamate Tert-butyl (1-(4-(7-bromo-1-methyl-2-oxo-2,3-dihydro-1H-pyrido[2,3-b][1,4]oxazin-6-yl)phenyl)cyclobutyl)carbamate (70 mg, 0.143 mmol), thiophen-2-yl boronic acid (30 mg, 0.215 momol), triphenylphosphine (11 mg, 0.043 mmol), cesium fluoride (109 mg, 0.717 mmol) were dissolved in 1,2-dimethoxyethane (3 ml) to give an orange solution. The reaction mixture was degassed by bubbling nitrogen for 10 minutes.

Palladium(II)acetate (4 mg, 0.018 mmol) was added at RT. The resulting reaction was degassed, bubbling $N_2$ and heated to 80° C. for 18 hours.

The reaction mixture was concentrated to dryness under reduced pressure. The crude was purified by Biotage silica gel chromatography (gradient 0% to 70% ethyl acetate in n-hexanes) to give the title compound as a mixture of two regioisomers (15 mg, 22%, 7:3). [2] LCMS (Method D): RT 1.524 min, M+1=492. $^1$H NMR (500 MHz, CDCl$_3$): 7.69-7.32 (7H, m), 6.81-6.76 (1H, m), 4.93 (2H, s), 3.43 (3H, s), 2.58-2.48 (4H, m), 2.20-2.07 (1H, m), 1.96-1.81 (1H, m), 1.46-1.20 (9H, br s).

[2] This was a mixture of two regioisomers (7:3 in ratio).

Step 2: 6-(4-(1-aminocyclobutyl)phenyl)-1-methyl-7-(thiophen-2-yl)-1H-pyrido[2,3-b][1,4]oxazin-2(3H)-one Tert-butyl (1-(4-(1-methyl-2-oxo-7-(thiophen-2-yl)-2,3-dihydro-1H-pyrido[2,3-b][1,4]oxazin-6-yl)phenyl)cyclobutyl)carbamate (12 mg, 0.024 mmol) was dissolved in dichloromethane (1.5 ml). TFA (1 ml) was added at room temperature and the reaction mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent was removed by pipette. This was repeated three times. The remaining solvent was removed under reduced pressure and dried to give the desired product as an off-white solid (14 mg, 78% yield). LCMS (Method D): RT=0.781 min, M+1=393. $^1$H-NMR (500 MHz, CD$_3$OD) δ 7.66 (1H, s), 7.53-7.49 (2H, dd), 7.48-7.44 (2H, dd), 7.42-7.39 (1H, dd), 7.01-7.97 (1H, dd), 6.97-6.95 (1H, dd), 4.97 (2H, s), 3.44 (3H, s), 2.84-2.74 (2H, m), 2.64-2.55 (2H, m), 2.31-2.21 (1H, m), 2.07-1.93 (1H, m).

Example 127

2-(4-(1-aminocyclobutyl)phenyl)-3-phenyl-6,8-dihydro-5H-pyrano[3,4-b]pyridin-5-one

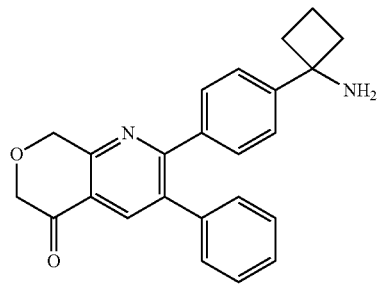 [SMILES: NC1(c2ccc(-c3nc4c(cc3-c3ccccc3)C(=O)COC4)cc2)CCC1]

Step 1: tert-butyl(1-(4-(5-oxo-3-phenyl-6,8-dihydro-5H-pyrano[3,4-b]pyridin-2-yl)phenyl)cyclobutyl) carbamate In a 5 mL reaction tube was added acetic acid (5 ml) followed by (E)-tert-butyl 1-(4-(3-(dimethylamino)-2-phenylacryloyl)phenyl)cyclobutylcarbamate (750 mg, 1.783 mmol), 2H-pyran-3,5(4H,6H)-dione (305 mg, 2.68 mmol), ammonium acetate (412 mg, 5.35 mmol) and molecular sieves (100 mg) to give a brown suspension. The reaction mixture was stirred at 100° C. under a nitrogen atmosphere for 2 hours, then allowed to cool to room temperature and concentrated under reduced pressure. The residue was partitioned between water (10 mL) and dichloromethane (10 mL) and decanted from the molecular sieves. The layers were separated and the aqueous phase extracted into dichloromethane (2×10 mL). The combined organic phases were washed with saturated sodium bicarbonate solution (2×10 mL), brine (10 mL), dried over Na$_2$SO$_4$, filtered and concentrated to dryness under reduced pressure to give a yellow/brown solid. This was purified twice by Biotage chromatography (cyclohexane:ethyl acetate, gradient elution from 93:7 to 60:40) and then preparative HPLC (Method F) to give the desired product as a white solid (12 mg, 1.4% yield). $^1$H-NMR (500 MHz, CDCl$_3$) δ 8.29 (1H, s), 7.16-7.41 (9H, m), 5.05 (2H, s), 5.02 (1H, br s), 4.44 (2H, s), 2.21-2.66 (4H, br m), 2.01-2.16 (1H, m), 1.74-1.88 (1H, m), 1.10-1.50 (9H, br m).

Step 2: 2-(4-(1-aminocyclobutyl)phenyl)-3-phenyl-6,8-dihydro-5H-pyrano[3,4-b]pyridin-5-one tert-Butyl (1-(4-(5-oxo-3-phenyl-6,8-dihydro-5H-pyrano[3,4-b]pyridin-2-yl)phenyl)cyclobutyl)carbamate (12 mg, 0.026 mmol) was dissolved in TFA (1 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as an off-white solid (10 mg, 77% yield). $^1$H-NMR (500 MHz, MeOD) δ 8.19 (1H, s), 7.41 (2H, d), 7.32 (2H, d), 7.20-7.24 (3H, m), 7.11-7.15 (2H, m), 4.94 (2H, s), 4.37 (2H, s), 2.59-2.68 (2H, m), 2.39-2.49 (2H, m), 2.06-2.16 (1H, m), 1.79-1.95 (1H, m). LCMS (Method D) RT=0.86 min, M+H$^+$=371.00.

Example 128

(1r,3r)-3-amino-3-(4-(1-(difluoromethyl)-8-phenyl-4H-pyrido[2,3-b][1,2,4]triazolo[4,3-d][1,4]oxazin-7-0)phenyl)-1-methylcyclobutanol

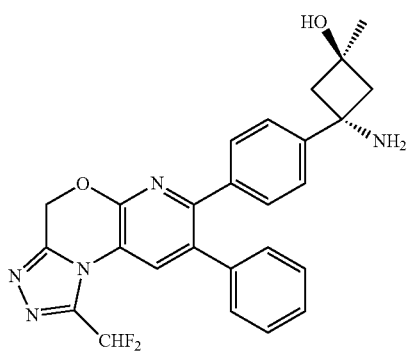 [SMILES: C[C@]1(O)C[C@@](N)(c2ccc(-c3nc4c(cc3-c3ccccc3)-n3c(nnc3C(F)F)CO4)cc2)C1]

Step 1: 6-bromo-7-phenyl-1H-pyrido[2,3-b][1,4]oxazine-2(3H)-thione

A mixture of 6-bromo-7-phenyl-1H-pyrido[2,3-b][1,4]oxazin-2(3H)-one (0.26 g, 0.852 mmol) and Lawesson's Reagent (0.34 g, 0.852 mmol) in toluene (10 ml) was heated at 120 degree for 16 h. The reaction mixture was concentrated to dryness and was added DCM (5 ml) and diisopropyl ether (20 ml). The precipitate was filtered to give product (0.18 g). $^1$H NMR (500 MHz, DMSO-d$_6$): 12.9 (br, 1H), 7.35-7.55 (m, 5H), 7.32 (s, 1H), 5.16 (s, 2H).

Step 2: 7-bromo-1-(difluoromethyl)-8-phenyl-4H-pyrido[2,3-b][1,2,4]triazolo[4,3-d][1,4]oxazine A mixture of 6-bromo-7-phenyl-1H-pyrido[2,3-b][1,4]oxazin-2(3H)-thione (0.21 g, 0.654 mmol) and 2,2-difluoroacetohydrazide (0.14 g, 1.3 mmol) in xylene (6 ml) was heated at 150 degree under microwave for 60 min. The reaction solution was concentrated and the residue was partitioned between ethyl acetate (10 ml) and water (10 ml). The organic phase was separated and the aqueous phase was extracted with ethyl acetate (10 ml). The combined organic phase was concentrated and purified by column (biotage 25 g) eluted with ethyl acetate/cyclohexane (0-60%) to afford product (55 mg). $^1$H NMR (500 MHz, CDCl$_3$) 8.09 (s, 1H), 7.4-7.55 (m, 5H), 7.06 (t, 1H), 5.66 (s, 2H).

Step 3: 2-((1r,3r)-1-(4-(1-(difluoromethyl)-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione A mixture of 7-bromo-1-(difluoromethyl)-8-phenyl-4H-pyrido[2,3-b][1,2,4]triazolo[4,3-d][1,4]oxazine (30 mg, 0.079 mmol), 24(1r,3r)-3-hydroxy-3-methyl-1-(4-(4,4,5,5-tetramethyl-1,3,2-dioxaborolan-2-yl)phenyl)cyclobutyl) isoindoline-1,3-dione (46 mg, 0.106 mmol), and sodium carbonate (16.7721 mg, 0.158 mmol) in dioxane (Ratio: 4.00, Volume: 4 ml) and Water (Ratio: 1.000, Volume: 1 ml) to give a yellow suspension. The suspension was degassed for 5 min. Pd(PPh$_3$)$_4$ (6.4614 mg, 7.91 μmol) was added and the mixture was heated under microwave condition at 100 degree for 20 min. The reaction mixture was concentrated to dryness. The residue was partitioned between ethyl acetate (15 ml) and water (15 ml). The organic phase was separated. The aqueous phase was extracted with ethyl acetate (2×15 ml). The combined organic phase was washed with water (2×30 ml), brine (25 ml) then concentrated. The crude product was purified by column (biotage 10 g) eluted with ethyl acetate/cyclohexane (0-50%) to afford product (10 mg). $^1$H NMR (500 MHz, CDCl$_3$): 8.14 (s, 1H), 7.74 (m, 2H), 7.69 (m, 2H), 7.54 (d, 2H), 7.33 (d, 2H), 7.27-7.31 (m, 3H), 7.05-7.19 (m, 3H), 5.61 (s, 2H), 3.35 (d, 2H), 3.09 (d, 2H), 1.4 (s, 3H).

Step 4: (1r,3r)-3-amino-3-(4-(1-(difluoromethyl)-8-phenyl-4H-pyrido[2,3-b][1,2,4]triazolo[4,3-d][1,4]oxazin-7-yl)phenyl)-1-methylcyclobutanol A mixture of 2-((1r,3r)-1-(4-(1-(difluoromethyl)-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione (10 mg, 0.017 mmol) and HYDRAZINE (0.1 ml, 3.19 mmol) hydrate in ethanol (3 ml) was heated under microwave irradiation at 120° C. for 30 min. The mixture was concentrated to dryness. The residue was partitioned between ethyl acetate (10 ml) and water (10 ml). The organic phase was separated. The aqueous phase was extracted with ethyl acetate (2×10 ml). The combined organic phase was washed with water (2×15 ml), brine (15 ml) and concentrated. The crude product was purified by SCX-2 column (2 g) eluted with ammonia in methanol (2M) to give product (3 mg). $^1$H NMR (500 MHz, CD$_3$OD): 8.05 (s, 1H), 7.4 (t, 1H), 7.2-7.3 (m, 7H), 7.11-7.15 (m, 2H), 5.63 (s, 2H), 2.59 (d, 3H), 2.34 (d, 2H). 1.43 (s, 3H). LCMS (Method D): R$_T$=0.78 min, M+H$^+$=476.0

Example 129

1-(4-(1,8-diphenyl-4H-pyrido[2,3-b][1,2,4]triazolo[4,3-d][1,4]oxazin-7-yl)phenyl)cyclobutanamine

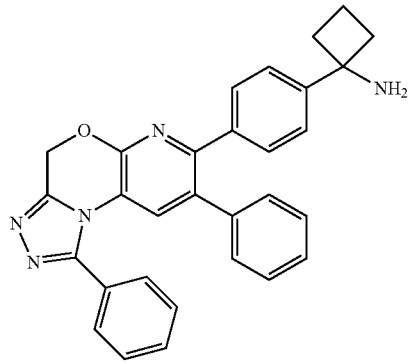 [SMILES: NC1(c2ccc(-c3nc4c(cc3-c3ccccc3)-n3c(nnc3-c3ccccc3)CO4)cc2)CCC1]

Step 1: Tert-butyl (1-(4-(1,8-diphenyl-4H-pyrido[2, 3-b][1,2,4]triazolo[4,3-d][1,4]oxazin-7-yl)phenyl) cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (100 mg, 0.205 mmol) and benzoic acid hydrazide (84 mg, 0.615 mmol) in p-xylene (2 ml) was heated to 150° C. for 15 minutes under microwave irradiation. The resulting reaction mixture was concentrated to dryness under reduced pressure and purified by Biotage silica gel chromatography (gradient 0% to 20% ethyl acetate in n-hexane) to give the title compound (46 mg, 40%). LCMS (Method D): $R_T$=1.546 min, M+1=572. $^1$H NMR (500 MHz, CDCl$_3$): 7.77-7.69 (2H, m), 7.64-7.57 (2H, m), 7.56-7.50 (1H, t), 7.49-7.41 (2H, t), 7.34-7.30 (2H, m), 7.28 (1H, s), 7.22-7.14 (3H, m), 6.95-6.90 (2H, dd), 5.65 (2H, s), 2.55-2.40 (3H, m), 2.15-2.01 (2H, m), 1.89-1.77 (1H, m), 1.46-1.24 (9H, bs).

Step 2: 1-(4-(1,8-diphenyl-4H-pyrido[2,3-b][1,2,4]triazolo[4,3-d][1,4]oxazin-7-yl)phenyl)cyclobutanamine Tert-butyl (1-(4-(1,8-diphenyl-4H-pyrido[2,3-b][1,2,4]triazolo[4,3-d][1,4]oxazin-7-yl)phenyl)cyclobutyl)carbamate (15 mg, 0.026 mmol) was dissolved in dichloromethane (1 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexanes (2 ml) and after settling the supernatant solvent removed by pipette. This was repeated three times. The remaining solvent was removed under reduced pressure and dried to give the desired product as an off-white solid (5 mg, 40% yield). LCMS (Method D) RT=0.846 min, M+1=472. $^1$H NMR (500 MHz, CDCl$_3$): 7.91-7.86 (2H, dd), 7.83-7.76 (3H, m), 7.59-7.54 (2H, d), 7.53-7.48 (2H, d), 7.42 (1H, s), 7.37-7.28 (3H, m), 7.09-7.03 (2H, dd), 5.86 (2H, s), 2.91-2.81 (2H, m), 2.74-2.63 (2H, m), 2.40-2.29 (1H, m), 2.13-2.02 (1H, m).

Example 130

1-(4-(8-phenyl-1-(pyridin-2-yl)-4H-pyrido[2,3-b][1,2,4]triazolo[4,3-d][1,4]oxazin-7-yl)phenyl)cyclobutanamine

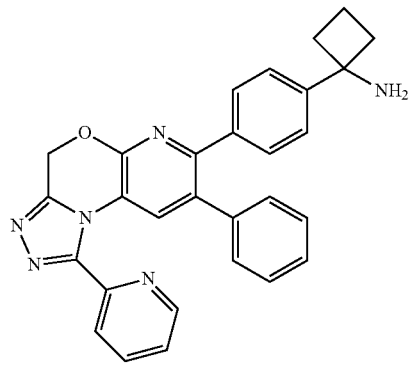 [SMILES: NC1(c2ccc(-c3nc4c(cc3-c3ccccc3)-n3c(nnc3-c3ccccn3)CO4)cc2)CCC1]

Step 1: 2-Picolynil hydrazide

Ethyl 2-picolinate (5 g, 33.1 mmol) and hydrazine monohydrate (5.3 g, 165 mmol) in ethanol (70 ml) were heated to reflux for 15 hour. The reaction mixture was concentrated under reduced pressure and the residue was treated with toluene to azeotrope hydrazine in excess.

This was repeated three times. The crude residue was used for the next step without further purification.

Step 2: Tert-butyl (1-(4-(8-phenyl-1-(pyridin-4-yl)-4H-pyrido[2,3-b][1,2,4]triazolo[4,3-d][1,4]oxazin-7-yl)phenyl)cyclobutyl)carbamate A suspension of tert-butyl(1-(4-(7-phenyl-2-thioxo-2,3-dihydro-1H-pyrido[2,3-b][1,4]oxazin-6-yl)phenyl)cyclobutyl)carbamate (100 mg, 0.205 mmol) and 2-picolinylhydrazide (56.2 mg, 0.410 mmol) in p-xylene (1 ml) was heated to 150° C. for 15 minutes under microwave irradiation. The resulting reaction mixture was concentrated to dryness under reduced pressure and purified by Biotage silica gel chromatography (gradient 0% to 4% methanol in dichloromethane) to give the title compound (15 mg, 13%). LCMS (Method A): $R_T$=6.95 min, M+1=573. $^1$H NMR (500 MHz, CDCl$_3$): 8.78-8.74 (1H, dd), 8.45 (1H, s), 8.27-8.23 (1H, dd), 7.96-7.91(1H, dt), 7.53-7.48 (1H, dd), 7.38-7.33 (2H, dd), 7.31-7.27 (3H, m), 7.25-7.23 (2H, m), 7.19-7.13 (2H,dd), 5.63 (2H, s), 2.56-2.41 (4H, m), 2.14-2.01 (1H, m), 1.88-1.75 (1H, m), 1.46-1.21 (9H, bs).

Step 3: 1-(4-(8-phenyl-1-(pyridin-2-yl)-4H-pyrido[2, 3-b][1,2,4]triazolo[4,3-d][1,4]oxazin-7-yl)phenyl) cyclobutanamine Tert-butyl (1-(4-(8-phenyl-1-(pyridin-2-yl)-4H-pyrido[2,3-b][1,2,4]triazolo[4,3-d][1,4]oxazin-7-yl)phenyl)cyclobutyl)carbamate (15 mg, 0.026 mmol) was dissolved in dichloromethane (1 ml); TFA (0.5 ml) was added at room temperature and the resulting mixture was stirred for 30 seconds. The solution was immediately concentrated to dryness under reduced pressure. The residue was dissolved in diethyl ether (~2 ml) and concentrated to dryness under reduced pressure. This was repeated three times. The residue was then slurred in diethyl ether (2 ml) and after settling the supernatant solvent was removed by pipette. This was repeated three times. The residue was then slurred in n-hexane (2 ml) and after settling the supernatant solvent was removed by pipette. This was repeated three times. The remaining solvent was removed under reduced pressure. The resulting residue was purified via preparative HPLC to give the desired product as a white solid (8 mg, 64% yield). LCMS (Method D) RT=0.825 min, M+H$^+$=474. $^1$H NMR (500 MHz, d$_6$-DMSO): 8.79 (1H, d), 8.44 (1H, bs), 8.13 (1H, s), 8.11-8.05 (1H, m), 7.62-7.59 (1H, m), 7.41 (2H, s), 7.42-7.38 (2H, d), 7.25-7.27 (3H, m), 7.10 (2H, m), 5.71 (2H, s), 2.60-2.51 (4H, m), 2.27-2.19 (1H, m), 1.88-1.76 (1H, m).

Example 131

6-(4-(aminomethyl)phenyl)-1-methyl-7-phenyl-1H-pyrido[2,3-b][1,4]oxazin-2(3H)-one

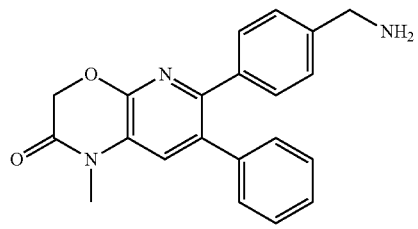 [SMILES: CN1C(=O)COc2nc(-c3ccc(CN)cc3)c(-c3ccccc3)cc21]

Step 1: tert-butyl 4-(1-methyl-2-oxo-7-phenyl-2,3-dihydro-1H-pyrido[2,3-b][1,4]oxazin-6-yl)benzylcarbamate In a 15 mL reaction tube was added 6-bromo-1-methyl-7-phenyl-1H-pyrido[2,3-b][1,4]oxazin-2(3H)-one (40 mg, 0.125 mmol) and tert-butyl 4-(4,4,5,5-tetramethyl-1,3,2-dioxaborolan-2-yl)benzylcarbamate (50 mg, 0.150 mmol) in 1,4-dioxane (2 ml), followed by a solution of sodium carbonate (40 mg, 0.3 mmol) in water (0.5 ml) to give a white suspension. This was degassed by bubbling nitrogen for 10 minutes, followed by the addition of [1,1-bis(diphenylphosphino)ferrocene]dichloropalladium(II)dichloromethane adduct (9 mg, 0.013 mmol). The reaction mixture was heated to 80° C. overnight. The reaction mixture was allowed to cool to room temperature, diluted with brine (4 ml) and extracted into ethyl acetate (3×4 ml). The combined organic phases were dried over $Na_2SO_4$, filtered and concentrated to dryness under reduced pressure. The residue was purified by Biotage chromatography (cyclohexane:ethyl acetate, gradient elution from 90:10 to 20:80) to give the desired product as a white solid (40 mg, 72% yield). $^1$H-NMR (500 MHz, $CDCl_3$) δ 7.27-7.32 (5H, m), 7.25 (1H, s), 7.16-7.20 (2H, m), 7.10 (2H, d), 4.89 (2H, s), 4.81 (1H, br s), 4.26 (2H, br s), 3.39 (3H, s), 1.23 (9H, br s). LCMS (Method D): RT=1.40 min, M+H$^+$=446.20.

Step 2: 6-(4-(aminomethyl)phenyl)-1-methyl-7-phenyl-1H-pyrido[2,3-b][1,4]oxazin-2(3H)-one tert-Butyl 4-(1-methyl-2-oxo-7-phenyl-2,3-dihydro-1H-pyrido[2,3-b][1,4]oxazin-6-yl)benzylcarbamate (40 mg, 0.090 mmol) was dissolved in TFA (2 mL) and stirred for 30 seconds. The solution was immediately concentrated to dryness under reduced pressure. The residue was dissolved in diethyl ether (~2 mL) and concentrated to dryness under reduced pressure three times. The residue was then slurried in diethyl ether (2 mL) and after settling the supernatant solvent removed by pipette. This was repeated three times. The remaining solvent was removed by freeze drying overnight to give the desired compound as a white solid (35 mg, 85% yield). $^1$H-NMR (500 MHz, MeOD) δ 7.54 (1H, s), 7.36 (2H, d), 7.31 (2H, d), 7.25-7.29 (3H, m), 7.18-7.23 (2H, m), 4.95 (2H, s), 4.07 (2H, s), 3.41 (3H, s). LCMS (Method D): RT=0.69 min, M+H$^+$=346.20.

Example 132

6-(4-(1-aminocyclobutyl)phenyl)-7-(4-fluorophenyl)-1-methyl-1H-pyrido[2,3-b][1,4]oxazin-2(3H)-one

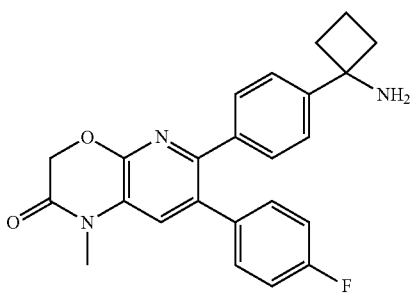 [SMILES: CN1C(=O)COc2nc(-c3ccc(C4(N)CCC4)cc3)c(-c3ccc(F)cc3)cc21]

Step 1: tert-butyl 1-(4-(7-(4-fluorophenyl)-1-methyl-2,3-dihydro-1H-pyrido[2,3-b][1,4]oxazin-6-yl)phenyl)cyclobutylcarbamate In a sealed tube was added tert-butyl 1-(4-(7-bromo-1-methyl-2-oxo-2,3-dihydro-1H-pyrido[2,3-b][1,4]oxazin-6-yl)phenyl)cyclobutylcarbamate (82 mg, 0.168 mmol), 4-fluorophenylboronic acid (35.2 mg, 0.252 mmol), triphenylphosphine (13.21 mg, 0.05 mmol) and cesium fluoride (128 mg, 0.84 mmol) in 1,2-dimethoxyethane (2 ml). The reaction mixture was degassed by bubbling nitrogen for 10 min and palladium acetate (5.65 mg, 0.025 mmol) was added and the mixture was heated at 80° C. overnight. The reaction mixture was concentrated and the residue was diluted with ethyl acetate and the suspension was pass through silica. The filtration was concentrated and to the residue was added methanol (2.5 ml) to form a suspension. The solid was filtered and dried to give tert-butyl 1-(4-(7-(4-fluorophenyl)-1-methyl-2,3-dihydro-1H-pyrido[2,3-b][1,4]oxazin-6-yl)phenyl)cyclobutylcarbamate (19 mg). LCMS (Method D): $R_T$=1.54 min, M+H$^+$=504.

Step 2: 6-(4-(1-aminocyclobutyl)phenyl)-7-(4-fluorophenyl)-1-methyl-1H-pyrido[2,3-b][1,4]oxazin-2(3H)-one TRIFLUOROACETIC ACID (0.5 ml, 6.49 mmol) was added to tert-butyl(1-(4-(7-(4-fluorophenyl)-1-methyl-2-oxo-2,3-dihydro-1H-pyrido[2,3-b][1,4]oxazin-6-yl)phenyl)cyclobutyl)carbamate (16 mg, 0.032 mmol) in a RBF (5 ml), The resulting solution was stirred for 60 seconds then concentrated to dryness under reduced pressure. The residue was suspended in diethyl ether (1 ml) and concentrated to dryness three times to give the trifluoroacetic acid salt of the product (7 mg). LCMS (Method D): $R_T$=0.78 min, M+H$^+$=404. $^1$H NMR (500 MHz, $CD_3OD$) 7.44 (s, 1H), 7.29 (m, 4H), 7.12-

7.15 (m, 2H), 6.91-6.95 (m, 2H), 4.85 (s, 2H), 3.31 (s, 3H), 2.62-2.69 (m, 2H), 2.43-2.49 (m, 2H), 2.10-2.15 (m, 1H), 1.80-1.86 (m, 1H).

Example 133

6-(4-(1-aminocyclobutyl)phenyl)-7-(cyclopropylmethyl)-1-methyl-1H-pyrido[2,3-b][1,4]oxazin-2(3H)-one

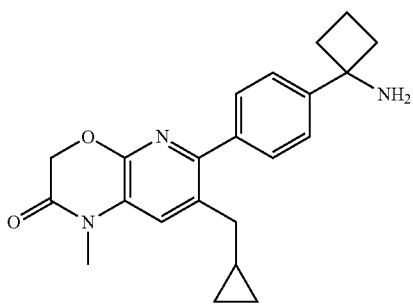 [SMILES: CN1C(=O)COc2nc(-c3ccc(C4(N)CCC4)cc3)c(CC3CC3)cc21]

Step 1: Tert-butyl (1-(4-(7-allyl-1-methyl-2-oxo-2,3-dihydro-1H-pyrido[2,3-b][1,4]oxazin-6-yl)phenyl)cyclobutyl)carbamate Tert-butyl (1-(4-(7-bromo-1-methyl-2-oxo-2,3-dihydro-1H-pyrido[2,3-b][1,4]oxazin-6-yl)phenyl)cyclobutyl)carbamate (100 mg, 0.205 mmol) and allyl-tributyl stannane were dissolved in anhydrous dimethylformamide (1 ml) to give a white solution. The reaction mixture was degassed by bubbling nitrogen for 30 minutes.

Bis(triphenylphosphine)palladium(II)dichloride (15 mg, 0.020 mmol) was added at room temperature. The resulting reaction was degassed and heated to 80° C. for 2 hours. The reaction mixture was diluted with ethyl acetate (3 ml), washed with water (5 ml) and brine (5 ml); the organic phase was concentrated to dryness under reduced pressure. The crude was purified by Biotage silica gel chromatography (gradient 0% to 20% ethyl acetate in n-hexanes) to give the title compound (52 mg, 56%). LCMS (Method A) $R_T$ 6.83 min, M+1=450. $^1$H NMR (500 MHz, CDCl$_3$): 7.57-7.40 (4H, m), 7.15 (1H, s), 6.04-5.88 (1H, m), 5.20-5.13 (1H, m), 5.11-4.99 (2H, m), 4.85 (2H, s), 3.52-3.41(1H, dd), 3.37 (3H, s), 2.67-2.41 (4H, m), 2.15-2.04 (1H, m), 1.90-1.80 (1H, m), 1.47-1.31 (9H, br s).

Step 2: Tert-butyl (1-(4-(7-(cyclopropylmethyl)-1-methyl-2-oxo-2,3-dihydro-1H-pyrido[2,3-b][1,4]oxazin-6-yl)phenyl)cyclobutyl)carbamate In a 50 ml 3 necks round-bottomed flask was tert-butyl(1-(4-(7-allyl-1-methyl-2-oxo-2,3-dihydro-1H-pyrido[2,3-b][1,4]oxazin-6-yl)phenyl)cyclobutyl)carbamate (52 mg, 0.116 mmol), palladium acetate (32 mg, 0.180 mmol) in diethyl ether (5 ml) to give a yellow solution at room temperature under a nitrogen atmosphere. The reaction mixture was cooled to 0° C. and trimethylsilyldiazomethane (2 ml) was added via a plastic syringe. The reaction mixture was left stirring at 0° C. for 10 minutes and warmed up to room temperature overnight.

The reaction was quenched with aqueous acetic acid (3 ml).

The reaction was then diluted with ethyl acetate (5 ml) and concentrated under reduced pressure.

The crude residue was dissolved in ethyl acetate (10 ml) and filtered through celite. The filtrate was concentrated under reduced pressure. The crude residue was purified by preparatory HPLC (Method E).

Fractions containing product were combined and concentrated under reduced pressure to give the title compound (3 mg, 5%). LCMS (Method D) RT 1.561 min, M+1=464. $^1$H NMR (500 MHz, CDCl$_3$): 7.58-7.39 (4H, m), 7.36 (1H, s), 4.85 (2H, s), 3.41(3H, s), 2.64-2.60 (2H, m), 2.59-2.52 (4H, m), 2.15-2.04 (1H, m), 1.91-1.84 (2H, m), 1.46-1.35 (9H, br s), 1.33-1.27 (1H, m), 0.95-0.84 (2H, m), 0.17-0.10 (1H, m).

Step 3: 6-(4-(1-aminocyclobutyl)phenyl)-7-(cyclopropylmethyl)-1-methyl-1H-pyrido[2,3-b][1,4]oxazin-2(3H)-one Tert-butyl (1-(4-(7-(cyclopropylmethyl)-1-methyl-2-oxo-2,3-dihydro-1H-pyrido[2,3-b][1,4]oxazin-6-yl)phenyl)cyclobutyl)carbamate (0.5 mg, 1.79 µmol) was dissolved in dichloromethane (1 ml). TFA (0.5 ml) was added at room temperature and the reaction mixture was stirred for 30 seconds. The solution was immediately concentrated to dryness under reduced pressure. The residue was dissolved in diethyl ether (~1 ml) and concentrated to dryness under reduced pressure. This was repeated three times. The residue was then slurred in diethyl ether (1 ml) and after settling the supernatant solvent was removed by pipette. This was repeated twice. The residue was then slurred in n-hexane (1 ml) and after settling the supernatant solvent was removed by pipette. This was repeated twice. The residue remaining solvent was dried to give the desired product as an off-white solid as the title compound (0.3 mg, 77% yield). LCMS (Method D) RT=0.77 min, M+1=364. $^1$H-NMR (500 MHz, CD$_3$OD) δ 7.66-7.50 (4H, m), 7.47 (1H, s), 4.48 (2H, s), 4.15-4.09 (2H,m), 3.06 (3H, s), 2.75-2.65 (2H, m), 2.51-2.42 (2H, m), 2.28-2.20 (1H, m), 1.97-1.90 (1H, m), 1.76-1.71 (1H, m), 1.66-1.55 (2H, m), 1.38-1.31 (2H, m).

Example 134

6-(4((1s,3s)-1-amino-3-hydroxy-3-methylcyclobutyl)phenyl)-1-methyl-7-phenyl-1H-pyrido[2,3-b][1,4]oxazin-2(3H)-one

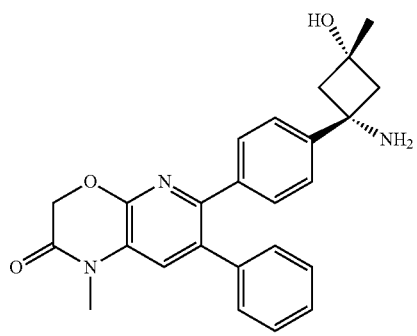 [SMILES: CN1C(=O)COc2nc(-c3ccc([C@]4(N)C[C@@](C)(O)C4)cc3)c(-c3ccccc3)cc21]

Step 1: 2-((1s,3s)-3-Hydroxy-3-methyl-1-(4-(1-methyl-2-oxo-7-phenyl-2,3-dihydro-1H-pyrido[2,3-b][1,4]oxazin-6-yl)phenyl)cyclobutyl)isoindoline-1,3-dione In a 15 ml reaction tube was added 6-bromo-1-methyl-7-phenyl-1H-pyrido[2,3-b][1,4]oxazin-2(3H)-one (50 mg, 0.157 mmol), 2-((1s,3s)-3-hydroxy-3-methyl-1-(4-(4,4,5,5-tetramethyl-1,3,2-dioxaborolan-2-yl)phenyl)cyclobutyl)isoindoline-1,3-dione (56.6 mg, 0.131 mmol) and cesium carbonate (213 mg, 0.652 mmol) in a mixture of 1,4-dioxane (2 ml) and water (667 µl) to give a colourless solution. This was degassed by bubbling nitrogen for 15 minutes, followed by the addition of PdCl$_2$(dppf)-CH$_2$Cl$_2$ adduct and degassing for a further 15 minutes. The reaction mixture was heated to 50° C. under a nitrogen atmosphere for 1.5 hrs. The reaction mixture was cooled to room temperature and water was added (7 ml). The resulting mixture was extracted with ethyl acetate (10 ml×3). The combined organic layers were dried over anhydrous Na$_2$SO$_4$, filtered and concentrated under reduced pressure. The crude was purified by Biotage silica gel chromatography (gradient 0% to 30% ethyl acetate in n-hexanes) to give the title compound (35 mg, 50%). $^1$H NMR (500 MHz, CDCl$_3$): 7.75-7.70 (2H, m), 7.66-7.63 (2H, m), 7.58-7.54 (2H, m), 7.32-7.29 (2H+1H, m), 7.25-7.21 (2H+1H, m), 7.18-7.14 (2H, m), 4.90 (2H, s), 3.37 (3H, s), 3.34-3.25 (2H, m), 3.10-3.01 (2H, m), 1.09 (3H, s). LCMS (Method D) RT 1.252 min, M+1=546.

Step 2: 6-(4-((1s,3s)-1-amino-3-hydroxy-3-methylcyclobutyl)phenyl)-1-methyl-7-phenyl-1H-pyrido[2,3-b][1,4]oxazin-2(3H)-one In a 10 ml microwave vial was 2-((1s,3s)-3-hydroxy-3-methyl-1-(4-(1-methyl-2-oxo-7-phenyl-2,3-dihydro-1H-pyrido[2,3-b][1,4]oxazin-6-yl)phenyl)cyclobutyl)isoindoline-1,3-dione (35 mg, 0.064 mmol) and hydrazine monohydrate (0.040 ml, 1.2 mmol) in ethanol (1.5 ml) and 1,4-dioxane (0.5 ml) to give a yellow solution. The reaction mixture was heated to 120° C. for 1 hr under microwave conditions.

The reaction mixture was cooled to room temperature and filtered to remove the solid. This was washed thoroughly with ethanol. The filtrates were combined and concentrated under reduced pressure.

The crude residue (20 mg) was dissolved in 1 ml of a solution of methanol:dichloromethane (1:1) and added to a scx-2 catch-and-release cartridge (5 g). After allowing to binding for 15 minutes, the column was washed with methanol (4×2 ml) then the product eluted with 2M ammonia in methanol (4×2 ml). The combined product fractions were concentrated to dryness to give an off-white solid (15 mg). This was re-dissolved in methanol/water (2 ml, 1:3) and freeze dried overnight to give the title compound (13 mg, 50%). $^1$H-NMR (500 MHz, CD$_3$OD) δ 7.54(1H, s), 7.39-7.18 (4H, m), 4.95 (2H, s), 3.43 (3H, s), 2.76-2.68 (2H, m), 2.46-2.33 (2H, m), 1.14 (3H, s). LCMS (Method D) RT=0.747 min, M+1=416.

Example 135

2-(6-(4-(aminomethyl)phenyl)-2-oxo-7-phenyl-2,3-dihydro-1H-pyrido[2,3-b][1,4]oxazin-1-yl)acetonitrile

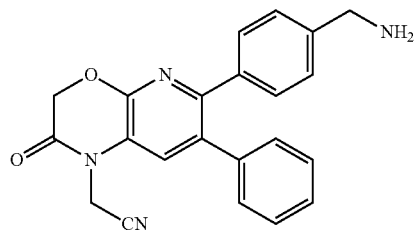 [SMILES: N#CCN1C(=O)COc2nc(-c3ccc(CN)cc3)c(-c3ccccc3)cc21]

Step 1: tert-butyl 4-(2-oxo-7-phenyl-2,3-dihydro-1H-pyrido[2,3-b][1,4]oxazin-6-yl)benzylcarbamate In a reaction tube was added 6-bromo-7-phenyl-1H-pyrido[2,3-b][1,4]oxazin-2(3H)-one (0.19 g, 0.623 mmol) and tert-butyl 4-(4,4,5,5-tetramethyl-1,3,2-dioxaborolan-2-yl)benzylcarbamate (0.25 g, 0.750 mmol) in 1,4-Dioxane (10 ml), followed by a solution of sodium carbonate (0.198 g, 1.868 mmol) in water (2.5 ml) to give a suspension. This was degassed followed by the addition of PdCl$_2$(dppf)-CH$_2$Cl$_2$ adduct (0.051 g, 0.062 mmol). The resulting mixture was heated at 80° C. for 20 h. The reaction mixture was cooled down to room temperature and diluted with saturated sodium bicarbonate solution (30 ml) and extracted with ethyl acetate (20 ml×3). The combined organic phase was washed with water, brine and concentrated to give product (0.21 g) used for next step without further purification. LCMS (Method D): R$_T$=1.25 min, M+H$^+$=433.2.

Step 2: tert-butyl 4-(1-(cyanomethyl)-2-oxo-7-phenyl-2,3-dihydro-1H-pyrido[2,3-b][1,4]oxazin-6-yl)benzylcarbamate A mixture of tert-butyl 4-(2-oxo-7-phenyl-2,3-dihydro-1H-pyrido[2,3-b][1,4]oxazin-6-yl)benzylcarbamate (70 mg, 0.162 mmol), 2-bromoacetonitrile (58.4 mg, 0.487 mmol) and potassium carbonate (67.3 mg, 0.487 mmol) in DMF (2 ml) was stirred at 40° C. for 16 h. The reaction mixture was cooled and diluted with water (10 ml) and extracted with DCM (8 ml×3). The combined organic phase was concentrated and the residue was purified by column (biotage, 10 g) eluted with Ethyl acetate/cyclohexane 0-30% to give product 12 mg. $^1$H NMR (500 MHz, CDCl$_3$) 7.29 (s, 1H), 7.19-7.26 (m, 5H), 7.13 (m, 2H), 7.05 (d, 2H), 4.88 (s, 2H), 4.81 (s, 2H), 4.73 (br, 1H), 4.21 (d, 2H), 1.38 (br, 9H). LCMS (Method D): R$_T$=1.35 min, M+H$^+$=472.2.

Step 3: 2-(6-(4-(aminomethyl)phenyl)-2-oxo-7-phenyl-2,3-dihydro-1H-pyrido[2,3-b][1,4]oxazin-1-yl)acetonitrile to a round bottomed flask containing tert-butyl 4-(1-(cyanomethyl)-2-oxo-7-phenyl-2,3-dihydro-1H-pyrido[2,3-b][1,4]oxazin-6-yl)benzylcarbamate (12 mg, 0.026 mmol) was added TFA (0.5 ml, 6.49 mmol). The resulting solution was stirred for 60 seconds then concentrated to dryness under reduced pressure. The residue was dissolved in diethyl ether (1 ml) and concentrated to dryness three times to give the trifluoroacetic acid salt of the product (9.5 mg). $^1$H NMR (500 MHz, CD$_3$OD) 7.58 (s, 1H), 7.29 (m, 2H), 7.19-7.23 (m, 5H), 7.13 (m, 2H), 5.03 (s, 2H), 4.93 (s, 2H), 3.98 (s, 2H). LCMS (Method D): R$_T$=0.65 min, M+H$^+$=372.2.

Example 136

(1s,3s)-3-Amino-3-(4-(1-ethyl-8-phenyl-4H-pyrido[2,3-b][1,2,4]triazolo[4,3-d][1,4]oxazin-7-yl)phenyl)cyclobutanol

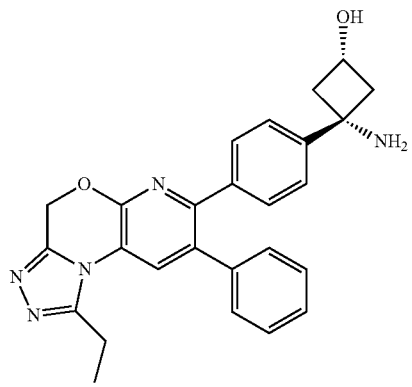 [SMILES: CCc1nnc2n1-c1cc(-c3ccccc3)c(-c3ccc([C@]4(N)C[C@@H](O)C4)cc3)nc1OC2]

Step 1: 6-bromo-7-phenyl-1H-pyrido[2,3-b][1,4]oxazine-2(3H)-thione

In a 500 ml round-bottomed flask were 6-bromo-7-phenyl-1H-pyrido[2,3-b][1,4]oxazin-2(3H)-one (2 g, 6.55 mmol) and Lawesson's reagent (2.65 g, 6.55 mmol) in toluene (150 ml) to give an orange suspension.

The reaction mixture was heated to reflux for 2 hours.

The reaction mixture was cooled to room temperature and toluene was removed under reduced pressure.

The crude residue was then dissolved in minimum amount of dichloromethane. Di-isopropyl ether was added and a precipitate developed. It was filtered and dried until constant weigh to give the title compound (1.5 g, 71%). It was used for the next step without further purification.

LCMS (Method D): RT 1.274 min, M+1=323.

Step 2: (E)-6-bromo-2-hydrazono-7-phenyl-2,3-dihydro-1H-pyrido[2,3-b][1,4]oxazine In a 15 ml vial was 6-bromo-7-phenyl-1H-pyrido[2,3-b][1,4]oxazine-2(3H)-thione (100 mg, 0.311 mmol) and hydrazine monohydrate (0.049 ml, 1.557 mmol) in tetrahydrofuran (5 ml) to give a brown solution. The reaction mixture was stirred at room temperature for 1 hour. The reaction mixture was concentrated under reduced pressure and the crude residue was slurred in diethyl ether. The supernatant solvent was removed and the brown solid vas dried until constant weigh to afford the title compound (90 mg, 90%). It was used for the next step without further purification. LCMS (Method D): RT 0.770 min, M+1=321.

Step 3: 7-bromo-1-ethyl-8-phenyl-4H-pyrido[2,3-b][1,2,4]triazolo[4,3-d][1,4]oxazine In a 10 ml microwave vial was (E)-6-bromo-2-hydrazono-7-phenyl-2,3-dihydro-1H-pyrido[2,3-b][1,4]oxazine (90 mg, 0.282 mmol) in 1,1,1-triethoxypropane to give a yellow suspension. The reaction mixture was heated to 120° C. for 20 minutes. The crude residue was concentrated under reduced pressure and purified by Biotage silica gel chromatography (gradient 100% to 100% n-hexane in ethyl acetate) to give the title compound (41 mg, 40%). $^1$H NMR (500 MHz, CDCl$_3$): 7.73 (1H, s), 7.54-7.48 (3H, m), 7.45-7.41 (2H, m), 5.56 (2H, s), 3.10-3.00 (2H, q), 1.53-1.48 (3H, t). LCMS (Method D) RT 1.117 min, M+1=358.

Step 4: Tert-butyl((1s,3s)-1-(4-(1-ethyl-8-phenyl-4H-pyrido[2,3-b][1,2,4]triazolo[4,3-d][1,4]oxazin-7-yl)phenyl)-3-hydroxycyclobutyl)carbamate In a 15 ml reaction tube was 7-bromo-1-ethyl-8-phenyl-4H-pyrido[2,3-b][1,2,4]triazolo[4,3-d][1,4]oxazine (40 mg, 0.112 mmol), tert-butyl((1s,3s)-3-hydroxy-1-(4-(4,4,5,5-tetramethyl-1,3,2-dioxaborolan-2-yl)phenyl)cyclobutyl)carbamate (36.3 mg, 0.093 mmol), and cesium carbonate (152 mg, 0.467 mmol) in 1,4-dioxane (1.8 ml) and water (0.6 ml) to give an orange suspension. The reaction was degassed by bubbling nitrogen for 15 minutes. PdCl$_2$(dppf)-CH$_2$Cl$_2$ adduct (15.24 mg, 0.019 mmol) was added and the reaction mixture degassed by bubbling nitrogen for further 15 minutes. The reaction mixture was heated to 50° C. for 1 hr.

The reaction mixture was allowed to cool to RT and water was added (7 ml). The reaction mixture was extracted using ethyl acetate (10 ml×3). The combined organic layers were concentrated under reduced pressure.

The crude was purified by Biotage silica gel chromatography (gradient 0% to 5% methanol in dichloromethane) to give the title compound (27 mg, 53%). LCMS (Method D) RT 1.091 min, M+1=530. $^1$H NMR (500 MHz, CDCl$_3$): 7.82 (1H, s), 7.39-7.32 (5H, m), 7.25-7.19 (4H, m), 5.57 (2H, s), 3.53-3.46 (2H, d), 3.18-3.09 (2H, q), 3.08-2.96 (2H, bs), 2.19 (1H, s), 1.82-1.75 (3H, t), 1.59-1.53 (9H, bs

Step 5: (1s,3s)-3-Amino-3-(4-(1-ethyl-8-phenyl-4H-pyrido[2,3-b][1,2,4]triazolo[4,3-d][1,4]oxazin-7-yl)phenyl)cyclobutanol Tert-butyl((1s,3s)-1-(4-(1-ethyl-8-phenyl-4H-pyrido[2,3-b][1,2,4]triazolo[4,3-d][1,4]oxazin-7-yl)phenyl)-3-hydroxycyclobutyl)carbamate (34 mg, 0.063 mmol) was dissolved in dichloromethane (1 ml). TFA (1 ml) was added at room temperature and the reaction mixture was stirred for 30 seconds. The solution was immediately concentrated to dryness under reduced pressure. The residue was dissolved in diethyl ether (~0.1 ml) and concentrated to dryness under reduced pressure. This was repeated three times. The residue was then slurred in diethyl ether (1 ml) and after settling the supernatant solvent was removed by pipette. This was repeated twice. The residue was then slurred in n-hexane (1 ml) and after settling the supernatant solvent was removed by pipette. This was repeated twice. The remaining solvent was removed under reduced pressure and the residue was dried until constant weigh. It was further purified by preparatory HPLC to give the desired product as an off-white solid (7 mg, 25% yield). LCMS (Method D) RT=0.658 min, M+1=440. $^1$H-NMR (500 MHz, CD$_3$OD) δ 7.95 (1H, s), 7.31-7.13 (8H, m), 5.52 (2H, s), 3.84-3.76 (1H, m), 3.17-3.10 (2H, q), 2.75-2.65 (2H, m), 2.86-2.77 (2H, m), 2.13-2.02 (1H, m), 1.43-1.38 (3H, t).

Example 137

6-(4-((1r,3r)-1-amino-3-hydroxycyclobutyl)phenyl)-1-methyl-7-phenyl-1H-pyrido[2,3-b][1,4]oxazin-2(3H)-one

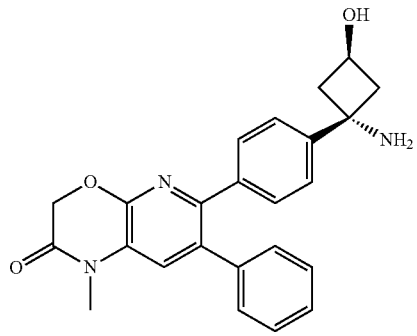 [SMILES: CN1C(=O)COc2nc(-c3ccc([C@]4(N)C[C@H](O)C4)cc3)c(-c3ccccc3)cc21]

Step 1: 1-(4-bromophenyl)-3,3-dimethoxycyclobutanecarbonitrile

A suspension of sodium hydride (2 g, 50.0 mmol) in DMF (20 ml) was cooled to 0 degree before 2-(4-bromophenyl)acetonitrile (4 g, 20.40 mmol) was added slowly, The suspension was stirred at 0 degree for another 10 min before 1,3-dibromo-2,2-dimethoxypropane (2.62 g, 10.00 mmol) was added. The reaction mixture was stirred at 60° C. for 20 h before cooled to room temperature, poured into water (75 ml) and extracted with ethyl acetate (2×50 ml). The combined organic phase was washed with water (75 ml), brine (50 ml) and concentrated. The crude product was purified by column (100 g, biotage) eluted with ethyl acetate/cyclohexane (0-10%) to afford product 1.7 g (59% yield). $^1$H NMR (500 MHz, DMSO-d$_6$): 7.46 (d, 2H), 7.29 (d, 2H), 3.21 (s, 3H), 3.11 (s, 3H), 3.03 (d, 2H), 2.62 (d, 2H).

Step 2: 1-(4-bromophenyl)-3,3-dimethoxycyclobutanecarboxamide

Hydrogen peroxide (2.05 ml, 20.07 mmol) was added over 2 h to a stirred mixture of 1-(4-bromophenyl)-3,3-dimethoxycyclobutanecarbonitrile (3.18 g, 10.74 mmol) and Potassium carbonate (0.297 g, 2.15 mmol) in DMSO (11 ml) at 40 degree under a nitrogen atmosphere. After the addition, the reaction mixture was heated to 80 degree for 3 h. The reaction mixture was allowed to cool down to room temperature and water (30 ml) was added. The reaction mixture was extracted with ethyl acetate (3×20 ml). The combined organic phase was washed with water (2×30 ml), brine (30 ml), concentrated to give light yellow oil (3.3 g). $^1$H NMR (500 MHz, CDCl$_3$) 7.40 (d, 2H), 7.11 (d, 2H), 5.89 (br, 1H), 5.58 (br, 1H), 3.12 (s, 3H), 3.02 (s, 3H), 2.97 (d, 2H), 2.52 (d, 2H).

Step 3
1-(4-bromophenyl)-3,3-dimethoxycyclobutanamine

To a solution of 1-(4-bromophenyl)-3,3-dimethoxycyclobutanecarboxamide (2.3 g, 7.32 mmol) in acetonitrile (9 ml) and Water (9.00 ml) was added phenyliodine bis(trifluoroacetate) (4.73 g, 11.00 mmol) and the resulting mixture was stirred at room temperature for 18 h. The reaction mixture was slowly poured into sodium bicarnate sat. solution (~45 ml) and extracted with ethyl acetate (3×30 ml). The combined organic phase was washed with water, brine and concentrated to give crude product (3.4 g). The crude product was purified by column (biotage, 50 g) eluted with 0-5% DCM/Methanol (mixture of 500 ml methanol and 60 ml 2M NH$_4$OH in methanol) to give product 1-(4-bromophenyl)-3,3-dimethoxycyclobutanamine (1.06 g), $^1$H NMR (500 MHz, CDCl$_3$): 7.48 (d, 2H), 7.32 (d, 2H), 3.27 (d, 3H), 3.17 (d, 3H), 2.66 (d, 2H), 2.44 (d, 2H).

Step 4: 2-(1-(4-bromophenyl)-3,3-dimethoxycyclobutyl)isoindoline-1,3-dione

A mixture of 1-(4-bromophenyl)-3,3-dimethoxycyclobutanamine (0.66 g, 2.306 mmol), ethyl 1,3-dioxoisoindoline-2-carboxylate (0.56 g, 2.55 mmol) and triethylamine (1.3 ml, 9.33 mmol) in CHCl3 (15 ml) was heated at 70° C. for 16 h. The reaction mixture was concentrated to as dry as possible. Methanol (~5 ml) was added. The solution was concentrated to dryness. Methanol (~5 ml) was added again and the resulted solid was collected by filtration to afford product as a white solid (0.39 g). $^1$H NMR (500 MHz, CDCl$_3$): 7.70 (dd, 2H), 7.60 (dd, 2H), 7.44 (dd, 2H), 7.37 (dd, 2H), 3.18 (m, 4H), 3.10 (s, 3H), 3.02 (s, 3H).

Step 5: 2-(1-(4-bromophenyl)-3-oxocyclobutyl)isoindoline-1,3-dione

A solution of 2-(1-(4-bromophenyl)-3,3-dimethoxycyclobutyl)isoindoline-1,3-dione (0.3 g, 0.72 mmol) in Acetone (30 ml) was added 6M HCl (3 ml) and the resulting solution was stirred at 50° C. for 2 h. The reaction mixture was concentrated to give product 0.26 g.).
$^1$H NMR (500 MHz, CDCl$_3$): 7.76 (dd, 2H), 7.67 (dd, 2H), 7.41 (m, 4H), 4.21 (m, 2H), 3.87 (m, 2H).

Step 6: 2-((1r,3r)-1-(4-bromophenyl)-3-hydroxycyclobutyl)isoindoline-1,3-dione

A solution of 2-(1-(4-bromophenyl)-3-oxocyclobutyl) isoindoline-1,3-dione (194 mg, 0.524 mmol) in THF (5 ml) was added L-Selectride (0.524 ml, 0.524 mmol)(1M THF solution) at −78° C. to give a yellow solution and stirred at −78° C. for 1 h. The reaction mixture was quenched with saturated sodium bicarbonate solution at −78° C. and extracted with ethyl acetate (3×10 ml). The combined organic phase was concentrated and purified by column (biotage 25 g) to give product (99 mg). $^1$H NMR (500 MHz, CDCl$_3$): 7.76-7.79 (m, 2H), 7.67-7.71 (m, 2H), 7.42-7.50 (m, 4H), 4.5-4.6 (m, 1H), 3.73-3.84 (m, 2H), 2.76-2.83 (m, 2H).

Step 7: 2-((1r,3r)-3-hydroxy-1-(4-(4,4,5,5-tetramethyl-1,3,2-dioxaborolan-2-yl)phenyl)cyclobutyl) isoindoline-1,3-dione A mixture of 2-((1r,3r)-1-(4-bromophenyl)-3-hydroxycyclobutyl)isoindoline-1,3-dione (99 mg, 0.266 mmol), 4,4,4', 4',5,5,5',5'-octamethyl-2,2'-bi(1,3,2-dioxaborolane) (67.5 mg, 0.266 mmol) and potassium acetate (131 mg, 1.330 mmol) in Dioxane (10 ml) was evacuated and flushed with nitrogen three times. Pd(dppf)Cl$_2$.CH$_2$Cl$_2$ (21.72 mg, 0.027 mmol) was added and the resulting mixture was evacuated and flushed with nitrogen 3 times. The mixture was then heated at 90° C. for 22 h. The reaction mixture was concentrated and the residue was purified by chromatography (biotage 25 g) eluted with ethyl acetate/cyclohexane 0-70% to give product (45 mg). $^1$H NMR (500 MHz, CDCl$_3$): 7.73-7.78 (m, 4H), 7.65 (m, 2H), 7.57-7.59 (m, 2H), 4.45-4.55 (m, 1H), 3.81-3.85 (m, 2H), 2.79-2.82 (m, 2H), 1.30 (s, 12H).

Step 8: 2-((1r,3r)-3-hydroxy-1-(4-(1-methyl-2-oxo-7-phenyl-2,3-dihydro-1H-pyrido[2,3-b][1,4]oxazin-6-yl)phenyl)cyclobutyl)isoindoline-1,3-dione A mixture of 6-bromo-1-methyl-7-phenyl-1H-pyrido[2,3-b][1,4]oxazin-2(3H)-one (45 mg, 0.141 mmol), 2-((1r,3r)-3-hydroxy-1-(4-(4,4,5,5-tetramethyl-1,3,2-dioxaborolan-2-yl) phenyl)cyclobutyl)isoindoline-1,3-dione (49.3 mg, 0.117 mmol) and cesium carbonate (191 mg, 0.587 mmol) in Dioxane (3 ml) and Water (1 ml) was degassed. Then PdCl$_2$(dppf) .CH$_2$Cl$_2$ (19.19 mg, 0.023 mmol) was added. The reaction mixture was degassed again and heated at 50° C. under stirring for 16 h.
The reaction mixture was cooled down to room temperature and diluted with water (15 ml) and extracted with ethyl acetate (3×15 ml). The combined organic phase was washed with water, dried over sodium sulfate and concentrated to give crude product which was purified by column chromatography (biotage 10 g) eluted with ethyl acetate/cyclohexane 0-80% to afford product (26 mg)). $^1$H NMR (500 MHz, CDCl$_3$): 7.74-7.76 (m, 2H), 7.66-7.68 (m, 2H), 7.40-7.42 (m, 2H), 7.23-7.30 (m, 6H), 7.17-7.19 (m, 2H), 4.87 (s, 2H), 4.45-4.55 (m, 1H), 3.79-3.82 (m, 2H), 3.38 (s, 3H), 2.74-2.78 (m, 2H), LCMS (Method D): R$_T$=1.22 min, M+H$^+$=533.0.

Step 9: 6-(4-((1r,3r)-1-amino-3-hydroxycyclobutyl) phenyl)-1-methyl-7-phenyl-1H-pyrido[2,3-b][1,4] oxazin-2(3H)-one A mixture of 2-((1r,3r)-3-hydroxy-1-(4-(1-methyl-2-oxo-7-phenyl-2,3-dihydro-1H-pyrido[2,3-b][1,4]oxazin-6-yl)

phenyl)cyclobutyl)isoindoline-1,3-dione (26 mg, 0.049 mmol) in Dioxane (1 ml) and MeOH (1.0 ml) was added hydrazine (0.25 ml, 7.97 mmol) monohydrate. The reaction mixture was heated at 120° C. for 30 min under microwave condition. The reaction mixture was diluted with saturated bicarbonate solution (10 ml) and extracted with DCM (3×10 ml). The combined organic phase was washed with water, brine and dried over sodium sulfate, filtered and concentrated to give crude product which was purified by prepHPLC (method F) to give product (5 mg). $^1$H NMR (500 MHz, CD$_3$OD): 7.44 (s, 1H), 7.28-7.29 (m, 2H), 7.18-7.20 (m, 5H), 7.11-7.13 (m, 2H), 4.85 (s, 2H), 4.52-4.54 (m, 1H), 3.32 (s, 3H), 32.83-2.87 (m, 2H), 2.46-2.51 (m, 2H), LCMS (Method D): R$_T$=0.67 min, M+H$^+$=403.2.

Example 138

(1r,3r)-3-amino-3-(4-(1-ethyl-8-phenyl-4H-pyrido[2,3-b][1,2,4]triazolo[4,3-d][1,4]oxazin-7-yl)phenyl)-1-methylcyclobutanol

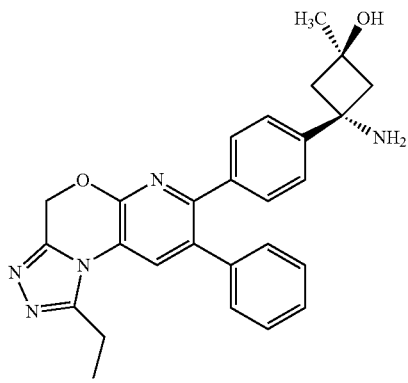 [SMILES: CCc1nnc2n1-c1cc(-c3ccccc3)c(-c3ccc([C@]4(N)C[C@](C)(O)C4)cc3)nc1OC2]

Step 1: 2-((1r,3r)-1-(4-(1-ethyl-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione In a 15 ml reaction tube was 7-bromo-1-ethyl-8-phenyl-4H-pyrido[2,3-b][1,2,4]triazolo[4,3-d][1,4]oxazine (62 mg, 0.174 mmol), 2-((1r,3r)-3-hydroxy-3-methyl-1-(4-(4,4,5,5-tetramethyl-1,3,2-dioxaborolan-2-yl)phenyl)cyclobutyl)isoindoline-1,3-dione (62.7 mg, 0.145 mmol), and cesium carbonate (236 mg, 0.723 mmol) in 1,4-dioxane (2.5 ml) to give a yellow solution. The reaction mixture was degassed by bubbling nitrogen for 15 minutes, following by addition of PdCl$_2$(dppf)-CH$_2$Cl$_2$ adduct. The reaction mixture was heated to 50° C. for 1 hr.

The reaction mixture was allowed to cool to RT and water was added (7 ml). The reaction mixture was extracted using ethyl acetate (10 ml×3). The combined organic layers were concentrated under reduced pressure.

The crude was purified by Biotage silica gel chromatography (gradient 0% to 100% ethyl acetate in n-hexanes, then 0% to 3% methanol in dichloromethane) to give the title compound (65 mg, 77%). LCMS (Method D) RT 1.212 min, M+1=584. $^1$H NMR (500 MHz, CDCl$_3$): 7.79 (1H, s), 7.77-7.72 (2H, m), 7.71-7.64 (2H, m), 7.58-7.51 (2H, m), 7.38-7.28 (5H, m), 7.22 7.16 (1H, m), 5.54 (2H, s), 3.39-3.29 (2H, m), 3.16-3.06 (2H+2H, m), 1.52-1.50 (3H, t), 1.42 (3H, s).

Step 2: (1r,3r)-3-amino-3-(4-(1-ethyl-8-phenyl-4H-pyrido[2,3-b][1,2,4]triazolo[4,3-d][1,4]oxazin-7-yl)phenyl)-1-methylcyclobutanol In a 10 ml microwave vial was 2-((1r,3r)-1-(4-(1-ethyl-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione (30 mg, 0.051 mmol) and hydrazine monohydrate (0.016 ml, 0.514 mmol) in 1,4-dioxane (1.5 ml) and ethanol (0.5 ml) to give a yellow solution. The reaction mixture was heated to 140° C. for 3 hours under microwave conditions.

The reaction mixture was cooled to room temperature and filtered to remove the solid, which has formed during the reaction. This was washed thoroughly with ethanol. The filtrates were combined and concentrated under reduced pressure.

The crude residue (20 mg) was dissolved in 1 ml of a solution of methanol:dichloromethane (1:1) and added to a scx-2 catch-and-release cartridge (5 g). After allowing to binding for 15 minutes, the column was washed with methanol (4×2 ml) then the product eluted with 2M ammonia in methanol (4×2 ml). The combined product fractions were concentrated to dryness under reduced pressure to give an off-white solid (15 mg). This was re-dissolved in methanol/water and freeze dried overnight to give the title compound (15 mg, 64%). LCMS (Method D) RT=0.630 min, M+1=454.

$^1$H-NMR (500 MHz, CD$_3$OD) δ 7.95 (1H, s), 7.26-7.23 (3H, m), 7.22-7.20 (3H, m), 7.18-7.13 (3H, m), 5.52 (2H, s), 3.15-3.09 (2H, q), 2.59-2.52 (2H, m), 2.33-2.24 (2H, m), 1.43 (3H, s), 1.41-1.36 (3H, t).

Example 139

6-(4-((1s,3s)-1-amino-3-hydroxycyclobutyl)phenyl)-1-ethyl-7-phenyl-1H-pyrido[2,3-b][1,4]oxazin-2(3H)-one

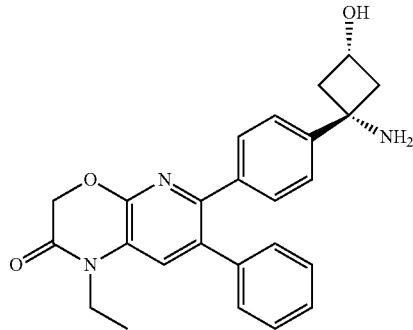 [SMILES: CCN1C(=O)COc2nc(-c3ccc([C@]4(N)C[C@@H](O)C4)cc3)c(-c3ccccc3)cc21]

Step 1: tert-butyl((1s,3s)-1-(4-(1-ethyl-2-oxo-7-phenyl-2,3-dihydro-1H-pyrido[2,3-b][1,4]oxazin-6-yl)phenyl)-3-hydroxycyclobutyl)carbamate In a 15 mL reaction tube was added 6-bromo-1-ethyl-7-phenyl-1H-pyrido[2,3-b][1,4]oxazin-2(3H)-one (50 mg, 0.150 mmol), tert-butyl((1s,3s)-3-hydroxy-1-(4-(4,4,5,5-tetramethyl-1,3,2-dioxaborolan-2-yl)phenyl)cyclobutyl)carbamate (49 mg, 0.125 mmol) and cesium carbonate (204 mg, 0.625 mmol) in a mixture of 1,4-dioxane (2.3 ml) and water (0.8 ml) to give a colourless solution. This was degassed by bubbling nitrogen for 15 minutes, followed by the addition of [1,1'-bis(diphenylphosphino)ferrocene]dichloropalladium (II)dichloromethane adduct (20 mg, 0.025 mmol) and degassing for a further 5 minutes. The reaction mixture was heated to 50° C. under a nitrogen atmosphere for one hour then allowed to cool to room temperature, diluted with water (5 ml) and extracted into ethyl acetate (3×5 ml). The combined organic phases were dried over Na$_2$SO$_4$, filtered and concentrated to dryness under reduced pressure. The residue was purified by Biotage chromatography (cyclohexane:ethyl acetate, gradient elution from 90:10 to 0:100) to give the desired product as an off-white solid (45 mg, 70% yield). $^1$H-NMR (500 MHz, CDCl$_3$) δ 7.29-7.35 (5H, m), 7.28 (1H, s), 7.18-7.24 (4H, m), 4.96 (1H, br s), 4.88 (2H, s), 4.05 (1H, br s), 4.01 (2H, q), 2.98 (2H, br s), 2.75 (2H, br s), 1.20-1.51 (9H, br m), 1.32 (3H, t). LCMS (Method D) RT=1.25 min, M+H$^+$=516.20.

Step 2: 6-(4-(1s,3s)-1-amino-3-hydroxycyclobutyl)phenyl)-1-ethyl-7-phenyl-1H-pyrido[2,3-b][1,4]oxazin-2(3H)-one tert-butyl((1s,3s)-1-(4-(1-ethyl-2-oxo-7-phenyl-2,3-dihydro-1H-pyrido[2,3-b][1,4]oxazin-6-yl)phenyl)-3-hydroxycyclobutyl)carbamate (45 mg, 0.087 mmol) was dissolved in TFA (1 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as an off-white solid (33 mg, 71% yield).
$^1$H-NMR (500 MHz, MeOD) δ 7.55 (1H, s), 7.39-7.42 (4H, m), 7.27-7.31 (3H, m), 7.20-7.24 (2H, m), 4.93 (2H, s), 4.01-4.11 (3H, m), 3.03-3.11 (2H, m), 2.42-2.50 (2H, m), 1.28 (3H, t). LCMS (Method D) RT=0.74 min, M+H$^+$=416.20.

Example 140

6-(4-((1s,3s)-1-amino-3-hydroxycyclobutyl)phenyl)-1-(cyclopropylmethyl)-7-phenyl-1H-pyrido[2,3-b][1,4]oxazin-2(3H)-one

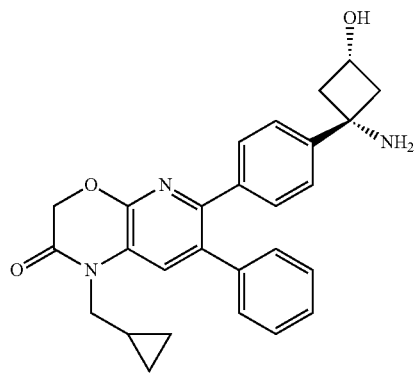 [SMILES: N[C@]1(c2ccc(-c3nc4c(cc3-c3ccccc3)N(CC3CC3)C(=O)CO4)cc2)C[C@H](O)C1]

Step 1: tert-butyl((1s,3s)-1-(4-(1-(cyclopropylmethyl)-2-oxo-7-phenyl-2,3-dihydro-1H-pyrido[2,3-b][1,4]oxazin-6-yl)phenyl)-3-hydroxycyclobutyl)carbamate In a 15 mL reaction tube was added 6-bromo-1-(cyclopropylmethyl)-7-phenyl-1H-pyrido[2,3-b][1,4]oxazin-2(3H)-one (50 mg, 0.139 mmol), tert-butyl((1s,3s)-3-hydroxy-1-(4-(4,4,5,5-tetramethyl-1,3,2-dioxaborolan-2-yl)phenyl)cyclobutyl)carbamate (45 mg, 0.116 mmol) and cesium carbonate (189 mg, 0.580 mmol) in a mixture of 1,4-dioxane (2.2 ml) and water (0.7 ml) to give a colourless solution. This was degassed by bubbling nitrogen for 15 minutes, followed by the addition of [1,1'-bis(diphenylphosphino)ferrocene]dichloropalladium(II)dichloromethane adduct (19 mg, 0.023 mmol) and degassing for a further 5 minutes. The reaction mixture was heated to 50° C. under a nitrogen atmosphere for one hour then allowed to cool to room temperature, diluted with water (5 mL) and extracted into ethyl acetate (3×5 mL). The combined organic phases were dried over Na$_2$SO$_4$, filtered and concentrated to dryness under reduced pressure. The residue was purified by Biotage chromatography (cyclohexane:ethyl acetate, gradient elution from 90:10 to 0:100) to give the desired product as an off-white solid (43 mg, 68% yield). $^1$H-NMR (500 MHz, CDCl$_3$) δ 7.40 (1H, s), 7.28-7.34 (5H, m), 7.18-7.24 (4H, m), 4.96 (1H, br s), 4.90 (2H, s), 4.05 (1H, br s), 3.87 (2H, d), 2.99 (2H, br s), 2.75 (2H, br s), 1.14-1.54 (9H, br m), 1.11-1.22 (1H, m), 0.54-0.62 (2H, m), 0.43-0.50 (2H, m). LCMS (Method D) RT=1.36 min, M+H$^+$=542.20.

Step 2: 6-((1s,3s)-1-amino-3-hydroxycyclobutyl)phenyl)-1-(cyclopropylmethyl)-7-phenyl-1H-pyrido[2,3-b][1,4]oxazin-2(3H)-one tert-butyl((1s,3s)-1-(4-(1-(cyclopropylmethyl)-2-oxo-7-phenyl-2,3-dihydro-1H-pyrido[2,3-b][1,4]oxazin-6-yl)phenyl)-3-hydroxycyclobutyl)carbamate (43 mg, 0.079 mmol) was dissolved in TFA (1 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as a yellow solid (31 mg, 70% yield). $^1$H-NMR (500 MHz, MeOD) δ 7.65 (1H, s), 3.60 (4H, s), 7.28-7.31 (3H, m), 7.20-7.24 (2H, m), 4.94 (2H, s), 4.06 (1H, quin), 3.96 (2H, d), 3.02-3.12 (2H, m), 2.40-2.51 (2H, m), 1.14-1.25 (1H, m), 0.53-0.60 (2H, m), 0.40-0.47 (2H, m). LCMS (Method D) RT=0.83 min, M+H$^+$=442.20.

Example 141

7-(4-((1s,3s)-1-amino-3-hydroxycyclobutyl)phenyl)-8-phenyl-2,4-dihydro-1H-pyrido[2,3-b][1,2,4]triazolo[4,3-d][1,4]oxazin-1-one

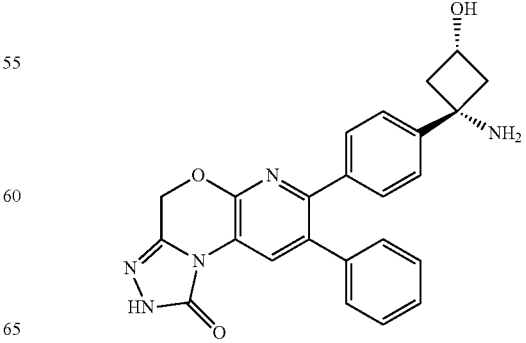

Step 1: 7-bromo-8-phenyl-2,4-dihydro-1H-pyrido[2,3-b][1,2,4]triazolo[4,3-d][1,4]oxazin-1-one In a 10 ml microwave vial was 6-bromo-7-phenyl-1H-pyrido[2,3-b][1,4]oxazine-2(3H)-thione (1 g, 3.11 mmol) and ethylhydrazine carboxylate (1.2 g, 12.44 mmol) in p-xylene (10 ml) to give a yellow suspension. The reaction mixture was heated to 180° C. for 45 minutes under microwave conditions. The crude residue was concentrated under reduced pressure and purified by Biotage silica gel chromatography (gradient 0% to 100% ethyl acetate in n-hexane) to give the title compound (293 mg, 27%). LCMS (Method D) RT 1.069 min, M+1=346.

Step 2: tert-butyl((1s,3s)-3-hydroxy-1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate In a 15 ml reaction tube was 7-bromo-8-phenyl-2,4-dihydro-1H-pyrido[2,3-b][1,2,4]triazolo[4,3-d][1,4]oxazin-1-one (70 mg, 0.203 mmol), tert-butyl((1s,3s)-3-hydroxy-1-(4-(4,4,5,5-tetramethyl-1,3,2-dioxaborolan-2-yl)phenyl)cyclobutyl)carbamate (65.8 mg, 0.169 mmol), and cesium carbonate (275 mg, 0.845 mmol) in 1,4-dioxane (3 ml) and water (0.733 ml) to give a yellow solution.

The reaction mixture was degassed by bubbling nitrogen for 15 minutes, following by the addition of PdCl$_2$(dppf)-CH$_2$Cl$_2$ adduct (20 mg) and degassing for further 15 minutes. The reaction mixture was heated to 70° C. for 96 hours under nitrogen atmosphere. Reaction mixture was allowed to cool to room temperature and water was added (7 ml). The reaction mixture was extracted using ethyl acetate (10 ml×3). The combined organic layers were concentrated under reduced pressure.

The crude was purified by Biotage silica gel chromatography (gradient 0% to 100% ethyl acetate in n-hexanes) to give the title compound (15 mg, 16%). LCMS (Method D) RT 1.034 min, M+1=528. $^1$H NMR (500 MHz, CDCl$_3$): 8.57 (1H, s), 7.48-7.27 (5H, m), 7.25-7.19 (4H, m), 5.30 (2H, s), 3.09-2.94 (2H, m), 2.84-2.70 (2H, m), 2.04 (1H, s), 1.47-1.32 (9H, bs).

Step 3: 7-(4-((1s,3s)-1-amino-3-hydroxycyclobutyl)phenyl)-8-phenyl-2,4-dihydro-1H-pyrido[2,3-b][1,2,4]triazolo[4,3-d][1,4]oxazin-1-one Tert-butyl((1s,3s)-3-hydroxy-1-(4-(1-oxo-8-phenyl-2,4-dihydro-1H-pyrido[2,3-b][1,2,4]triazolo[4,3-d][1,4]oxazin-7-yl)phenyl)cyclobutyl)carbamate (15 mg, 0.028 mmol) was dissolved in dichloromethane (1 ml). TFA (1 ml) was added at room temperature and the reaction mixture was stirred for 30 seconds. The solution was immediately concentrated to dryness under reduced pressure. The residue was dissolved in diethyl ether (~1 ml) and concentrated to dryness under reduced pressure. This was repeated three times. The residue was then slurred in diethyl ether (1 ml) and after settling the supernatant solvent was removed by pipette. This was repeated twice. The residue was then slurred in n-hexanes (1 ml) and after settling the supernatant solvent was removed by pipette. This was repeated twice. The remaining solvent was removed under reduced pressure and the residue was dried until constant weigh. It was further purified by preparatory HPLC to give the desired product as an off-white solid (4 mg, 33% yield). LCMS (Method D) RT=0.613 min, M-NH$_2$=410.

$^1$H-NMR (500 MHz, CD$_3$OD) δ 8.56 (1H, s), 7.42-7.37 (2H, m), 7.36-7.28 (5H, m), 7.25-7.20 (2H, m), 5.41 (2H, s), 3.96-3.87 (1H, m), 3.00-2.88 (2H, m), 2.28-2.13 (2H, m).

Example 142

(4-(1-ethyl-8-phenyl-4H-pyrido[2,3-b][1,2,4]triazolo[4,3-d][1,4]oxazin-7-yl)phenyl)methanamine

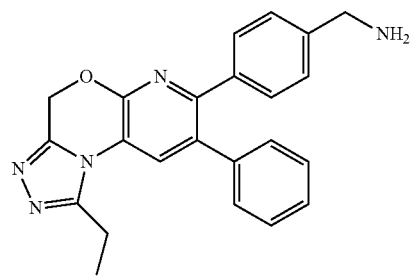 [SMILES: CCc1nnc2n1-c1cc(-c3ccccc3)c(-c3ccc(CN)cc3)nc1OC2]

Step 1: 24(1r,3r)-1-(4-(1-ethyl-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione In a 15 ml reaction tube was 7-bromo-1-ethyl-8-phenyl-4H-pyrido[2,3-b][1,2,4]triazolo[4,3-d][1,4]oxazine (75 mg, 0.210 mmol), tert-butyl 4-(4,4,5,5-tetramethyl-1,3,2-dioxaborolan-2-yl)benzylcarbamate (84 mg, 0.252 mmol), and cesium carbonate (342 mg, 1.050 mmol) in 1,4-dioxane (3 ml) and water (1 ml) to give a yellow solution. The reaction mixture was degassed by bubbling nitrogen for 15 minutes, following by addition of PdC12(dppf)-CH$_2$Cl$_2$ adduct (34 mg). The reaction mixture was heated to 50° C. for 1 hour.

The reaction mixture was allowed to cool to RT and water was added (7 ml). The reaction mixture was extracted using ethyl acetate (10 ml×3). The combined organic layers were concentrated under reduced pressure.

The crude was purified by Biotage silica gel chromatography (gradient 0% to 100% ethyl acetate cyclohexane) to give the title compound (51 mg, 50%). LCMS (Method B) RT 1.292 min, M+1=484. $^1$H NMR (500 MHz, CDCl$_3$): 7.81 (1H, s), 7.38-7.30 (5H, m), 7.23-7.18 (2H, m), 7.16-7.12 (2H, m), 5.57 (2H, s), 4.29 (2H, bs), 3.19-3.09 (2H, q), 1.58-1.50 (3H, t), 1.48-1.39 (9H, bs).

Step 2: (4-(1-ethyl-8-phenyl-4H-pyrido[2,3-b][1,2,4]triazolo[4,3-d][1,4]oxazin-7-yl)phenyl)methanamine Following the procedure for 1-((1H-imidazol-2-yl)methyl)-6-(4-(1-aminocyclobutyl)phenyl)-7-phenyl-1H-pyrido[2,3-b][1,4]oxazin-2(3H)-one, 2-((1r,3r)-1-(4-(1-ethyl-8-phenyl-4H-pyrido[2,3-b][1,2,4]triazolo[4,3-d][1,4]oxazin-7-yl)phenyl)-3-hydroxy-3-methylcyclobutyl)isoindoline-1,3-dione (21 mg, 0.04 mmol) was reacted to afford the title compound (26 mg, quantitative). LCMS: R$_T$=0.669 min, M+1=384. $^1$H NMR (500 MHz, MeOD): 7.99 (1H, s), 7.36-

7.32 (2H, m), 7.29-7.20 (5H, m), 7.19-7.15 (2H, m), 5.55 (2H, s), 4.00 (2H, s), 3.25-3.16 (2H, q), 1.69-1.43 (3H, q).

Example 143

6-(4-((1r,3r)-1-amino-3-hydroxy-3-methylcyclobutyl)phenyl)-1-ethyl-7-phenyl-1H-pyrido[2,3-b][1,4]oxazin-2(3H)-one

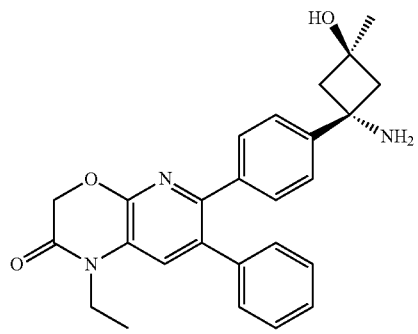 [SMILES: CCN1C(=O)COc2nc(-c3ccc([C@]4(N)C[C@](C)(O)C4)cc3)c(-c3ccccc3)cc21]

Step 1: 2-((1r,3r)-1-(4-(1-ethyl-2-oxo-7-phenyl-2,3-dihydro-1H-pyrido[2,3-b][1,4]oxazin-6-yl)phenyl)-3-hydroxy-3-methylcyclobutyl)isoindoline-1,3-dione In a 15 mL reaction tube was added 6-bromo-1-ethyl-7-phenyl-1H-pyrido[2,3-b][1,4]oxazin-2(3H)-one (40 mg, 0.120 mmol), 2-((1r,3r)-3-hydroxy-3-methyl-1-(4-(4,4,5,5-tetramethyl-1,3,2-dioxaborolan-2-yl)phenyl)cyclobutyl)isoindoline-1,3-dione (43 mg, 0.100 mmol) and cesium carbonate (163 mg, 0.500 mmol) in a mixture of 1,4-dioxane (1.9 ml) and water (0.6 ml) to give a colourless solution. This was degassed by bubbling nitrogen for 15 minutes, followed by the addition of [1,1'-bis(diphenylphosphino)ferrocene]dichloropalladium(II)dichloromethane adduct (16 mg, 0.020 mmol) and degassing for a further 5 minutes. The reaction mixture was heated to 50° C. under a nitrogen atmosphere for one hour. The reaction mixture was allowed to cool to room temperature, diluted with water (5 ml) and extracted into ethyl acetate (3×5 ml). The combined organic phases were dried over Na$_2$SO$_4$, filtered and concentrated to dryness under reduced pressure. The residue was purified by Biotage chromatography (cyclohexane:ethyl acetate, gradient elution from 90:10 to 0:100) to give the desired product as an off-white solid (40 mg, 71% yield). $^1$H-NMR (500 MHz, CDCl$_3$) δ 7.71-7.77 (2H, m), 7.63-7.69 (2H, m), 7.50 (2H, d), 7.23-7.33 (6H, m), 7.15-7.20 (2H, m), 4.84 (2H, s), 3.99 (2H, q), 3.32 (2H, d), 3.08 (2H, d), 1.40 (3H, s), 1.30 (3H, q). LCMS (Method D) RT=1.36 min, M+H$^+$=560.20.

Step 2: 6-(4-((1r,3r)-1-amino-3-hydroxy-3-methylcyclobutyl)phenyl)-1-ethyl-7-phenyl-1H-pyrido[2,3-b][1,4]oxazin-2(3H)-one To a solution of 2-((1r,3r)-1-(4-(1-ethyl-2-oxo-7-phenyl-2,3-dihydro-1H-pyrido[2,3-b][1,4]oxazin-6-yl)phenyl)-3-hydroxy-3-methylcyclobutyl)isoindoline-1,3-dione (40 mg, 0.071 mmol) in a mixture of methanol (1 mL) and 1,4-dioxane (1 ml) was added hydrazine monohydrate (0.25 ml, 5.15 mmol) and heated to 120° C. under microwave irradiation for 30 minutes. The reaction mixture was diluted with dichloromethane (8 ml) and washed with saturated sodium bicarbonate solution (8 ml), brine (8 ml) and water (8 mL), dried over Na$_2$SO$_4$, filtered and concentrated to dryness under reduced pressure. The residue was redissoved in 1,4-dioxane (1 mL) followed by the dropwise addition of 4M HCl in 1,4-dioxane (0.054 mL, 0.214 mmol). The resulting suspension was stirred at room temperature for 15 minutes, then diluted with diethyl ether (6 mL) and slurried for 10 minutes. After settling, the supernatant solvent was removed by pipette. The solid was slurried in diethyl ether (3 mL) and after settling the supernatant solvent removed by pipette. This was repeated two times. The remaining solvent was removed by concentration under reduced pressure and freeze drying overnight to give the desired compound as a white solid (27 mg, 81% yield). $^1$H-NMR (500 MHz, MeOD) δ 7.56 (1H, s), 7.37-7.44 (4H, m), 7.27-7.31 (3H, m), 7.20-7.25 (2H, m), 4.93 (2H, s), 4.07 (2H, q), 2.85 (2H, d), 2.67 (2H, d), 1.49 (3H, s), 1.28 (3H, q), LCMS (Method D) RT=0.72 min, M+H$^+$=430.20.

Example 144

6-(4-((1r,3r)-1-amino-3-hydroxy-3-methylcyclobutyl)phenyl)-1-(cyclopropylmethyl)-7-phenyl-1H-pyrido[2,3-b][1,4]oxazin-2(3H)-one

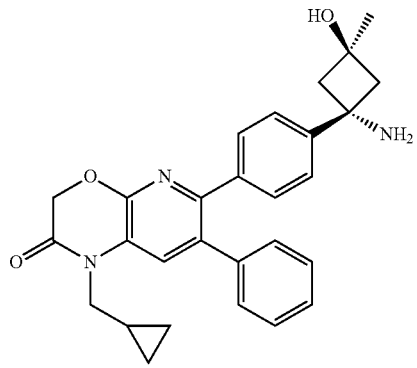 [SMILES: C[C@]1(O)C[C@@](N)(c2ccc(-c3nc4c(cc3-c3ccccc3)N(CC3CC3)C(=O)CO4)cc2)C1]

Step 1: 2-(1r,3r)-1-(4-(1-(cyclopropylmethyl)-2-oxo-7-phenyl-2,3-dihydro-1H-pyrido[2,3-b][1,4]oxazin-6-yl)phenyl)-3-hydroxy-3-methylcyclobutyl)isoindoline-1,3-dione In a 15 mL reaction tube was added 6-bromo-1-(cyclopropylmethyl)-7-phenyl-1H-pyrido[2,3-b][1,4]oxazin-2(3H)-one (40 mg, 0.111 mmol), 2-((1r,3r)-3-hydroxy-3-methyl-1-(4-(4,4,5,5-tetramethyl-1,3,2-dioxaborolan-2-yl)phenyl)cyclobutyl)isoindoline-1,3-dione (40 mg, 0.093 mmol) and cesium carbonate (151 mg, 0.464 mmol) in a mixture of 1,4-dioxane (1.7 ml) and water (0.6 ml) to give a colourless solution. This was degassed by bubbling nitrogen for 15 minutes, followed by the addition of [1,1'-bis(diphenylphosphino)ferrocene]dichloropalladium(II)dichloromethane adduct (15 mg, 0.019 mmol) and degassing for a further 5 minutes. The reaction mixture was heated to 50° C. under a nitrogen atmosphere for one hour. The reaction mixture was allowed to cool to room temperature, diluted with water (5 mL) and extracted into ethyl acetate (3×5 mL). The combined organic phases were dried over Na$_2$SO$_4$, filtered and concentrated to dryness under reduced pressure. The residue was purified by Biotage chromatography (cyclohexane:ethyl acetate, gradient elution from 90:10 to 0:100) then Biotage chromatography (dichloromethane:methanol, gradient elution from 100:0 to 90:10) to give the desired product as an off-white solid (20 mg, 37% yield). $^1$H-NMR (500 MHz, CDCl$_3$) δ 7.71-7.76 (2H, m), 7.63-7.69 (2H, m), 7.50 (2H, d), 7.36 (1H, s), 7.24-7.33 (5H, m), 7.15-7.19 (2H, m), 4.85 (2H, s), 3.84 (2H, d), 3.32 (2H, d), 3.08 (2H, d), 1.40 (3H, s), 1.09-1.19 (1H, m), 0.52-0.59 (2H, m), 0.42-0.48 (2H, m). LCMS (Method D) RT=1.45 min, M+H$^+$=586.20.

Step 2: 6-(4-((1r,3r)-1-amino-3-hydroxy-3-methylcyclobutyl)phenyl)-1-(cyclopropylmethyl)-7-phenyl-1H-pyrido[2,3-b][1,4]oxazin-2(3H)-one To a solution of 2-((1r,3r)-1-(4-(1-(cyclopropylmethyl)-2-oxo-7-phenyl-2,3-dihydro-1H-pyrido[2,3-b][1,4]oxazin-6-yl)phenyl)-3-hydroxy-3-methylcyclobutyl)isoindoline-1,3-dione (20 mg, 0.034 mmol) in a mixture of methanol (1 ml) and 1,4-dioxane (1 ml) was added hydrazine monohydrate (0.25 mL, 5.15 mmol) and heated to 120° C. under microwave irradiation for 30 minutes. The reaction mixture was diluted with dichloromethane (8 ml) and washed with saturated sodium bicarbonate solution (8 ml), brine (8 ml) and water (8 ml), dried over Na$_2$SO$_4$, filtered and concentrated to dryness under reduced pressure. The residue was redissoved in 1,4-dioxane (1 ml) followed by the dropwise addition of 4M HCl in 1,4-dioxane (0.026 mL, 0.102 mmol). The resulting suspension was stirred at room temperature for 15 minutes, then diluted with diethyl ether (6 ml) and slurried for 10 minutes. After settling, the supernatant solvent was removed by pipette. The solid was slurried in diethyl ether (3 ml) and after settling the supernatant solvent removed by pipette. This was repeated two times. The remaining solvent was removed by concentration under reduced pressure and freeze drying overnight to give the desired compound as a white solid (18 mg, quantitative yield). $^1$H-NMR (500 MHz, MeOD) δ 7.65 (1H, s), 7.39-7.45 (4H, m), 7.27-7.31 (3H, m), 7.20-7.25 (2H, m), 4.94 (2H, s), 3.96 (2H, d), 2.85 (2H, d), 2.68 (2H, d), 1.49 (3H, s), 1.14-1.26 (1H, m), 0.54-0.61 (2H, m), 0.40-0.46 (2H, m). LCMS (Method D) RT=0.81 min, M+H$^+$=456.20.

Example 145

6-(4-((1r,3r)-1-amino-3-hydroxy-3-methylcyclobutyl)phenyl)-1-(2-fluoroethyl)-7-phenyl-1H-pyrido[2,3-b][1,4]oxazin-2(3H)-one

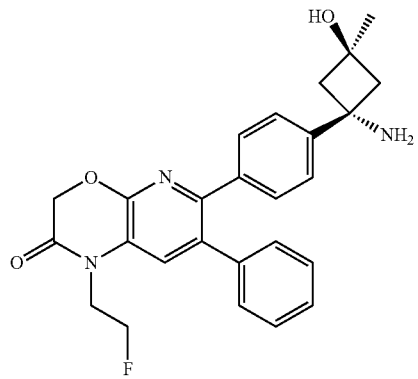 [SMILES: C[C@]1(O)C[C@@](N)(c2ccc(-c3nc4c(cc3-c3ccccc3)N(CCF)C(=O)CO4)cc2)C1]

Step 1: 6-bromo-1-(2-fluoroethyl)-7-phenyl-1H-pyrido[2,3-b][1,4]oxazin-2(3H)-one A mixture of 6-bromo-7-phenyl-1H-pyrido[2,3-b][1,4]oxazin-2(3H)-one (400 mg, 1.311 mmol), 1-fluoro-2-iodoethane (684 mg, 3.93 mmol) and potassium carbonate (544 mg, 3.93 mmol) in DMF (4 ml) was heated under stirring for 3 h. The reaction mixture was cooled down and diluted with water (20 ml), the resulted mixture was extracted with DCM (3×20 ml). The combined organic phase was washed with water, brine, dried over sodium sulfate, concentrated to give the crude material which was purified by column chromatography eluted with ethyl acetate/cyclohexane 0-40% to give product 0.21 g. $^1$H NMR (500 MHz, CDCl$_3$): 7.39-7.48 (m, 5H), 4.89 (s, 2H), 4.77 (t, 1H), 4.67 (t, 1H), 4.21 (t, 1H), 4.16 (t, 1H), LCMS (Method D): R$_T$=1.24 min, M+H$^+$=353.0.

Step 2: 2-((1r,3r)-1-(4-(1-(2-fluoroethyl)-2-oxo-7-phenyl-2,3-dihydro-1H-pyrido[2,3-b][1,4]oxazin-6-yl)phenyl)-3-hydroxy-3-methylcyclobutyl)isoindoline-1,3-dione A mixture of 6-bromo-1-(2-fluoroethyl)-7-phenyl-1H-pyrido[2,3-b][1,4]oxazin-2(3H)-one (38.9 mg, 0.111 mmol), 2-((1r,3r)-3-hydroxy-3-methyl-1-(4-(4,4,5,5-tetramethyl-1,3,2-dioxaborolan-2-yl)phenyl)cyclobutyl)isoindoline-1,3-dione (40 mg, 0.092 mmol) and cesium carbonate (150 mg, 0.462 mmol) in Dioxane (3 ml) and Water (1 ml) was degassed, Pd(dppf)Cl$_2$.CH$_2$Cl$_2$ (15.08 mg, 0.018 mmol) was added, after degassed, The reaction mixture was heating at 50° C. under stirring for 2 h. The reaction mixture was cooled down to room temperature and diluted with water (20 ml) and the resulted mixture was extracted with ethyl acetate (3×20 ml). The combined organic phase was washed with water (30 ml) and dried with sodium sulfate, filtered and concentrated to give crude product which was purified by chromatography (biotage 10 g) eluted with ethyl acetate/cyclohexane 0-60% to afford product (31 mg). LCMS (Method D): R$_T$=1.31 min, M+H$^+$=578.2.

Step 3: 6-(4-((1r,3r)-1-amino-3-hydroxy-3-methylcyclobutyl)phenyl)-1-(2-fluoroethyl)-7-phenyl-1H-pyrido[2,3-b][1,4]oxazin-2(3H)-one A mixture of 2-((1r,3r)-1-(4-(1-(2-fluoroethyl)-2-oxo-7-phenyl-2,3-dihydro-1H-pyrido[2,3-b][1,4]oxazin-6-yl)phenyl)-3-hydroxy-3-methylcyclobutyl)isoindoline-1,3-dione (31 mg, 0.054 mmol) in Dioxane (1 ml) and Methanol (1.000 ml) was added HYDRAZINE monohydrate (0.25 ml, 7.97 mmol). The reaction mixture was heated at 120° C. for 30 min under microwave condition. The reaction mixture was diluted with saturated bicarbonate solution (10 ml) and extracted with DCM (3×10 ml). The combined organic phase was washed with water, brine and dried over sodium sulfate, filtered and concentrated to give product (13 mg) $^1$H NMR (500 MHz, CD$_3$OD) 7.54 (s, 1H), 7.20-7.22 (m, 2H), 7.15-7.17 (m, 5H), 7.07-7.09 (m, 2H), 4.86 (s, 2H), 4.66 (t, 1H), 4.57 (t, 1H), 4.27 (t, 1H), 4.22 (t, 1H), 2.53 (d, 2H), 2.56 (d, 2H). LCMS (Method D): R$_T$=0.63 min, M+H$^+$=448.2.

Example 146

6-(4-(Aminomethyl)phenyl)-7-phenyl-1-(2,2,2-trifluoroethyl)-1H-pyrido[2,3-b][1,4]oxazin-2(3H)-one

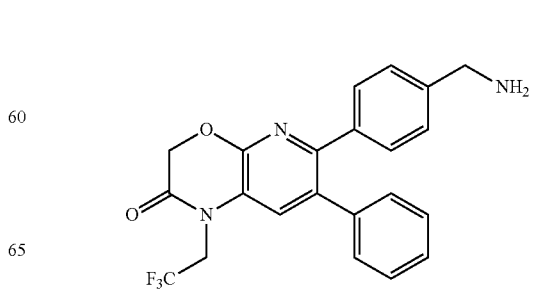

Step 1: tert-Butyl 4-(2-oxo-7-phenyl-1-(2,2,2-trifluoroethyl)-2,3-dihydro-1H-pyrido[2,3-b][1,4]oxazin-6-yl)benzylcarbamate In a 15 mL reaction tube was added 6-bromo-7-phenyl-1-(2,2,2-trifluoroethyl)-1H-pyrido[2,3-b][1,4]oxazin-2(3H)-one (40 mg, 0.103 mmol), tert-butyl 4-(4,4,5,5-tetramethyl-1,3,2-dioxaborolan-2-yl)benzylcarbamate (41.3 mg, 0.124 mmol), and cesium carbonate (168 mg, 0.517 mmol) in a mixture of 1,4-Dioxane (1937 µl) and water (646 µl) to give a colourless solution. This was degassed by bubbling nitrogen for 15 minutes, followed by the addition of PdCl2(dppf)-CH$_2$Cl$_2$Adduct (16.87 mg, 0.021 mmol) and degassing for a further 5 minutes. The reaction mixture was heated to 50° C. under a nitrogen atmosphere for one hour. LC-MS analysis showed reaction completion. The reaction mixture was allowed to cool to room temperature, diluted with water (5 mL) and extracted into ethyl acetate (3×5 mL). The combined organic phases were dried over Na$_2$SO$_4$, filtered and concentrated to dryness under reduced pressure to give a brown solid. The resulting residue was purified via Biotage (0-45% cyclohexane:EtOAc; 10 g column) to give the title compound (45 mg, 85%) as off-white solid. $^1$H NMR (500 MHz, CDCl$_3$): 7.36 (1H, s), 7.32-7.26 (5H, m), 7.17-7.13 (4H, m), 4.96 (2H, s), 4.77 (1H, br), 4.63-4.58 (2H, q), 4.28 (2H, s), 1.48-1.45 (9H, br).

Step 2: 6-(4-(Aminomethyl)phenyl)-7-phenyl-1-(2,2,2-trifluoroethyl)-1H-pyrido[2,3-b][1,4]oxazin-2(3H)-one tert-Butyl 4-(2-oxo-7-phenyl-1-(2,2,2-trifluoroethyl)-2,3-dihydro-1H-pyrido[2,3-b][1,4]oxazin-6-yl)benzylcarbamate (45 mg, 0.088 mmol) was dissolved in TFA (1 mL). The resulting mixture was stirred for 30 seconds at room temperature and evaporated under reduced pressure. The deprotected compound was taken back twice into diethyl ether and the solid formed was washed twice with diethylether. The remaining solvent was removed under reduced pressure and dried to afford the title compound (34 mg, 94%) as off-white solid. LCMS (Method D): R$_T$=0.82 min, M+H$^+$=414. $^1$H NMR (500 MHz, CDCl$_3$): 8.25 (2H, br), 7.47 (1H, s), 7.28-7.26 (4H, m), 7.20-7.18 (3H,m), 7.10-7.08 (2H, m), 4.88 (2H, s), 4.64-4.59 (2H, q), 3.92 (2H, s).

Example 147

2-(6-(4-((1s,3s)-1-amino-3-hydroxycyclobutyl)phenyl)-2-oxo-7-phenyl-2,3-dihydro-1H-pyrido[2,3-b][1,4]oxazin-1-yl)acetonitrile

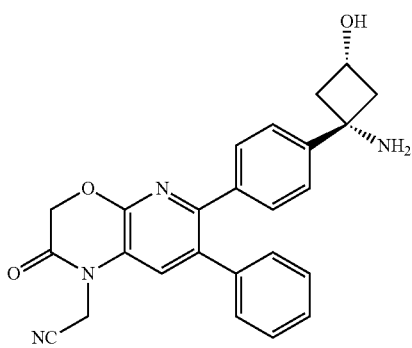 [SMILES: N#CCN1C(=O)COc2nc(-c3ccc([C@]4(N)C[C@@H](O)C4)cc3)c(-c3ccccc3)cc21]

Step 1: 2-(6-bromo-2-oxo-7-phenyl-2,3-dihydro-1H-pyrido[2,3-b][1,4]oxazin-1-yl)acetonitrile A mixture of 6-bromo-7-phenyl-1H-pyrido[2,3-b][1,4]oxazin-2(3H)-one (0.4 g, 1.311 mmol), 2-bromoacetonitrile (0.472 g, 3.93 mmol) and potassium carbonate (0.544 g, 3.93 mmol) in DMF (4 ml) was stirred at 50° C. for 2 h. The reaction mixture was diluted with water (20 ml) and extracted with dichloromethane (3×20 ml). The combined organic phase was washed with water, brine, dried over sodium sulfate and concentrated to give crude product which was purified by column chromatography (biotage 25 g) eluted with 0-50% ethyl acetate/cyclohexane to afford product (0.19 g) $^1$H NMR (500 MHz, CDCl$_3$) 7.45-7.50 (m, 3H), 7.4-7.43 (m, 2H), 7.31 (s, 1H), 4.93 (s, 2H), 4.83 (s, 2H).

Step 2: tert-butyl((1s,3s)-1-(4-(1-(cyanomethyl)-2-oxo-7-phenyl-2,3-dihydro-1H-pyrido[2,3-b][1,4]oxazin-6-yl)phenyl)-3-hydroxycyclobutyl)carbamate A mixture of 2-(6-bromo-2-oxo-7-phenyl-2,3-dihydro-1H-pyrido[2,3-b][1,4]oxazin-1-yl)acetonitrile (42.4 mg, 0.123 mmol), tert-butyl((1s,3s)-3-hydroxy-1-(4-(4,4,5,5-tetraethyl-1,3,2-dioxaborolan-2-yl)phenyl)cyclobutyl)carbamate (40 mg, 0.103 mmol) and CESIUM CARBONATE (167 mg, 0.514 mmol) in Dioxane (3 ml) and Water (1 ml) was degassed. Pd(dppf)Cl$_2$.CH$_2$Cl$_2$ (16.78 mg, 0.021 mmol) was added, after degassed, The reaction mixture was heating at 50° C. under stirring for 1 h.

The reaction mixture was cooled down to room temperature and diluted with water (20 ml) and the resulted mixture was extracted with ethyl acetate (3×20 ml). The combined organic phase was washed with water (30 ml) and dried with sodium sulfate, filtered and concentrated to give crude product which was purified by chromatography (biotage 10 g) eluted with ethyl acetate/cyclohexane 0-70% to afford product (21 mg). LCMS (Method D): R$_T$=1.15 min, M+H$^+$=527.2.

Step 3: 2-(6-(4-(aminomethyl)phenyl)-2-oxo-7-phenyl-2,3-dihydro-1H-pyrido[2,3-b][1,4]oxazin-1-yl)acetonitrile To o a round bottomed flask containing tert-butyl((1s,3s)-1-(4-(1-(cyanomethyl)-2-oxo-7-phenyl-2,3-dihydro-1H-pyrido[2,3-b][1,4]oxazin-6-yl)phenyl)-3-hydroxycyclobutyl)carbamate (18 mg, 0.034 mmol) was added TRIFLUOROACETIC ACID (0.5 ml, 6.49 mmol). The resulting solution was stirred for 60 seconds then concentrated to dryness under reduced pressure. The residue was suspended in diethyl ether (1 ml) and concentrated to dryness three times to give the trifluoroacetic acid salt of the product (8.5 mg) $^1$H NMR (500 MHz, CD$_3$OD) 7.58 (s, 1H), 7.31-7.35 (m, 4H), 7.19-7.22 (m, 3H), 7.13-7.15 (m, 2H), 5.02 (s, 2H), 4.92 (s, 2H), 3.92-3.96 (m, 1H), 2.95-2.99 (m, 2H), 2.35-2.39 (m, 2H). LCMS (Method A): R$_T$=3.53 min, M+H$^+$=428.11.

Example 148

6-(4-((1s,3s)-1-amino-3-hydroxycyclobutyl)phenyl)-7-phenyl-1-(2,2,2-trifluoroethyl)-1H-pyrido[2,3-b][1,4]oxazin-2(3H)-one

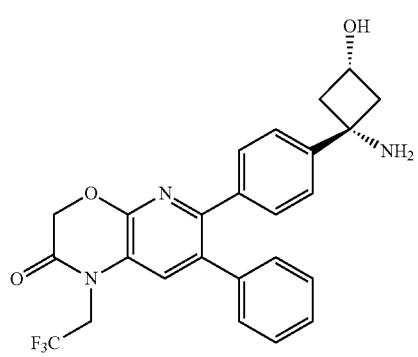 [SMILES: N[C@]1(c2ccc(-c3nc4c(cc3-c3ccccc3)N(CC(F)(F)F)C(=O)CO4)cc2)C[C@H](O)C1]

Step 1: 6-bromo-7-phenyl-1-(2,2,2-trifluoroethyl)-1H-pyrido[2,3-b][1,4]oxazin-2(3H)-one A mixture of 6-bromo-7-phenyl-1H-pyrido[2,3-b][1,4]oxazin-2(3H)-one (0.4 g, 1.311 mmol), potassium carbonate (0.544 g, 3.93 mmol) and 1,1,1-trifluoro-2-iodoethane (0.826 g, 3.93 mmol) in DMF (2 ml) was heated at 70° C. under stirring for 18 h The reaction mixture was cooled down and diluted with water (15 ml) and extracted with DCM (15 mlX3). The combined organic phase was washed with water (25 ml) and dried with $Na_2SO_4$ and concentrated. The residue was purified by column chromatography (biotage 25 g) eluted with ethyl acetate/cyclohexane 0-60% to afford product 6-bromo-7-phenyl-1-(2,2,2-trifluoroethyl)-1H-pyrido[2,3-b][1,4]oxazin-2(3H)-one (0.17 g) $^1$H NMR (500 MHz, $CDCl_3$) 7.45-7.50 (m, 3H), 7.38-7.40 (m, 2H), 7.28 (s, 1H), 4.94 (s, 2H), 4.55 (q, 2H).

Step 2: tea-butyl((1s,3s)-3-hydroxy-1-(4-(2-oxo-7-phenyl-1-(2,2,2-trifluoroethyl)-2,3-dihydro-1H-pyrido[2,3-b][1,4]oxazin-6-yl)phenyl)cyclobutyl)carbamate A mixture of 6-bromo-7-phenyl-1-(2,2,2-trifluoroethyl)-1H-pyrido[2,3-b][1,4]oxazin-2(3H)-one (47.7 mg, 0.123 mmol), tert-butyl ((1s,3s)-3-hydroxy-1-(4-(4,4,5,5-tetramethyl-1,3,2-dioxaborolan-2-yl)phenyl)cyclobutyl)carbamate (40 mg, 0.103 mmol) and cesium carbonate (167 mg, 0.514 mmol) in Dioxane (3 ml) and Water (1 ml) was degassed. Pd(dppf)$Cl_2$.$CH_2Cl_2$ (16.78 mg, 0.021 mmol) was added, after degassed, The reaction mixture was heating at 50° C. under stirring for 1 h.

The reaction mixture was cooled down to room temperature and diluted with water (20 ml) and the resulted mixture was extracted with ethyl acetate (3×20 ml). The combined organic phase was washed with water (30 ml) and dried with sodium sulfate, filtered and concentrated to give crude product which was purified by chromatography (biotage 10 g) eluted with ethyl acetate/cyclohexane 0-70% to afford product (32 mg). $^1$H NMR (500 MHz, $CDCl_3$) 7.31-7.37 (m, 5H), 7.16-7.22 (m, 5H), 4.96 (s, 2H), 4.95 (br, 1H), 4.61 (q, 2H), 4.09 (m, 1H), 2.95-3.05 (m, 2H), 2.7-2.8 (m, 2H), 1.40 (br, 9H). LCMS (Method D): $R_T$=1.31 min, M+H$^+$=571.0

Step 3: 6-(44(1s,3s)-1-amino-3-hydroxycyclobutyl) phenyl)-7-phenyl-1-(2,2,2-trifluoroethyl)-1H-pyrido[2,3-b][1,4]oxazin-2(3H)-one to a round bottomed flask containing to a round bottomed flask containing tert-butyl ((1s,3s)-3-hydroxy-1-(4-(2-oxo-7-phenyl-1-(2,2,2-trifluoroethyl)-2,3-dihydro-1H-pyrido[2,3-b][1,4]oxazin-6-yl)phenyl)cyclobutyl)carbamate (30 mg, 0.053 mmol) was added TRIFLUOROACETIC ACID (0.5 ml, 6.49 mmol). The resulting solution was stirred for 60 seconds then concentrated to dryness under reduced pressure. The residue was dissolved in diethyl ether (1 ml) and concentrated to dryness three times to give the trifluoroacetic acid salt of the product (21 mg) $^1$H NMR (500 MHz, $CD_3OD$) 7.76 (s, 1H), 7.45 (m, 4H), 7.31-7.32 (m, 3H), 7.21-7.23 (m, 2H), 5.03 (s, 2H), 4.92 (q, 2H), 4.06-4.09 (m, 1H), 3.08-3.11 (m, 2H), 2.46-2.50 (m, 2H). LCMS (Method A): $R_T$=3.94 min, M+H$^+$=471.04.

Example 149

6-(4-(1-aminocyclopropyl)phenyl)-1-methyl-7-phenyl-1H-pyrido[2,3-b][1,4]oxazin-2(3H)-one

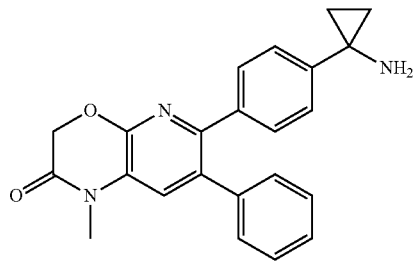 [SMILES: CN1C(=O)COc2nc(-c3ccc(C4(N)CC4)cc3)c(-c3ccccc3)cc21]

Step 1: 1-(4-(4,4,5,5-tetramethyl-1,3,2-dioxaborolan-2-yl)phenyl)cyclopropanamine In a 40 mL reaction tube was added 4-(4,4,5,5-tetramethyl-1,3,2-dioxaborolan-2-yl)benzonitrile (500 mg, 2.18 mmol) and titanium(IV) isopropoxide (710 µl, 2.40 mmol) in anhydrous tetrahydrofuran (11 ml) to give a colourless solution. The reaction mixture was cooled to −70° C. under a nitrogen atmosphere, followed by the dropwise addition of ethylmagnesium bromide (1M in THF, 4.80 ml, 4.80 mmol) over a period of 30 minutes. The resulting orange solution was stirred at −78° C. for 10 minutes, followed by warming to room temperature and stirring for 60 minutes. After this period, boron trifluoride diethyl etherate (540 µl, 4.37 mmol) was added and the mixture stirred at room temperature for 60 minutes. To the reaction was then added 1M HCl solution (6 ml) and stirred for 15 minutes before basification with 2M NaOH solution. The organic phase was separated and the aqueous washed with ethyl acetate (3×4 mL). The combined organic phases were dried over $Na_2SO_4$, filtered and concentrated to dryness under reduced pressure. The residue was purified by Biotage chromatography (cyclohexane:ethyl acetate, gradient elution from 90:10 to 0:100) to give the desired product as an off-white solid (70 mg, 12% yield). $^1$H-NMR (500 MHz, $CDCl_3$) δ 7.76 (2H, d), 7.29 (2H, d), 2.32 (2H, br s), 1.34 (12H, s), 1.12 (2H, dd), 1.01 (2H, dd). LCMS RT=0.68 min, M+H$^+$=260.20.

Step 2: tert-butyl(1-(4-(4,4,5,5-tetramethyl-1,3,2-dioxaborolan-2-yl)phenyl)cyclopropyl)carbamate To a solution of 1-(4-(4,4,5,5-tetramethyl-1,3,2-dioxaborolan-2-yl)phenyl)cyclopropanamine (70 mg, 0.270 mmol) in anhydrous THF (1.35 ml) was added triethylamine (83 µl, 0.594 mmol) and di-tert-butyl dicarbonate (69 µl, 0.297 mmol). The reaction mixture was stirred at room temperature under a nitrogen atmosphere for 3 hours then concentrated to dryness under reduced pressure. The residue was purified by Biotage chromatography (cyclohexane:ethyl acetate, gradient elution from 90:10 to 40:60) to give the desired product as a white solid (54 mg, 56% yield). $^1$H-NMR (500 MHz, CDCl$_3$) δ 7.73 (2H, d), 7.19 (2H, d), 1.39-1.59 (9H, br m), 1.33 (12H, s), 1.30 (2H, br s), 1.25 (2H, br s).

Step 3: tert-butyl(1-(4-(1-methyl-2-oxo-7-phenyl-2,3-dihydro-1H-pyrido[2,3-b][1,4]oxazin-6-yl)phenyl)cyclopropyl)carbamate In a 15 mL reaction tube was added 6-bromo-1-methyl-7-phenyl-1H-pyrido[2,3-b][1,4]oxazin-2(3H)-one (40 mg, 0.125 mmol) and tert-butyl(1-(4-(4,4,5,5-tetramethyl-1,3,2-dioxaborolan-2-yl)phenyl)cyclopropyl)carbamate (54 mg, 0.150 mmol) in 1,4-dioxane (1 ml), followed by a solution of sodium carbonate (40 mg, 0.3 mmol) in water (0.25 ml) to give a white suspension. This was degassed by bubbling nitrogen for 10 minutes, followed by the addition of [1,1'-bis(diphenylphosphino)ferrocene]dichloropalladium(II)dichloromethane adduct (9 mg, 0.013 mmol). The reaction mixture was heated to 80° C. overnight. The reaction mixture was allowed to cool to room temperature, diluted with brine (4 ml) and extracted into ethyl acetate (3×4 ml). The combined organic phases were dried over Na$_2$SO$_4$, filtered and concentrated to dryness under reduced pressure. The residue was purified by Biotage chromatography (cyclohexane:ethyl acetate, gradient elution from 90:10 to 20:80) to give the desired product as a white solid (60 mg, quantitative yield). $^1$H-NMR (500 MHz, CDCl$_3$) δ 7.14-7.26 (6H, m), 7.08-7.14 (2H, m), 6.93 (2H, d), 4.99-5.27 (1H, br m), 4.80 (2H, s), 3.31 (3H, s), 1.35 (9H, br s), 1.25 (2H, br s), 1.03 (2H, br s). LCMS (Method D): RT=1.44 min, M+H$^+$=472.20.

Step 4: 6-(4-(1-aminocyclopropyl)phenyl)-1-methyl-7-phenyl-1H-pyrido[2,3-b][1,4]oxazin-2(3H)-one To a solution of tert-butyl(1-(4-(1-methyl-2-oxo-7-phenyl-2,3-dihydro-1H-pyrido[2,3-b][1,4]oxazin-6-yl)phenyl)cyclopropyl)carbamate (60 mg, 0.127 mmol) in 1,4-dioxane (1 mL) was added dropwise 4M HCl in 1,4-dioxane (0.5 mL, 2.00 mmol) and the resulting solution stirred at room temperature for 1 hour. The reaction mixture was diluted by the dropwise addition of diethyl ether (6 mL) and stirred for 15 minutes to give a white precipitate. The layers were allowed to settle and the supernatant solution removed. The solid was washed twice more with diethyl ether (6 mL), allowing to settle and removing the supernatant solvent each time. The remaining solvent was removed by concentration to dryness under reduced pressure, then freeze-drying over the weekend to give the desired product as an off-white solid (27 mg, 52% yield). $^1$H-NMR (500 MHz, MeOD) δ 7.53 (1H, s), 7.34 (2H, d), 7.31 (2H, d), 7.25-7.29 (3H, m), 7.18-7.23 (2H, m), 4.94 (2H, s), 3.41 (3H, s), 1.29-1.35 (2H, m), 1.24-1.29 (2H, m). LCMS (Method D): RT=0.75 min, M+H$^+$=372.10.

Example 150

2-(6-(4-((1r,3r)-1-amino-3-hydroxy-3-methylcyclobutyl)phenyl)-2-oxo-7-phenyl-2,3-dihydro-1H-pyrido[2,3-b][1,4]oxazin-1-yl)acetonitrile

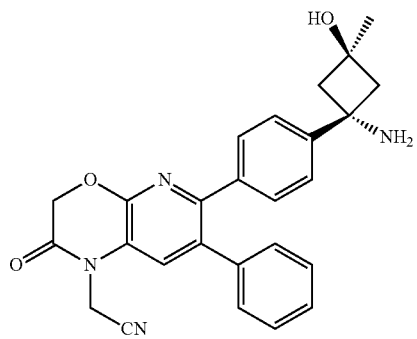 [SMILES: C[C@]1(O)C[C@@](N)(c2ccc(-c3nc4c(cc3-c3ccccc3)N(CC#N)C(=O)CO4)cc2)C1]

Step 1: tert-butyl((1r,3r)-(4-(1-(cyanomethyl)-2-oxo-7-phenyl-2,3-dihydro-1H-pyrido[2,3-b][1,4]oxazin-6-yl)phenyl)-3-hydroxy-3-methylcyclobutyl)carbamate In a 15 mL reaction tube was added 2-(6-bromo-2-oxo-7-phenyl-2,3-dihydro-1H-pyrido[2,3-b][1,4]oxazin-1-yl)acetonitrile (40 mg, 0.116 mmol), tert-butyl((1r,3r)-3-hydroxy-3-methyl-1-(4-(4,4,5,5-tetramethyl-1,3,2-dioxaborolan-2-yl)phenyl)cyclobutyl)carbamate (39 mg, 0.097 mmol) and cesium carbonate (158 mg, 0.484 mmol) in a mixture of 1,4-dioxane (1.8 ml) and water (0.6 ml) to give a colourless solution. This was degassed by bubbling nitrogen for 15 minutes, followed by the addition of [1,1'-bis(diphenylphosphino)ferrocene]dichloropalladium(II)dichloromethane adduct (16 mg, 0.019 mmol) and degassing for a further 5 minutes. The reaction mixture was heated to 50° C. under a nitrogen atmosphere for one hour. The reaction mixture was allowed to cool to room temperature, diluted with water (5 mL) and extracted into ethyl acetate (3×5 mL). The combined organic phases were dried over Na$_2$SO$_4$, filtered and concentrated to dryness under reduced pressure. The residue was purified twice by Biotage chromatography (cyclohexane:ethyl acetate, gradient elution from 90:10 to 0:100) to give the desired product as an off-white solid (30 mg, 57% yield). $^1$H-NMR (500 MHz, d$_6$-Acetone) δ 7.67 (1H, s), 7.23-7.35 (9H, m), 6.55 (1H, br s), 5.21 (2H, s), 5.04 (2H, s), 2.70-2.78 (2H, m), 2.45-2.60 (2H, m), 1.49 (3, s), 1.15-1.40 (br m, 9H). LCMS (Method D) RT=1.22 min, M+H$^+$=541.15.

Step 2: 2-(6-(4-((1r,3r)-1-amino-3-hydroxy-3-methylcyclobutyl)phenyl)-2-oxo-7-phenyl-2,3-dihydro-1H-pyrido[2,3-b][1,4]oxazin-1-yl)acetonitrile tert-Butyl((1r,3r)-1-(4-(1-(cyanomethyl)-2-oxo-7-phenyl-2,3-dihydro-1H-pyrido[2,3-b][1,4]oxazin-6-yl)phenyl)-3-hydroxy-3-methylcyclobutyl)carbamate (30 mg, 0.055 mmol) was dissolved in TFA (1 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as a white solid (18 mg, 59% yield). $^1$H-NMR (500 MHz, MeOD) δ 7.68 (1H, s), 7.40-7.45 (4H, m), 7.28-7.31 (3H, m), 7.22-7.26 (2H, m), 5.12 (2H, s), 5.00 (2H, s), 2.85 (2H, d), 2.68 (2H, d), 1.48 (3H, s). LCMS (Method D) RT=0.64 min, M+H$^+$=441.10.

Example 151

6-(4-(Aminomethyl)phenyl)-1-ethyl-7-phenyl-1H-pyrido[2,3-b][1,4]oxazin-2(3H)-one

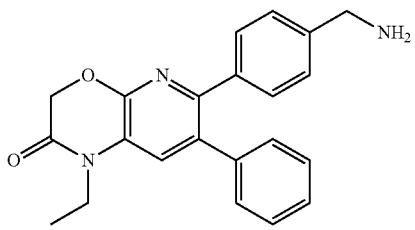 [SMILES: CCN1C(=O)COc2nc(-c3ccc(CN)cc3)c(-c3ccccc3)cc21]

Step 1: tert-Butyl 4-(1-ethyl-2-oxo-7-phenyl-2,3-dihydro-1H-pyrido[2,3-b][1,4]oxazin-6-yl)benzyl-carbamate In a 15 mL reaction tube was added 6-bromo-1-ethyl-7-phenyl-1H-pyrido[2,3-b][1,4]oxazin-2(3H)-one (50 mg, 0.150 mmol), tert-butyl 4-(4,4,5,5-tetramethyl-1,3,2-dioxaborolan-2-yl)benzylcarbamate (60.0 mg, 0.180 mmol), and CESIUM CARBONATE (244 mg, 0.750 mmol) in a mixture of 1,4-Dioxane (2814 μl) and water (938 μl) to give a colourless solution. This was degassed by bubbling nitrogen for 15 minutes, followed by the addition of PdCl2(dppf)-CH$_2$Cl$_2$Adduct (24.51 mg, 0.030 mmol) and degassing for a further 5 minutes. The reaction mixture was heated to 50° C. under a nitrogen atmosphere for one hour. LC-MS analysis showed reaction completion. The reaction mixture was allowed to cool to room temperature, diluted with water (5 mL) and extracted into ethyl acetate (3×5 mL). The combined organic phases were dried over Na$_2$SO$_4$, filtered and concentrated to dryness under reduced pressure to give an off-white solid. The resulting residue was purified via Biotage (15-85% cyclohexane:EtOAc; 10 g column) to give the title compound (45 mg, 65.3%) as off-white solid. $^1$H NMR (500 MHz, CDCl$_3$): 7.31-7.27 (6H, m), 7.19-7.18 (2H, d), 7.11-7.10 (2H, d), 4.87 (2H, s), 4.84 (1H, br), 4.27 (2H, s), 4.03-3.98 (2H, q), 1.45 (9H, br), 1.32-1.30 (3H, t).

Step 2: 6(4-(Aminomethyl)phenyl)-1-ethyl-7-phenyl-1H-pyrido[2,3-b][1,4]oxazin-2(3H)-one tert-Butyl 4-(1-ethyl-2-oxo-7-phenyl-2,3-dihydro-1H-pyrido[2,3-b][1,4]oxazin-6-yl)benzylcarbamate (45 mg, 0.098 mmol) was dissolved in TFA (1 mL). The resulting mixture was stirred for 30 seconds at room temperature and evaporated under reduced pressure. The deprotected compound was taken back twice into diethyl ether and the solid formed was washed twice with diethylether. The remaining solvent was removed under reduced pressure and dried to afford the title compound (35 mg, 99%) as white solid. LCMS: R$_T$=0.75 min, M+H$^+$=360. $^1$H NMR (500 MHz, CDCl$_3$): 8.34 (2H, br), 7.30-7.27 (5H, m), 7.18 (3H, m), 7.13-7.11 (2H, m), 4.80 (2H, s), 4.03-3.99 (2H, q), 3.96 (2H, s), 1.32-1.30 93H, t).

Example 152

6-(4-(((1r,3r)-1-amino-3-hydroxy-3-methylcyclobutyl)phenyl)-7-phenyl-1-(2,2,2-trifluoroethyl)-1H-pyrido[2,3-b][1,4]oxazin-2(3H)-one

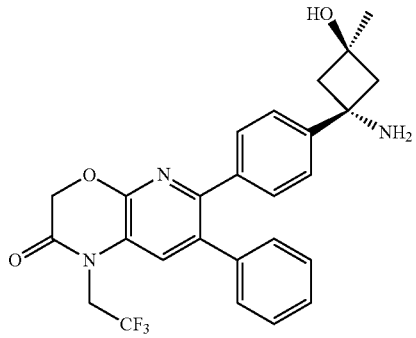 [SMILES: C[C@]1(O)C[C@@](N)(c2ccc(-c3nc4c(cc3-c3ccccc3)N(CC(F)(F)F)C(=O)CO4)cc2)C1]

Step 1: tert-butyl((1r,3r)-3-hydroxy-3-methyl-1-(4-(2-oxo-7-phenyl-1-(2,2,2-trifluoroethyl)-2,3-dihydro-1H-pyrido[2,3-b][1,4]oxazin-6-yl)phenyl)cyclobutyl)carbamate In a 15 mL reaction tube was added 6-bromo-7-phenyl-1-(2,2,2-trifluoroethyl)-1H-pyrido[2,3-b][1,4]oxazin-2(3H)-one (45 mg, 0.116 mmol), tert-butyl((1r,3r)-3-hydroxy-3-methyl-1-(4-(4,4,5,5-tetramethyl-1,3,2-dioxaborolan-2-yl)phenyl)cyclobutyl)carbamate (39 mg, 0.097 mmol) and cesium carbonate (158 mg, 0.484 mmol) in a mixture of 1,4-dioxane (1.8 ml) and water (0.6 ml) to give a colourless solution. This was degassed by bubbling nitrogen for 15 minutes, followed by the addition of [1,1'-bis(diphenylphosphino)ferrocene]dichloropalladium(II)dichloromethane adduct (16 mg, 0.019 mmol) and degassing for a further 5 minutes. The reaction mixture was heated to 50° C. under a nitrogen atmosphere for one hour. The reaction mixture was allowed to cool to room temperature, diluted with water (5 mL) and extracted into ethyl acetate (3×5 mL). The combined organic phases were dried over Na$_2$SO$_4$, filtered and concentrated to dryness under reduced pressure. The residue was purified twice by Biotage chromatography (cyclohexane:ethyl acetate, gradient elution from 90:10 to 0:100) to give the desired product as an off-white solid (25 mg, 44% yield). $^1$H-NMR (500 MHz, CDCl$_3$) δ 7.35 (1H, s), 7.26-7.32 (5H, m), 7.21-7.25 (2H, m), 7.14-7.18 (2H, m), 4.94 (2H, s), 2.93 (1H, br s), 4.60 (2H, q), 2.40-2.68 (4H, m), 1.55 (3H, s), 1.20-1.40 (9H, br m). LCMS (Method D) RT=1.38 min, M+H$^+$=584.10.

Step 2: 6-(4-((1r,3r)-1-amino-3-hydroxy-3-methylcyclobutyl)phenyl)-7-phenyl-1-(2,2,2-trifluoroethyl)-1H-pyrido[2,3-b][1,4]oxazin-2(3H)-one tert-Butyl((1r,3r)-3-hydroxy-3-methyl-1-(4-(2-oxo-7-phenyl-1-(2,2,2-trifluoroethyl)-2,3-dihydro-1H-pyrido[2,3-b][1,4]oxazin-6-yl)phenyl)cyclobutyl)carbamate (25 mg, 0.043 mmol) was dissolved in TFA (1 mL) and stirred for 30 seconds. The solution was immediately concentrated to dryness under reduced pressure. The residue was dissolved in diethyl ether (~3 mL) and concentrated to dryness under reduced pressure three times. The residue was then slurried in diethyl ether (3 mL) and after settling the supernatant solvent removed by pipette. This was repeated three times. The remaining solvent was removed by freeze drying overnight to give the desired compound as a white solid (8 mg, 31% yield). ¹H-NMR (500 MHz, MeOD) δ 7.73 (1H, s), 7.39-7.44 (4H, m), 7.26-7.32 (3H, m), 7.17-7.23 (2H, m), 5.01 (2H, s), 4.89 (2H, q), 2.85 (2H, d), 2.66 (2H, d), 1.49 (3H, s). LCMS (Method D) RT=0.80 min, M+H⁺=484.05.

Example 153

6-(4-(Aminomethyl)phenyl)-1-(cyclopropylmethyl)-7-phenyl-1H-pyrido[2,3-b][1,4]oxazin-2(3H)-one

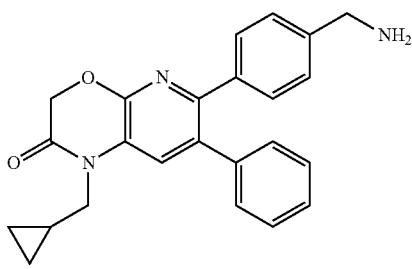 [SMILES: NCc1ccc(-c2nc3c(cc2-c2ccccc2)N(CC2CC2)C(=O)CO3)cc1]

Step 1: tert-Butyl 4-(1-(cyclopropylmethyl)-2-oxo-7-phenyl-2,3-dihydro-1H-pyrido[2,3-b][1,4]oxazin-6-yl)benzylcarbamate In a 15 mL reaction tube was added 6-bromo-1-(cyclopropylmethyl)-7-phenyl-1H-pyrido[2,3-b][1,4]oxazin-2(3H)-one (80 mg, 0.223 mmol), tert-butyl 4-(4,4,5,5-tetramethyl-1,3,2-dioxaborolan-2-yl)benzylcarbamate (89 mg, 0.267 mmol) and CESIUM CARBONATE (363 mg, 1.114 mmol) in a mixture of 1,4-Dioxane (3341 NI) and water (1114 µl) to give a colourless solution. This was degassed by bubbling nitrogen for 15 minutes, followed by the addition of PdCl2(dppf)-CH₂Cl₂Adduct (36.4 mg, 0.045 mmol) and degassing for a further 5 minutes. The reaction mixture was heated to 50° C. under a nitrogen atmosphere for one hour. LC-MS analysis showed reaction completion. The reaction mixture was allowed to cool to room temperature, diluted with water (5 mL) and extracted into ethyl acetate (3×5 mL). The combined organic phases were dried over Na₂SO₄, filtered and concentrated to dryness under reduced pressure to give an off-white solid. The resulting residue was purified via Biotage (15-85% cyclohexane:EtOAc; 10 g column) to give the title compound (80 mg, 74%). ¹H NMR (500 MHz, CDCl₃): 7.39 (1H, s), 7.32-7.26 (5H, m), 7.20-7.18 (2H, dd), 7.12-7.10 (2H, d), 4.89 (2H, s), 4.80 (1H, br), 4.27 (2H, s), 3.87-3.86 (2H, d), 1.48-1.45 (9H, br), 1.18-1.15 (1H, m), 0.60-0.56 (2H, m), 0.48-0.45 (2H, m).

Step 2: 6-(4-(Aminomethyl)phenyl)-1-(cyclopropylmethyl)-7-phenyl-1H-pyrido[2,3-b][1,4]oxazin-2(3H)-one tert-Butyl 4-(1-(cyclopropylmethyl)-2-oxo-7-phenyl-2,3-dihydro-1H-pyrido[2,3-b][1,4]oxazin-6-yl)benzylcarbamate (80 mg, 0.165 mmol) was dissolved in TFA (1 mL). The resulting mixture was stirred for 30 seconds at room temperature and evaporated under reduced pressure. The deprotected compound was taken back twice into diethyl ether and the solid formed was washed twice with diethylether. The remaining solvent was removed under reduced pressure and dried to afford the title compound (45 mg, 70.9%) as white solid. LCMS: R_T=0.84 min, M+H⁺=386. ¹H NMR (500 MHz, CDCl₃): 8.33 (2H, br), 7.41 (1H, s), 7.27-7.26 (4H, m), 7.18 (3H, m), 7.13-7.12 (2H, m), 4.82 (2H, s), 3.94 (2H, s), 3.87-3.85 (2H, d), 1.16-1.14 (1H, m), 0.60-0.57 (2H, m), 0.48-0.45 (2H, m).

tert-butyl 1-(4-(6-chloro-5-nitro-3-phenylpyridin-2-yl)phenyl)cyclobutylcarbamate

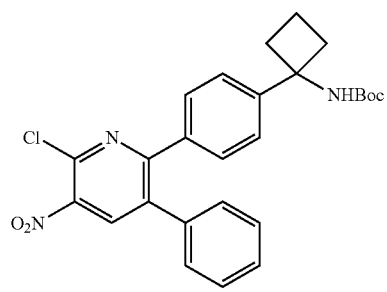 [SMILES: CC(C)(C)OC(=O)NC1(c2ccc(-c3nc(Cl)c([N+](=O)[O-])cc3-c3ccccc3)cc2)CCC1]

Step 1: tert-butyl(1-(4-(5-nitro-6-oxo-3-phenyl-1,6-dihydropyridin-2-yl)phenyl)cyclobutyl)carbamate A solution of (E)-tert-butyl 1-(4-(3-(dimethylamino)-2-phenylacryloyl)phenyl)cyclobutyl carbamate (95 g, 214 mmol) and 2-nitroacetamide (20 g, 192 mmol) in acetic acid (600 mL) was stirred at 45° C. for 3 hours, then at room temperature for 18 hours. The resulting precipitate was filtered, washed with acetic acid (150 mL), diethyl ether (400 mL) and dried at ambient temperature to afford the title compound as a yellow solid (41 g). The filtrate was concentrated under reduced pressure. The residue was taken up in diethyl ether. The resulting precipitate was filtered and dried at ambient temperature to afford a second crop of product (9 g). The overall yield of title compound was 48%. ¹H NMR (500 MHz, d₆-DMSO): 13.02 (1H, brs), 8.42 (1H, s), 7.6-7.1 (9H, m), 2.35 (4H, m), 1.98 (1H, m), 1.76 (1H, m), 1.3-1.1 (9H, m).

Step 2: tert-butyl 1-(4-(6-chloro-5-nitro-3-phenylpyridin-2-yl)phenyl)cyclobutylcarbamate A solution of tert-butyl 1-(4-(6-hydroxy-5-nitro-3-phenylpyridin-2-yl)phenyl)cyclobutyl carbamate (50 g, 2.16 mmol) and 10% Pd/C (0.2 g) in THF (2 L) was hydrogenated in an autoclave (2 bar) for 15 hours at room temperature. The solution was then filtered through celite and the celite was washed with THF (0.5 L). The combined filtrates were concentrated under reduced pressure. The residue was triturated in diethyl ether. The resulting white precipitate was filtered and dried at ambient to afford the title compound (50 g, 91%).

It was used for the next step without further purification.

Step 3: tert-butyl 1-(4-(6-chloro-5-nitro-3-phenylpyridin-2-yl)phenyl)cyclobutylcarbamate To a Schlenck tube were added tert-butyl 1-(4-(6-chloro-5-nitro-3-phenylpyridin-2-yl)phenyl)cyclobutylcarbamate (10 g, 21.67 mmol), triphenylphosphine (17.05 g, 65 mmol), DCE (200 mL) and carbon tetrachloride (2.19 mL, 22.75 mmol). The resulting heterogeneous solution was heated at 100° C. for 35 minutes. It was then concentrated under reduced pressure. The residue was purified by Biotage chromatography (gradient 0% to 3% methanol in dichloromethane) to afford the title compound as a white solid (6 g, 57%). $^1$H NMR (500 MHz, CDCl$_3$): 8.30 (1H, s), 7.4-7.2 (9H, m), 2.51 (4H, m), 2.10 (1H, m), 1.88 (1H, m), 1.3-1.1 (9H, m).

tert-butyl(1-(4-(5-amino-6-oxo-3-phenyl-1,6-dihydropyridin-2-yl)phenyl)cyclobutyl)carbamate

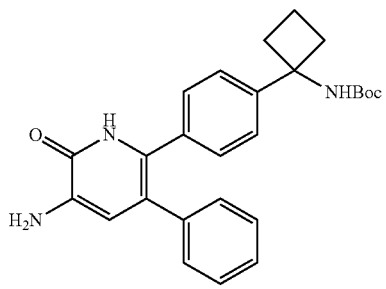 [SMILES: CC(C)(C)OC(=O)NC1(c2ccc(-c3[nH]c(=O)c(N)cc3-c3ccccc3)cc2)CCC1]

Step 1: tert-butyl(1-(4-(5-nitro-6-oxo-3-phenyl-1,6-dihydropyridin-2-yl)phenyl)cyclobutyl)carbamate (E)-tert-butyl-1-(4-(3-(dimethylamino)phenyl)cyclobutylcarbamate (10 g, 23.78 mmol) and 2-nitroacetamide (2.45 g, 23.78 mmol) were dissolved in acetic acid (125 mL) to give a yellow solution. This reaction mixture was heated to 50° C. for 2 hours and then it was stirred at room temperature for 16 hours. The obtained precipitate was filtered, washed with diethyl ether and dried until constant weight to give the title compound as a yellow solid (4.1 g, 37.4%).

Step 2: tert-butyl(1-(4-(5-amino-6-oxo-3-phenyl-1,6-dihydropyridin-2-yl)phenyl)cyclobutyl)carbamate Tert-butyl (1-(4-(5-nitro-6-oxo-3-phenyl-1,6-dihydropyridin-2-yl)phenyl)cyclobutyl)carbamate (10.95 g, 23.77 mmol) was dissolved in acetic acid (250 mL) at room temperature. Zinc powder (10 g, 153 mmol) was added at 30° C. and the resulting suspension was stirred at room temperature for 18 hours. The reaction mixture was concentrated under reduced pressure and the obtained residue was partitioned between water (250 mL) and ethyl acetate (250 mL). The aqueous phase was extracted with fresh ethyl acetate (3×200 mL) and the combined organic layers were washed with water (200 mL), brine (200 mL), dried on anhydrous Na$_2$SO$_4$, filtered and concentrated to dryness under reduced pressure. The obtained crude was purified by Biotage silica gel chromatography (gradient 0% to 3% methanol in dichloromethane) to give the title compound (4.3 g, 43%). It was used for the next step without further purification. LCMS (Method A) RT 5.96 min, M+1=432.

tert-butyl(1-(4-(1-methyl-7-phenyl-2-thioxo-2,3-dihydro-1H-pyrido[2,3-b][1,4]oxazin-6-yl)phenyl)cyclobutyl)carbamate

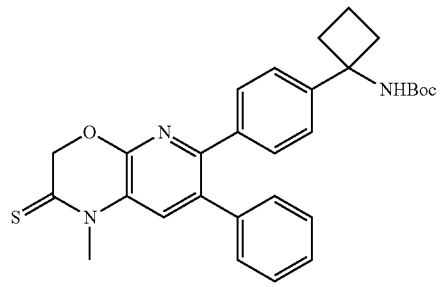 [SMILES: CN1C(=S)COc2nc(-c3ccc(C4(NC(=O)OC(C)(C)C)CCC4)cc3)c(-c3ccccc3)cc21]

Tert-butyl (1-(4-(1-methyl-7-phenyl-2-oxo-2,3-dihydro-1H-pyrido[2,3-b][1,4]oxazin-6-yl)phenyl)cyclobutyl)carbamate (200 mg, 0.412 mmol) was suspended in toluene (5 ml). Lawesson's reagent (125 mg, 0.309 mmol) was added at room temperature. The resulting mixture was heated under reflux for 5 hours. After it was cooled down to room temperature, the mixture was concentrated to dryness under reduced pressure. The resulting residue was dissolved in the minimum amount of dichloromethane (1 mL) and treated with diisopropyl ether (7 mL). A yellow solid crushed out. It was filtered and dried until constant weight (200 mg, 96%). LCMS (Method A): R$_T$=7.08 min, M+1=502.

6-bromo-1-methyl-7-phenyl-1H-pyrido[2,3-b][1,4]oxazin-2(3H)-one

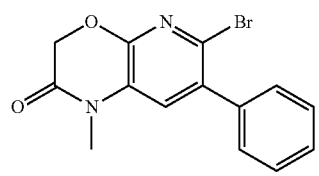 [SMILES: CN1C(=O)COc2nc(Br)c(-c3ccccc3)cc21]

In a 15 mL reaction tube was added 6-bromo-7-phenyl-1H-pyrido[2,3-b][1,4]oxazin-2(3H)-one (1.00 g, 3.28 mmol) in anhydrous N,N-dimethylformamide (5 mL), potassium carbonate (1.359 g, 9.83 mmol) and iodomethane (0.246 mL, 3.93 mmol) to give a brown suspension. The reaction mixture was stirred at room temperature under a nitrogen atmosphere for 1 hour. The reaction mixture was diluted with saturated sodium bicarbonate solution (30 mL) and extracted into dichloromethane (3×15 mL). The combined organic phases were dried over anhydrous Na$_2$SO$_4$, filtered and concentrated to dryness under reduced pressure to give a brown oil. The residue was purified via Biotage chromatography (silica 50 g column, cyclohexane:ethyl acetate, gradient elution from 88:12 to 0:100) to give a pale yellow solid (780 mg, 74.6% yield). ¹H NMR (500 MHz, CDCl₃): 7.51-7.44 (5H, m), 7.20 (1H, s), 4.91 (2H, s), 3.36 (3H, s).

7-bromo-1H-pyrido[2,3-b][1,4]oxazin-2(3H)-one

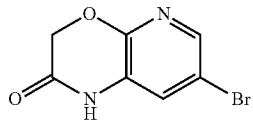

In a 500 mL round-bottomed flask was added ethyl 2-(5-bromo-3-nitropyridin-2-yloxy)acetate (5.2 g, 17.04 mmol) in hydrochloric acid, 37% (50 mL) to give a yellow suspension. The mixture was cooled to 0-5° C. followed by the portion wise addition of tin powder (10.1168 g, 85 mmol). Caution must be taken during the addition as it is very exothermic. The mixture was stirred at room temperature for a further 30 minutes after the addition. The reaction mixture was heated to 80° C. under a nitrogen atmosphere for 3 hours. The reaction mixture was diluted with water (250 mL). The precipitate was filtered, washed with water (200 mL) and diethyl ether (200 mL) and dried until constant weight to give the title compound (3.2 g, 82%). ¹H NMR (500 MHz, d₆-DMSO): 10.41 (2H, s), 7.88 (2H, s), 7.34 (2H, s), 4.85 (2H, s).

ethyl 2-((5-bromo-3-nitropyridin-2-yl)oxy)acetate

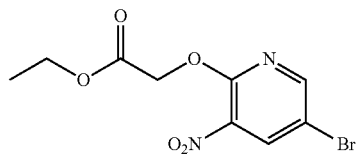 [SMILES: CCOC(=O)COc1ncc(Br)cc1[N+](=O)[O-]]

To a suspension of sodium hydride (5.31 g, 133 mmol) in 1,4-dioxane (250 mL) was added drop wise ethyl glycolate (12.56 ml, 133 mmol) over a period of 30 minutes ensuring that the temperature was maintained below 30° C. The resulting thick suspension was stirred at room temperature for 15 minutes. In a separate 1 L round-bottomed flask was added 5-bromo-2-chloro-3-nitropyridine (21 g, 88 mmol) in 1,4-dioxane (150 mL) to give a brown solution. The sodium hydride/ethyl glycolate slurry was added drop wise over a period of 30 minutes. The resulting reaction mixture was heated to 80° C. overnight. The reaction mixture was concentrated under reduced pressure and the residue was purified via Biotage chromatography (silica 340 g column, gradient elution from 0% to 10% ethyl acetate in cyclohexane) to give a pale yellow solid (11.8 g, 43% yield). ¹H NMR (500 MHz, CDCl₃): 8.48 (1H, d), 8.42 (1H, d), 5.07 (2H, s), 4.25 (2H, q), 1.30 (3H, s).

6-bromo-1-ethyl-7-phenyl-1H-pyrido[2,3-b][1,4]oxazin-2(3H)-one

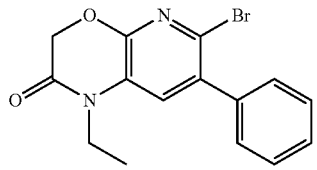 [SMILES: CCN1C(=O)COc2nc(Br)c(-c3ccccc3)cc21]

In a 15 mL reaction tube was added 6-bromo-7-phenyl-1H-pyrido[2,3-b][1,4]oxazin-2(3H)-one (300 mg, 0.983 mmol), iodoethane (0.095 mL, 1.180 mmol) and potassium carbonate (408 mg, 2.95 mmol) in anhydrous N,N-dimethylformamide (1 mL) to give a brown suspension. This was stirred at 50° C. under a nitrogen atmosphere for 60 minutes. The reaction mixture was diluted with saturated sodium bicarbonate solution (5 mL) and extracted into ethyl acetate (3×5 mL). The combined organic phases were washed with 50:50 water:brine (3×5 mL), dried over Na₂SO₄, filtered and concentrated to dryness under reduced pressure to give a brown solid. This was purified by Biotage chromatography (25 g silica cartridge, cyclohexane:ethyl acetate, gradient elution from 90:10 to 20:80) to give the title compound as a beige solid (160 mg, 48.8% yield).

¹H NMR (500 MHz, CDCl₃): 7.58-7.37 (5H, m), 7.21 (1H, s), 4.86 (2H, s), 3.96 (2H, q), 1.27 (3H, t). LCMS (Method D) RT 1.293 min, M+1=334.

6-bromo-1-(cyclopropylmethyl)-7-phenyl-1H-pyrido[2,3-b][1,4]oxazin-2(3H)-one

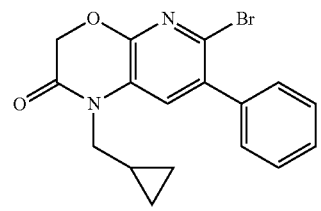 [SMILES: O=C1COc2nc(Br)c(-c3ccccc3)cc2N1CC1CC1]

In a 15 mL reaction tube was added 6-bromo-7-phenyl-1H-pyrido[2,3-b][1,4]oxazin-2(3H)-one (300 mg, 0.983 mmol), (bromomethyl)cyclopropane (0.114 mL, 1.180 mmol) and potassium carbonate (408 mg, 2.95 mmol) in anhydrous N,N-dimethylformamide (1 mL) to give a brown suspension. This was stirred at 50° C. under a nitrogen atmosphere for 60 minutes. The reaction mixture was diluted with saturated sodium bicarbonate solution (5 mL) and extracted into ethyl acetate (3×5 mL). The combined organic phases were washed with 50:50 water:brine (3×5 mL), dried over Na₂SO₄, filtered and concentrated to dryness under reduced pressure to give a brown solid. This was purified by Biotage chromatography (25 g silica cartridge, cyclohexane:ethyl acetate, gradient elution from 90:10 to 20:80) to give the title compound as a beige solid (160 mg, 0.445 mmol, 45.3% yield). ¹H NMR (500 MHz, CDCl₃): 7.58-7.37 (5H, m), 7.32 (1H, s), 4.88 (2H, s), 3.81 (2H, d), 1.14-1.01 (1H, m), 0.60-0.53 (2H, m), 0.47-0.40 (2H, m).

tert-butyl((1r,3r)-1-(4-(5,5-dimethyl-1,3,2-dioxaborinan-2-yl)phenyl)-3-hydroxy-3-methylcyclobutyl)carbamate

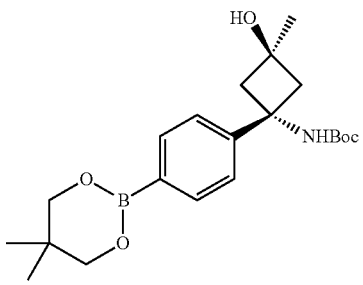 [SMILES: CC1(C)COB(c2ccc([C@]3(NC(=O)OC(C)(C)C)C[C@](C)(O)C3)cc2)OC1]

Step 1: 2-((1r,3r)-1-(4-(5,5-dimethyl-1,3,2-dioxaborinan-2-yl)phenyl)-3-hydroxy-3-methylcyclobutyl)isoindoline-1,3-dione In a 100 mL round-bottomed flask was added 2-((1r,3r)-1-(4-bromophenyl)-3-hydroxy-3-methylcyclobutyl)isoindoline-1,3-dione (0.710 g, 1.838 mmol), 5,5,5',5'-tetramethyl-2,2'-bi(1,3,2-dioxaborinane) (0.700 g, 3.10 mmol) and potassium acetate (0.361 g, 3.68 mmol) in anhydrous DMSO (35.4 ml) to give a colourless suspension. This was degassed by bubbling nitrogen for 15 minutes, followed by the addition of PdC12(dppf)-$CH_2Cl_2$ adduct (0.150 g, 0.184 mmol). The resulting suspension was heated to 80° C. under a nitrogen atmosphere overnight. The reaction mixture was allowed to cool to room temperature, diluted with ethyl acetate (180 mL), filtered through celite, washed with water (2×180 mL) then brine (180 mL), dried over $Na_2SO_4$, filtered and concentrated to dryness under reduced pressure to give a brown oil. This was purified by Biotage chromatography (silica 50 g cartridge, cyclohexane:ethyl acetate, gradient elution from 90:10 to 0:100) to give the title compound as an off-white solid (263 mg, 0.627 mmol, 34.1% yield). $^1$H NMR (500 MHz, $CDCl_3$): 7.82-7.72 (5H, m), 7.70-7.63 (4H, m), 3.73 (3H, s), 3.36 (2H, d), 3.19 (2H, d). LCMS (Method D) RT 0.890 min, M+1=420.

Step 2: tert-butyl((1r,3r)-1-(4-(5,5-dimethyl-1,3,2-dioxaborinan-2-yl)phenyl)-3-hydroxy-3-methylcyclobutyl)carbamate In a 15 mL reaction tube was added 2-((1r,3r)-1-(4-(5,5-dimethyl-1,3,2-dioxaborinan-2-yl)phenyl)-3-hydroxy-3-methylcyclobutyl)isoindoline-1,3-dione (220 mg, 0.525 mmol) and hydrazine monohydrate (0.2 mL, 4.12 mmol) in ethanol (4 mL) to give a pale yellow solution. This was heated to 80° C. overnight giving a white suspension. The reaction mixture was filtered and the filtrates concentrated to dryness under reduced pressure. The residue was redissolved in methanol (4 mL) followed by the addition of di-tert-butyl dicarbonate (0.244 mL, 1.049 mmol) and triethylamine (0.183 mL, 1.312 mmol). The reaction mixture was heated to 50° C. overnight. The reaction mixture was diluted with ethyl acetate (16 mL) and washed with water (8 mL), dried over $Na_2SO_4$, filtered and concentrated to dryness under reduced pressure to give a yellow solid. This was purified by Biotage chromatography (25 g silica cartridge, cyclohexane:ethyl acetate, gradient elution from 90:10 to 20:80) to give the title compound as an off-white solid (88 mg, 0.226 mmol, 43.1% yield). $^1$H-NMR (500 MHz, $CD_3Cl_3$) δ 7.75 (2H, m), 7.38 (2H, s), 3.76 (3H, s), 2.80-2.63 (4H, m), 2.60-2.45 (2H, m), 2.16-2.03 (2H, m), 1.49-1.29 (9H, m), 1.01 (6H, s). LCMS (Method D) RT=0.814 min, M+1=390.

AKT Kinase Assay Testing

Testing of the compounds was performed using an AKT Kinase Assay:

Activated AKT isoforms 1, 2 and 3 were assayed utilising a 5' FAM Crosstide (Seq. GRPRTSSFAEG-OH)(SEQ ID NO: 1). The extent of kinase phosphorylation was determined by fluorescent polarisation using IMAP progressive binding reagent, which introduces binding beads which allow the reagent to specifically bind to phosphate residues via covalent co-ordination complex bonds.

iMAP binding solution stops Crosstide/kinase interaction and specifically binds phosphorylated substrates. The degree of phosphorylation is determined by fluorescent polarisation (excitation 485 nm; emission 528 nm) or the reduction in speed of rotation of the excited substrate.

The following materials were used in the assay:
a) Activated AKT isoforms (SignalChem.) dissolved in Complete Reaction buffer at a pre-determined concentration selected so that the assay was carried out in the linear range.
b) AKT substrate peptide: FAM Crosstide (R7110) Molecular Devices, diluted in complete reaction buffer.
c) iMAP Progressive Screening Express Kit (R8127) Molecular Devices
d) Complete Reaction Buffer containing 0.1% BSA, 10 mM Tris-HCl, 10 mM $MgCl_2$, 0.05% $NaN_3$ and 0.01% phosphate free BSA, 1 mM DTT
e) Progressive Binding Solution containing 75% Buffer A, 25% Buffer B and low volume Binding Reagent which contains the binding entity for the assay
f) ATP diluted in complete reaction buffer
g) Black polystyrene 384 well assay plates (Nunc).
h) Biotek Synergy 4 Hybrid Plate reader.

5 µl of test compound was dissolved in DMSO (Sigma Aldrich) and serially diluted in complete reaction buffer to give a fourteen point half log dose response and plated into 384 well black plates. The compound was incubated at room temperature with activated AKT isoform (50µl) at the pre-determined concentration, for 45 minutes.

2.5 µl of ATP solution mixed with 2.5 µl of AKT substrate peptide (FAM Crosstide (R7110) Molecular Devices) were dispensed into each well and the plate centrifuged at 1000 rpm for 20 seconds to ensure homogenous mixing of reagents. The reaction mix was incubated in the dark for one hour at room temperature.

The kinase reaction was stopped by the addition of Progressive Binding Solution and the mixture allowed to equilibrate for one hour in the dark, at room temperature.

The fluorescent polarisation generated in each well was determined using a Biomek Synergy 4 Hybrid plate reader. In brief, each reaction solution was excited at 485 nm with the emission measured at 528 nm in both the parallel and perpendicular pathway.

The polarisation value generated in each well was calculated by Gen5 software (Biotek) and the % inhibition of kinase activity compared to vehicle control was calculated via GraphPad Prism. $IC_{50}$ values for each compound were calculated by non-linear regression analysis using Prism software.

All plates were internally controlled by two methods. Firstly, by calculating the signal:noise ratio; based on kinase polarisation without inhibitor and polarisation generated by complete reaction buffer in the absence of activated kinase. Secondly by determining $IC_{50}$ values generated by known inhibitors of the AKT isoforms.

Testing of the compounds was also performed using in vitro cell proliferation assays:

Cell Titre Glo (Promega) is a highly sensitive homogeneous reagent used to determine the viability of cells. The reagent uses a stable form of luciferase to measure ATP as an output of viability. The luminescent values generated in the assay are directly proportional to the number of viable cells in your assay.

The following materials were used: White, clear bottomed 96 well assay plates (Costar); Cell titre Glo reagents; LnCaP (ECACC) cells grown in RPMI medium (Invitrogen) supplemented with 10 mM HEPES (Invitrogen), 1 mM Sodium pyruvate (Invitrogen), 2 mM L-Glutamine (Invitrogen) and 10% Foetal calf serum (Invitrogen); PC3 (ECACC) cells grown in RPMI medium supplemented with 10% Foetal calf serum (Invitrogen); Trypsin (Invitrogen); PBS (Invitrogen); Biotek Synergy 4 Hybrid Plate reader; 96 well plate shaker (Stuart SSL5); Eppendorf 5414 desk-top centrifuge; Beckman Coulter cell counter Z1 single threshold system.

Prostate cell lines, PC3 and LnCaP, were washed, detached and re-suspended in their respective fresh media. The cells were pelleted by centrifugation (Eppendorf 5414) and spent supernatant discarded. The cells were re-suspended by vortex mixing, counted and seeded into clear bottom white 96 well plates at a density of 5000 cells per well. The cells were incubated (Sanyo) overnight at 37° C. (95% $O_2$/5% $CO_2$), and next day treated with increasing concentrations of test compound formulated in fresh medium. The plates were returned to the incubator for 72 hours.

Cell Titre Glo (Promega) was prepared by mixing the supplied reagents as per manufacturer's instructions and left to stand at room temperature. The cell plates were removed from the incubator and 800l of the Cell Titre Glo solution added to each well. The plate was shaken for five minutes to ensure homogenous mixing of reagents and cells, then left to stand for ten minutes at room temperature.

The cell viability post compound treatment was determined by the luminescent intensity emitted from the drug treated wells in the plate. In brief, the assay plate was placed in the Biotex Synergy 4 Hybrid plate reader and the luminescence read in each well. The compound treated wells were compared to vehicle treated wells and the % inhibition of cell viability calculated.

The data was analysed using GraphPad Prism, with $IC_{50}$ values generated using non-linear regression of the data set.

Analysis of Compound Effects on AKT Signalling Pathways

Phosphorylation status of various members of the AKT/ PI3K pathway were investigated via western blotting.

Materials Required for this Assay: 20× Running buffer (Invitrogen); Rainbow marker ladder (GE Healthcare); Reducing buffer (Invitrogen); 20× Transfer buffer (Invitrogen); 4-12% Bis-Tris Gels (Invitrogen); Filter paper (Whatman); Nitrocellulose (Amersham); ECL plus detection reagents (GE Healthcare); Radiographic film (Kodak); Biorad Protein determination reagent (Biorad); AKT pathway signalling antibodies (Cell Signalling) LnCaP and PC3 cell lines were washed, detached and re-suspended in fresh medium. They were seeded in 90 mm² dishes and incubated overnight (95% $O_2$/5% $CO_2$) to allow adherence. When the cells had reached 60% confluence, the medium was removed and replaced with compound or vehicle supplemented medium. The plates were incubated for a range of time points.

The medium was removed and the cells placed on ice and washed in PBS. 300 μl of lysis buffer was added to the dish and left for a few minutes, before the cells were scraped into the solution and pipetted into a centrifuge tube. The tube was placed on ice for 10 minutes and then vortexed to aid cellular lysis. The sample was centrifuged (Eppendorf bench-top ultra-fuge) at 13.2 k rpm for 10 minutes at 4° C. The resultant supernatant was assayed for protein content using the Bradford method (Biorad) and equal quantities of protein calculated and heated in sample reducing buffer to 95° C. for ten minutes.

The samples were run on 4-12% Bis-Tris gels (Invitrogen), transferred onto nitrocellulose membrane (Amersham) and blocked with a 5% non-fat milk solution.

The membranes were used to determine difference in total AKT, pSer473 AKT, pGSK3β and total GSK3β (all sourced from Cell Signalling) The respective primary antibodies were diluted in 1% non-fat milk blocking solution and incubated on the membranes overnight at 4° C. The membranes were washed three times in PBS and incubated with the respective secondary antibodies (Sigma Aldrich) for two hours and the proteins were detected using ECL plus detection reagents (GE Healthcare).

The invention claimed is:

1. A compound according to Formula (I):

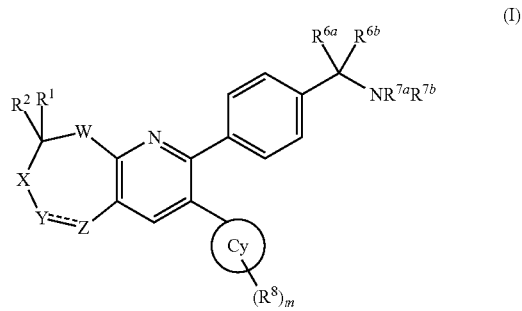

wherein:

$R^1$ and $R^2$ are each independently selected from hydrogen, aryl, C1-C10 alkyl, CN, CHO, $CO_2H$, $CONH_2$, $CONHR^3$, $CONR^{3a}R^{3b}$, $COR^3$, $CO_2R^3$, $NH_2$, $NHR^3$, $NR^{3a}R^{3b}$, $NHCOR^3$, $NHSO_2R^3$, $NR^{3a}COR^{3b}$, $NR^{3a}SO_2R^{3b}$, OH, $OR^3$, SH, $SR^3$, $SOR^3$, $SO_2R^3$, $SO_2NHR^3$, $SO_2NR^{3a}R^{3b}$, F, Cl, Br and I, wherein each $R^3$, $R^{3a}$ and $R^{3b}$ is independently selected from C1-C10 alkyl, including wherein $R^{3a}$ and $R^{3b}$ are joined to one another to form a heterocycle that includes the nitrogen to which they are attached;

wherein separate $R^1$ and $R^2$ may be joined to one another to form an optionally substituted and optionally saturated heterocycle or carbocycle that includes the C atom to which they are attached; or $R^1$ and $R^2$ together are oxo or optionally C1-C10 alkyl O-substituted oxime;

W is O;

X is absent;

Y and Z are independently either substituted or unsubstituted nitrogen or carbon and where carbon is substituted by substituents independently selected from the members of the group from which $R^1$ and $R^2$ are selected above or when nitrogen then the substituent is selected from aryl, C1-C10 alkyl, $SO_2R^3$, $CONHR^3$, $CONR^{3a}R^{3b}$, $COR^3$ and $CO_2R^3$ where $R^3$, $R^{3a}$ and $R^{3b}$ are as defined above, or where Y and Z together form an optionally substituted heterocyclyl or carbocyclic group, or where Y is $SO_2$;

$R^{7a}$ and $R^{7b}$ are independently selected from H and alkyl, including wherein $R^{7a}$ and $R^{7b}$ are joined to one another to form a heterocycle that includes the nitrogen to which they are attached;

$R^{6a}$ and $R^{6b}$ are taken together to form a monocyclic or bicyclic carbo- or heterocycle with 3-7 members in each ring, said heterocycle having one or more heteroatoms selected from N, O and S, and said carbo or heterocycle is optionally substituted with one or more substituents selected from: $(C_1-C_6)$alkyl, $(C_3-C_6)$cycloalkyl, $(C_1-C_6)$ alkoxy, $CO_2H$, halo, OH, CN and $NR^{3a}R^{3b}$, said alkyl, cycloalkyl and alkoxy is optionally substituted with one or more substituents selected from halo, CN, OH and $NR^{3a}R^{3b}$; and ring Cy is selected from $(C_3$ to $C_8)$heteroaryl and $(C_3$ to $C_8$ aryl, wherein m is 0, 1, 2, 3, 4 or 5, and each $R^8$ is independently selected from alkyl, CN, CHO, $CO_2H$, $CONH_2$, $CONHR^9$, $CONHR^{9a}R^{9b}$, $COR^9$, $CO_2R^9$, $NH_2$, $NHR^9$, $NR^{9a}R^{9b}$, $NHCOR^9$, $NHSO_2R^9$, $NR^{9a}COR^{9b}$, $NR^{9a}SO_2R^{9b}$, OH, $OR^9$, SH, $SR^9$, F, Cl, Br and I, wherein each $R^9$, $R^{9a}$ and $R^{9b}$ is independently selected from alkyl, including wherein $R^{9a}$ and $R^{9b}$ form a heterocycle that includes the nitrogen to which they are attached;

or a compound selected from the group:

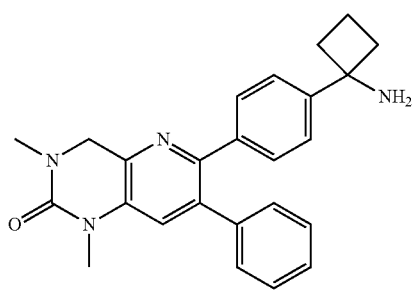

-continued

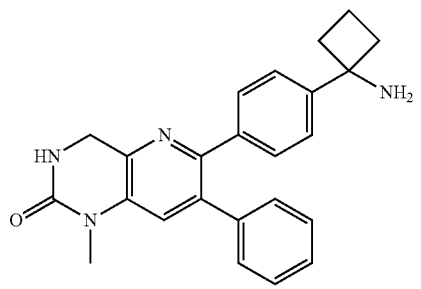

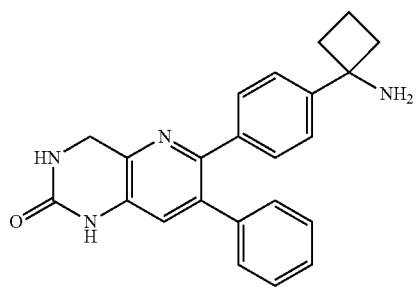

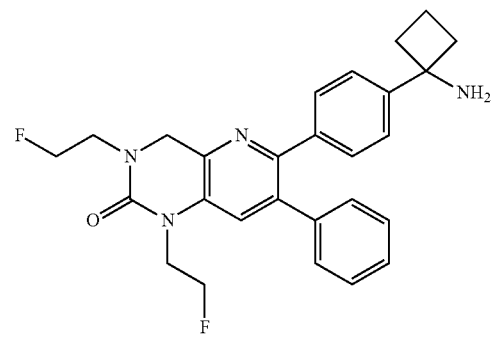

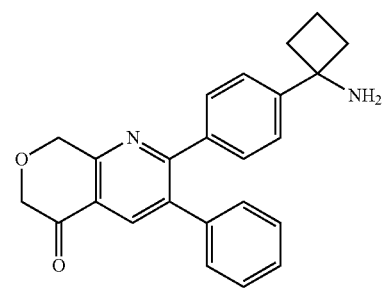

and pharmaceutically acceptable salts, stereoisomers and tautomers thereof.

2. The compound of claim 1, wherein $R^{6a}$ and $R^{6b}$ together form

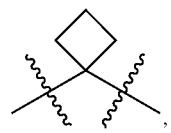 [SMILES: *C1(*)CCC1]

3. The compound of claim 2, wherein $R^{7a}$ and $R^{7b}$ are hydrogen.

4. The compound of claim 1, wherein the bond between Y and Z is a single bond.

5. The compound of claim 1 where Y is carbonyl and Z is optionally substituted amino, or Z is carbonyl and Y is optionally substituted amino.

6. The compound of claim 5 wherein $R^1$ and $R^2$ are hydrogen.

7. The compound of claim 5 wherein, when amino is substituted, it is methyl or acetamido substituted.

8. The compound of claim 1, wherein the substituents bound to Y and Z together with Y and Z themselves form a 5 or 6 membered optionally substituted heterocyclic ring.

9. The compound of claim 1, wherein the substituents bound to Y and Z together with Y and Z themselves form a moiety selected from the group:

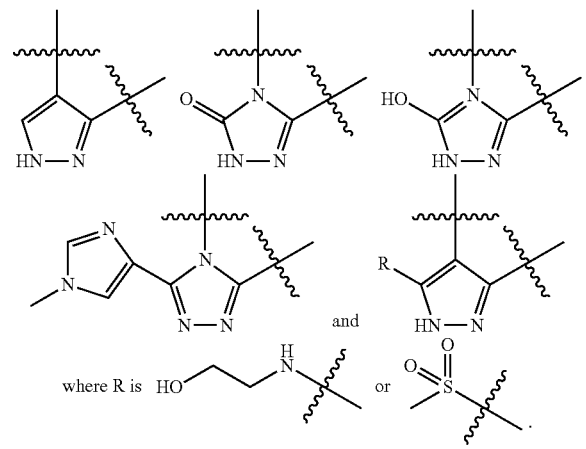

10. The compound of claim 1, wherein Cy is phenyl and m is 0.

11. The compound of claim 1 being:
6-(4-(1-aminocyclobutyl)phenyl)-7-phenyl-1H-pyrido[2,3-b][1,4]oxazin-2(3H)-one
6-(4-(1-aminocyclobutyl)phenyl)-1-methyl-7-phenyl-1H-pyrido[2,3-b][1,4]oxazin-2(3H)-one
6-(4-(1-aminocyclobutyl)phenyl)-7-phenyl1(prop-2yn-1-yl)1H-pyrido[2,3-b][1,4]oxazin2(3H)-one
2-(6-(4-(1-aminocyclobutyl)phenyl)-2-oxo-7-phenyl-2,3-dihydro1H-pyrido[2,3-b][1,4]oxazin1-yl)acetonitrile
6-(4-(1-aminocyclobutyl)phenyl)1(2(dimethylamino)ethyl)-7-phenyl1H-pyrido[2,3-b][1,4]oxazin-2(3H)-one
2-(6-(4-(1-aminocyclobutyl)phenyl)-2-oxo-7-phenyl-2,3-dihydro1H-pyrido[2,3-b][1,4]oxazin1-yl)acetamide
6-(4-(1-aminocyclobutyl)phenyl)1-(2-oxopropyl)-7-phenyl1H-pyrido[2,3-b][1,4]oxazin-2(3H)one
1-(4-(7-phenyl-2,3-dihydro1H-pyrido[2,3-b][1,4]oxazin-6-yl)phenyl)cyclobutanamine
7-(4-(1-aminocyclobutyl)phenyl)8-phenyl-2,4-dihydro1H-pyrido[2,3-b][1,2,4]triazolo[4,3-d][1,4]oxazin1-one
1-(4-(8-phenyl-4H-pyrido[2,3-b][1,2,4]triazolo[4,3-d][1,4]oxazin-7-yl)phenyl)cyclobutanamine
1-(4(1-methyl-7-phenyl-2,3-dihydro1H-pyrido[2,3-b][1,4]oxazin-6-yl)phenyl)cyclobutanamine
1-(6-(4-(1-aminocyclobutyl)phenyl)-7-phenyl-2,3-dihydro1H-pyrido[2,3-b][1,4]oxazin1yl)ethanone
1-((1H-imidazol-2-yl)methyl)-6(4(1-aminocyclobutyl)phenyl)-7-phenyl1H-pyrido[2,3-b][1,4]oxazin-2(3H)-one
2-(6-(4-(1-aminocyclobutyl)phenyl)-7-phenyl-2,3-dihydro1H-pyrido[2,3-b][1,4]oxazin1-yl)acetonitrile
2-(6-(4-(1-aminocyclobutyl)phenyl)-7-phenyl-2,3-dihydro1H-pyrido[2,3-b][1,4]oxazin1-yl)acetamide
6-(4-(1-aminocyclobutyl)phenyl)-7-phenyl1(pyridin-4-ylmethyl)1H-pyrido[2,3-b][1,4]oxazin-2(3H)-one
6-(4-(1-aminocyclobutyl)phenyl)-7-phenyl1(pyridin-3-ylmethyl)1H-pyrido[2,3-b][1,4]oxazin-2(3H)-one
1-(4-(1-ethyl8-phenyl-4H-pyrido[2,3-b][1,2,4]triazolo[4,3-d][1,4]oxazin-7-yl)phenyl)cyclobutanamine
6-(4-(1-aminocyclobutyl)phenyl)1(cyclobutylmethyl)-7-phenyl1H-pyrido[2,3-b][1,4]oxazin-2(3H)-one
ethyl 2-(6-(4-(1-aminocyclobutyl)phenyl)-2-oxo-7-phenyl-2,3-dihydro-1H-pyrido[2,3-b][1,4]oxazin-1-yl)acetate
7-(4-(1-aminocyclobutyl)phenyl)-8-phenyl-4H-pyrido[2,3-b][1,2,4]triazolo[4,3-d][1,4]oxazin-1-amine
6-(4-(1-aminocyclobutyl)phenyl)-1-(2-methoxyethyl)-7-phenyl-1H-pyrido[2,3-b][1,4]oxazin-2(3H)-one
6-(4-(1-aminocyclobutyl)phenyl)-1-ethyl-7-phenyl-1H-pyrido[2,3-b][1,4]oxazin-2(3H)-one
1-((1H-imidazol-5-yl)methyl)-6-(4-(1-aminocyclobutyl)phenyl)-7-phenyl-1H-pyrido[2,3-b][1,4]oxazin-2(3H)-one
2-(6-(4-(1-aminocyclobutyl)phenyl)-2-oxo-7-phenyl-2,3-dihydro-1H-pyrido[2,3-b][1,4]oxazin-1-yl)propanenitrile
6-(4-(1-aminocyclobutyl)phenyl)-1-(cyclopropylmethyl)-7-phenyl-1H-pyrido[2,3-b][1,4]oxazin-2(3H)-one
6-(4-(1-aminocyclobutyl)phenyl)-7-phenyl-1-(pyridin-2-ylmethyl)-1H-pyrido[2,3-b][1,4]oxazin-2(3H)-one
6-(4-(1-aminocyclobutyl)phenyl)-1-isopropyl-7-phenyl-1H-pyrido[2,3-b][1,4]oxazin-2(3H)-one
6-(4-(1-aminocyclobutyl)phenyl)-1-cyclopentyl-7-phenyl-1H-pyrido[2,3-b][1,4]oxazin-2(3H)one
6-(4-(1-aminocyclobutyl)phenyl)-7-phenyl-1-(thiazol-4-ylmethyl)-1H-pyrido[2,3-b][1,4]oxazin-2(3H)-one
6-(4-(1-aminocyclobutyl)phenyl)-7-phenyl-1-(2,2,2-trifluoroethyl)-1H-pyrido[2,3-b][1,4]oxazin-2(3H)-one
6-(4-(1-aminocyclobutyl)phenyl)-1-cyclobutyl-7-phenyl-1H-pyrido[2,3-b][1,4]oxazin-2(3H)-one
3-(6-(4-(1-aminocyclobutyl)phenyl)-2-oxo-7-phenyl-2,3-dihydro-1H-pyrido[2,3-b][1,4]oxazin-1-yl)propanenitrile
1-(4-(1-methyl-8-phenyl-4H-pyrido[2,3-b][1,2,4]triazolo[4,3-d][1,4]oxazin-7-yl)phenyl)cyclobutanamine
4-(6-(4-(1-aminocyclobutyl)phenyl)-2-oxo-7-phenyl-2,3-dihydro-1H-pyrido[2,3-b][1,4]oxazin-1-yl)butanenitrile
6-(4-(1-aminocyclobutyl)phenyl)-7-phenyl-1-(tetrahydro-2H-pyran-4-yl)-1H-pyrido[2,3-b][1,4]oxazin-2(3H)-one
5-(6-(4-(1-aminocyclobutyl)phenyl)-2-oxo-7-phenyl-2,3-dihydro-1H-pyrido[2,3-b][1,4]oxazin-1-yl)pentanenitrile
1-allyl-6-(4-(1-aminocyclobutyl)phenyl)-7-phenyl1H-pyrido[2,3-b][1,4]oxazin-2(3H)-one
6-(4-(1-aminocyclobutyl)phenyl)-1-(2-hydroxyethyl)-7-phenyl-1H-pyrido[2,3-b][1,4]oxazin-2(3H)-one
1-(4-(8-phenyl-1-propyl-4H-pyrido[2,3-b][1,2,4]triazolo[4,3-d][1,4]oxazin-7-yl)phenyl)cyclobutanamine
1-(4-(1-(methylsulfonyl)-7-phenyl-2,3-dihydro-1H-pyrido[2,3-b][1,4]oxazin-6-yl)phenyl)cyclobutanamine
6-(4-(1-aminocyclobutyl)phenyl)-3-(2-hydroxyethyl)-7-phenyl-1H-pyrido[2,3-b][1,4]oxazin-2(3H)-one
6-(4-(1-aminocyclobutyl)phenyl)-1-methyl-7-phenyl-1H-pyrido[3,2-e][1,3,4]oxathiazine 2,2-dioxide 6-(4-(1-aminocyclobutyl)phenyl)-7-phenyl-1-(pyridin-3-yl)-1H-pyrido[3,2-e][1,3,4]oxathiazine 2,2-dioxide
6-(4-(1-aminocyclobutyl)phenyl)-7-phenyl-1-(pyridin-3-yl)-1H-pyrido[2,3-b][1,4]oxazin-2(3H)one
2-(6-(4-(1-aminocyclobutyl)phenyl)-2,2-dioxido-7-phenyl-1H-pyrido[3,2-e][1,3,4]oxathiazin-1-yl )acetonitrile
6-(4-(1-aminocyclobutyl)phenyl)-3-(2-hydroxyethyl)-1-methyl-7-phenyl-1H-pyrido[2,3-b][1,4]oxazin-2(3H)-one
2-(6-(4-(1-aminocyclobutyl)phenyl)-3-(2-hydroxyethyl)-2-oxo-7-phenyl-2,3-dihydro-1H-pyrido[2,3-b][1,4]oxazin-1-yl)acetonitrile
6-(4-(1-aminocyclobutyl)phenyl)-3-methyl-7-phenyl-1H-pyrido[2,3-b][1,4]oxazin-2(3H)-one
2-(6-(4-(1-aminocyclobutyl)phenyl)-3-methyl-2-oxo-7-phenyl-2,3-dihydro-1H-pyrido[2,3-b][1,4]oxazin-1-yl)acetonitrile
6-(4-(1-aminocyclobutyl)phenyl)-1-(methylsulfonylmethyl)-7-phenyl-1H-pyrido[2,3-b][1,4]oxazin-2(3H)-one
6(4(1-aminocyclobutyl)phenyl)1(1-methyl-1H-pyrazol-4-yl)-7-phenyl-1H-pyrido[2,3-b][1,4]oxazin-2(3H)-one
6-(4-(1-aminocyclobutyl)phenyl)-1,3-dimethyl-7-phenyl-1H-pyrido[2,3-b][1,4]oxazin-2(3H)-one
6-(4-(1-aminocyclobutyl)phenyl)-1-(2,2-difluoroethyl)-7-phenyl-1H-pyrido[2,3-b][1,4]oxazin-2(3H)-one
6-(4-(1-aminocyclobutyl)phenyl)-1-(2-fluoroethyl)-7-phenyl-1H-pyrido[2,3-b][1,4]oxazin2(3H)-one
6-(4-(1-aminocyclobutyl)phenyl)-7-phenyl-3,4-dihydropyrido[3,2-d]pyrimidin-2(1H)-one
6-(4-(1-aminocyclobutyl)phenyl)-N-ethyl-7-phenyl-2,3-dihydro-1H-pyrido[2,3-b][1,4]oxazine-1-carboxamide
6-(4-(1-aminocyclobutyl)phenyl)-1,3-dimethyl-7-phenyl-3,4-dihydropyrido[3,2-d]pyrimidin-2(1H)-one
6-(4-(1-Aminocyclobutyl)phenyl)-1-methyl-7-phenyl-1H-pyrido[2,3-b][1,4]oxazin-2(3H)-one O-methyl oxime
1-(4-(7-phenyl-1-(pyridin-3-yl)-2,3-dihydro-1H-pyrido[2,3-b][1,4]oxazin-6-yl)phenyl)cyclobutanamine
1-(4-(1-bromo-8-phenyl-4H-pyrido[2,3-b][1,2,4]triazolo[4,3-d][1,4]oxazin-7-yl)phenyl)cyclobutanamine
(R)-2-(6-(4-(1-aminocyclobutyl)phenyl)-3-methyl-2-oxo-7-phenyl-2,3-dihydro-1H-pyrido[2,3-b][1,4]oxazin-1-yl)acetonitrile
2-(6-(4-(1-aminocyclobutyl)phenyl)-3-(methoxymethyl)-2-oxo-7-phenyl-2,3-dihydro-1H-pyrido[2,3-b][1,4]oxazin-1-yl)acetonitrile
6-(4-(1-aminocyclobutyl)phenyl)-3-(methoxymethyl)-1-methyl-7-phenyl-1H-pyrido[2,3-b][1,4]oxazin-2(3H)-one
6-(4-((1s,3s)-1-amino-3-hydroxycyclobutyl)phenyl)-1-methyl-7-phenyl-1H-pyrido[2,3-b][1,4]oxazin-2(3H)-one
1-(4-(1-(difluoromethyl)-8-phenyl-4H-pyrido[2,3-b][1,2,4]triazolo[4,3-d][1,4]oxazin-7-yl)phenyl)cylobutanamine
7-(4-(1-aminocyclobutyl)phenyl)-2-methyl-8-phenyl-2,4-dihydro-1H-pyrido[2,3-b][1,2,4]triazolo[4,3-d][1,4]oxazin-1-one
1-(4-(8-phenyl-1-(trifkoromethyl)-4H-pyrido[2,3-b][1,2,4]triazolo[4,3-d][1,4]oxazin-7-yl )phenyl)cyclobutanamine
2-(7-(4-(1-aminocyclobutyl)phenyl)-1-oxo-8-phenyl-1H-pyrido[2,3-b][1,2,4]triazolo[4,3-d][1,4]oxazin-2(4H)-yl)acetonitrile
6-(4-(1-aminocyclobutyl)phenyl)-1-isobutyl-7-phenyl-1H-pyrido[2,3-b][1,4]oxazin-2(3H)-one
7-(4-(1-aminocyclobutyl)phenyl)-8-phenyl-2-(2,2,2-trifluoroethyl)-2,4-dihydro-1H-pyrido[2,3-b][1,2,4]triazolo[4,3-d][1,4]oxazin-1-one
6-(4-(1-aminocyclobutyl)phenyl)-7-phenyl-1-propyl-1H-pyrido[2,3-b][1,4]oxazin-2(3H)-one
6-(4-(1-aminocyclobutyl)phenyl)-1-(3-hydroxy-2-(hydroxymethyl)-2-methylpropyl)-7-phenyl1H-pyrido[2,3-b][1,4]oxazin-2(3H)-one
7-(4-(1-Aminocyclobutyl)phenyl)-8-phenyl-4H-pyrido[2,3-b][1,2,4]triazolo[4,3-d][1,4]oxazin-1-yl)phenyl)methanol
6-(4-(1-aminocyclobutyl)phenyl)-1-methyl-7-phenyl-3,4-dihydropyrido[3,2-d]pyrimidin-2(1H)-one
6-(4-(1-aminocyclobutyl)phenyl)-1,3-bis(2-fluoroethyl)-7-phenyl-3,4-dihydropyrido[3,2-d]pyrimidin-2(1H)-one
1-(4-(1-cyclopropyl-8-phenyl-4H-pyrido[2,3-b][1,2,4]triazolo[4,3-d][1,4]oxazin-7-yl)phenyl)cyclobutanamine
1-(4-(1-isopropyl-8-phenyl-4H-pyrido[2,3-b][1,2,4]triazolo[4,3-d][1,4]oxazin-7-yl)phenyl)cyclobutanamine
6-(4-((1r,3r)-1-amino-3-hydroxy-3-methylcyclobutyl)phenyl)-1-methyl-7-phenyl-1H-pyrido[2,3-b][1,4]oxazin-2(3H)-one
1-(4-(1-isobutyl-8-phenyl-4H-pyrido[2,3-b][1,2,4]triazolo[4,3-d][1,4]oxazin-7-yl)phenyl)cyclobutanamine
7-(4-(1-aminocyclobutyl)phenyl)-N,N-dimethyl-8-phenyl-4H-pyrido[2,3-b][1,2,4]triazolo[4,3-d][1,4]oxazin-1-amine
1-(4-(8-phenyl-1-(2,2,2-trifluoroethyl)-4H-pyrido[2,3-b][1,2,4]triazolo[4,3-d][1,4]oxazin-7yl)phenyl)cyclobutanamine
7-(4-(1-aminocyclobutyl)phenyl)-8-phenyl-4H-pyrido[2,3-b][1,2,4]triazolo[4,3-d][1,4]oxazine-1-carboxamide
1-(4-(1-(fluoromethyl)-8-phenyl-4H-pyrido[2,3-b][1,2,4]triazolo[4,3-d][1,4]oxazin-7-yl)phenyl)cyclobutanamine
1-(4-(1-(2-methoxyethyl)-8-phenyl-4H-pyrido[2,3-b][1,2,4]triazolo[4,3-d][1,4]oxazin-7yl)phenyl)cyclobutanamine
1-(4-(8-phenyl-1-(pyridin-3yl)-4H-pyrido[2,3-b][1,2,4]triazolo[4,3-d][1,4]oxazin-7-yl)phenyl)cyclobutanamine
1-(4-(8-phenyl-1-(pyridin-4yl)-4H-pyrido[2,3-b][1,2,4]triazolo[4,3-d][1,4]oxazin-7-yl)phenyl)cyclobutanamine
6-(4-(1-aminocyclobutyl)phenyl)-1-methyl-7-(pyridin-3yl)-1H-pyrido[2,3-b][1,4]oxazin-2(3H)-one
6-(4-(1-aminocyclobutyl)phenyl)-1-methyl-7-(thiophen-3yl)-1H-pyrido[2,3-b][1,4]oxazin-2(3H)-one
6-(4-(1-aminocyclobutyl)phenyl)-1-methyl-7-(thiophen-2yl)-1H-pyrido[2,3-b][1,4]oxazin-2(3H)-one
2-(4-(1-aminocyclobutyl)phenyl)-3-phenyl-6,8-dihydro-5H-pyrano[3,4-b]pyridin-5-one
(1r,3r)-3-amino-3-(4-(1-(difluoromethyl)-8-phenyl-4H-pyrido[2,3-b][1,2,4]triazolo[4,3-d][1,4]oxazin-7-yl)phenyl)-1-methylcyclobutanol
1-(4-(1,8-diphenyl-4H-pyrido[2,3-b][1,2,4]triazolo[4,3-d][1,4]oxazin-7-yl)phenyl)cyclobutanamine
1-(4-(8-phenyl-1-(pyridin-2yl)-4H-pyrido[2,3-b][1,2,4]triazolo[4,3-d][1,4]oxazin-7-yl)phenyl)cyclobutanamine
6(4(1-aminocyclobutyl)phenyl)-7(4-fluorophenyl)1-methyl1H-pyrido[2,3-b][1,4]oxazin-2(3H)-one 6-(4-((1s,3s)-1-amino-3-hydroxy-3-methylcyclobutyl)
phenyl)-1-methyl-7-phenyl-1H-pyrido[2,3-b][1,4]oxazin-2(3H)-one (1s,3s)-3-Amino-3-(4-(1-ethyl-8-phenyl-4H-pyrido[2,3-b][1,2,4]triazolo[4,3-d][1,4]oxazin-7-yl)phenyl)cyclobutanol 6-(4-((1r,3r)-1-amino-3-hydroxycyclobutyl)phenyl)-1-methyl-7-phenyl-1H-pyrido[2,3-b][1,4]oxazin-2(3H)-one (1r,3r)-3-amino-3-(4-(1-ethyl-8-phenyl-4H-pyrido[2,3-b][1,2,4]triazolo[4,3-d][1,4]oxazin-7- yl)phenyl)-1-methylcyclobutanol 6-(4-((1s,3s)-1-amino-3-hydroxycyclobutyl)phenyl)-1-ethyl-7-phenyl-1H-pyrido[2,3b][1,4]oxazin-2(3H)-one 6-(4-((1s,3s)-1-amino-3-hydroxycyclobutyl)phenyl)-1-(cyclopropylmethyl)-7-phenyl-1Hpyrido[2,3-b][1,4]oxazin-2(3H)-one 7-(4-((1s,3s)-1-amino-3-hydroxycyclobutyl)phenyl)-8-phenyl-2,4-dihydro-1H-pyrido[2,3b][1,2,4]triazolo[4,3-d][1,4]oxazin-1-one 6-(4-((1r,3r)-1-amino-3-hydroxy-3-methylcyclobutyl)phenyl)-1-ethyl-7-phenyl-1H-pyrido[2,3-b][1,4]oxazin-2(3H)-one 6-(4-((1r,3r)-1-amino-3-hydroxy-3-methylcyclobutyl)phenyl)-1-(cyclopropylmethyl)-7phenyl-1H-pyrido[2,3-b][1,4]oxazin-2(3H)- one 6-(4-((1r,3r)-1-amino-3-hydroxy-3-methylcyclobutyl)phenyl)-1-(2-fluoroethyl)-7-phenyl-1Hpyrido[2,3-b][1,4]oxazin-2(3H)- one 2-(6-(4-((1s,3s)-1-amino-3-hydroxycyclobutyl)phenyl)-2-oxo-7-phenyl-2,3-dihydro-1Hpyrido[2,3-b][1,4]oxazin-1-yl)acetonitrile 6-(4-((1s,3s)-1-amino-3-hydroxycyclobutyl)phenyl)-7-phenyl-1-(2,2,2-trifluoroethyl)-1H-pyrido[2,3-b][1,4]oxazin-2(3H)-one 6-(4-(1-aminocyclopropyl)phenyl)-1-methyl-7-phenyl-1H-pyrido[2,3-b][1,4]oxazin-2(3H)-one 2-(6-(4-((1r,3r)-1-amino-3-hydroxy-3-methylcyclobutyl)phenyl)-2-oxo-7-phenyl-2,3-dihydro-1H-pyrido[2,3-b][1,4]oxazin-1-yl)acetonitrile 6-(4-((1r,3r)-1-amino-3-hydroxy-3-methylcyclobutyl)phenyl)-7-phenyl-1-(2,2,2-trifluoroethyl)-1H-pyrido[2,3-b][1,4]oxazin-2(3H)-one 7-(4-((1r,3r)-1-amino-3-hydroxy-3-methylcyclobutyl)phenyl)-8-phenyl-2,4-dihydro-1H-pyrido [2,3-b][1,2,4]triazolo[4,3-d][1,4]oxazin-1-one and pharmaceutically acceptable salts, stereoisomers and tautomers thereof.

12. The compound of claim 1 being:
6-(4-(1-aminocyclobutyl)phenyl)-1 -methyl-7phenyl-1H-pyrido[2,3-b][1,4]oxazin-2(3H)-one 2-(6-(4-(1-aminocyclobutyl)phenyl)-2-oxo-7-phenyl-2,3-dihydro-1H-pyrido[2,3-b][1,4]oxazin-1yl)acetonitrile and pharmaceutically acceptable salts, stereoisomers and tautomers thereof.

13. The compound of claim 1 being:
2-(6-(4-(1-aminocyclobutyl)phenyl)-2-oxo-7-phenyl-2,3-dihydro-1H-pyrido[2,3-b][1,4]oxazin-1yl)acetonitrile and pharmaceutically acceptable salts, stereoisomers and tautomers thereof.

14. The compound of claim 1 being:
6-(4-(1-aminocyclobutyl)phenyl)-7-phenyl-1-(prop-2-yn-1-yl)-1H-pyrido[2,3-b][1,4]oxazin-2(3H)-one 1-(4-(1-ethyl-8-phenyl-4H-pyrido[2,3-b][1,2,4]triazolo[4,3-d][1,4]oxazin-7-yl)phenyl)cyclobutanamine 6-(4-(1-aminocyclobutyl)phenyl)-1-ethyl-7-phenyl-1H-pyrido[2,3-b][1,4]oxazin-2(3H)-one 6-(4-(1-aminocyclobutyl)phenyl)-1-(cyclopropylmethyl)-7-phenyl-1H-pyrido[2,3-b][1,4]oxazin-2(3H)-one 6-(4-(1-aminocyclobutyl)phenyl)-7-phenyl-1-(2,2,2-trifluoroethyl)-1H-pyrido[2,3-b][1,4]oxazin-2(3H)-one 6-(4-(1-aminocyclobutyl)phenyl)-1-(2-fluoroethyl)-7-phenyl-1H-pyrido[2,3-b][1,4]oxazin-2(3H)-one 1-(4-(1-(difluoromethyl)-8-phenyl-4H-pyrido[2,3-b][1,2,4]triazolo[4,3-d][1,4]oxazin-7-yl)phenyl)cylobutanamine 1-(4-(1-(fluoromethyl)-8-phenyl-4H-pyrido[2,3-b][1,2,4]triazolo[4,3-d][1,4]oxazin-7-yl)phenyl)cyclobutanamine 6-(4-((1r,3r)-1-amino-3-hydroxycyclobutyl)phenyl)-1-methyl-7-phenyl-1H-pyrido[2,3-b][1,4]oxazin-2(3H)-one (1r,3r)-3-amino-3-(4-(1-ethyl-8-phenyl-4H-pyrido[2,3-b][1,2,4]triazolo[4,3-d][1,4]oxazin-7yl)phenyl)-1-methylcyclobutanol 6-(4-((1r,3r)-1-amino-3-hydroxy-3-methylcyclobutyl)phenyl)-1-ethyl-7-phenyl-1H-pyrido[2,3-b][1,4]oxazin-2(3H)-one 6-(4-((1r,3r)-1-amino-3-hydroxy-3-methylcyclobutyl)phenyl)-1-(cyclopropylmethyl)-7-phenyl-1H-pyrido[2,3-b][1,4]oxazin-2(3H)- one 6-(4-((1r,3r)-1-amino-3-hydroxy-3-methylcyclobutyl)phenyl)-1-(2-fluoroethyl)-7phenyl-1H-pyrido[2,3-b][1,4]oxazin-2(3H)- one 2-(6-(4-((1r,3r)-1-amino-3-hydroxy-3-methylcyclobutyl)phenyl)-2-oxo-7-phenyl-2,3-dihydro-1H-pyrido[2,3-b][1,4]oxazin-1yl)acetonitrile 6-(4-((1r,3r)-1-amino-3-hydroxy-3-methylcyclobutyl)phenyl)-7-phenyl-1-(2,2,2-trifkoroethyl)-1H-pyrido[2,3-b][1,4]oxazin-2(3H)-one and pharmaceutically acceptable salts, stereoisomers and tautomers thereof.

15. A pharmaceutical composition comprising a pharmaceutical carrier and, dispersed therein, a compound of claim 1.

16. A compound selected from:
2-(4-(1-aminocyclobutyl)phenyl)-3-phenyl-7,8-dihydroquinolin-5(6H)-one 2-(4-(1-aminocyclobutyl)phenyl)-3-phenyl-7,8-dihydroquinolin-5(6H)-one oxime 2-(4-(1-aminocyclobutyl)phenyl)-3-phenyl-7,8-dihydroquinolin-5(6H)-one O-methyl oxime 1-(4-(8-phenyl-4,5-dihydro-2H-pyrazolo[3,4-f]quinolin-7yl)phenyl)cyclobutanamine 1-(4-(2-methyl-8-phenyl-4,5-dihydro-2H-pyrazolo[3,4-f]quinolin-7yl)phenyl)cyclobutanamine 1-(4-(1-methyl-8-phenyl-4,5-dihydro-1H-pyrazolo[3,4-f]quinolin-7yl)phenyl)cyclobutanamine 7-(4-(1-aminocyclobutyl)phenyl)-8-phenyl-4,5-dihydro-2H-pyrazolo[3,4-f]quinolin-3-ol 7-(4-(1-aminocyclobutyl)phenyl)-3a-methyl-8-phenyl-4,5-dihydro-2H-pyrazolo[3,4-f]quinolin-3(3aH)-one 1-(4-(3-(methylthio)-8-phenyl-4,5-dihydro-2H-pyrazolo[3,4-f]quinolin-7yl)phenyl)cyclobutanamine 1-(4-(3-(methylsulfonyl)-8-phenyl-4,5-dihydro-2H-pyrazolo[3,4-f]quinolin-7yl)phenyl)cyclobutanamine 7-(4-(1-aminocyclobutyl)phenyl)-N-methyl-8-phenyl-4,5-dihydro-2H-pyrazolo[3,4-f]quinolin-3-amine 2-((7-(4-(1-aminocyclobutyl)phenyl)-8-phenyl-4,5-dihydro-2H-pyrazolo[3,4-f]quinolin3yl)amino)ethanol 1-(4-(3-morpholino-8-phenyl-4,5-dihydro-2H-pyrazolo[3,4-f]quinolin-7yl)phenyl)cyclobutanamine 7-(4-(1-aminocyclobutyl)phenyl)-2-methyl-8-phenyl-4,5-dihydro-3H-imidazo[4,5-f]quinolin-3-ol 1-(4-(2-methyl-8-phenyl-4,5-dihydro-3H-imidazo[4,5-f]quinolin-7y1 )phenyl)cyclobutanamine 1-(4-(9-phenyl-5,6-dihydropyrido[2,3-h]quinazolin-8yl) phenyl)-cyclobutanamine 8-(4-(9-phenyl-5,6-dihydropyrido[2,3-h]quinazolin-2-amine 2-(4-(1-aminocyclobutyl)phenyl)-7,7-dimethyl-3-phenyl-7,8-dihydroquinolin-5(6H)-one 1-(4-(4,4-dimethyl-8-phenyl-4,5-dihydro-2H-pyrazolo[3,4-f]quinolin-7yl)phenyl)cyclobutanamine 2-(4-(1-aminocyclobutyl)phenyl)-3-phenyl-6,7,8,9-tetrahydro-5H-cyclohepta[b]pyridin5-one 1-(4-(9-phenyl-2,4,5,6-tetrahydropyrazolo[3',4':3,4]cyclohepta[1,2-b]pyridin-8yl)phenyl)cyclobutanamine 2-(4-(1-aminocyclobutyl)phenyl)-3-phenyl-7,8-dihydro-1,6-naphthyridin-5(6H)-one 2-(4-(1-aminocyclobutyl)phenyl)-6-methyl-3-phenyl-7,8-dihydro-1,6-naphthyridin5(6H)-one 2-(2-(4-(1-aminocyclobutyl)phenyl)-5-oxo-3-phenyl-7,8-dihydro-1,6naphthyridin-6(5H)-yl)acetonitrile 2-(4-(1-aminocyclobutyl)phenyl)-6-(2-dimethylamino) ethyl)-3-phenyl-7,8-dihydro-1,6naphthyridin-5 (6H)-one 8-(4-(1-aminocyclobutyl)phenyl)-9-phenyl-5,6-dihydro-[1,2,4]triazolo[3,4-f][1,6]naphthyridin-3(2H)-one 1-(4-(6-ethyl-3-phenyl-5,6,7,8-tetrahydro-1,6-naphthyridin-2yl)phenyl)cyclobutanamine 1-(4-(9-phenyl-5,6-dihydro-[1,2,4]triazolo[3,4-f][1,6] naphthyridin-8yl)phenyl)cyclobutanamine 1-(4-(3-(1-methyl-1H-imidazol-4yl)-9-phenyl-5,6-dihydro-[1,2,4]triazolo[3,4-f][1,6]naphthyridin-8yl)phenyl) cyclobutanamine 6-(4-(1-aminocyclobutyl)phenyl)-4-methyl-7-phenyl-3,4-dihydropyrido[2,3-b]pyrazin-2(1H)-one 7-(4-(1-aminocyclobutyl)phenyl)-8-phenyl-4,5-dihydro-1H-pyrido[2,3-b][1,4]diazepin-2(3H)-one 7-(4-(1-aminocyclobutyl)phenyl)-1,5-dimethyl-8-phenyl-4,5-dihydro-1H-pyrido[2,3-b][1,4]diazepin-2(3H)-one 7-(4-(1-aminocyclobutyl)phenyl)-1-methyl-8-phenyl-4,5-dihydro-1H-pyrido[2,3-b][1,4]diazepin-2(3H)-one 7-(4-(1-aminocyclobutyl)phenyl)-1-(2-fluoroethyl)-8-phenyl-4,5-dihydro-1H-pyrido[2,3-b][1,4]diazepin-2 (3H)-one 6-(4-(aminomethyl)phenyl)-1-methyl-7-phenyl-1H-pyrido[2,3-b][1,4]oxazin-2(3H)-one 6(4(1-aminocyclobutyl)phenyl)-7-(cyclopropylmethyl)-1methyl-1H-pyrido [2,3-b][1,4]oxazin-2(3H)-one 2-(6-(4-(aminomethyl)phenyl)-2-oxo-7-phenyl-2,3-dihydro-1H-pyrido[2,3-b][1,4]oxazin1-yl)acetonitrile 6-(4-(Aminomethyl)phenyl)-1-ethyl-7-phenyl-1H-pyrido [2,3-b][1,4]oxazin-2(3H)-one 6-(4-(Aminomethyl)phenyl)-1-(cyclopropylmethyl)-7-phenyl-1H-pyrido [2,3-b][1,4]oxazin-2(3H)-one 1-(4-(8-phenyl-4,5-dihydro-2H-pyrazolo[3,4-f]quinolin-7yl)phenyl)cyclobutanamine (4-(1-ethyl-8-phenyl-4H-pyrido [2,3-b][1,2,4]triazolo[4,3-d][1,4]oxazin-7-yl)phenyl)methanamine, (6(4(aminomethyl)phenyl)-7-phenyl-1-(2,2,2-trifluoroethyl)-1H-pyrido[2,3-b][1,4]oxazin-2(3H)-one, (4-(1-ethyl-8-phenyl-4H-pyrido[2,3-b][1,2,4]triazolo[4,3-d][1,4]oxazin-7-yl)phenyl)methanamine, (6(4(aminomethyl)phenyl)-7-phenyl-1-(2,2,2-trifluoroethyl)-1H-pyrido[2,3-b][1,4]oxazin-2(3H)-one, and pharmaceutically acceptable salts, stereoisomers and tautomers thereof.

\* \* \* \* \*